(12) United States Patent
Player et al.

(10) Patent No.: US 9,249,163 B2
(45) Date of Patent: Feb. 2, 2016

(54) PDE10A INHIBITORS FOR THE TREATMENT OF TYPE II DIABETES

(71) Applicant: Janssen Pharmaceutica, NV, Beerse (BE)

(72) Inventors: Mark R. Player, Phoenixville, PA (US); Sanath K. Meegalla, Garnet Valley, PA (US); Carl R. Illig, Phoenixville, PA (US); Jinsheng Chen, Exton, PA (US); Kenneth J. Wilson, Guanacaste (CR); Yu-Kai Lee, Exton, PA (US); Daniel J. Parks, Downingtown, PA (US); Hui Huang, Blue Bell, PA (US); Sharmila Patel, Jamison, PA (US); Tianbao Lu, Churchville, PA (US)

(73) Assignee: JANSSEN PHARMACEUTICA NV., Beerse (BE)

(*) Notice: Subject to any disclaimer, the term of this patent is extended or adjusted under 35 U.S.C. 154(b) by 0 days.

(21) Appl. No.: 14/299,512

(22) Filed: Jun. 9, 2014

(65) Prior Publication Data

US 2014/0364414 A1    Dec. 11, 2014

Related U.S. Application Data

(60) Provisional application No. 61/833,495, filed on Jun. 11, 2013.

(51) Int. Cl.
*C07D 519/00* (2006.01)
*C07D 487/04* (2006.01)

(52) U.S. Cl.
CPC ............ *C07D 519/00* (2013.01); *C07D 487/04* (2013.01)

(58) Field of Classification Search
CPC .............................. C07D 519/00; C07D 487/04
USPC ........................................ 544/117; 514/233.2
See application file for complete search history.

(56) References Cited

U.S. PATENT DOCUMENTS

| 2007/0078136 | A1 | 4/2007 | Vaccaro et al. |
| 2009/0162286 | A1 | 6/2009 | Black et al. |
| 2009/0176778 | A1 | 7/2009 | Schmitz et al. |
| 2011/0269752 | A1 | 11/2011 | Pastor-Fernandez et al. |
| 2012/0329792 | A1 | 12/2012 | Bartolome-Nebreda et al. |
| 2013/0116233 | A1 | 5/2013 | Geneste et al. |

FOREIGN PATENT DOCUMENTS

| WO | WO 2011/110545 A1 | 9/2011 |
| WO | WO 2011/150156 A2 | 12/2011 |
| WO | WO 2012/146644 A1 | 11/2012 |

OTHER PUBLICATIONS

International Search Report dated Sep. 8, 2014 for corresponding Application No. PCT/US2014/841472.
International Search Report dated Sep. 1, 2014 for corresponding Application No. PCT/US2014/041466.
Cantin, Louis-David, "PDE-10A inhibitors as insulin secretagogues", *Bioorg. Med. Chem. Lett.*, 2007, vol. 17, pp. 2869-2873.

*Primary Examiner* — Kahsay Habte
(74) *Attorney, Agent, or Firm* — Roberts Mlotkowski Safran & Cole, P.C.

(57) ABSTRACT

Disclosed are compounds, compositions and methods for treating Type II diabetes and other disorders affected by activity of the enzyme PDE10a. Such compounds are represented by Formula (I) below, wherein $R^1$, $R^2$, L and Q are defined herein.

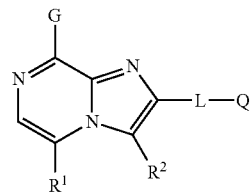

Formula (I)

19 Claims, No Drawings

PDE10A INHIBITORS FOR THE TREATMENT OF TYPE II DIABETES

CROSS-REFERENCE TO RELATED APPLICATIONS

This Application claims priority to U.S. Provisional Patent Application No. 61/833,495, filed Jun. 11, 2013 which is hereby incorporated by reference in its entirety.

FIELD OF THE INVENTION

The present invention relates to novel substituted imidazo[1,2-a]pyrazine derivatives which are inhibitors of the phosphodiesterase 10 enzyme (PDE10) and are useful for the treatment of disorders that are affected by the PDE10a enzyme. The invention also relates to pharmaceutical compositions comprising such compounds, to processes to prepare such compounds and compositions, and to the use of such compounds or pharmaceutical compositions for the treatment of various diseases, syndromes and disorders, including Type II diabetes.

BACKGROUND OF THE INVENTION

Phosphodiesterases (PDEs) are a family of enzymes encoded by 21 genes and subdivided into 11 distinct families according to structural and functional properties. These enzymes are hydrolases that metabolically inactivate widely occurring intracellular second messengers, 3',5'-cyclic adenosine monophosphate (cAMP) and 3',5'-cyclic guanosine monophosphate (cGMP) by catalytic hydrolysis of the 3'-ester bond, forming the inactive 5'-monophosphate. These two messengers regulate a wide variety of biological processes, including pro-inflammatory mediator production and action, ion channel function, muscle contraction, learning, differentiation, apoptosis, lipogenesis, glycogenolysis, and gluconeogenesis. They do this by activation of protein kinase A (PKA) and protein kinase G (PKG), which in turn phosphorylate a wide variety of substrates including transcription factors and ion channels that regulate innumerable physiological responses. In neurons, this includes the activation of cAMP and cGMP-dependent kinases and subsequent phosphorylation of proteins involved in acute regulation of synaptic transmission as well as in neuronal differentiation and survival.

On the basis of substrate specificity, the PDE families can be divided into three groups: i) the cAMP-specific PDEs, which include PDE4, 7 and 8; ii) the cGMP-selective enzymes PDE5 and 9; and iii) the dual-substrate PDEs, PDE1, 2 and 3, as well as PDE10 and 11.

Furthermore, PDEs are expressed differentially throughout the organism, including the central nervous system. Different PDE isozymes therefore may play different physiological functions. Compounds that selectively inhibit PDE families or isozymes may display particular therapeutic activity, fewer side effects, or both.

PDE10a is highly expressed in the brain with the highest expression residing in the nAcc olfactory tubercle, striatum and spiny neurons. There is a high co-incidence of PDE10a, D2 and D1 expression in these areas. Antipsychotics normalize a dopamine-evoked cAMP decrease, i.e. agonists at Gs-coupled D1 receptors result in increased intracellular cAMP and antagonists of the Gi-coupled D2 receptor also elevate the intracellular cAMP.

Since PDE10a hydrolyzes cAMP and cGMP, it is to be expected that PDE10a inhibitors will increase intracellular levels of cAMP and cGMP, thereby mimicking dopamine transmission at D1 mediated synapses (D1 agonism) and decreasing dopamine transmission at D2 mediated synapses (D2 antagonism). Therefore, PDE10a inhibitors are expected to have antipsychotic and cognitive-improving properties and may provide benefits for the treatment of schizophrenia.

Besides being a potential treatment for psychiatric disorders, PDE10a inhibitors may also be beneficial for the treatment of metabolic diseases. Although PDE10a is predominantly expressed in the brain, it is also expressed in neuroendocrine tissues such as pancreatic islets, adrenal gland, pituitary gland, and in the neuronal ganglion throughout the intestine. Because cAMP is a major regulator of glucose-stimulated insulin secretion from pancreatic islet β cells, PDE10a inhibitors may enhance insulin secretion and reduce blood glucose levels. They may also potentiate the actions of GLP-1, GPR119 agonists and other Gs-coupled GPCR agonists which signal via increased cAMP and the protein kinase A pathway. In addition, PDE10a inhibitors may potentiate incretin effects such as β cell proliferation and survival. A peripherally restricted PDE10a inhibitor has been shown to enhance insulin secretion and reduce the glucose excursion in lean Wistar rats (*Bioorg. Med. Chem. Lett.* 17 (2007) 2869-2873).

Further validation that PDE10a inhibition may have beneficial effects on metabolism includes the phenotype of the PDE10a knockout mice (US Patent Appl. US2009/0162286 A1). These mice are resistant to weight gain on a high fat diet, without an appreciable change in food consumption, and the differences in weight between the PDE10a knockout and wild type mice are predominantly due to differences in adiposity and not lean mass. When compared to wild type mice, the PDE10a knockout mice have lower plasma insulin, triglycerides, non-esterified free fatty acids and leptin. Although there does not appear to be a difference in the glucose excursion between knockout and wild type mice on a chow diet, there is a reduction in the glucose excursion during an oral glucose tolerance test. Additionally, there was a slight increase in oxygen consumption. Furthermore, PDE10a inhibitor treatment in mice fed a high fat diet showed similar changes to those observed between wild type and PDE10a knockout mice. PDE10a inhibitor treated mice exhibited 6% weight loss during the 14 day study with little changes in food intake and slight increases in oxygen consumption. In addition, they exhibited improvements in the glucose excursion during an oral glucose tolerance test.

Taken together, these data suggest that PDE10a inhibitors may be beneficial for the treatment of type II diabetes and obesity with potentiation of glucose-stimulated insulin secretion and the potential for weight loss. Additivity and/or synergy may be expected between PDE10a inhibitors and DPPIV inhibitors, GLP-1 mimetics and GPR119 agonists. They may work well as monotherapy or in conjunction with common treatments of type II diabetes, such as metformin, SGLT2 inhibitors, PPAR gamma agonists and DPPIV inhibitors.

Therefore, there is a need in the art for PDE10a inhibitors that are useful for the treatment of a disease, syndrome, or condition in a mammal in which the disease, syndrome, or condition is affected by the inhibition of the PDE10a receptor, such as Type II diabetes. It has been suggested in the scientific literature that compounds that do not accumulate in the brain tissue may possess fewer potential CNS side effects. Therefore, it is an objective of the present invention to identify compounds of Formula (I) that do not accumulate in the brain tissue where they may exert CNS effects.

SUMMARY OF THE INVENTION

The present invention is directed to compounds of Formula (I)

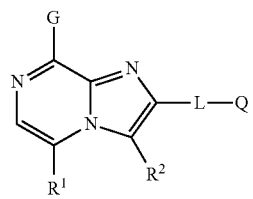

Formula (I)

wherein

G is a substituent selected from the group consisting of

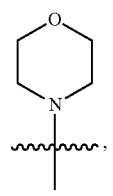
g-1

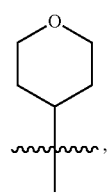
g-2

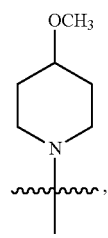
g-3

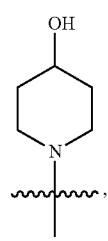
g-4

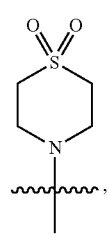
g-5

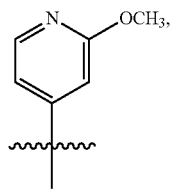
g-6

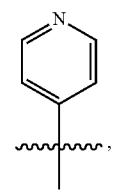
g-7

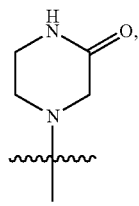
g-8

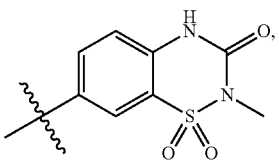
g-9, and g-10

R¹ is
(i) hydrogen;
(ii) a substituent selected from the group consisting of pyridinyl, 1H-pyrazol-4-yl, 5-pyrimidinyl, 5-hydroxy-1,2,4-oxadiazol-3-yl, 1H-imidazo[4,5-b]pyridin-6-yl, 2-hydroxy-1H-imidazo[4,5-b]pyridin-6-yl, and a ring 1-a to 1-h 1-a

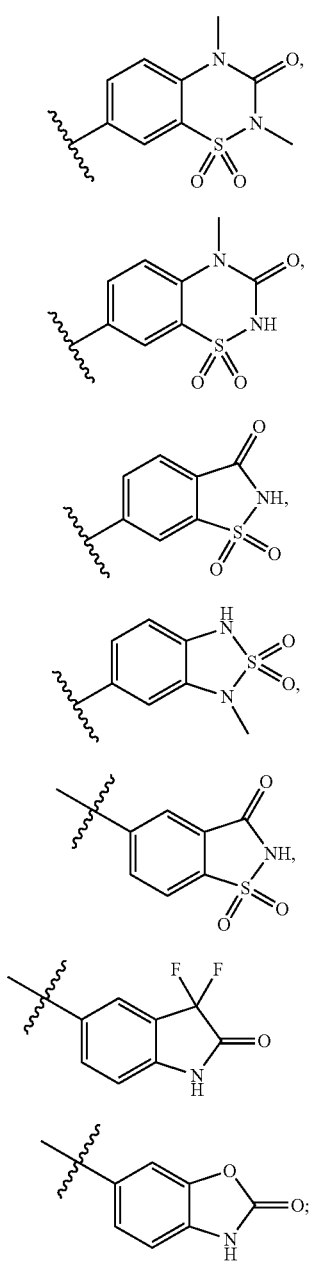

wherein the pyridinyl and 5-pyrimidinyl rings of group (iii) are optionally substituted with one substituent selected from the group consisting of $C_{1-4}$alkyl, carboxy($C_{1-4}$alkyl, aminocarbonyl, aminosulfonyl, 1,2,3,6-tetrahydropyridin-4-yl, carboxy, amino, dimethylamino, carboxymethylamino, piperidin-4-yl, piperazin-1-yl, 4-methylpiperazin-1-yl, morpholin-4-yl, $C_{1-4}$alkylsulfonylamino, $C_{1-4}$alkylsulfonylaminocarbonyl, 5-hydroxy-1,2,4-oxadiazol-3-yl, 1,2,4-oxadiazol-5(4H)-one-3-yl, tetrazolyl, triazolyl, or triazolylthio; wherein said tetrazolyl, and triazolyl are optionally substituted with one hydroxy or $C_{1-4}$alkoxy substituent;

and wherein said pyridinyl of group (iii) is optionally further substituted with one or two substituents selected from the group consisting of fluoro, chloro, and hydroxy;

wherein said 1H-pyrazol-4-yl of group (iii) is optionally substituted at the 1-position with methoxy-ethyl or carboxy($C_{1-4}$)alkyl;

(iii) phenyl optionally substituted at the 4-position with one substituent that is $C_{1-4}$alkoxycarbonyl, $C_{1-4}$alkylcarbonylaminosulfonyl, $C_{1-4}$alkylaminosulfonyl, (2-hydroxyethyl)aminosulfonyl, aminosulfonyl, $C_{1-4}$alkylsulfonylaminocarbonyl, carboxy, —O(CH$_2$CH$_2$O)$_{2-5}$CH$_3$, —OCH$_2$OCH$_3$, carboxy($C_{1-4}$)alkylaminocarbonyl, 2-carboxypyrrolidin-1-ylcarbonyl, carboxy($C_{1-4}$)alkylcarbonylamino, $C_{1-4}$alkylsulfonylaminocarbonylamino, carboxy($C_{1-4}$)alkylamino, bis(2-hydroxyethyl)aminocarbonylamino, (2-hydroxyethyl)aminocarbonylamino, 1,1,1,3,3,3-hexafluoro-2-hydroxypropan-2-yl, 4-carboxypiperidin-1-yl, piperazin-1-yl, triazolylthio, tetrazolyl, triazolyl, imidazolyl, or oxazolyl; wherein said tetrazolyl, triazolyl, imidazolyl, or oxazolyl substituents are optionally independently substituted with one or two substituents selected from the group consisting of $C_{1-4}$alkyl and hydroxy;

and wherein said phenyl ring of group (iii) is optionally independently further substituted with one or two substituents selected from the group consisting of $C_{1-4}$alkyl, $C_{1-4}$alkoxy, and fluoro;

(iv) phenyl substituted at the 4-position with one substituent that is r-1, r-2, or r-3;

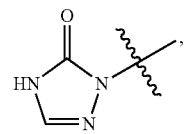

r-1

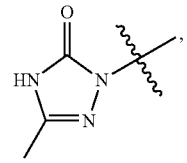

r-2

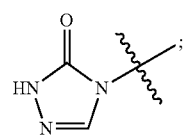

r-3 wherein said phenyl ring of group (iv) is optionally further substituted with one additional fluoro substituent;

(v) phenyl substituted at the 4-position with p-1 or p-2;

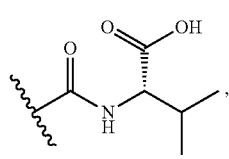

p-1

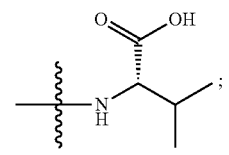

p-2 or (vi) piperidin-4-yl optionally substituted at the 1-position with aminosulfonyl or carboxy($C_{1-4}$)alkyl;

$R^2$ is hydrogen; or $R^2$ is chloro when L is azetidin-1-yl;

L is a bivalent linker that is ethyl, E-ethenyl, ethynyl, trans-1,3-cyclobutyl, cis-1,3-cyclobutyl, azetidinyl, —CH$_2$X-Q, or —NHC(O)-Q; wherein X is O or S;

Q is quinolin-2-yl, pyridinyl, pyrimidinyl, quinazolin-2-yl, benzimidazol-2-yl, or benzothiazol-2-yl;

wherein said Q is optionally independently substituted with one or two substituents selected from the group consisting of $C_{1-4}$alkyl, carboxy-methoxy, $C_{1-4}$alkoxy, and carboxy;

or an enantiomer, diastereomer, or pharmaceutically acceptable salt form thereof.

The present invention also provides a pharmaceutical composition comprising, consisting of and/or consisting essentially of a pharmaceutically acceptable carrier, a pharmaceutically acceptable excipient, and/or a pharmaceutically acceptable diluent and a compound of Formula (I) or a pharmaceutically acceptable salt form thereof.

Also provided are processes for making a pharmaceutical composition comprising, consisting of, and/or consisting essentially of admixing a compound of Formula (I) and a pharmaceutically acceptable carrier, a pharmaceutically acceptable excipient, and/or a pharmaceutically acceptable diluent.

The present invention further provides methods for treating or ameliorating a disease, syndrome, or condition in a subject, including a mammal and/or human in which the disease, syndrome, or condition is affected by the inhibition of PDE10a, such as Type II diabetes, using a compound of Formula (I).

The present invention also is also directed to the use of any of the compounds described herein in the preparation of a medicament wherein the medicament is prepared for treating a disease or condition that is affected by the inhibition of PDE10a enzyme, such as Type II diabetes, in a subject in need thereof.

The present invention is also directed to the preparation of substituted imidazo[1,2-a]pyrazine derivatives that act as selective inhibitors of the PDE10a enzyme and are peripherally restricted, thereby reducing centrally-mediated side effects.

Exemplifying the invention are methods of treating a disorder modulated by PDE10a, wherein the disorder is Type II diabetes, comprising administering to a subject in need thereof a therapeutically effective amount of any of the compounds or pharmaceutical compositions described above.

In another embodiment, the present invention is directed to a compound of Formula (I) for use in the treatment of a disorder affected by the inhibition of PDE10a wherein the disorder is Type II diabetes.

In another embodiment, the present invention is directed to a composition comprising a compound of Formula (I) for the treatment of a disorder affected by the inhibition of PDE10a, wherein the disorder is Type II diabetes.

DETAILED DESCRIPTION OF THE INVENTION

With reference to substituents, the term "independently" refers to the situation where when more than one substituent is possible, the substituents may be the same or different from each other.

The term "alkyl" whether used alone or as part of a substituent group, refers to straight and branched carbon chains having 1 to 8 carbon atoms. Therefore, designated numbers of carbon atoms (e.g., $C_{1-8}$) refer independently to the number of carbon atoms in an alkyl moiety or to the alkyl portion of a larger alkyl-containing substituent. In substituent groups with multiple alkyl groups such as, ($C_{1-6}$alkyl)$_2$-amino-, the $C_{1-6}$alkyl groups of the dialkylamino may be the same or different.

The term "alkoxy" refers to an —O-alkyl group, wherein the term "alkyl" is as defined above.

The terms "alkenyl" and "alkynyl" refer to straight and branched carbon chains having 2 to 8 carbon atoms, wherein an alkenyl chain contains at least one double bond and an alkynyl chain contains at least one triple bond.

The term "cycloalkyl" refers to saturated or partially saturated, monocyclic or polycyclic hydrocarbon rings of 3 to 14 carbon atoms. Examples of such rings include cyclopropyl, cyclobutyl, cyclopentyl, cyclohexyl, cycloheptyl, and adamantyl.

The term "heterocyclyl" refers to a nonaromatic monocyclic or bicyclic ring system having 3 to 10 ring members that include at least 1 carbon atom and from 1 to 4 heteroatoms independently selected from N, O, and S. Included within the term heterocyclyl is a nonaromatic cyclic ring of 5 to 7 members in which 1 to 2 members are N, or a nonaromatic cyclic ring of 5 to 7 members in which 0, 1 or 2 members are N and up to 2 members are O or S and at least one member must be either N, O, or S; wherein, optionally, the ring contains 0 to 1 unsaturated bonds, and, optionally, when the ring is of 6 or 7 members, it contains up to 2 unsaturated bonds. The carbon atom ring members that form a heterocycle ring may be fully saturated or partially saturated. The term "heterocyclyl" also includes two 5 membered monocyclic heterocycloalkyl groups bridged to form a bicyclic ring. Such groups are not considered to be fully aromatic and are not referred to as heteroaryl groups. When a heterocycle is bicyclic, both rings of the heterocycle are non-aromatic and at least one of the rings contains a heteroatom ring member. Examples of heterocycle groups include, and are not limited to, pyrrolinyl (including 2H-pyrrole, 2-pyrrolinyl or 3-pyrrolinyl), pyrrolidinyl, imidazolinyl, imidazolidinyl, pyrazolinyl, pyrazolidinyl, piperidinyl, morpholinyl, thiomorpholinyl, and piperazinyl. Unless otherwise noted, the heterocycle is attached to its pendant group at any heteroatom or carbon atom that results in a stable structure.

The term "aryl" refers to an unsaturated, aromatic monocyclic or bicyclic ring of 6 to 10 carbon members. Examples of aryl rings include phenyl and naphthalenyl.

The term "heteroaryl" refers to an aromatic monocyclic or bicyclic aromatic ring system having 5 to 10 ring members and which contains carbon atoms and from 1 to 4 heteroatoms independently selected from the group consisting of N, O, and S. Included within the term heteroaryl are aromatic rings of 5 or 6 members wherein the ring consists of carbon atoms and has at least one heteroatom member. Suitable heteroatoms include nitrogen, oxygen, and sulfur. In the case of 5 membered rings, the heteroaryl ring preferably contains one member of nitrogen, oxygen or sulfur and, in addition, up to 3 additional nitrogens. In the case of 6 membered rings, the heteroaryl ring preferably contains from 1 to 3 nitrogen atoms. For the case wherein the 6 membered ring has 3 nitrogens, at most 2 nitrogen atoms are adjacent. Examples of heteroaryl groups include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinolinyl, isoquinolinyl and quinazolinyl. Unless otherwise noted, the heteroaryl is attached to its pendant group at any heteroatom or carbon atom that results in a stable structure.

The term "halogen" or "halo" refers to fluorine, chlorine, bromine and iodine atoms.

The term "azetidin-1-yl" refers to the group

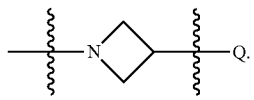

The term "carboxy" refers to the group —C(=O)OH.
The term "formyl" refers to the group —C(=O)H.
The term "oxo" refers to the group (=O).

Whenever the term "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example $C_{1-6}$ alkyl would include methyl, ethyl, propyl, butyl, pentyl and hexyl individually as well as subcombinations thereof (e.g., $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment. Thus, for example, a "$C_1$-$C_6$ alkylcarbonyl" substituent refers to a group of the formula:

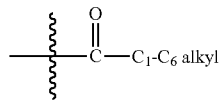

The term "R" at a stereocenter designates that the stereocenter is purely of the R-configuration as defined in the art; likewise, the term "S" means that the stereocenter is purely of the S-configuration. As used herein, the terms "*R" or "*S" at a stereocenter are used to designate that the stereocenter is of pure but unknown configuration. As used herein, the term "RS" refers to a stereocenter that exists as a mixture of the R- and S-configurations. Similarly, the terms "*RS" or "*SR" refer to a stereocenter that exists as a mixture of the R- and S-configurations and is of unknown configuration relative to another stereocenter within the molecule.

Compounds containing one stereocenter drawn without a stereo bond designation are a mixture of two enantiomers. Compounds containing two stereocenters both drawn without stereo bond designations are a mixture of four diastereomers. Compounds with two stereocenters both labeled "RS" and drawn with stereo bond designations are a two-component mixture with relative stereochemistry as drawn. Compounds with two stereocenters both labeled "*RS" and drawn with stereo bond designations are a two-component mixture with relative stereochemistry unknown. Unlabeled stereocenters drawn without stereo bond designations are a mixture of the R- and S-configurations. For unlabeled stereocenters drawn with stereo bond designations, the absolute stereochemistry is as depicted.

Unless otherwise noted, it is intended that the definition of any substituent or variable at a particular location in a molecule be independent of its definitions elsewhere in that molecule. It is understood that substituents and substitution patterns on the compounds of Formula (I) can be selected by one of ordinary skill in the art to provide compounds that are chemically stable and that can be readily synthesized by techniques known in the art as well as those methods set forth herein.

The term "subject" refers to an animal, preferably a mammal, most preferably a human, who has been the object of treatment, observation or experiment.

The term "therapeutically effective amount" refers to an amount of an active compound or pharmaceutical agent, including a compound of the present invention, which elicits the biological or medicinal response in a tissue system, animal or human that is being sought by a researcher, veterinarian, medical doctor or other clinician, which includes alleviation or partial alleviation of the symptoms of the disease, syndrome, condition, or disorder being treated.

The term "composition" refers to a product that includes the specified ingredients in therapeutically effective amounts, as well as any product that results, directly, or indirectly, from combinations of the specified ingredients in the specified amounts.

The term "PDE10a inhibitor" is intended to encompass a compound that interacts with PDE10a to substantially reduce or eliminate its catalytic activity, thereby increasing the concentrations of its substrate(s).

The term "PDE10a-modulated" is used to refer to the condition of being affected by the modulation of the PDE10a enzyme, including but not limited to, the state of being mediated by the PDE10a enzyme, for the treatment of a disease or condition such as type II diabetes.

As used herein, unless otherwise noted, the term "affect" or "affected" (when referring to a disease, syndrome, condition or disorder that is affected by inhibition of PDE10a) includes a reduction in the frequency and/or severity of one or more symptoms or manifestations of said disease, syndrome, condition or disorder; and/or include the prevention of the development of one or more symptoms or manifestations of said disease, syndrome, condition or disorder or the development of the disease, condition, syndrome or disorder.

The compounds of Formula (I) are useful in methods for treating or ameliorating a disease, a syndrome, a condition or a disorder that is affected by the inhibition of PDE10a. Such methods comprise, consist of and/or consist essentially of administering to a subject, including an animal, a mammal, and a human in need of such treatment, amelioration and/or prevention, a therapeutically effective amount of a compound of Formula (I), or an enantiomer, diastereomer, solvate or pharmaceutically acceptable salt thereof.

In particular, the compounds of Formula (I), or an enantiomer, diastereomer, solvate or pharmaceutically acceptable salt thereof are useful for treating or ameliorating diseases, syndromes, conditions, or disorders such as Type II diabetes.

More particularly, the compounds of Formula (I), or an enantiomer, diastereomer, solvate or pharmaceutically acceptable salt thereof are useful for treating or ameliorating Type II diabetes, comprising administering to a subject in need thereof a therapeutically effective amount of a compound of Formula (I), or an enantiomer, diastereomer, solvate or pharmaceutically acceptable salt thereof as herein defined.

Embodiments of the present invention include a compound of Formula (I)
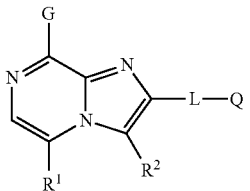
Formula (I)
wherein
a) G is
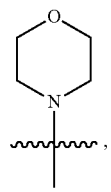
g-1
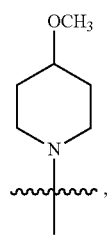
g-3
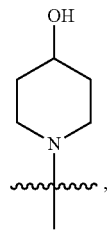
g-4
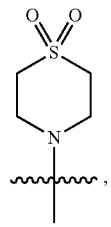
g-5
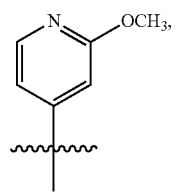
g-6
-continued
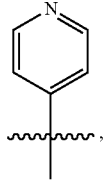
g-7
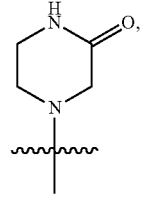
g-8
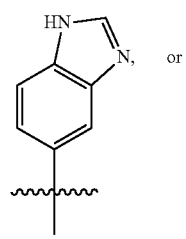
g-9 or
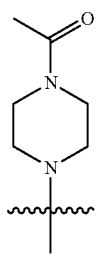
g-10
b) G is
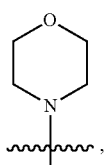
g-1
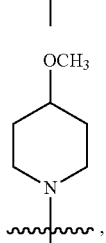
g-3
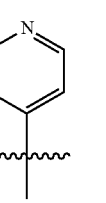
g-7 or c) G is

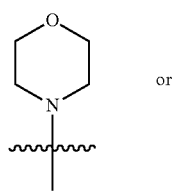 or

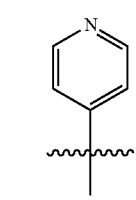

d) G is

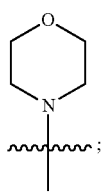

e) R¹ is
(i) hydrogen;
(ii) a substituent selected from the group consisting of pyridinyl, 1H-pyrazol-4-yl, 5-pyrimidinyl, 5-hydroxy-1,2,4-oxadiazol-3-yl, 1H-imidazo[4,5-b]pyridin-6-yl, 2-hydroxy-1H-imidazo[4,5-b]pyridin-6-yl, and a ring 1-a to 1-h

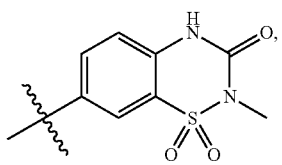 1-a

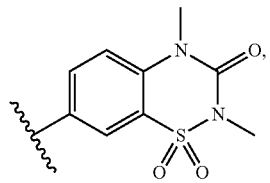 1-b

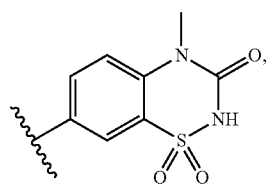 1-c

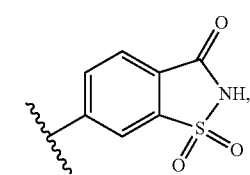 1-d

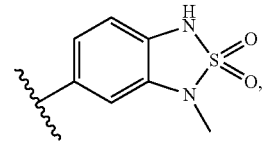 1-e

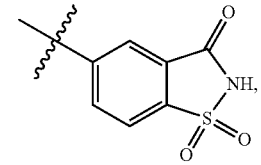 1-f

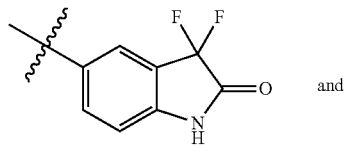 1-g and

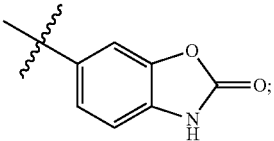 1-h wherein the pyridinyl and 5-pyrimidinyl rings of group (iii) are optionally substituted with one substituent selected from the group consisting of $C_{1-4}$alkyl, carboxy($C_{1-4}$)alkyl, aminocarbonyl, aminosulfonyl, 1,2,3,6-tetrahydropyridin-4-yl, carboxy, amino, dimethylamino, carboxymethylamino, 4-methylpiperazin-1-yl, morpholin-4-yl, $C_{1-4}$alkylsulfonylamino, $C_{1-4}$alkylsulfonylaminocarbonyl, 1,2,4-oxadiazol-5(4H)-one-3-yl, tetrazolyl, triazolyl, or triazolylthio; wherein said tetrazolyl and triazolyl are optionally substituted with one hydroxy substituent;

and wherein said pyridinyl of group (iii) is optionally further substituted with one or two substituents selected from the group consisting of fluoro, chloro, and hydroxy;

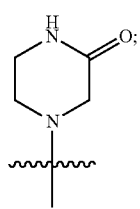 g-8 wherein said 1H-pyrazol-4-yl of group (iii) is optionally substituted at the 1-position with methoxy-ethyl or carboxy($C_{1-4}$)alkyl;

(iii) phenyl optionally substituted at the 4-position with one substituent that is $C_{1-4}$alkoxycarbonyl, $C_{1-4}$alkylcarbonylaminosulfonyl, (2-hydroxyethyl)aminosulfonyl, aminosulfonyl, $C_{1-4}$alkylsulfonylaminocarbonyl, carboxy, —O($CH_2CH_2O$)$_{2-5}CH_3$, —$OCH_2OCH_3$, carboxy($C_{1-4}$)alkylaminocarbonyl, 2-carboxypyrrolidin-1-ylcarbonyl, carboxy($C_{1-4}$)alkylcarbonylamino, $C_{1-4}$alkylsulfonylaminocarbonylamino, carboxy($C_{1-4}$)alkylamino, bis(2-hydroxyethyl)aminocarbonylamino, (2-hydroxyethyl)aminocarbonylamino, 1,1,1,3,3,3-hexafluoro-2-hydroxy-propan-2-yl, 4-carboxypiperidin-1-yl, piperazin-1-yl, triazolylthio, tetrazolyl, triazolyl, imidazolyl, or oxazolyl;

wherein said tetrazolyl, triazolyl, imidazolyl, or oxazolyl substituents are optionally independently substituted with one or two substituents selected from the group consisting of $C_{1-4}$alkyl and hydroxy;

and wherein said phenyl ring of group (iii) is optionally independently further substituted with one or two substituents selected from the group consisting of $C_{1-4}$alkyl, $C_{1-4}$alkoxy, and fluoro;

(iv) phenyl substituted at the 4-position with one substituent that is r-1 or r-3;

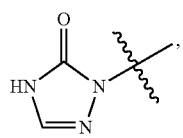
r-1

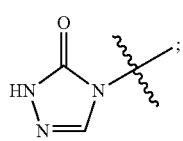
r-3 wherein said phenyl ring of group (iv) is optionally further substituted with one additional fluoro substituent;

(v) phenyl substituted at the 4-position with p-1 or p-2;

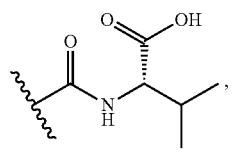
p-1

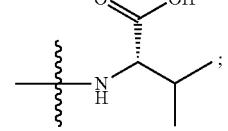
p-2 or (vi) piperidin-4-yl optionally substituted at the 1-position with aminosulfonyl;

f) $R^1$ is
(i) hydrogen;
(ii) a substituent selected from the group consisting of pyridinyl, 1H-pyrazol-4-yl, 5-pyrimidinyl, 5-hydroxy-1,2,4-oxadiazol-3-yl, 1H-imidazo[4,5-b]pyridin-6-yl, 2-hydroxy-1H-imidazo[4,5-b]pyridin-6-yl, and a ring 1-a to 1-h

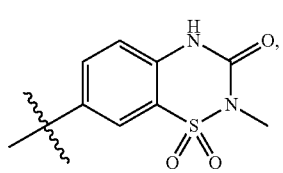
1-a

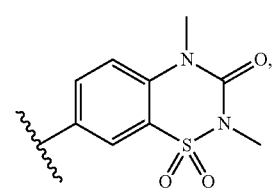
1-b

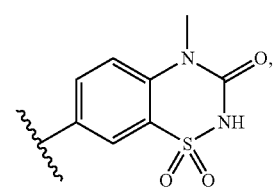
1-c

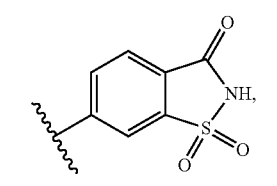
1-d

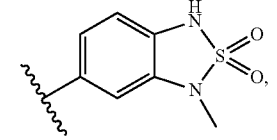
1-e

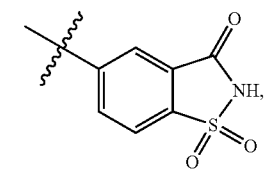
1-f

1-g and

-continued 1-h wherein the pyridinyl and 5-pyrimidinyl rings of group (iii) are optionally substituted with one substituent selected from the group consisting of $C_{1-4}$alkyl, carboxy($C_{1-4}$)alkyl, aminocarbonyl, aminosulfonyl, 1,2,3,6-tetrahydropyridin-4-yl, carboxy, amino, dimethylamino, carboxymethylamino, 4-methylpiperazin-1-yl, morpholin-4-yl, $C_{1-4}$alkylsulfonylamino, $C_{1-4}$alkylsulfonylaminocarbonyl, 1,2,4-oxadiazol-5(4H)-one-3-yl, tetrazolyl, triazolyl, or triazolylthio; wherein said tetrazolyl and triazolyl are optionally substituted with one hydroxy substituent;

and wherein said pyridinyl of group (iii) is optionally further substituted with one or two substituents selected from the group consisting of fluoro, chloro, and hydroxy;

wherein said 1H-pyrazol-4-yl of group (iii) is optionally substituted at the 1-position with methoxyethyl or carboxy($C_{1-4}$)alkyl;

(iii) phenyl optionally substituted at the 4-position with one substituent that is $C_{1-4}$alkoxycarbonyl, $C_{1-4}$alkylcarbonylaminosulfonyl, (2-hydroxyethyl)aminosulfonyl, aminosulfonyl, $C_{1-4}$alkylsulfonylaminocarbonyl, carboxy, —O(CH$_2$CH$_2$O)$_{2-5}$CH$_3$, —OCH$_2$OCH$_3$, carboxy($C_{1-4}$)alkylaminocarbonyl, 2-carboxypyrrolidin-1-ylcarbonyl, carboxy($C_{1-4}$)alkylcarbonylamino, $C_{1-4}$alkylsulfonylaminocarbonylamino, carboxy($C_{1-4}$)alkylamino, bis(2-hydroxyethyl)aminocarbonylamino, (2-hydroxyethyl)aminocarbonylamino, 1,1,1,3,3,3-hexafluoro-2-hydroxy-propan-2-yl, 4-carboxypiperidin-1-yl, piperazin-1-yl, triazolylthio, tetrazolyl, triazolyl, imidazolyl, or oxazolyl;

wherein said tetrazolyl, triazolyl, imidazolyl, or oxazolyl substituents are optionally independently substituted with one or two substituents selected from the group consisting of $C_{1-4}$alkyl and hydroxy;

and wherein said phenyl ring of group (iii) is optionally independently further substituted with one or two substituents selected from the group consisting of $C_{1-4}$alkyl, $C_{1-4}$alkoxy, and fluoro;

(iv) phenyl substituted at the 4-position with one substituent that is r-1 or r-3;

r-1 or r-3 wherein said phenyl ring of group (iv) is optionally further substituted with one additional fluoro substituent;

or (v) phenyl substituted at the 4-position with p-1 or p-2;

p-1 p-2 g) $R^2$ is hydrogen;

h) L is a bivalent linker that is ethyl, E-ethenyl, ethynyl, trans-1,3-cyclobutyl, cis-1,3-cyclobutyl, azetidinyl, —CH$_2$X-Q, or —NHC(O)-Q; wherein X is O or S;

i) L is a bivalent linker that is ethyl, E-ethenyl, ethynyl, trans-1,3-cyclobutyl, azetidinyl, or —CH$_2$X-Q; wherein X is O or S;

j) $R^2$ is hydrogen;

k) Q is quinolin-2-yl, pyridinyl, pyrimidinyl, benzimidazol-2-yl, or benzothiazol-2-yl;

wherein said Q is optionally independently substituted with one or two substituents selected from the group consisting of $C_{1-4}$alkyl, carboxy-methoxy, $C_{1-4}$alkoxy, and carboxy;

l) Q is quinolin-2-yl, pyridinyl, benzimidazol-2-yl, or benzothiazol-2-yl; wherein said Q is optionally independently substituted with one substituent selected from the group consisting of $C_{1-4}$alkyl, carboxy-methoxy, $C_{1-4}$alkoxy, and carboxy;

and any combination of embodiments a) through l) above, provided that it is understood that combinations in which different embodiments of the same substituent would be combined are excluded;

or an enantiomer, diastereomer, or pharmaceutically acceptable salt form thereof.

An embodiment of the present invention includes a compound of Formula (I)

Formula (I)

wherein
G is
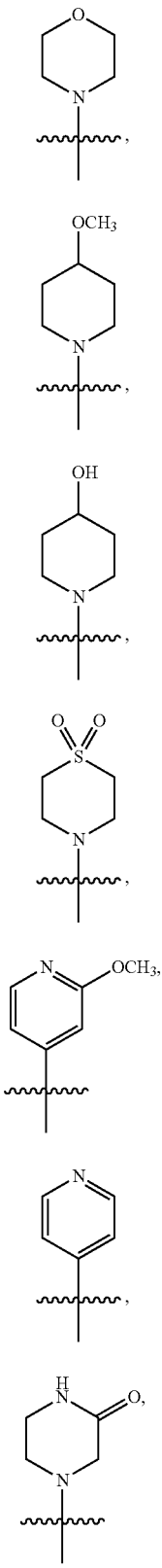
g-1
g-3
g-4
g-5
g-6
g-7
g-8
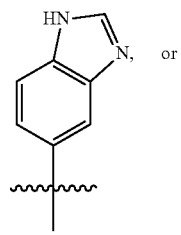
g-9
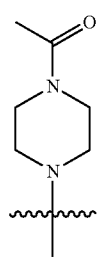
g-10
R¹ is
(i) hydrogen;
(ii) a substituent selected from the group consisting of pyridinyl, 1H-pyrazol-4-yl, 5-pyrimidinyl, 5-hydroxy-1,2,4-oxadiazol-3-yl, 1H-imidazo[4,5-b]pyridin-6-yl, 2-hydroxy-1H-imidazo[4,5-b]pyridin-6-yl, and a ring 1-a to 1-h
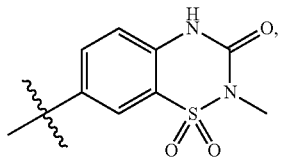
1-a
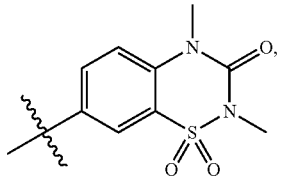
1-b
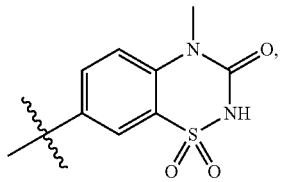
1-c
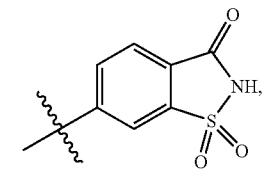
1-d
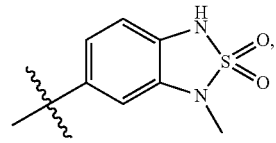
1-e -continued

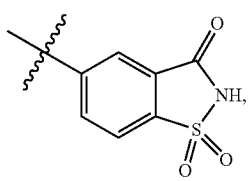
1-f

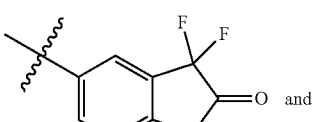
1-g

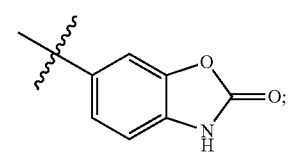
1-h wherein the pyridinyl and 5-pyrimidinyl rings of group (iii) are optionally substituted with one substituent selected from the group consisting of $C_{1-4}$alkyl, carboxy($C_{1-4}$)alkyl, aminocarbonyl, aminosulfonyl, 1,2,3,6-tetrahydropyridin-4-yl, carboxy, amino, dimethylamino, carboxymethylamino, 4-methylpiperazin-1-yl, morpholin-4-yl, $C_{1-4}$alkylsulfonylamino, $C_{1-4}$alkylsulfonylaminocarbonyl, 1,2,4-oxadiazol-5(4H)-one-3-yl, tetrazolyl, triazolyl, or triazolylthio; wherein said tetrazolyl and triazolyl are optionally substituted with one hydroxy substituent;

and wherein said pyridinyl of group (iii) is optionally further substituted with one or two substituents selected from the group consisting of fluoro, chloro, and hydroxy;

wherein said 1H-pyrazol-4-yl of group (iii) is optionally substituted at the 1-position with methoxy-ethyl or carboxy($C_{1-4}$)alkyl;

(iii) phenyl optionally substituted at the 4-position with one substituent that is $C_{1-4}$alkoxycarbonyl, $C_{1-4}$alkylcarbonylaminosulfonyl, (2-hydroxyethyl)aminosulfonyl, aminosulfonyl, $C_{1-4}$alkylsulfonylaminocarbonyl, carboxy, —O(CH$_2$CH$_2$O)$_{2-5}$CH$_3$, —OCH$_2$OCH$_3$, carboxy($C_{1-4}$)alkylaminocarbonyl, 2-carboxypyrrolidin-1-ylcarbonyl, carboxy($C_{1-4}$)alkylcarbonylamino, $C_{1-4}$alkylsulfonylaminocarbonylamino, carboxy($C_{1-4}$)alkylamino, bis(2-hydroxyethyl)aminocarbonylamino, (2-hydroxyethyl)aminocarbonylamino, 1,1,1,3,3,3-hexafluoro-2-hydroxypropan-2-yl, 4-carboxypiperidin-1-yl, piperazin-1-yl, triazolylthio, tetrazolyl, triazolyl, imidazolyl, or oxazolyl;

wherein said tetrazolyl, triazolyl, imidazolyl, or oxazolyl substituents are optionally independently substituted with one or two substituents selected from the group consisting of $C_{1-4}$alkyl and hydroxy;

and wherein said phenyl ring of group (iii) is optionally independently further substituted with one or two substituents selected from the group consisting of $C_{1-4}$alkyl, $C_{1-4}$alkoxy, and fluoro;

(iv) phenyl substituted at the 4-position with one substituent that is r-1 or r-3;

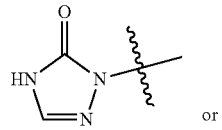
r-1 or

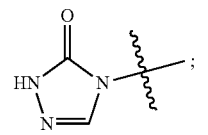
r-3 wherein said phenyl ring of group (iv) is optionally further substituted with one additional fluoro substituent;

(v) phenyl substituted at the 4-position with p-1 or p-2; or

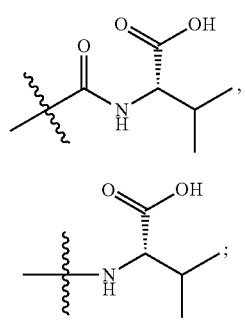
p-1 p-2

(vi) piperidin-4-yl optionally substituted at the 1-position with aminosulfonyl;

$R^2$ is hydrogen;

L is a bivalent linker that is ethyl, E-ethenyl, ethynyl, trans-1,3-cyclobutyl, cis-1,3-cyclobutyl, azetidinyl, —CH$_2$X-Q, or —NHC(O)-Q; wherein X is O or S;

Q is quinolin-2-yl, pyridinyl, pyrimidinyl, benzimidazol-2-yl, or benzothiazol-2-yl; wherein said Q is optionally independently substituted with one or two substituents selected from the group consisting of $C_{1-4}$alkyl, carboxy-methoxy, $C_{1-4}$alkoxy, and carboxy;

or an enantiomer, diastereomer, or pharmaceutically acceptable salt form thereof.

An embodiment of the present invention includes a compound of Formula (I)

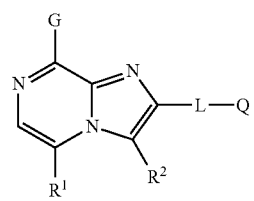
Formula (I)

wherein
G is

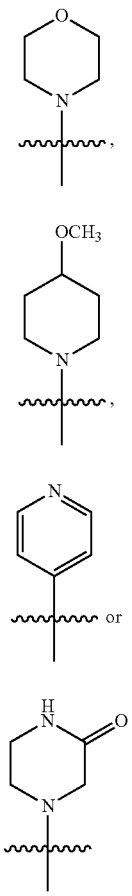

g-1 g-3 g-7 g-8

R¹ is
(i) hydrogen;
(ii) a substituent selected from the group consisting of pyridinyl, 1H-pyrazol-4-yl, 5-pyrimidinyl, 5-hydroxy-1,2,4-oxadiazol-3-yl, 1H-imidazo[4,5-b]pyridin-6-yl, 2-hydroxy-1H-imidazo[4,5-b]pyridin-6-yl, and a ring 1-a to 1-h

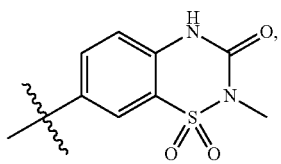

1-a

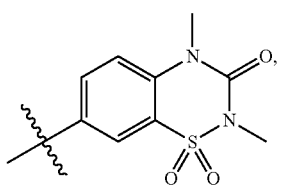

1-b

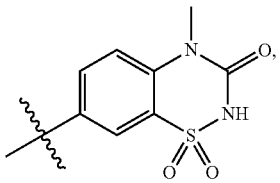

1-c

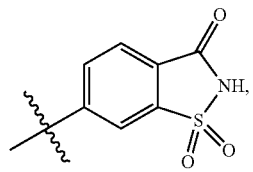

1-d

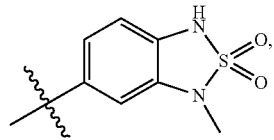

1-e

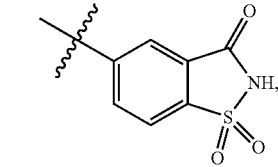

1-f

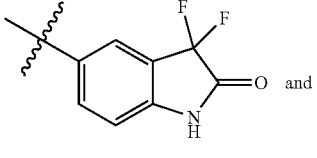

1-g and

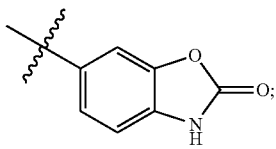

1-h wherein the pyridinyl and 5-pyrimidinyl rings of group (iii) are optionally substituted with one substituent selected from the group consisting of $C_{1-4}$alkyl, carboxy($C_{1-4}$) alkyl, aminocarbonyl, aminosulfonyl, 1,2,3,6-tetrahydropyridin-4-yl, carboxy, amino, dimethylamino, carboxymethylamino, 4-methylpiperazin-1-yl, morpholin-4-yl, $C_{1-4}$alkylsulfonylamino, $C_{1-4}$alkylsulfonylaminocarbonyl, 1,2,4-oxadiazol-5(4H)-one-3-yl, tetrazolyl, triazolyl, or triazolylthio; wherein said tetrazolyl and triazolyl are optionally substituted with one hydroxy substituent;
and wherein said pyridinyl of group (iii) is optionally further substituted with one or two substituents selected from the group consisting of fluoro, chloro, and hydroxy;
wherein said 1H-pyrazol-4-yl of group (iii) is optionally substituted at the 1-position with methoxy-ethyl or carboxy($C_{1-4}$)alkyl;
(iii) phenyl optionally substituted at the 4-position with one substituent that is $C_{1-4}$alkoxycarbonyl, $C_{1-4}$alkylcarbonylaminosulfonyl, (2-hydroxyethyl)aminosulfonyl, aminosulfonyl, $C_{1-4}$alkylsulfonylaminocarbonyl, carboxy, —O(CH$_2$CH$_2$O)$_{2-5}$CH$_3$, —OCH$_2$OCH$_3$, carboxy($C_{1-4}$)

alkylaminocarbonyl, 2-carboxypyrrolidin-1-ylcarbonyl, carboxy($C_{1-4}$)alkylcarbonylamino, $C_{1-4}$alkylsulfonylaminocarbonylamino, carboxy($C_{1-4}$)alkylamino, bis(2-hydroxyethyl)aminocarbonylamino, (2-hydroxyethyl)aminocarbonylamino, 1,1,1,3,3,3-hexafluoro-2-hydroxypropan-2-yl, 4-carboxypiperidin-1-yl, piperazin-1-yl, triazolylthio, tetrazolyl, triazolyl, imidazolyl, or oxazolyl;

wherein said tetrazolyl, triazolyl, imidazolyl, or oxazolyl substituents are optionally independently substituted with one or two substituents selected from the group consisting of $C_{1-4}$alkyl and hydroxy;

and wherein said phenyl ring of group (iii) is optionally independently further substituted with one or two substituents selected from the group consisting of $C_{1-4}$alkyl, $C_{1-4}$alkoxy, and fluoro;

(iv) phenyl substituted at the 4-position with one substituent that is r-1 or r-3;

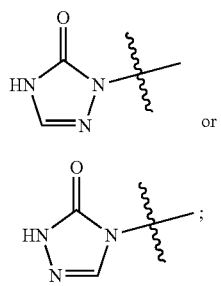

r-1 or

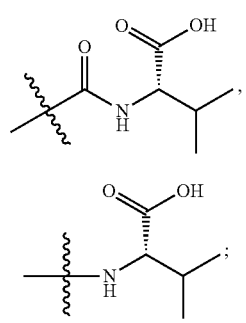

r-3 wherein said phenyl ring of group (iv) is optionally further substituted with one additional fluoro substituent;

or (v) phenyl substituted at the 4-position with p-1 or p-2;

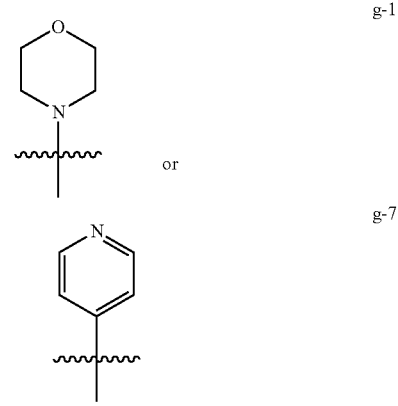

p-1 p-2

$R^2$ is hydrogen;

L is a bivalent linker that is ethyl, E-ethenyl, ethynyl, trans-1,3-cyclobutyl, cis-1,3-cyclobutyl, azetidinyl, —CH$_2$X-Q, or —NHC(O)-Q; wherein X is O or S;

Q is quinolin-2-yl, pyridinyl, pyrimidinyl, benzimidazol-2-yl, or benzothiazol-2-yl; wherein said Q is optionally independently substituted with one or two substituents selected from the group consisting of $C_{1-4}$alkyl, carboxy-methoxy, $C_{1-4}$alkoxy, and carboxy;

or an enantiomer, diastereomer, or pharmaceutically acceptable salt form thereof.

An embodiment of the present invention includes a compound of Formula (I)

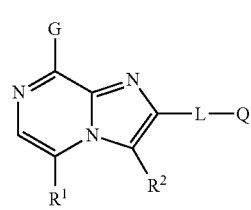

Formula (I)

wherein
G is

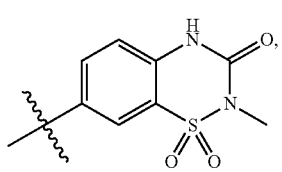

g-1 or g-7

$R^1$ is
(i) hydrogen;
(ii) a substituent selected from the group consisting of pyridinyl, 1H-pyrazol-4-yl, 5-pyrimidinyl, 5-hydroxy-1,2,4-oxadiazol-3-yl, 1H-imidazo[4,5-b]pyridin-6-yl, 2-hydroxy-1H-imidazo[4,5-b]pyridin-6-yl, and a ring 1-a to 1-h

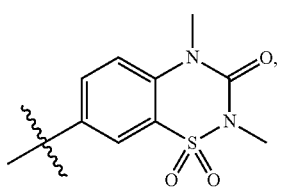

1-a 1-b

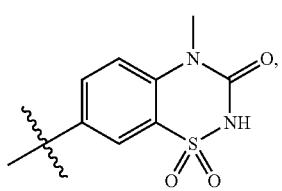

1-c

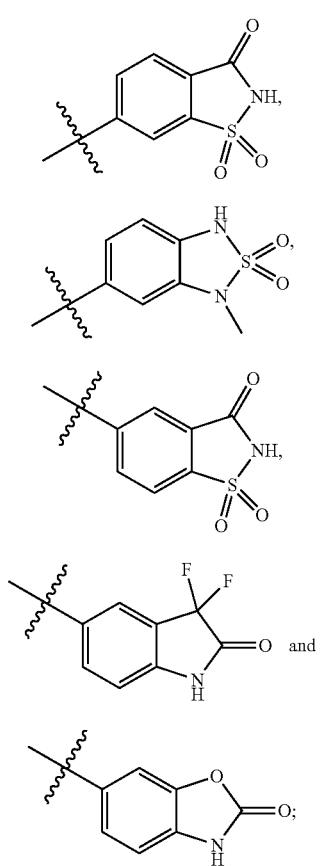

wherein the pyridinyl and 5-pyrimidinyl rings of group (iii) are optionally substituted with one substituent selected from the group consisting of $C_{1-4}$alkyl, carboxy($C_{1-4}$)alkyl, aminocarbonyl, aminosulfonyl, 1,2,3,6-tetrahydropyridin-4-yl, carboxy, amino, dimethylamino, carboxymethylamino, 4-methylpiperazin-1-yl, morpholin-4-yl, $C_{1-4}$alkylsulfonylamino, $C_{1-4}$alkylsulfonylaminocarbonyl, 1,2,4-oxadiazol-5(4H)-one-3-yl, tetrazolyl, triazolyl, or triazolylthio; wherein said tetrazolyl and triazolyl are optionally substituted with one hydroxy substituent;

and wherein said pyridinyl of group (iii) is optionally further substituted with one or two substituents selected from the group consisting of fluoro, chloro, and hydroxy;

wherein said 1H-pyrazol-4-yl of group (iii) is optionally substituted at the 1-position with methoxy-ethyl or carboxy($C_{1-4}$)alkyl;

(iii) phenyl optionally substituted at the 4-position with one substituent that is $C_{1-4}$alkoxycarbonyl, $C_{1-4}$alkylcarbonylaminosulfonyl, (2-hydroxyethyl)aminosulfonyl, aminosulfonyl, $C_{1-4}$alkylsulfonylaminocarbonyl, carboxy, —O(CH$_2$CH$_2$O)$_{2-5}$CH$_3$, —OCH$_2$OCH$_3$, carboxy($C_{1-4}$)alkylaminocarbonyl, 2-carboxypyrrolidin-1-ylcarbonyl, carboxy($C_{1-4}$)alkylcarbonylamino, $C_{1-4}$alkylsulfonylaminocarbonylamino, carboxy($C_{1-4}$)alkylamino, bis(2-hydroxyethyl)aminocarbonylamino, (2-hydroxyethyl)aminocarbonylamino, 1,1,1,3,3,3-hexafluoro-2-hydroxypropan-2-yl, 4-carboxypiperidin-1-yl, piperazin-1-yl, triazolylthio, tetrazolyl, triazolyl, imidazolyl, or oxazolyl;

wherein said tetrazolyl, triazolyl, imidazolyl, or oxazolyl substituents are optionally independently substituted with one or two substituents selected from the group consisting of $C_{1-4}$alkyl and hydroxy;

and wherein said phenyl ring of group (iii) is optionally independently further substituted with one or two substituents selected from the group consisting of $C_{1-4}$alkyl, $C_{1-4}$alkoxy, and fluoro;

(iv) phenyl substituted at the 4-position with one substituent that is r-1 or r-3;

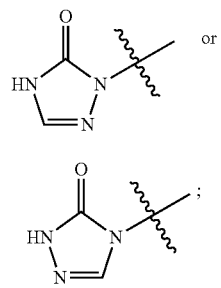

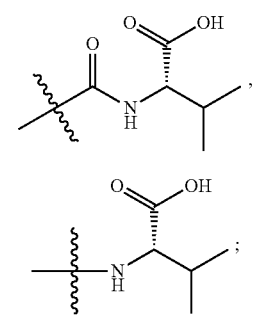

wherein said phenyl ring of group (iv) is optionally further substituted with one additional fluoro substituent; or (v) phenyl substituted at the 4-position with p-1 or p-2;

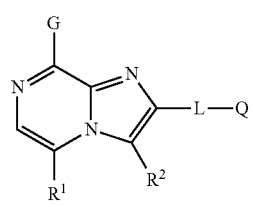

L is a bivalent linker that is -ethyl, E-ethenyl, ethynyl, trans-1,3-cyclobutyl, azetidinyl, or —CH$_2$X-Q; wherein X is O or S;

Q is quinolin-2-yl, pyridinyl, benzimidazol-2-yl, or benzothiazol-2-yl; wherein said Q is optionally independently substituted with one substituent selected from the group consisting of $C_{1-4}$alkyl, carboxy-methoxy, $C_{1-4}$alkoxy, and carboxy;

or an enantiomer, diastereomer, or pharmaceutically acceptable salt form thereof.

An embodiment of the present invention includes a compound of Formula (I)

Formula (I)

wherein
G is

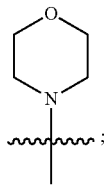
g-1

$R^1$ is
(i) hydrogen;
(ii) a substituent selected from the group consisting of pyridinyl, 1H-pyrazol-4-yl, 5-pyrimidinyl, 5-hydroxy-1,2,4-oxadiazol-3-yl, 1H-imidazo[4,5-b]pyridin-6-yl, 2-hydroxy-1H-imidazo[4,5-b]pyridin-6-yl, and a ring 1-a to 1-h

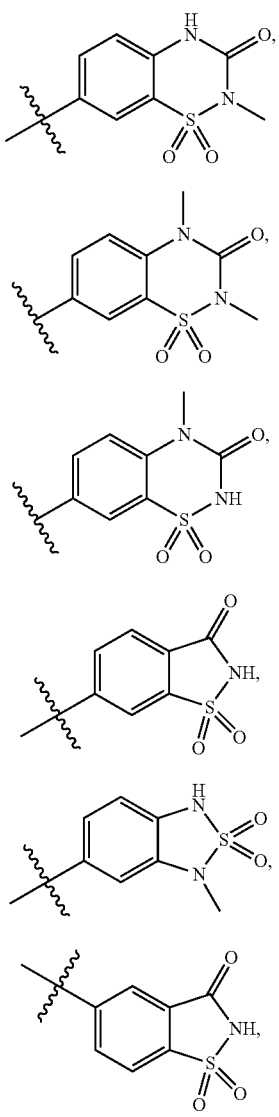

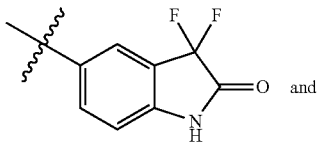
1-g

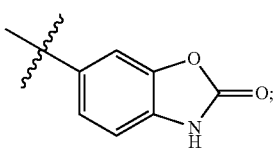
1-h wherein the pyridinyl and 5-pyrimidinyl rings of group (iii) are optionally substituted with one substituent selected from the group consisting of $C_{1-4}$alkyl, carboxy($C_{1-4}$)alkyl, aminocarbonyl, aminosulfonyl, 1,2,3,6-tetrahydropyridin-4-yl, carboxy, amino, dimethylamino, carboxymethylamino, 4-methylpiperazin-1-yl, morpholin-4-yl, $C_{1-4}$alkylsulfonylamino, $C_{1-4}$alkylsulfonylaminocarbonyl, 1,2,4-oxadiazol-5(4H)-one-3-yl, tetrazolyl, triazolyl, or triazolylthio; wherein said tetrazolyl and triazolyl are optionally substituted with one hydroxy substituent;

and wherein said pyridinyl of group (iii) is optionally further substituted with one or two substituents selected from the group consisting of fluoro, chloro, and hydroxy;

wherein said 1H-pyrazol-4-yl of group (iii) is optionally substituted at the 1-position with methoxy-ethyl or carboxy($C_{1-4}$)alkyl;

(iii) phenyl optionally substituted at the 4-position with one substituent that is $C_{1-4}$alkoxycarbonyl, $C_{1-4}$alkylcarbonylaminosulfonyl, (2-hydroxyethyl)aminosulfonyl, aminosulfonyl, $C_{1-4}$alkylsulfonylaminocarbonyl, carboxy, —O(CH$_2$CH$_2$O)$_{2-5}$CH$_3$, —OCH$_2$OCH$_3$, carboxy($C_{1-4}$)alkylaminocarbonyl, 2-carboxypyrrolidin-1-ylcarbonyl, carboxy($C_{1-4}$alkylcarbonylamino, $C_{1-4}$alkylsulfonylaminocarbonylamino, carboxy($C_{1-4}$)alkylamino, bis(2-hydroxyethyl)aminocarbonylamino, (2-hydroxyethyl)aminocarbonylamino, 1,1,1,3,3,3-hexafluoro-2-hydroxypropan-2-yl, 4-carboxypiperidin-1-yl, piperazin-1-yl, triazolylthio, tetrazolyl, triazolyl, imidazolyl, or oxazolyl;

wherein said tetrazolyl, triazolyl, imidazolyl, or oxazolyl substituents are optionally independently substituted with one or two substituents selected from the group consisting of $C_{1-4}$alkyl and hydroxy;

and wherein said phenyl ring of group (iii) is optionally independently further substituted with one or two substituents selected from the group consisting of $C_{1-4}$alkyl, $C_{1-4}$alkoxy, and fluoro;

(iv) phenyl substituted at the 4-position with one substituent that is r-1 or r-3;

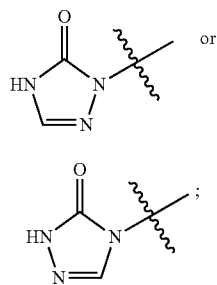

wherein said phenyl ring of group (iv) is optionally further substituted with one additional fluoro substituent;
or
(v) phenyl substituted at the 4-position with p-1 or p-2;

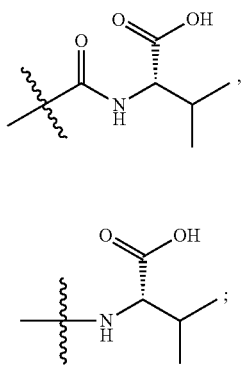

$R^2$ is hydrogen;

L is a bivalent linker that is ethyl, E-ethenyl, ethynyl, trans-1,3-cyclobutyl, azetidinyl, or —CH$_2$X-Q; wherein X is O or S;

Q is quinolin-2-yl, pyridinyl, benzimidazol-2-yl, or benzothiazol-2-yl; wherein said Q is optionally independently substituted with one substituent selected from the group consisting of C$_{1-4}$alkyl, carboxy-methoxy, C$_{1-4}$alkoxy, and carboxy;

or an enantiomer, diastereomer, or pharmaceutically acceptable salt form thereof.

Additional embodiments of the present invention include compounds of Formula (I) as herein defined, or an enantiomer, diastereomer, solvate, or a pharmaceutically acceptable salt form thereof, wherein the substituents selected from one or more of the variables defined herein (e.g. G, $R^1$, $R^2$, L, and Q) are independently selected to be any individual substituent or any subset of substituents from those exemplified in the listing in Table 1, below.

In the tables that follow, the linkers (under column "L") are depicted such that they can be directly inserted into the structure of Formula (I). More specifically, the right terminus of the linker is attached to Q, while the left terminus of the linker is attached to the core ring structure.

TABLE 1

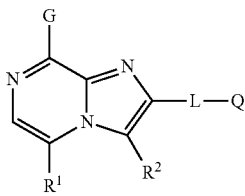

| Cpd No. | G | $R^1$ | $R^2$ | L | Q |
|---|---|---|---|---|---|
| 1 | g-1 | 4-carboxyphenyl | H | cis-cyclobutyl | quinolin-2-yl |
| 2 | g-1 | 4-(1,1,1,3,3,3-hexafluoro-2-hydroxy-propan-2-yl)phenyl | H | E-ethenyl | quinolin-2-yl |
| 3 | g-1 | 4-carboxy-3-fluorophenyl | H | E-ethenyl | quinolin-2-yl |
| 4 | g-1 | 4-carboxy-3-methoxyphenyl | H | E-ethenyl | quinolin-2-yl |
| 5 | G-1 | 4-carboxyphenyl | H | trans-cyclobutyl | quinolin-2-yl |
| 6 | g-1 | 5-carboxypyridin-2-yl | H | E-ethenyl | quinolin-2-yl |

TABLE 1-continued

Compounds of Formula (I)

Formula (I)

| Cpd No. | G | R¹ | R² | L | Q |
|---|---|---|---|---|---|
| 7 | g-1 | 4-carboxyphenyl | H | E-ethenyl | 6-methoxy pyridin-2-yl |
| 8 | g-1 | H | H | E-ethenyl | 4-carboxy quinolin-2-yl |
| 9 | g-1 | 1-carboxymethyl-pyrazol-4-yl | H | ethynyl | quinolin-2-yl |
| 10 | g-1 | 4-carboxyphenyl | H | ethynyl | pyridin-2-yl |
| 11 | g-1 | 4-carboxyphenyl | H | ethynyl | benzothiazol-2-yl |
| 12 | g-1 | 4-(methanesulfonyl aminocarbonyl) phenyl | H | CH₂S | quinolin-2-yl |
| 13 | g-1 | 4-carboxyphenyl | H | CH₂S | quinolin-2-yl |
| 14 | g-1 | 4-(4-carboxy piperidin-1-yl) phenyl | H | E-ethenyl | quinolin-2-yl |
| 15 | g-1 | [4-(N-(1-carboxy-2-methylpropyl)amino)phenyl] | H | E-ethenyl | quinolin-2-yl |
| 16 | g-1 | 4-carboxyphenyl | H | E-ethenyl | quinolin-2-yl |
| 17 | g-1 | 4-carboxyphenyl | H | ethyl | quinolin-2-yl |
| 18 | g-1 | 4-(CH₃(OCH₂CH₂)₂O) phenyl | H | E-ethenyl | quinolin-2-yl |
| 19 | g-1 | 1-a | H | E-ethenyl | quinolin-2-yl |
| 20 | g-1 | 1-b | H | E-ethenyl | quinolin-2-yl |
| 21 | g-1 | [4-(5-oxo-4,5-dihydro-1H-1,2,4-triazol-1-yl)phenyl] | H | ethyl | quinolin-2-yl |

TABLE 1-continued

Compounds of Formula (I)

Formula (I)

| Cpd No. | G | R¹ | R² | L | Q |
|---|---|---|---|---|---|
| 22 | g-1 | 4-(2-carboxyethylamino)phenyl | H | E-ethenyl | quinolin-2-yl |
| 23 | g-1 | 4-(2-carboxyethylamino)phenyl | H | ethyl | quinolin-2-yl |
| 24 | g-1 | 1-c | H | E-ethenyl | quinolin-2-yl |
| 25 | g-1 | 5-(methanesulfonyl-aminocarbonyl)pyridin-3-yl | H | E-ethenyl | quinolin-2-yl |
| 26 | g-1 | 2,4-dihydro-oxazol-5-yl | H | ethyl | quinolin-2-yl |
| 27 | g-1 | 5-carboxy pyridin-3-yl | H | E-ethenyl | quinolin-2-yl |
| 28 | g-1 | 5-(5-hydroxy-1,2,4-oxadiazol-3-yl)pyridin-3-yl | H | E-ethenyl | quinolin-2-yl |
| 29 | g-1 | 4-(carboxymethyl amino)phenyl | H | E-ethenyl | quinolin-2-yl |
| 30 | g-1 | 4-(carboxymethyl amino)phenyl | H | ethyl | quinolin-2-yl |
| 31 | g-1 | 4-($CH_3(OCH_2CH_2)_2O$)phenyl | H | ethyl | quinolin-2-yl |
| 32 | g-1 | 4-(carboxyethyl carbonylamino)phenyl | H | E-ethenyl | quinolin-2-yl |
| 33 | g-1 | 4-(1-methyl-5-hydroxy-1,2,4-triazol-3-yl)phenyl | H | ethyl | quinolin-2-yl |
| 34 | g-1 | | H | ethyl | quinolin-2-yl |
| 35 | g-1 | 4-(2(S)-carboxy pyrrolidin-1-yl carbonyl)phenyl | H | ethyl | quinolin-2-yl |
| 36 | g-1 | 4-(1H-1,2,3-triazol-4-ylthio)phenyl | H | ethyl | quinolin-2-yl |

TABLE 1-continued

Compounds of Formula (I)

Formula (I)

| Cpd No. | G | R¹ | R² | L | Q |
|---|---|---|---|---|---|
| 37 | g-1 | 4-(carboxyethyl carbonylamino) phenyl | H | ethyl | quinolin-2-yl |
| 38 | g-1 | 4-(carboxyethyl aminocarbonyl) phenyl | H | ethyl | quinolin-2-yl |
| 39 | g-1 | 4-(carboxyethylamino carbonyl)phenyl | H | E-ethenyl | quinolin-2-yl |
| 40 | g-1 | 4-(methanesulfonyl aminocarbonyl amino)phenyl | H | ethyl | quinolin-2-yl |
| 41 | g-1 | 3,5-dimethyl-4-methoxymethoxy-phenyl | H | E-ethenyl | quinolin-2-yl |
| 42 | g-1 | (3-oxo-2,3-dihydro-1,2-benzisothiazol-1,1-dioxide-5-yl) | H | E-ethenyl | quinolin-2-yl |
| 43 | g-1 | (3-methyl-2,2-dioxo-2,3-dihydro-1H-2,1,3-benzothiadiazol-5-yl) | H | E-ethenyl | quinolin-2-yl |
| 44 | g-1 | 4-(N-(1-carboxy-2-methylpropyl)carbamoyl)phenyl | H | E-ethenyl | quinolin-2-yl |
| 45 | g-1 | 4-(2(S)-carboxy pyrrolidin-1-yl carbonyl)phenyl | H | E-ethenyl | quinolin-2-yl |
| 46 | g-1 | 4-(carboxymethyl aminocarbonyl) phenyl | H | ethyl | quinolin-2-yl |
| 47 | g-1 | 4-(1-methyl-5-hydroxy-1,2,4-triazol-3-yl)phenyl | H | E-ethenyl | quinolin-2-yl |
| 48 | g-1 | 2,4-dihydrox-oxazol-5-yl | H | E-ethenyl | quinolin-2-yl |
| 49 | g-1 | 2-methyl-4-isopropylamino sulfonyl-phenyl | H | E-ethenyl | quinolin-2-yl |
| 50 | g-1 | 4-(carboxymethyl aminocarbonyl) phenyl | H | E-ethenyl | quinolin-2-yl |

TABLE 1-continued

Compounds of Formula (I)

Formula (I)

| Cpd No. | G | R¹ | R² | L | Q |
|---|---|---|---|---|---|
| 51 | g-1 | 4-(3-hydroxy-1H-1,2,4-triazol-1-yl)phenyl | H | ethyl | quinolin-2-yl |
| 52 | g-1 | 6-(3-hydroxy-1H-1,2,4-triazol-1-yl)pyridin-3-yl | H | E-ethenyl | quinolin-2-yl |
| 53 | g-1 | 4-(5-hydroxy-1H-1,2,3,4-tetrazol-1-yl)phenyl | H | ethyl | quinolin-2-yl |
| 54 | g-1 | (1,1-dioxo-3-oxo-2,3-dihydro-1,2-benzisothiazol-5-yl) | H | ethyl | quinolin--2yl |
| 55 | g-1 | 4-(5-hydroxy-1H-tetrazol-1-yl)phenyl | H | E-ethenyl | quinolin-2-yl |
| 56 | g-1 | 4-(3-hydroxy-1H-1,2,4-triazol-1-yl)phenyl | H | E-ethenyl | quinolin-2-yl |
| 57 | g-1 | 4-(2,5-dihydroxy-imidazol-4-yl)phenyl | H | E-ethenyl | quinolin-2-yl |
| 58 | g-1 | 4-(5-oxo-4,5-dihydro-1H-1,2,4-triazol-4-yl)phenyl | H | E-ethenyl | quinolin-2-yl |
| 59 | g-1 | (3,3-difluoro-2-oxo-2,3-dihydro-1H-indol-5-yl) | H | ethyl | quinolin-2-yl |
| 60 | g-1 | 5-(1H-tetrazol-5-yl)pyridin-3-yl | H | E-ethenyl | quinolin-2-yl |
| 61 | g-1 | 4-(methanesulfonyl aminocarbonyl)phenyl | H | ethyl | quinolin-2-yl |
| 62 | g-1 | 4-(methanesulfonyl aminocarbonyl)phenyl | H | E-ethenyl | quinolin-2-yl |
| 63 | g-1 | 4-(methylcarbonyl aminosulfonyl)phenyl | H | ethyl | quinolin-2-yl |
| 64 | g-1 | (2-oxo-2,3-dihydro-1,3-benzoxazol-6-yl) | H | ethyl | quinolin-2-yl |

TABLE 1-continued

Compounds of Formula (I)

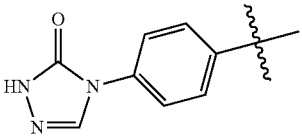 [SMILES: *c1ccc(-n2cn[nH]c2=O)cc1]

Formula (I)

| Cpd No. | G | R¹ | R² | L | Q |
|---|---|---|---|---|---|
| 65 | g-1 | 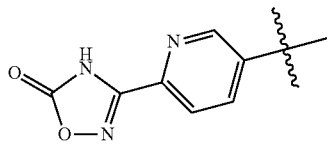 [SMILES: *c1ccc(-c2noc(=O)[nH]2)nc1] | H | ethyl | quinolin-2-yl |
| 66 | g-1 | 6-(carboxymethyl amino)pyridin-3-yl | H | E-ethenyl | quinolin-2-yl |
| 67 | g-1 | 6-(4H-1,2,4-triazol-3-yl)pyridin-3-yl | H | ethyl | quinolin-2-yl |
| 68 | g-1 | 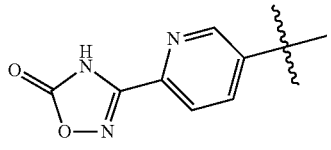 [SMILES: *c1ccc(-c2noc(=O)[nH]2)nc1] | H | CH₂O | quinolin-2-yl |
| 69 | g-1 | 4-(methylcarbonyl aminosulfonyl)phenyl | H | E-ethenyl | quinolin-2-yl |
| 70 | g-1 | 6-(1H-tetrazol-5-yl)pyridin-3-yl | H | CH₂S | quinolin-2-yl |
| 71 | g-1 | 4-(bis-(2-hydroxyethyl) aminocarbonyl amino)phenyl | H | E-ethenyl | quinolin-2-yl |
| 72 | g-1 | 4-((2-hydroxyethyl) aminocarbonyl amino)phenyl | H | E-ethenyl | quinolin-2-yl |
| 73 | g-1 | 4-(2-hydroxyethylamino sulfonyl)phenyl | H | E-ethenyl | quinolin-2-yl |
| 74 | g-1 | 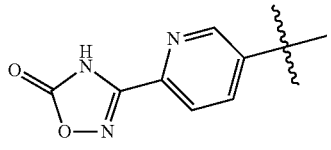 [SMILES: *c1ccc(-c2noc(=O)[nH]2)nc1] | H | ethyl | quinolin-2-yl |
| 75 | g-1 | 5-hydroxy-1,2,4-oxadiazol-3-yl | H | CH₂O | quinolin-2-yl |
| 76 | g-1 | 6-(methanesulfonyl aminocarbonyl)pyridin-3-yl | H | CH₂O | quinolin-2-yl |
| 77 | g-1 | 6-(1H-tetrazol-5-yl)pyridin-3-yl | H | ethyl | quinolin-2-yl |
| 78 | g-1 | 6-(methanesulfonyl amino)pyridin-3-yl | H | ethyl | quinolin-2-yl |
| 79 | g-1 | 2-hydroxy-1H-imidazo[4,5-b]pyridin-6-yl | H | ethyl | quinolin-2-yl |
| 80 | g-2 | 6-(piperazin-1-yl)pyridin-3-yl | H | E-ethenyl | quinolin-2-yl |
| 81 | g-6 | 6-(piperazin-1-yl)pyridin-3-yl | H | E-ethenyl | quinolin-2-yl |
| 82 | g-6 | 6-(piperazin-1-yl)pyridin-3-yl | H | CH₂O | quinolin-2-yl |
| 83 | g-2 | 6-(piperazin-1-yl)pyridin-3-yl | H | CH₂O | quinolin-2-yl |

TABLE 1-continued

Compounds of Formula (I)

Formula (I)

| Cpd No. | G | R¹ | R² | L | Q |
|---|---|---|---|---|---|
| 84 | g-1 | 6-aminocarbonyl-pyridin-3-yl | H | CH$_2$O | quinolin-2-yl |
| 85 | g-1 | 6-(methanesulfonyl amino)pyridin-3-yl | H | CH$_2$O | quinolin-2-yl |
| 86 | g-1 | 6-aminosulfonyl-pyridin-3-yl | H | CH$_2$O | quinolin-2-yl |
| 87 | g-1 | 4-aminosulfonyl-phenyl | H | CH$_2$O | quinolin-2-yl |
| 88 | g-1 | 4-(methylcarbonyl aminosulfonyl) phenyl | H | CH$_2$O | quinolin-2-yl |
| 89 | g-1 | 6-(methanesulfonyl amino)pyridin-3-yl | H | E-ethenyl | quinolin-2-yl |
| 90 | g-1 | 4-(1H-tetrazol-5-yl) phenyl | H | CH$_2$O | quinolin-2-yl |
| 91 | g-1 | 6-(4H-1,2,4-triazol-3-yl)pyridin-3-yl | H | E-ethenyl | quinolin-2-yl |
| 92 | g-1 | 6-(3H-1,2,3-triazol-4-ylthio) pyridin-3-yl | H | CH$_2$O | quinolin-2-yl |
| 93 | g-1 | 1H-imidazo[4,5-b] pyridin-6-yl | H | E-ethenyl | quinolin-2-yl |
| 94 | g-1 | 2-hydroxy-1H-imidazo[4,5-b] pyridin-6-yl | H | E-ethenyl | quinolin-2-yl |
| 95 | g-1 | (3-(5-oxo-4,5-dihydro-1,2,4-oxadiazol-3-yl)pyridin-2-yl substituent) | H | E-ethenyl | quinolin-2-yl |
| 96 | g-1 | 6-(1H-tetrazol-5-yl) pyridin-3-yl | H | E-ethenyl | quinolin-2-yl |
| 97 | g-1 | 6-(1H-tetrazol-5-yl) pyridin-3-yl | H | CH$_2$O | quinolin-2-yl |
| 98 | g-1 | 6-(piperazin-1-yl) pyridin-3-yl | H | CH$_2$S | quinolin-2-yl |
| 99 | g-1 | 6-(piperazin-1-yl) pyridin-3-yl | H | azetidine-1,3-diyl | quinolin-2-yl |
| 100 | g-1 | 6-(4H-1,2,4-triazol-3-ylthio) pyridin-3-yl | H | CH$_2$O | quinolin-2-yl |
| 101 | g-1 | 6-(carboxymethyl) pyridin-3-yl | H | CH$_2$O | quinolin-2-yl |
| 102 | g-1 | 6-(piperazin-1-yl) pyridin-3-yl | H | ethyl | quinolin-2-yl |
| 103 | g-1 | 6-(piperazin-1-yl) pyridin-3-yl | H | E-ethenyl | pyrimidin-2-yl |
| 104 | g-1 | 6-(piperazin-1-yl) pyridin-3-yl | H | E-ethenyl | quinazolin-2-yl |
| 105 | g-1 | 6-(piperazin-1-yl) pyridin-3-yl | H | E-ethenyl | quinolin-2-yl |
| 106 | g-1 | 6-(piperidin-4-yl) pyridin-3-yl | H | CH$_2$O | quinolin-2-yl |
| 107 | g-1 | 6-(carboxymethyl amino) pyridin-3-yl | H | CH$_2$O | quinolin-2-yl |

TABLE 1-continued

Compounds of Formula (I)

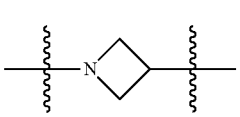 [SMILES: *C1CN(*)C1]

Formula (I)

| Cpd No. | G | R¹ | R² | L | Q |
|---|---|---|---|---|---|
| 108 | g-1 | 6-(1,2,3,6-tetrahydropyridin-4-yl)pyridin-3-yl | H | CH₂O | quinolin-2-yl |
| 109 | g-1 | 1-(aminosulfonyl)piperidin-4-yl | H | CH₂O | quinolin-2-yl |
| 110 | g-1 | 1-(carboxymethyl)piperidin-4-yl | H | CH₂O | quinolin-2-yl |
| 111 | g-1 | piperidin-4-yl | H | CH₂O | quinolin-2-yl |
| 112 | g-3 | 6-(piperazin-1-yl)pyridin-3-yl | H | CH₂O | quinolin-2-yl |
| 113 | g-10 | 6-(piperazin-1-yl)pyridin-3-yl | H | CH₂O | quinolin-2-yl |
| 114 | g-1 | 6-(piperazin-1-yl)pyridin-3-yl | H | 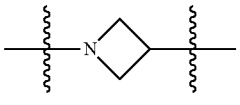 [SMILES: *C1CN(*)C1] | quinolin-2-yl |
| 115 | g-8 | 6-(piperazin-1-yl)pyridin-3-yl | H | CH₂O | quinolin-2-yl |
| 116 | g-1 | 6-(piperazin-1-yl)pyridin-3-yl | H | CH₂O | pyrimidin-2-yl |
| 117 | g-5 | 6-(piperazin-1-yl)pyridin-3-yl | H | CH₂O | quinolin-2-yl |
| 118 | g-4 | 6-(piperazin-1-yl)pyridin-3-yl | H | CH₂O | quinolin-2-yl |
| 119 | g-9 | 6-(piperazin-1-yl)pyridin-3-yl | H | CH₂O | quinolin-2-yl |
| 120 | g-7 | 6-(piperazin-1-yl)pyridin-3-yl | H | CH₂O | quinolin-2-yl |
| 121 | g-1 | 2-(piperazin-1-yl)pyrimidin-5-yl | H | CH₂O | quinolin-2-yl |
| 122 | g-1 | 6-amino pyridin-3-yl | H | CH₂O | quinolin-2-yl |
| 123 | g-1 | 2-(4-methylpiperazin-1-yl)pyrimidin-5-yl | H | CH₂O | quinolin-2-yl |
| 124 | g-1 | 6-(piperazin-1-yl)pyridin-3-yl | H | CH₂O | quinazolin-2-yl |
| 125 | g-1 | 6-(piperazin-1-yl)pyridin-3-yl | H | NHC(O) | quinolin-2-yl |
| 126 | g-1 | 6-(piperazin-1-yl)pyridin-3-yl | H | CH₂O | quinolin-2-yl |
| 127 | g-1 | 6-dimethylamino0 pyridin-3-yl | H | CH₂O | quinolin-2-yl |
| 128 | g-1 | 6-methyl pyridin-3-yl | H | CH₂O | quinolin-2-yl |
| 129 | g-1 | pyridin-3-yl | H | CH₂O | quinolin-2-yl |
| 130 | g-1 | 6-(4-methylpiperazin-1-yl)pyridin-3-yl | H | CH₂O | quinolin-2-yl |
| 131 | g-1 | 6-(morpholin-4-yl)pyridin-3-yl | H | CH₂O | quinolin-2-yl |
| 132 | g-1 | 6-(piperazin-1-yl)pyridin-3-yl | Cl | 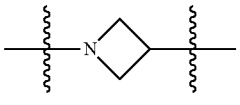 [SMILES: *C1CN(*)C1] | quinolin-2-yl |
| 133 | g-1 | 6-carboxy pyridin-3-yl | H | E-ethenyl | quinolin-2-yl |

Further embodiments of the present invention are directed to a compound of Formula (I)

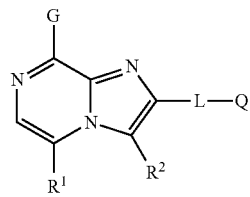

Formula (I)

selected from the group consisting of

Cpd 1, the compound of Formula (I) wherein G is g-1, $R^1$ is 4-carboxyphenyl, $R^2$ is hydrogen, L is cis-cyclobutyl, and Q is quinolin-2-yl;

Cpd 2, the compound of Formula (I) wherein G is g-1, $R^1$ is 4-(1,1,1,3,3,3-hexafluoro-2-hydroxy-propan-2-yl)phenyl, $R^2$ is hydrogen, L is E-ethenyl, and Q is quinolin-2-yl;

Cpd 3, the compound of Formula (I) wherein G is g-1, $R^1$ is 4-carboxy-3-fluorophenyl, $R^2$ is hydrogen, L is E-ethenyl, and Q is quinolin-2-yl;

Cpd 4, the compound of Formula (I) wherein G is g-1, $R^1$ is 4-carboxy-3-methoxyphenyl, $R^2$ is hydrogen, L is E-ethenyl, and Q is quinolin-2-yl;

Cpd 5, the compound of Formula (I) wherein G is g-1, $R^1$ is 4-carboxyphenyl, $R^2$ is hydrogen, L is trans-cyclobutyl, and Q is quinolin-2-yl;

Cpd 6, the compound of Formula (I) wherein G is g-1, $R^1$ is 5-carboxypyridin-2-yl, $R^2$ is hydrogen, L is E-ethenyl, and Q is quinolin-2-yl;

Cpd 7, the compound of Formula (I) wherein G is g-1, $R^1$ is 4-carboxyphenyl, $R^2$ is hydrogen, L is E-ethenyl, and Q is 6-methoxypyridin-2-yl;

Cpd 8, the compound of Formula (I) wherein G is g-1, $R^1$ is H, $R^2$ is hydrogen, L is E-ethenyl, and Q is 4-carboxyquinolin-2-yl;

Cpd 9, the compound of Formula (I) wherein G is g-1, $R^1$ is 1-carboxymethyl-pyrazol-4-yl, $R^2$ is hydrogen, L is ethynyl, and Q is quinolin-2-yl;

Cpd 10, the compound of Formula (I) wherein G is g-1, $R^1$ is 4-carboxyphenyl, $R^2$ is hydrogen, L is ethynyl, and Q is pyridin-2-yl;

Cpd 11, the compound of Formula (I) wherein G is g-1, $R^1$ is 4-carboxyphenyl, $R^2$ is hydrogen, L is ethynyl, and Q is benzothiazol-2-yl;

Cpd 12, the compound of Formula (I) wherein G is g-1, $R^1$ is 4-(methanesulfonylaminocarbonyl)phenyl, $R^2$ is hydrogen, L is —$CH_2$S-Q, and Q is quinolin-2-yl;

Cpd 13, the compound of Formula (I) wherein G is g-1, $R^1$ is 4-carboxyphenyl, L is —$CH_2$S-Q, and Q is quinolin-2-yl;

Cpd 14, the compound of Formula (I) wherein G is g-1, $R^1$ is 4-(4-carboxypiperidin-1-yl)phenyl, $R^2$ is hydrogen, L is E-ethenyl, and Q is quinolin-2-yl;

Cpd 15, the compound of Formula (I) wherein G is g-1, $R^1$ is

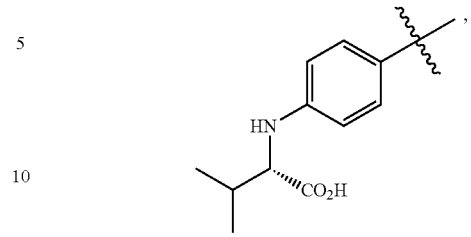

$R^2$ is hydrogen, L is E-ethenyl, and Q is quinolin-2-yl;

Cpd 16, the compound of Formula (I) wherein G is g-1, $R^1$ is 4-carboxyphenyl, $R^2$ is hydrogen, L is E-ethenyl, and Q is quinolin-2-yl;

Cpd 17, the compound of Formula (I) wherein G is g-1, $R^1$ is 4-carboxyphenyl, $R^2$ is hydrogen, L is ethyl, and Q is quinolin-2-yl;

Cpd 18, the compound of Formula (I) wherein G is g-1, $R^1$ is 4-($CH_3(OCH_2CH_2)_2O$)phenyl, $R^2$ is hydrogen, L is E-ethenyl, and Q is quinolin-2-yl Cpd 19, the compound of Formula (I) wherein G is g-1, $R^1$ is

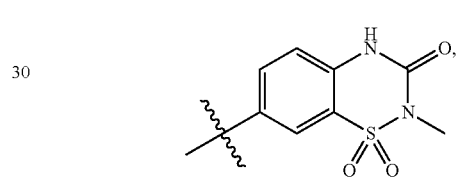

1-a $R^2$ is hydrogen, L is E-ethenyl, and Q is quinolin-2-yl;

Cpd 20, the compound of Formula (I) wherein G is g-1, $R^1$ is

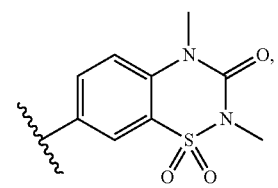

1-b $R^2$ is hydrogen, L is E-ethenyl, and Q is quinolin-2-yl;

Cpd 21, the compound of Formula (I) wherein G is g-1, $R^1$ is

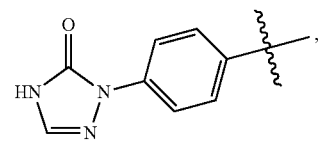 [SMILES: *c1ccc(-n2nc[nH]c2=O)cc1]

$R^2$ is hydrogen, L is ethyl, and Q is quinolin-2-yl;

Cpd 22, the compound of Formula (I) wherein G is g-1, $R^1$ is 4-(2-carboxyethylamino)phenyl, $R^2$ is hydrogen, L is E-ethenyl, and Q is quinolin-2-yl;

Cpd 23, the compound of Formula (I) wherein G is g-1, $R^1$ is 4-(2-carboxyethylamino)phenyl, $R^2$ is hydrogen, L is ethyl, and Q is quinolin-2-yl;

Cpd 24, the compound of Formula (I) wherein G is g-1, R¹ is

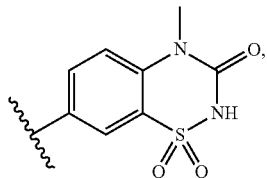

R² is hydrogen, L is E-ethenyl, and Q is quinolin-2-yl;
Cpd 25, the compound of Formula (I) wherein G is g-1, R¹ is 5-(methanesulfonylaminocarbonyl)pyridin-3-yl, R² is hydrogen, L is E-ethenyl, and Q is quinolin-2-yl;
Cpd 26, the compound of Formula (I) wherein G is g-1, R¹ is 2,4-dihydroxy-oxazol-5-yl, R² is hydrogen, L is ethyl, and Q is quinolin-2-yl;
Cpd 27, the compound of Formula (I) wherein G is g-1, R¹ is 5-carboxypyridin-3-yl, R² is hydrogen, L is E-ethenyl, and Q is quinolin-2-yl;
Cpd 28, the compound of Formula (I) wherein G is g-1, R¹ is 5-(5-hydroxy-1,2,4-oxadiazol-3-yl)pyridin-3-yl, R² is hydrogen, L is E-ethenyl, and Q is quinolin-2-yl;
Cpd 29, the compound of Formula (I) wherein G is g-1, R¹ is 4-(carboxymethylamino)phenyl, R² is hydrogen, L is E-ethenyl, and Q is quinolin-2-yl;
Cpd 30, the compound of Formula (I) wherein G is g-1, R¹ is 4-(carboxymethylamino)phenyl, R² is hydrogen, L is ethyl, and Q is quinolin-2-yl;
Cpd 31, the compound of Formula (I) wherein G is g-1, R¹ is 4-(CH₃(OCH₂CH₂)₂O)phenyl, R² is hydrogen, L is ethyl, and Q is quinolin-2-yl;
Cpd 32, the compound of Formula (I) wherein G is g-1, R¹ is 4-(carboxyethylcarbonylamino)phenyl, R² is hydrogen, L is E-ethenyl, and Q is quinolin-2-yl;
Cpd 33, the compound of Formula (I) wherein G is g-1, R¹ is 4-(1-methyl-5-hydroxy-1,2,4-triazol-3-yl)phenyl, R² is hydrogen, L is ethyl, and Q is quinolin-2-yl;
Cpd 34, the compound of Formula (I) wherein G is g-1, R¹ is

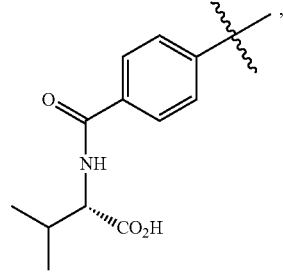 [SMILES: *c1ccc(C(=O)N[C@H](C(=O)O)C(C)C)cc1]

R² is hydrogen, L is ethyl, and Q is quinolin-2-yl;
Cpd 35, the compound of Formula (I) wherein G is g-1, R¹ is 4-(2(S)-carboxypyrrolidin-1-ylcarbonyl)phenyl, R² is hydrogen, L is ethyl, and Q is quinolin-2-yl;
Cpd 36, the compound of Formula (I) wherein G is g-1, R¹ is 4-(1H-1,2,3-triazol-4-ylthio)phenyl, R² is hydrogen, L is ethyl, and Q is quinolin-2-yl
Cpd 37, the compound of Formula (I) wherein G is g-1, R¹ is 4-(carboxyethylcarbonylamino)phenyl, R² is hydrogen, L is ethyl, and Q is quinolin-2-yl;
Cpd 38, the compound of Formula (I) wherein G is g-1, R¹ is 4-(carboxyethylaminocarbonyl)phenyl, R² is hydrogen, L is ethyl, and Q is quinolin-2-yl;
Cpd 39, the compound of Formula (I) wherein G is g-1, R¹ is 4-(carboxyethylaminocarbonyl)phenyl, R² is hydrogen, L is E-ethenyl, and Q is quinolin-2-yl;
Cpd 40, the compound of Formula (I) wherein G is g-1, R¹ is 4-(methanesulfonylaminocarbonylamino)phenyl, R² is hydrogen, L is ethyl, and Q is quinolin-2-yl;
Cpd 41, the compound of Formula (I) wherein G is g-1, R¹ is 3,5-dimethyl-4-methoxymethoxy-phenyl, R² is hydrogen, L is E-ethenyl, and Q is quinolin-2-yl;
Cpd 42, the compound of Formula (I) wherein G is g-1, R¹ is

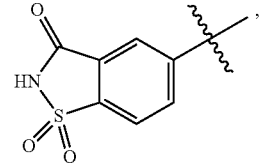 [SMILES: *c1ccc2c(c1)C(=O)NS2(=O)=O]

R² is hydrogen, L is E-ethenyl, and Q is quinolin-2-yl;
Cpd 43, the compound of Formula (I) wherein G is g-1, R¹ is

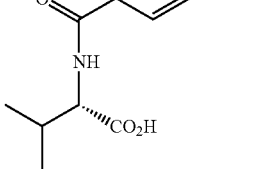

R² is hydrogen, L is E-ethenyl, and Q is quinolin-2-yl;
Cpd 44, the compound of Formula (I) wherein G is g-1, R¹ is R² is hydrogen, L is E-ethenyl, and Q is quinolin-2-yl;
Cpd 45, the compound of Formula (I) wherein G is g-1, R¹ is 4-(2(S)-carboxypyrrolidin-1-ylcarbonyl)phenyl, R² is hydrogen, L is E-ethenyl, and Q is quinolin-2-yl;
Cpd 46, the compound of Formula (I) wherein G is g-1, R¹ is 4-(carboxymethylaminocarbonyl)phenyl, R² is hydrogen, L is ethyl, and Q is quinolin-2-yl;
Cpd 47, the compound of Formula (I) wherein G is g-1, R¹ is 4-(1-methyl-5-hydroxy-1,2,4-triazol-3-yl)phenyl, R² is hydrogen, L is E-ethenyl, and Q is quinolin-2-yl;
Cpd 48, the compound of Formula (I) wherein G is g-1, R¹ is 2,4-dihydroxy-oxazol-5-yl, R² is hydrogen, L is E-ethenyl, and Q is quinolin-2-yl;
Cpd 49, the compound of Formula (I) wherein G is g-1, R¹ is 2-methyl-4-isopropylaminosulfonyl-phenyl, R² is hydrogen, L is E-ethenyl, and Q is quinolin-2-yl;
Cpd 50, the compound of Formula (I) wherein G is g-1, R¹ is 4-(carboxymethylaminocarbonyl)phenyl, L is E-ethenyl, and Q is quinolin-2-yl;

Cpd 51, the compound of Formula (I) wherein G is g-1, R¹ is 4-(3-hydroxy-1H-1,2,4-triazol-1-yl)phenyl, R² is hydrogen, L is ethyl, and Q is quinolin-2-yl;

Cpd 52, the compound of Formula (I) wherein G is g-1, R¹ is 6-(3-hydroxy-1H-1,2,4-triazol-1-yl)pyridin-3-yl, R² is hydrogen, L is E-ethenyl, and Q is quinolin-2-yl;

Cpd 53, the compound of Formula (I) wherein G is g-1, R¹ is 4-(5-hydroxy-1H-1,2,3,4-tetrazol-1-yl)phenyl, R² is hydrogen, L is ethyl, and Q is quinolin-2-yl;

Cpd 54, the compound of Formula (I) wherein G is g-1, R¹ is

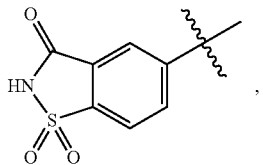 [SMILES: *c1ccc2c(c1)C(=O)NS2(=O)=O]

R² is hydrogen, L is ethyl, and Q is quinolin-2-yl;

Cpd 55, the compound of Formula (I) wherein G is g-1, R¹ is 4-(5-hydroxy-1H-tetrazol-1-yl)phenyl, R² is hydrogen, L is E-ethenyl, and Q is quinolin-2-yl;

Cpd 56, the compound of Formula (I) wherein G is g-1, R¹ is 4-(3-hydroxy-1H-1,2,4-triazol-1-yl)phenyl, R² is hydrogen, L is E-ethenyl, and Q is quinolin-2-yl;

Cpd 57, the compound of Formula (I) wherein G is g-1, R¹ is 4-(2,5-dihydroxy-imidazol-4-yl)phenyl, R² is hydrogen, L is E-ethenyl, and Q is quinolin-2-yl;

Cpd 58, the compound of Formula (I) wherein G is g-1, R¹ is

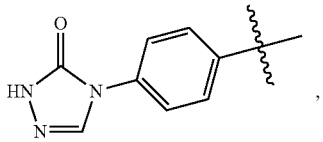 [SMILES: *c1ccc(-n2cn[nH]c2=O)cc1]

R² is hydrogen, L is E-ethenyl, and Q is quinolin-2-yl;

Cpd 59, the compound of Formula (I) wherein G is g-1, R¹ is

R² is hydrogen, L is ethyl, and Q is quinolin-2-yl;

Cpd 60, the compound of Formula (I) wherein G is g-1, R¹ is 5-(1H-tetrazol-5-yl)pyridin-3-yl, R² is hydrogen, L is E-ethenyl, and Q is quinolin-2-yl;

Cpd 61, the compound of Formula (I) wherein G is g-1, R¹ is 4-(methanesulfonylaminocarbonyl)phenyl, R² is hydrogen, L is ethyl, and Q is quinolin-2-yl;

Cpd 62, the compound of Formula (I) wherein G is g-1, R¹ is 4-(methanesulfonylaminocarbonyl)phenyl, R² is hydrogen, L is E-ethenyl, and Q is quinolin-2-yl;

Cpd 63, the compound of Formula (I) wherein G is g-1, R¹ is 4-(methylcarbonylaminosulfonyl)phenyl, R² is hydrogen, L is ethyl, and Q is quinolin-2-yl;

Cpd 64, the compound of Formula (I) wherein G is g-1, R¹ is

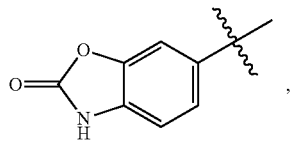 [SMILES: *c1ccc2[nH]c(=O)oc2c1]

R² is hydrogen, L is ethyl, and Q is quinolin-2-yl;

Cpd 65, the compound of Formula (I) wherein G is g-1, R¹ is

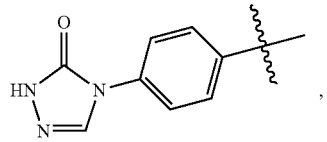 [SMILES: *c1ccc(-n2cn[nH]c2=O)cc1]

R² is hydrogen, L is ethyl, and Q is quinolin-2-yl;

Cpd 66, the compound of Formula (I) wherein G is g-1, R¹ is 6-(carboxymethylamino)pyridin-3-yl, R² is hydrogen, L is E-ethenyl, and Q is quinolin-2-yl;

Cpd 67, the compound of Formula (I) wherein G is g-1, R¹ is 6-(4H-1,2,4-triazol-3-yl)pyridin-3-yl, R² is hydrogen, L is ethyl, and Q is quinolin-2-yl;

Cpd 68, the compound of Formula (I) wherein G is g-1, R¹ is

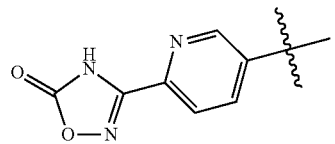

R² is hydrogen, L is —CH₂O-Q, and Q is quinolin-2-yl;

Cpd 69, the compound of Formula (I) wherein G is g-1, R¹ is 4-(methylcarbonylaminosulfonyl)phenyl, R² is hydrogen, L is E-ethenyl, and Q is quinolin-2-yl;

Cpd 70, the compound of Formula (I) wherein G is g-1, R¹ is 6-(1H-tetrazol-5-yl)pyridin-3-yl, R² is hydrogen, L is —CH₂S-Q, and Q is quinolin-2-yl;

Cpd 71, the compound of Formula (I) wherein G is g-1, R¹ is 4-(bis-(2-hydroxyethyl)aminocarbonylamino)phenyl, R² is hydrogen, L is E-ethenyl, and Q is quinolin-2-yl;

Cpd 72, the compound of Formula (I) wherein G is g-1, R¹ is 4-((2-hydroxyethyl)aminocarbonylamino)phenyl, R² is hydrogen, L is E-ethenyl, and Q is quinolin-2-yl;

Cpd 73, the compound of Formula (I) wherein G is g-1, R¹ is 4-(2-hydroxyethylaminosulfonyl)phenyl, R² is hydrogen, L is E-ethenyl, and Q is quinolin-2-yl;

Cpd 74, the compound of Formula (I) wherein G is g-1, R¹ is

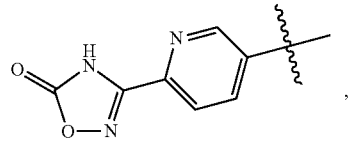 [SMILES: *c1ccc(-c2noc(=O)[nH]2)nc1]

R² is hydrogen, L is ethyl, and Q is quinolin-2-yl;

Cpd 75, the compound of Formula (I) wherein G is g-1, R¹ is 5-hydroxy-1,2,4-oxadiazol-3-yl, R² is hydrogen, L is —CH₂O-Q, and Q is quinolin-2-yl;

Cpd 76, the compound of Formula (I) wherein G is g-1, $R^1$ is 6-(methanesulfonylaminocarbonyl)pyridin-3-yl, $R^2$ is hydrogen, L is —$CH_2O$-Q, and Q is quinolin-2-yl;

Cpd 77, the compound of Formula (I) wherein G is g-1, $R^1$ is 6-(1H-tetrazol-5-yl)pyridin-3-yl, L is ethyl, and Q is quinolin-2-yl;

Cpd 78, the compound of Formula (I) wherein G is g-1, $R^1$ is 6-(methanesulfonylamino)pyridin-3-yl, $R^2$ is hydrogen, L is ethyl, and Q is quinolin-2-yl;

Cpd 79, the compound of Formula (I) wherein G is g-1, $R^1$ is 2-hydroxy-1H-imidazo[4,5-b]pyridin-6-yl, $R^2$ is hydrogen, L is ethyl, and Q is quinolin-2-yl;

Cpd 80, the compound of Formula (I) wherein G is g-2, $R^1$ is 6-(piperazin-1-yl)pyridin-3-yl, $R^2$ is hydrogen, L is E-ethenyl, and Q is quinolin-2-yl;

Cpd 81, the compound of Formula (I) wherein G is g-6, $R^1$ is 6-(piperazin-1-yl)pyridin-3-yl, $R^2$ is hydrogen, L is E-ethenyl, and Q is quinolin-2-yl;

Cpd 82, the compound of Formula (I) wherein G is g-6, $R^1$ is 6-(piperazin-1-yl)pyridin-3-yl, $R^2$ is hydrogen, L is —$CH_2O$-Q, and Q is quinolin-2-yl;

Cpd 83, the compound of Formula (I) wherein G is g-2, $R^1$ is 6-(piperazin-1-yl)pyridin-3-yl, $R^2$ is hydrogen, L is —$CH_2O$-Q, and Q is quinolin-2-yl;

Cpd 84, the compound of Formula (I) wherein G is g-1, $R^1$ is 6-aminocarbonyl-pyridin-3-yl, $R^2$ is hydrogen, L is —$CH_2O$-Q, and Q is quinolin-2-yl;

Cpd 85, the compound of Formula (I) wherein G is g-1, $R^1$ is 6-(methanesulfonylamino)pyridin-3-yl, $R^2$ is hydrogen, L is —$CH_2O$-Q, and Q is quinolin-2-yl;

Cpd 86, the compound of Formula (I) wherein G is g-1, $R^1$ is 6-aminosulfonyl-pyridin-3-yl, $R^2$ is hydrogen, L is —$CH_2O$-Q, and Q is quinolin-2-yl;

Cpd 87, the compound of Formula (I) wherein G is g-1, $R^1$ is 4-aminosulfonyl-phenyl, $R^2$ is hydrogen, L is —$CH_2O$-Q, and Q is quinolin-2-yl;

Cpd 88, the compound of Formula (I) wherein G is g-1, $R^1$ is 4-(methylcarbonylaminosulfonyl)phenyl, $R^2$ is hydrogen, L is —$CH_2O$-Q, and Q is quinolin-2-yl;

Cpd 89, the compound of Formula (I) wherein G is g-1, $R^1$ is 6-(methanesulfonylamino)pyridin-3-yl, $R^2$ is hydrogen, L is E-ethenyl, and Q is quinolin-2-yl;

Cpd 90, the compound of Formula (I) wherein G is g-1, $R^1$ is 4-(1H-tetrazol-5-yl)phenyl, $R^2$ is hydrogen, L is —$CH_2O$-Q, and Q is quinolin-2-yl;

Cpd 91, the compound of Formula (I) wherein G is g-1, $R^1$ is 6-(4H-1,2,4-triazol-3-yl)pyridin-3-yl, $R^2$ is hydrogen, L is E-ethenyl, and Q is quinolin-2-yl;

Cpd 92, the compound of Formula (I) wherein G is g-1, $R^1$ is 6-(3H-1,2,3-triazol-4-ylthio)pyridin-3-yl, $R^2$ is hydrogen, L is —$CH_2O$-Q, and Q is quinolin-2-yl;

Cpd 93, the compound of Formula (I) wherein G is g-1, $R^1$ is 1H-imidazo[4,5-b]pyridin-6-yl, $R^2$ is hydrogen, L is E-ethenyl, and Q is quinolin-2-yl;

Cpd 94, the compound of Formula (I) wherein G is g-1, $R^1$ is 2-hydroxy-1H-imidazo[4,5-b]pyridin-6-yl, $R^2$ is hydrogen, L is E-ethenyl, and Q is quinolin-2-yl;

Cpd 95, the compound of Formula (I) wherein G is g-1, $R^1$ is

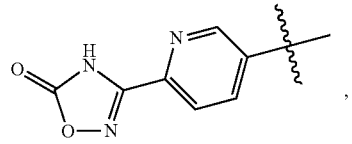 [SMILES: *c1ccc(-c2noc(=O)[nH]2)nc1]

$R^2$ is hydrogen, L is E-ethenyl, and Q is quinolin-2-yl;

Cpd 96, the compound of Formula (I) wherein G is g-1, $R^1$ is 6-(1H-tetrazol-5-yl)pyridin-3-yl, $R^2$ is hydrogen, L is E-ethenyl, and Q is quinolin-2-yl;

Cpd 97, the compound of Formula (I) wherein G is g-1, $R^1$ is 6-(1H-tetrazol-5-yl)pyridin-3-yl, $R^2$ is hydrogen, L is —$CH_2O$-Q, and Q is quinolin-2-yl;

Cpd 98, the compound of Formula (I) wherein G is g-1, $R^1$ is 6-(piperazin-1-yl)pyridin-3-yl, $R^2$ is hydrogen, L is —$CH_2O$-Q, and Q is quinolin-2-yl;

Cpd 99, the compound of Formula (I) wherein G is g-1, $R^1$ is 6-(piperazin-1-yl)pyridin-3-yl, $R^2$ is hydrogen, L is

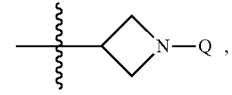

and Q is quinolin-2-yl;

Cpd 100, the compound of Formula (I) wherein G is g-1, $R^1$ is 6-(4H-1,2,4-triazol-3-ylthio)pyridin-3-yl, $R^2$ is hydrogen, L is —$CH_2O$-Q, and Q is quinolin-2-yl;

Cpd 101, the compound of Formula (I) wherein G is g-1, $R^1$ is 6-(carboxymethyl)pyridin-3-yl, $R^2$ is hydrogen, L is —$CH_2O$-Q, and Q is quinolin-2-yl;

Cpd 102, the compound of Formula (I) wherein G is g-1, $R^1$ is 6-(piperazin-1-yl)pyridin-3-yl, $R^2$ is hydrogen, L is ethyl, and Q is quinolin-2-yl;

Cpd 103, the compound of Formula (I) wherein G is g-1, $R^1$ is 6-(piperazin-1-yl)pyridin-3-yl, $R^2$ is hydrogen, L is E-ethenyl, and Q is pyrimidin-2-yl;

Cpd 104, the compound of Formula (I) wherein G is g-1, $R^1$ is 6-(piperazin-1-yl)pyridin-3-yl, $R^2$ is hydrogen, L is E-ethenyl, and Q is quinazolin-2-yl;

Cpd 105, the compound of Formula (I) wherein G is g-1, $R^1$ is 6-(piperazin-1-yl)pyridin-3-yl, $R^2$ is hydrogen, L is E-ethenyl, and Q is quinolin-2-yl;

Cpd 106, the compound of Formula (I) wherein G is g-1, $R^1$ is 6-(piperidin-4-yl)pyridin-3-yl, $R^2$ is hydrogen, L is —$CH_2O$-Q, and Q is quinolin-2-yl;

Cpd 107, the compound of Formula (I) wherein G is g-1, $R^1$ is 6-(carboxymethylamino)pyridin-3-yl, $R^2$ is hydrogen, L is —$CH_2O$-Q, and Q is quinolin-2-yl;

Cpd 108, the compound of Formula (I) wherein G is g-1, $R^1$ is 6-(1,2,3,6-tetrahydropyridin-4-yl)pyridin-3-yl, $R^2$ is hydrogen, L is —$CH_2O$-Q, and Q is quinolin-2-yl;

Cpd 109, the compound of Formula (I) wherein G is g-1, $R^1$ is 1-(aminosulfonyl)piperidin-4-yl, $R^2$ is hydrogen, L is —$CH_2O$-Q, and Q is quinolin-2-yl;

Cpd 110, the compound of Formula (I) wherein G is g-1, $R^1$ is 1-(carboxymethyl)piperidin-4-yl, $R^2$ is hydrogen, L is —$CH_2O$-Q, and Q is quinolin-2-yl;

Cpd 111, the compound of Formula (I) wherein G is g-1, $R^1$ is piperidin-4-yl, $R^2$ is hydrogen, L is —$CH_2O$-Q, and Q is quinolin-2-yl;

Cpd 112, the compound of Formula (I) wherein G is g-3, $R^1$ is 6-(piperazin-1-yl)pyridin-3-yl, $R^2$ is hydrogen, L is —CH$_2$O-Q, and Q is quinolin-2-yl;

Cpd 113, the compound of Formula (I) wherein G is g-10, $R^1$ is 6-(piperazin-1-yl)pyridin-3-yl, $R^2$ is hydrogen, L is —CH$_2$O-Q, and Q is quinolin-2-yl;

Cpd 114, the compound of Formula (I) wherein G is g-1, $R^1$ is 6-(piperazin-1-yl)pyridin-3-yl, $R^2$ is hydrogen, L is

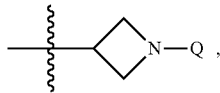

and Q is quinolin-2-yl;

Cpd 115, the compound of Formula (I) wherein G is g-8, $R^1$ is 6-(piperazin-1-yl)pyridin-3-yl, $R^2$ is hydrogen, L is —CH$_2$O-Q, and Q is quinolin-2-yl;

Cpd 116, the compound of Formula (I) wherein G is g-1, $R^1$ is 6-(piperazin-1-yl)pyridin-3-yl, $R^2$ is hydrogen, L is —CH$_2$O-Q, and Q is pyrimidin-2-yl;

Cpd 117, the compound of Formula (I) wherein G is g-5, $R^1$ is 6-(piperazin-1-yl)pyridin-3-yl, $R^2$ is hydrogen, L is —CH$_2$O-Q, and Q is quinolin-2-yl;

Cpd 118, the compound of Formula (I) wherein G is g-4, $R^1$ is 6-(piperazin-1-yl)pyridin-3-yl, $R^2$ is hydrogen, L is —CH$_2$O-Q, and Q is quinolin-2-yl;

Cpd 119, the compound of Formula (I) wherein G is g-9, $R^1$ is 6-(piperazin-1-yl)pyridin-3-yl, $R^2$ is hydrogen, L is —CH$_2$O-Q, and Q is quinolin-2-yl;

Cpd 120, the compound of Formula (I) wherein G is g-7, $R^1$ is 6-(piperazin-1-yl)pyridin-3-yl, $R^2$ is hydrogen, L is —CH$_2$O-Q, and Q is quinolin-2-yl;

Cpd 121, the compound of Formula (I) wherein G is g-1, $R^1$ is 2-(piperazin-1-yl)pyrimidin-5-yl, $R^2$ is hydrogen, L is —CH$_2$O-Q, and Q is quinolin-2-yl;

Cpd 122, the compound of Formula (I) wherein G is g-1, $R^1$ is 6-aminopyridin-3-yl, $R^2$ is hydrogen, L is —CH$_2$O-Q, and Q is quinolin-2-yl;

Cpd 123, the compound of Formula (I) wherein G is g-1, $R^1$ is 2-(4-methylpiperazin-1-yl)pyrimidin-5-yl, $R^2$ is hydrogen, L is —CH$_2$O-Q, and Q is quinolin-2-yl;

Cpd 124, the compound of Formula (I) wherein G is g-1, $R^1$ is 6-(piperazin-1-yl)pyridin-3-yl, $R^2$ is hydrogen, L is —CH$_2$O-Q, and Q is quinazolin-2-yl;

Cpd 125, the compound of Formula (I) wherein G is g-1, $R^1$ is 6-(piperazin-1-yl)pyridin-3-yl, $R^2$ is hydrogen, L is —NHC(O)-Q, and Q is quinolin-2-yl;

Cpd 126, the compound of Formula (I) wherein G is g-1, $R^1$ is 6-(piperazin-1-yl)pyridin-3-yl, $R^2$ is hydrogen, L is —CH$_2$O-Q, and Q is quinolin-2-yl;

Cpd 127, the compound of Formula (I) wherein G is g-1, $R^1$ is 6-dimethylamino-pyridin-3-yl, $R^2$ is hydrogen, L is —CH$_2$O-Q, and Q is quinolin-2-yl;

Cpd 128, the compound of Formula (I) wherein G is g-1, $R^1$ is 6-methylpyridin-3-yl, $R^2$ is hydrogen, L is —CH$_2$O-Q, and Q is quinolin-2-yl;

Cpd 129, the compound of Formula (I) wherein G is g-1, $R^1$ is pyridin-3-yl, $R^2$ is hydrogen, L is —CH$_2$O-Q, and Q is quinolin-2-yl;

Cpd 130, the compound of Formula (I) wherein G is g-1, $R^1$ is 6-(4-methylpiperazin-1-yl)pyridin-3-yl, $R^2$ is hydrogen, L is —CH$_2$O-Q, and Q is quinolin-2-yl;

Cpd 131, the compound of Formula (I) wherein G is g-1, $R^1$ is 6-(morpholin-4-yl)pyridin-3-yl, $R^2$ is hydrogen, L is —CH$_2$O-Q, and Q is quinolin-2-yl;

Cpd 132, the compound of Formula (I) wherein G is g-1, $R^1$ is 6-(piperazin-1-yl)pyridin-3-yl, $R^2$ is chloro, L is

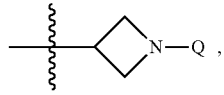

and Q is quinolin-2-yl;

Cpd 133, the compound of Formula (I) wherein G is g-1, $R^1$ is 6-carboxypyridin-3-yl, $R^2$ is hydrogen, L is E-ethenyl, and Q is quinolin-2-yl;

and pharmaceutically acceptable salt forms thereof.

For use in medicine, salts of compounds of Formula (I) refer to non-toxic "pharmaceutically acceptable salts." Other salts may, however, be useful in the preparation of compounds of Formula (I) or of their pharmaceutically acceptable salt forms thereof. Suitable pharmaceutically acceptable salts of compounds of Formula (I) include acid addition salts that can, for example, be formed by mixing a solution of the compound with a solution of a pharmaceutically acceptable acid such as, hydrochloric acid, sulfuric acid, fumaric acid, maleic acid, succinic acid, acetic acid, benzoic acid, citric acid, tartaric acid, carbonic acid or phosphoric acid. Furthermore, where the compounds of Formula (I) carry an acidic moiety, suitable pharmaceutically acceptable salts thereof may include alkali metal salts such as, sodium or potassium salts; alkaline earth metal salts such as, calcium or magnesium salts; and salts formed with suitable organic ligands such as, quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide, and valerate.

Representative acids and bases that may be used in the preparation of pharmaceutically acceptable salts include acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxoglutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methylglucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine, and zinc hydroxide.

Embodiments of the present invention include prodrugs of compounds of Formula (I). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula (I).

Where the processes for the preparation of the compounds according to certain embodiments of the invention give rise to mixture of stereoisomers, these isomers may be separated by conventional techniques such as, preparative chromatography. The compounds may be prepared in racemic form, or individual enantiomers may be prepared either by enantiospecific synthesis or by resolution. The compounds may, for example, be resolved into their component enantiomers by standard techniques such as, the formation of diastereomeric pairs by salt formation with an optically active acid such as, (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition, including a pharmaceutical composition, comprising, consisting of, and/or consisting essentially of the (+)-enantiomer of a compound of Formula (I) wherein said composition is substantially free from the (−)-isomer of said compound. In the present context, substantially free means less than about 25%, preferably less than about 10%, more preferably less than about 5%, even more preferably less than about 2% and even more preferably less than about 1% of the (−)-isomer calculated as $$\%(+)\text{-enantiomer} = \frac{(\text{mass}(+)\text{-enantiomer})}{(\text{mass}(+)\text{-enantiomer}) + (\text{mass}(-)\text{-enantiomer})} \times 100.$$

Another embodiment of the present invention is a composition, including a pharmaceutical composition, comprising, consisting of, and consisting essentially of the (−)-enantiomer of a compound of Formula (I) wherein said composition is substantially free from the (+)-isomer of said compound. In the present context, substantially free from means less than about 25%, preferably less than about 10%, more preferably less than about 5%, even more preferably less than about 2% and even more preferably less than about 1% of the (+)-isomer calculated as $$\%(-)\text{-enantiomer} = \frac{(\text{mass}(-)\text{-enantiomer})}{(\text{mass}(+)\text{-enantiomer}) + (\text{mass}(-)\text{-enantiomer})} \times 100.$$

During any of the processes for preparation of the compounds of the various embodiments of the present invention, it may be necessary and/or desirable to protect sensitive or reactive groups on any of the molecules concerned. This may be achieved by means of conventional protecting groups such as those described in *Protective Groups in Organic Chemistry, Second Edition*, J. F. W. McOmie, Plenum Press, 1973; T. W. Greene & P. G. M. Wuts, *Protective Groups in Organic Synthesis*, John Wiley & Sons, 1991; and T. W. Greene & P. G. M. Wuts, *Protective Groups in Organic Synthesis, Third Edition*, John Wiley & Sons, 1999. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising compounds of Formula (I) and at least one pharmaceutically acceptable carrier, pharmaceutically acceptable excipient, and/or pharmaceutically acceptable diluent.

By way of example, in the pharmaceutical compositions of embodiments of the present invention, the compounds of Formula (I) may be admixed with any suitable binder(s), lubricant(s), suspending agent(s), coating agent(s), solubilizing agent(s), and combinations thereof.

Solid oral dosage forms such as, tablets or capsules, containing the compounds of the present invention may be administered in at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, compounds of Formula (I) can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a wax or soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example, intracavernosally, intravenously, intramuscularly, subcutaneously, intradermally, or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing at least one of the compounds of Formula (I) as the active ingredient can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus, for liquid oral preparations such as, suspensions, syrups, elixirs and solutions, suitable carriers, excipients and diluents include water, glycols, oils, alcohols, flavoring agents, preservatives, stabilizers, coloring agents and the like; for solid oral preparations such as, powders, capsules, and tablets, suitable carriers, excipients and diluents include starches, sugars, diluents, granulating agents, lubricants, binders, disintegrating agents and the like. Solid oral preparations also may be optionally coated with substances such as, sugars, or be enterically coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives such as, solubilizers and preservatives.

A therapeutically effective amount of a compound of Formula (I) or a pharmaceutical composition thereof includes a dose range from about 0.1 mg to about 3000 mg, or any particular amount or range therein, in particular from about 1 mg to about 1000 mg, or any particular amount or range therein, or, more particularly, from about 10 mg to about 500 mg, or any particular amount or range therein, of active ingredient in a regimen of about 1 to about 4 times per day for an average (70 kg) human; although, it is apparent to one skilled in the art that the therapeutically effective amount for a compound of Formula (I) will vary as will the diseases, syndromes, conditions, and disorders being treated.

For oral administration, a pharmaceutical composition is preferably provided in the form of tablets containing about 1.0, about 10, about 50, about 100, about 150, about 200, about 250, and about 500 milligrams of a compound of Formula (I).

Advantageously, a compound of Formula (I) may be administered in a single daily dose, or the total daily dosage may be administered in divided doses of two, three and four times daily.

Optimal dosages of a compound of Formula (I) to be administered may be readily determined and will vary with the particular compound used, the mode of administration, the strength of the preparation and the advancement of the disease, syndrome, condition or disorder. In addition, factors associated with the particular subject being treated, including subject gender, age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

Compounds of Formula (I) may be administered in any of the foregoing compositions and dosage regimens or by means of those compositions and dosage regimens established in the art whenever use of a compound of Formula (I) is required for a subject in need thereof.

As PDE10a inhibitors, the compounds of Formula (I) are useful in methods for treating or preventing a disease, a syndrome, a condition or a disorder in a subject, including an animal, a mammal and a human in which the disease, the syndrome, the condition or the disorder is affected by the modulation, including inhibition, of the PDE10a enzyme. Such methods comprise, consist of and/or consist essentially of administering to a subject, including an animal, a mammal, and a human in need of such treatment or prevention, a therapeutically effective amount of a compound, salt or solvate of Formula (I).

In an embodiment, the present invention is directed to treating or preventing Type II diabetes; comprising administering to a subject, including an animal, a mammal, and a human in need thereof, a therapeutically effective amount of a compound, salt, or solvate of Formula (I).

GENERAL SYNTHETIC METHODS

Representative compounds of the present invention can be synthesized in accordance with the general synthetic methods described below and illustrated in the schemes and examples that follow. Since the schemes are an illustration, the invention should not be construed as being limited by the chemical reactions and conditions described in the schemes and examples. The various starting materials used in the schemes and examples are commercially available or may be prepared by methods well within the skill of persons versed in the art. The variables are as defined herein.

Abbreviations used in the instant specification, particularly the schemes and examples, are as follows:
ACN acetonitrile
AcOH glacial acetic acid
aq. aqueous
Bn or Bzl benzyl
BINAP 2,2'-bis(diphenylphosphino)-1,1'-binaphthyl
Boc tert-butyloxycarbonyl
BPO benzoyl peroxide
conc. concentrated
dba dibenzylideneacetone
DBU 1,8-diazabicyclo[5.4.0]undec-7-ene
DCC N,N'-dicyclohexyl-carbodiimide DCE 1,2-dichloroethane
DCM dichloromethane
DIPEA or DIEA diisopropyl-ethyl amine
DMA dimethylaniline
DMAP 4-dimethylaminopyridine
DMF N,N-dimethylformamide
DMSO dimethylsulfoxide
DPPA diphenylphosphoryl azide
dppf 1,1'-bis(diphenylphosphino)ferrocene
EGTA ethylene glycol tetraacetic acid
ESI electrospray ionization
EtOAc or EA ethyl acetate
EtOH ethanol
h or hr(s) hour or hours
HEK human embryonic kidney
HEPES (4-(2-hydroxyethyl)-1-piperazineethane sulfonic acid
HOBt hydroxybenzotriazole
HPLC high performance liquid chromatography
IBX 2-iodoxybenzoic acid
MEK methyl ethyl ketone
MeOH methanol
MHz megahertz
min minute or minutes
MS mass spectrometry
Ms methanesulfonyl
NBS N-bromosuccinimide
NMP N-methylpyrrolidone
NMR nuclear magnetic resonance
RP reverse-phase
rt or RT room temperature
$R_t$ retention time
Sec second or seconds
SEMCl 2-(trimethylsilyl)ethoxymethyl chloride
TBAF tetrabutylammonium fluoride
TBDMS t-butyldimethylsilyl
TEA or $Et_3N$ triethylamine
TFA trifluoroacetic acid
THF tetrahydrofuran
TLC thin layer chromatography
TMS tetramethylsilane
Ts 4-toluenesulfonyl General Schemes One of ordinary skill in the art will recognize that conventional protecting groups may be utilized in certain synthetic sequences in order to protect functional groups that may be sensitive to a particular set of reaction conditions. Such protecting groups may be subsequently removed at an appropriate stage using conventional deprotection reagents.

Scheme A illustrates a method for the preparation of certain compounds of Formula (I-A) of the present invention wherein L is a cyclobutyl in Formula (I).

Scheme A

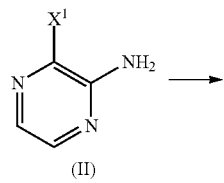

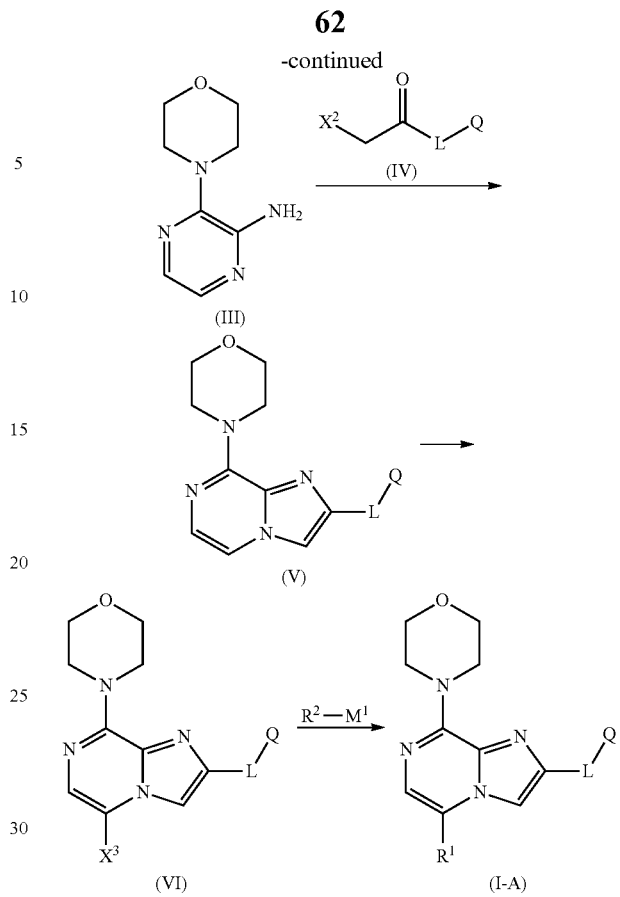

A compound of formula (II), wherein $X^1$ is chloro or bromo, is either commercially available or may be prepared according to methods described in the scientific literature. The compound of formula (II) may be reacted with morpholine in the presence or absence of a solvent such as DMF, DMA, DMSO, MeOH, DCE, EtOH and the like, preferably at a suitable temperature in the range of from about room temperature to about 180° C. to obtain a compound of formula (III). The preferred conditions for this transformation include the reaction of a compound of formula (II) with excess morpholine at 100° C. for 12 h. A compound of formula (III) may be transformed to a compound of formula (V) by reaction with a compound of formula (IV), wherein L is as defined herein, and $X^2$ is a leaving group such as Cl, Br, iodo, and the like, preferably Cl or Br. This reaction may be carried out in a solvent such as DMF, THF and the like, at a suitable temperature in the range of from about room temperature to about 180° C., in the presence or absence of a base. When used, preferred bases for this reaction include, but are not limited to, inorganic bases such as $K_2CO_3$ and $Na_2HPO_4$. If a compound of formula (IV) is not commercially available, it may be prepared according to methods described in the scientific literature. One known method for the preparation of compounds of formula (IV) involves conversion of an appropriately substituted methyl ketone of formula Q-L-COCH$_3$ (wherein L is as defined herein), either directly or indirectly, into its corresponding α-bromomethyl ketone of formula (IV) wherein $X^2$ is bromo.

A preferred method for this transformation includes the conversion of an appropriately substituted ketone of formula Q-L-COCH$_3$ to its corresponding silyl enol ether, followed by reaction with a bromine source such as $Br_2$ or NBS and the like, in a solvent such as $CH_3CN$, DCM, DCE, MeOH, DMF, THF or diethyl ether, in the presence of a base such as Na₂CO₃ at a suitable temperature in the range of from about −78° C. to about room temperature. One of ordinary skill in the art will recognize that certain ketones of the formula Q-L-COCH₃ may not be commercially available, but instead may be prepared using known conventional methods described in the scientific literature.

Another known method for the preparation of compounds of formula (IV) involves conversion of an appropriately substituted carboxylic acid of formula Q-L-COOH to its corresponding acyl halide, preferably an acyl chloride of formula Q-L-COCl. The acyl chloride may then be converted to its corresponding diazoketone before final conversion to a compound of formula (IV) wherein X² is bromo. The acyl chloride may be prepared using a number of conventional chlorinating agents such as thionyl chloride or, preferably, oxalyl chloride, in a solvent such as DCM, and preferably in the presence of DMF as a catalyst. A preferred method for the preparation of the diazoketone intermediate is the interception of the acyl chloride with TMSCHN₂, in a solvent such as DCM, at a suitable temperature in the range of from about −78° C. to about room temperature. A preferred method for the conversion of the diazoketone into a compound of formula (IV) wherein X² is bromo, is the reaction of diazoketone with HBr in HOAc, in a solvent such as DCM, diethyl ether, THF, acetonitrile and the like, at a suitable temperature in the range of from −20° C. to about room temperature.

A compound of formula (V) may be halogenated by using number of conventional halogenating agents to obtain a compound of formula (VI) wherein X³ is chloro, bromo, or iodo, preferably bromo. The preferred method of halogenation includes, but is not limited to, treatment of a compound of formula (V) with an electrophilic bromine source, such as NBS, in a solvent such as DCM, CH₃CN and the like, at a temperature ranging from about −20° C. to room temperature. A compound of formula (VI) may be reacted with a suitably substituted compound of formula R¹-M¹, wherein M¹ is a suitably selected activating group, under suitable coupling conditions, to yield the corresponding compound of formula (I-A). A compound of formula R¹-M¹ may be (a) a boronic acid to form a compound of formula R¹—B(OH)₂; (b) a suitably selected boronic ester such as pinacolatoboryl, neopentylglycolatoboryl, and the like; (c) a suitably selected trialkylstannyl such as tri(n-butyl)tin, and the like; (d) a suitably selected trialkylsilyl such as triallylsilyl, and the like; or (e) a suitably selected aryldialkylsilyl such as 2-(hydroxymethyl)phenyl-dimethylsilyl, and the like.

For example, a compound of formula R¹-M¹ where M¹ is preferably —B(OH)₂ or a suitably selected R¹-substituted boronic ester may be reacted with a compound of formula (VIII) under Suzuki coupling conditions, more particularly in the presence of a suitably selected palladium catalyst such as palladium (II) acetate, palladium (II) chloride, bis(acetonitrile)-dichloro-palladium(II), allylpalladium (II) chloride dimer, tris(dibenzylidineacetone)dipalladium (0) (Pd₂(dba)₃), 2-(di-tert-butylphosphino)biphenyl, dichlorobis(di-tert-butylphenylphosphine)-palladium (II), [1,1'-bis-(diphenylphosphino)-ferrocene]-palladium (II) dichloride dichloromethane adduct ((dppf)PdCl₂.DCM), tetrakis(triphenylphosphine) palladium(0) (Pd(PPh₃)₄), (1,1'-bis(di-tert-butylphosphino)ferrocene palladium (II) chloride, and the like; optionally in the presence of a suitably selected ligand such as triphenylphosphine, tri-o-tolylphosphine, tri(tert-butyl)-phosphine, tricyclohexylphosphine, 1,1'-bis(diphenylphosphino)-ferrocene, 2-(dicyclohexylphosphino)-2',4', 6'-tri-1-propyl-1,1'-biphenyl, S-Phos, Ru-Phos, bis[2-(diphenyl-phosphino)phenyl]ether, 2-dicyclohexylphosphino-2',6'-dimethoxybiphenyl, tris(2-furyl)phosphine, 1-butyl-3-methylimidazolium hexafluorophosphate, and the like; in the presence of a suitably selected inorganic base such as cesium carbonate, potassium carbonate, sodium carbonate, cesium fluoride, potassium fluoride, tetrabutylammonium fluoride, potassium tert-butoxide, sodium tert-butoxide, sodium hydroxide, sodium bicarbonate; potassium phosphate or preferably sodium carbonate; in a suitably selected solvent such as ethanol, THF, DMF, toluene, benzene, DME, H₂O, 1,4-dioxane, and the like, or a combination thereof; at a temperature in the range of from about room temperature to about 180° C.

It is understood that when R¹ contains a functional group that may be sensitive to the coupling reaction conditions described herein, the functional group may be suitably protected and, subsequently deprotected under appropriate conditions upon completion of the coupling reaction.

Scheme B illustrates a method for the preparation of certain compounds of formulae I-B1 and I-B2 of the present invention wherein L-Q in Formula (I) is —NHC(O)-Q.

Scheme B

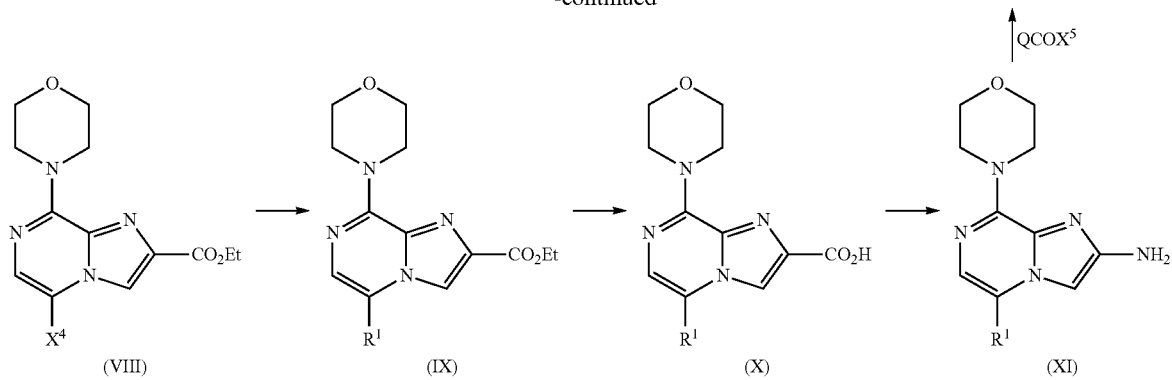

A compound of formula (VIII) may be obtained from a compound of formula (III) and a compound of formula (IVa) using the synthetic methods described in Scheme A, which may be halogenated to obtain a compound of formula (VIII) wherein $X^4$ is chloro, bromo, or iodo, preferably bromo, as described in Scheme A. The $R^1$ substituent may be then installed as previously described in Scheme A to yield a compound of formula (IX). The ester functionality of a compound of formula (IX) may be saponified using one of various conventional methods known to one of ordinary skill in the art to produce the corresponding carboxylic acid of formula (X). Such methods include the use of sodium hydroxide in water with a suitable co-solvent such as methanol, ethanol, THF, dioxane, or a co-solvent combination thereof.

Various L linkers of the present invention may be incorporated using the common intermediate of formula (X). For example, a compound of formula (X) may be converted to its corresponding amine of formula (XI) by one of numerous methods. For example, a compound of formula (X) may be converted to its corresponding acid chloride, followed by the reaction with hydrazine to obtain corresponding acyl hydrazide which can be converted to the corresponding diazonium salt. The diazonium salt can then be reacted with sodium azide to obtain the corresponding acyl azide. The preferred conditions for this transformation include the interception of the diazonium salt generated by the treatment of the acyl hydrazide in aqueous HCl with aqueous $NaNO_2$ dropwise below 15° C., with aqueous $NaN_3$.

The acyl azide may undergo a Curtius rearrangement in the presence of water to furnish a compound of formula (XI). If the reaction is carried out in the presence of an alcohol, such as EtOH, the amine compound of formula (XI) may be obtained as its ethyl carbamate, which may then be subjected to suitable deprotecting conditions to unmask the desired amino compound of formula (XI). The preferred conditions for this transformation include, but are not limited to, the thermal decomposition of the acyl azide in refluxing ethanol for about 6 h and the base hydrolysis of the resulting ethyl carbamate using aqueous NaOH in refluxing EtOH for 12 to 18 h.

A compound of formula (XI) may be reacted with a compound of formula $Q-C(O)X^5$ (wherein $X^5$ is chloro or hydroxy), under standard amide bond formation conditions to yield a compound of formula (I-B1). A preferred method for amide bond formation includes reaction of a compound of formula (XI) with Q-C(O)Cl in the presence of an organic base such as DIEA, in a solvent such as DCM, at room temperature.

Scheme C illustrates a method for the preparation of certain compounds of Formulae (I-C1) and (I-C2) of the present invention wherein L-Q are —$CH_2$S-Q and $CH_2$O-Q respectively.

Scheme C

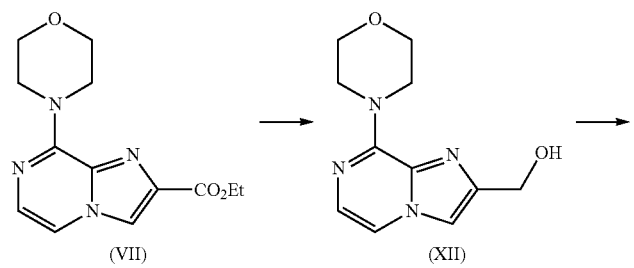

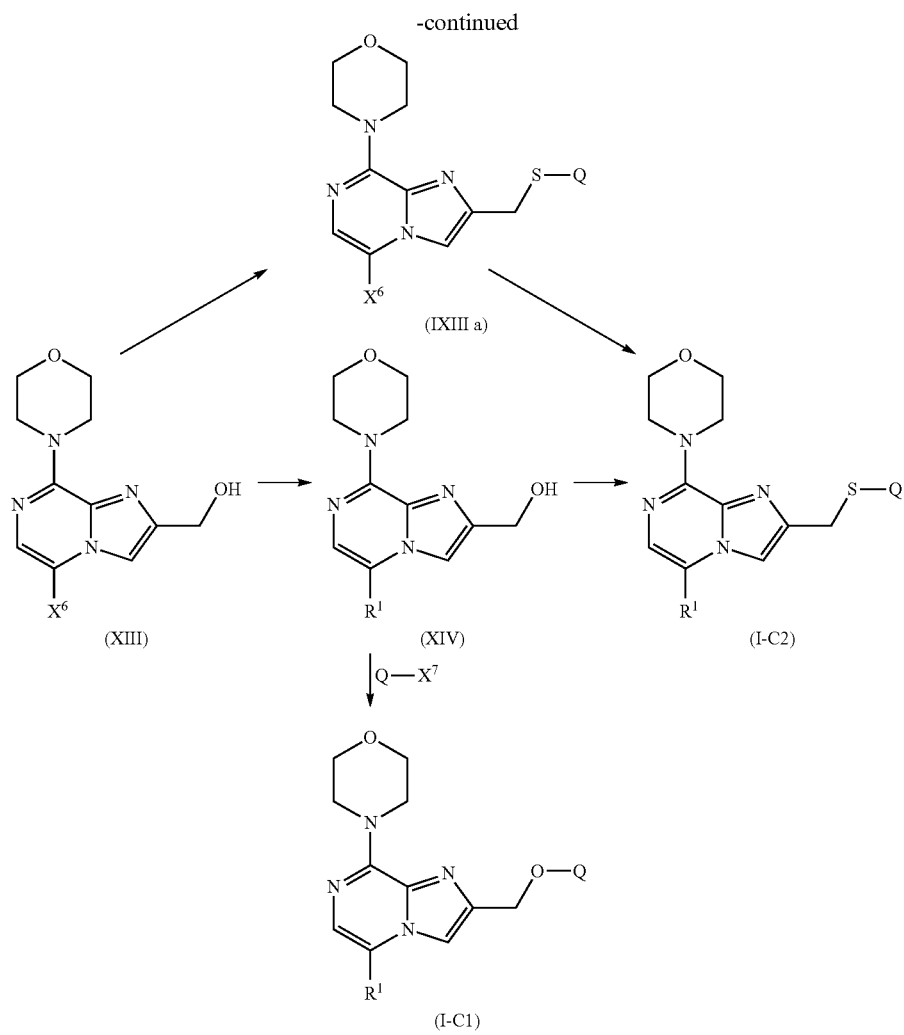

A compound of formula (VII) may be reduced to the corresponding alcohol of formula (XII) using a suitable reducing agent such as LAH and the like, in a solvent such as THF, diethyl ether, or DME, at a temperature ranging from about −78° C. to about room temperature and the resulting alcohol (XII) may be halogenated as described in Scheme A to obtain a compound of formula (XIII) where $X^6$ is chloro, bromo, or iodo, preferably bromo. The $R^1$ substituent can then be introduced to obtain a compound of formula (XIV). The primary alcohol of formula (XIV) may be reacted with a compound of formula Q-$X^7$, wherein $X^7$ is a leaving group such as fluoro, chloro, bromo, triflate, and the like, to afford a compound of formula (I-C1) wherein L-Q is —CH$_2$O-Q. A compound of formula Q-$X^7$ is either a known compound or a compound that may be prepared by known methods disclosed in the scientific literature. Preferred synthetic methods include the reaction of a metal salt of a compound of formula (XIV), preferably the potassium or sodium salt, which may be generated via treatment of a compound of formula (XIV) with either potassium-tert-butoxide or NaH, respectively, in a solvent such as THF or DMF, at a temperature in the range of from about room temperature to about 70° C., optionally in the presence of an additive such as a crown ether. Most preferred is the reaction of a potassium salt of a compound of formula (XIV) with a compound of formula Q-$X^7$, in the presence of 18-crown-6, in THF solvent, at a temperature of about 60° C.

A compound of formula (I-C2) may be prepared via a compound of formula (XIV). The primary alcohol functionality of the compound of formula (XIV) may be converted to a leaving group such as a mesylate, tosylate, Cl, Br, or I and the like, followed by reaction with a thiol of formula HS-Q to produce a compound of formula (I-C2). For example, the compound of formula (XIV) may be activated by reacting with MeSO$_2$Cl, in a solvent such as DCM, at about 0° C. to room temperature, in the presence of an organic base such as Et$_3$N, DIEA or pyridine and then be treated with a thiol of formula HS-Q, in a suitable solvent such as acetonitrile, in the presence of a base such as Na$_2$CO$_3$, at a suitable temperature in the range of from about −20° C. to about 100° C., preferably at about room temperature.

Alternately, a compound of formula (XIII) can be converted to a compound of formula (XIII a) wherein $X^6$ is Cl, Br or I, preferably bromo, by reacting with HS-Q after activating the alcohol. A compound of formula (XIIIa) may then be used as a substrate for the installation of an $R^1$ substituent as described above to obtain a compound of formula (I-C2).

Scheme D illustrates a method for the preparation of certain compounds of Formulae (I-D1) and (1-D2) of the present invention wherein L-Q are -ethenyl-Q and -ethyl-Q.

Scheme D

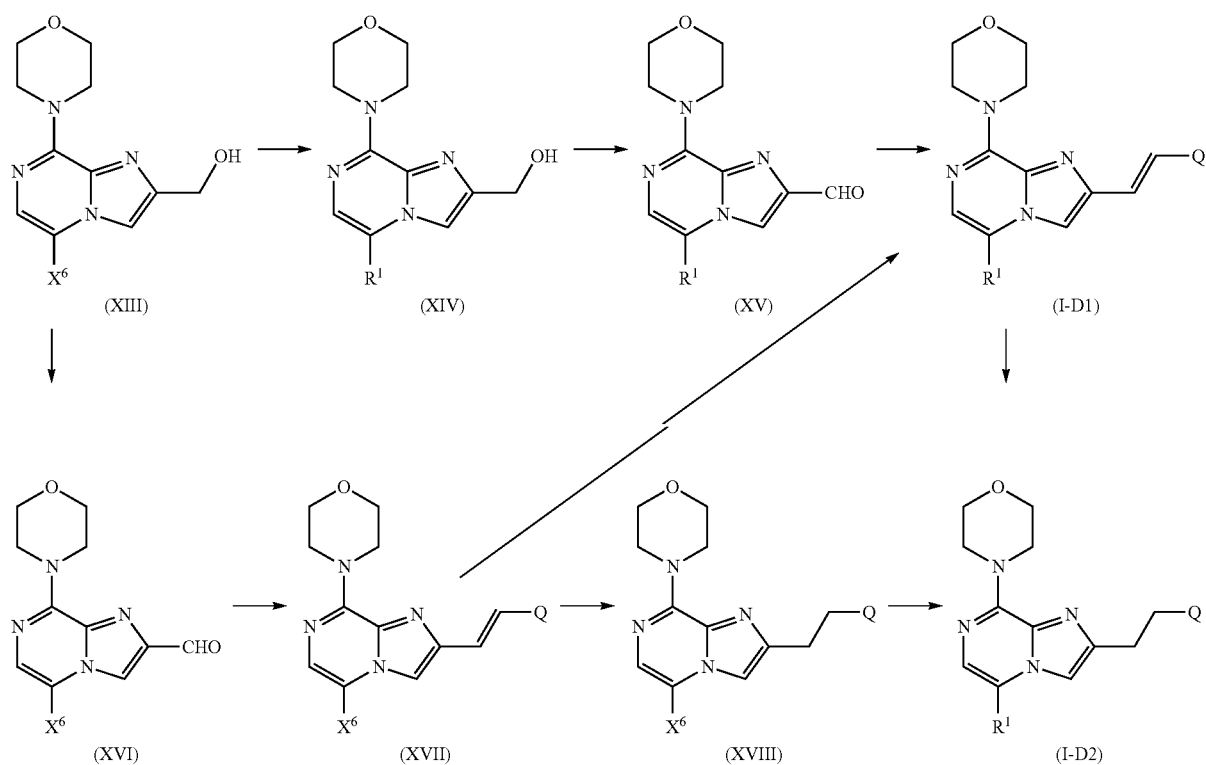

An aldehyde of formula (XV) or (XVI) may serve as central intermediates for the preparation of the compounds of the present invention wherein L in the Formula (I) is E-ethenyl, or ethyl. Oxidation of the primary alcohol of formula (XIII) with a suitable oxidizing agent such as PDC, NaOCl, active MnO$_2$, IBX, Dess-Martin periodinane, and the like, affords an aldehyde of formula (XVI). Preferred oxidation methods for this transformation include the treatment of a compound of formula (XIII), in a solvent such as DCM or DCE, with active MnO$_2$ or Dess-Martin periodinane, at about room temperature. Olefination of an aldehyde of formula (XVI) may then produce a compound of formula (XVII). Preferred synthetic methods include, but are not limited to, Wittig or Horner-Emmons olefination with an appropriate Wittig reagent (QCH$_2$P$^+$Ph$_3$X$^-$) or Horner-Emmons reagent (QCH$_2$P(=O)(OEt)$_2$) derived from the corresponding compounds of formula CH$_3$-Q, prepared by known methods. For example, a compound of formula QCH$_2$P(=O)(OEt)$_2$ may be reacted with an aldehyde of formula (XVI), in the presence of a suitable base such as NaH, in a suitable solvent such as THF, at a suitable temperature in the range of from about 0° C. to about 70° C., preferably at about 65° C., to obtain the compounds of formula (XVII).

Alternatively, a Knoevenagel condensation between a compound of formula CH$_3$-Q with an aldehyde of formula (XVI), in the presence of an activating agent such as acetic anhydride or TMSCl, may also provide a compound of formula (XVII). Preferred synthetic methods include heating an aldehyde of formula (XVI) with a 2-methyl-substituted Q ring (methyl substituent adjacent to the hetero atom), at a temperature ranging from about 35° C. to about 120° C., preferably at about 90° C., in the presence of excess TMSCl, in a solvent such as DMF. A compound of formula (XVII) may subsequently undergo a Suzuki-type coupling reaction, as described for the preparation of compounds of formula (I-A) from a compound of formula (VI), to provide a compound of formula (I-D1).

Similarly, a compound of formula (XIV) may first be oxidized as previously described to afford the corresponding aldehyde of formula (XV). The aldehyde of formula (XV) may serve as a substrate for an olefination, methods for which have been described herein above, to obtain a compound of formula (I-D1). The ethenyl linker in compounds of formula (I-D1) may be reduced using diimide to obtain a compound of formula (I-D2). Preferred reaction conditions include heating a compound of formula (I-D1) with diimide generated in-situ from tosylhydrazide, in the presence of sodium acetate, in a water-DME co-solvent system, at a temperature of about 80° C.

Alternatively, a compound of formula (XVII) can be reduced with diimide to obtain a compound of formula (XVIII) as described above and the resulting compound can be used as a substrate for Suzuki coupling reaction to install R$^1$ substituent to obtain a compound of formula (I-D2).

Scheme E illustrates a method for the preparation of certain compounds of Formula (I) of the present invention wherein L-Q is

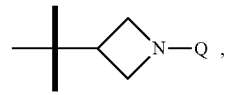

Scheme E

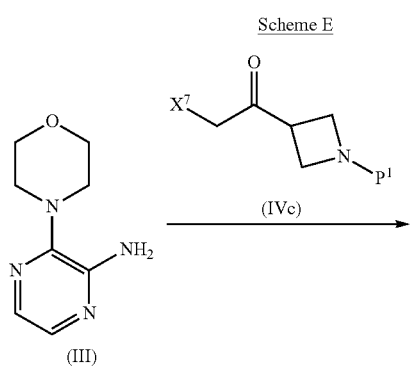

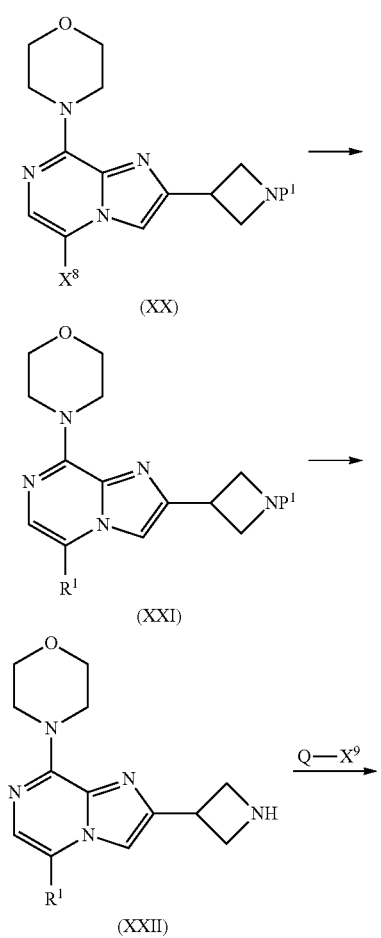

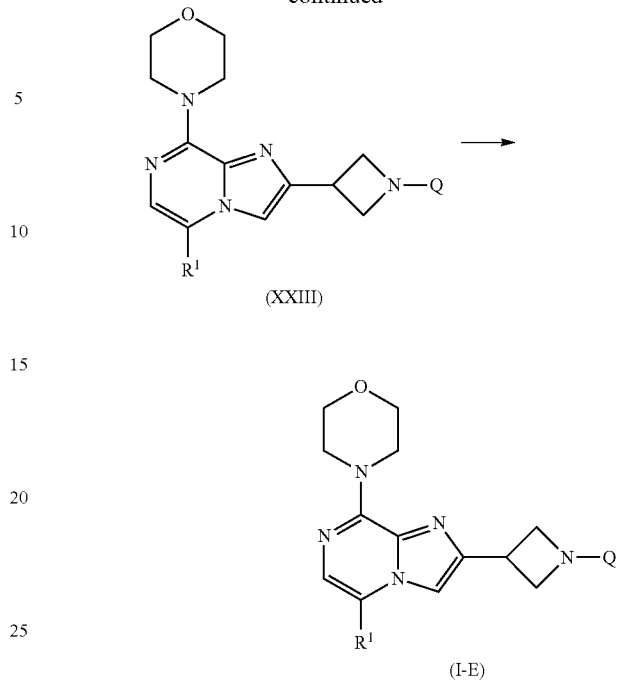

A compound of formula (XIX) may be obtained via the reaction of a compound of formula (III) with a compound of formula (IVc) wherein $P^1$ is a protecting group on the azetidinyl nitrogen and $X^7$ is a halogen, preferably a bromo or chloro, as described in Scheme A for the preparation of a compound of formula (XIX). As previously described in Scheme A, a compound of formula (XIX) can be brominated to yield a compound of formula (XX) wherein $X^8$ is bromo, which may be used in a Suzuki coupling reaction to introduce an $R^1$ substituent. The protecting group $P^1$ in the compound of formula (XXI) can be then removed to obtain a compound of formula (XXII). For example, when $P^1$ of a compound of formula (XXI) is a Boc group, deprotection may be accomplished by a treatment with an acid such as TFA, in a suitable solvent such as DCM, to obtain a compound of formula (XXII) after neutralization of the resulting product. A compound of formula (XXIII) may be prepared from a compound of formula (XXII) and a compound of formula Q-$X^9$ (wherein $X^9$ is a leaving group such as Cl, Br, I, triflate, and the like), by using transition metal-catalyzed amination conditions or an aromatic nucleophilic substitution reaction. Preferred reaction conditions include the reaction of the sodium salt of a compound of formula (XXII) with Q-$X^9$, a known compound or a compound that may be prepared by known methods disclosed in the scientific literature. at a temperature range of from about room temperature to about 180° C. in a solvent such as DMF.

Scheme F illustrates a method for the preparation of certain compounds of Formulae (I-F1 and I-F2) of the present invention wherein L-Q is

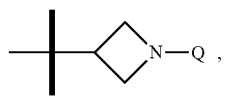

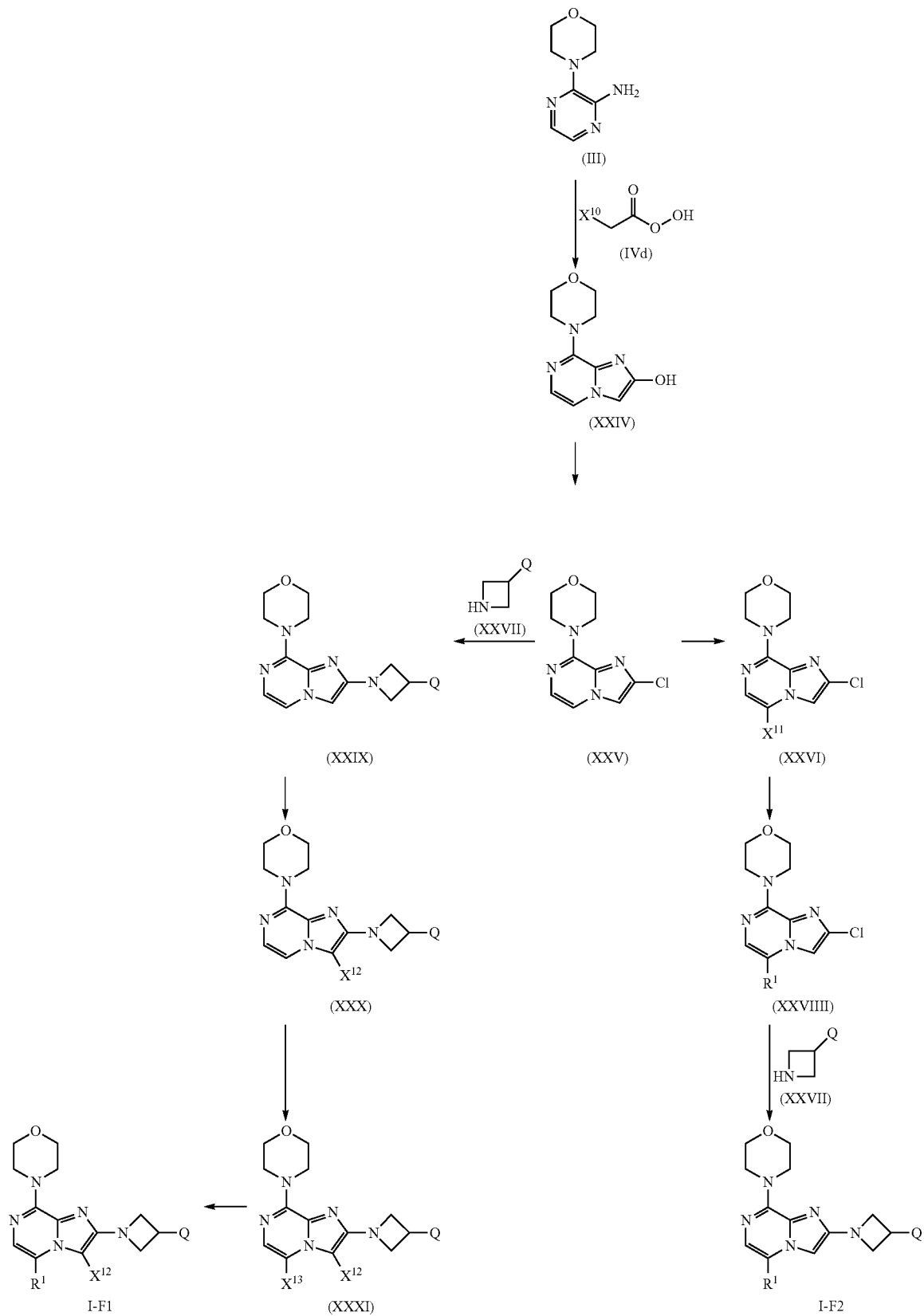
Scheme F

Compounds of formula (XXIV) may be obtained via the reaction of a compound of formula (III) with a compound of formula (IVd) as described in Scheme A for the preparation of a compound of formula (V). The hydroxy group of the compound of formula (XXIV) may be converted to a halogen, preferably a chloride, by the action of $POCl_3$ in a suitable solvent such as DCE, at a temperature in the range of from about $-20°$ C. to about $180°$ C., preferably at about $120°$ C. The bromination of the chloride of formula (XXV), as described in Scheme A, may furnish a compound of formula (XXVI) wherein $X^{10}$ is bromo, which may be used in a Suzuki coupling reaction to introduce $R^1$ substituent to yield a compound of formula (XXVIII). A compound of formula (XXVIII) may be treated with a suitable amine such as a compound of the formula (XXVII) under transition metal-catalyzed amination conditions to obtain a compound of formula (I-F2). Preferred conditions include the reaction of a compound of formula (XXVIII) with a compound of formula (XXVII) in the presence of a transition metal-catalyst such as $Pd_2(dba)_3$ and the like, a base such as sodium tert-butoxide or $Cs_2CO_3$, and a suitable metal catalyst ligand such as BINAP, 2-(dicyclohexylphosphino)-2',4',6'-tri-isopropyl-1,1'-biphenyl, and the like, under an inert atmosphere, at a temperature range of from about room temperature to about $180°$ C.

Similarly, a compound of formula (XXIX) may be obtained from a compound of formula (XXV) and a compound of formula (XXVII) as described above and then chlorinated to obtain a compound of formula (XXX) wherein $X^{12}$ is chloro. The preferred conditions for this transformation include the treatment of a compound of formula (XXIX) with a suitable chlorinating agent such as $SO_2Cl_2$ in a solvent such as DCM at a temperature ranging from about $-78°$ C. to room temperature. The compound of formula (XXX) may then be converted to a compound of Formula I-F1 via bromination to yield a compound of formula (XXXI) wherein $X^{12}$ is chloro and $X^{13}$ is bromo, followed by selective Suzuki coupling reaction of the bromine using coupling conditions described previously.

Compounds of the formula (XXVII) may be prepared by the transition metal-catalyzed cross coupling reaction of a 2-halo-quinoline, preferably 2-bromoquinoline, and an organozinc reagent derived from N-protected 3-halo-azetidine. The preferred conditions for this transformation include the coupling of an organozinc reagent generated from tert-butyl-3-iodo-azetidine with 2-bromoquinoline in the presence of a catalyst such as $Pd_2(dba)_3$ and the like, and a suitable metal catalyst ligand such as trifurylphosphine and the like, under an inert atmosphere, at a temperature range of from about room temperature to about $180°$ C. in a suitable solvent such as THF. Subsequent removal of the N-protecting group as previously described followed by the addition of a suitable base affords the desired free amine.

Scheme G illustrates a method for the preparation of certain compounds of Formula (I-G) of the present invention wherein L-Q in the Formula (I) is ethynyl-Q.

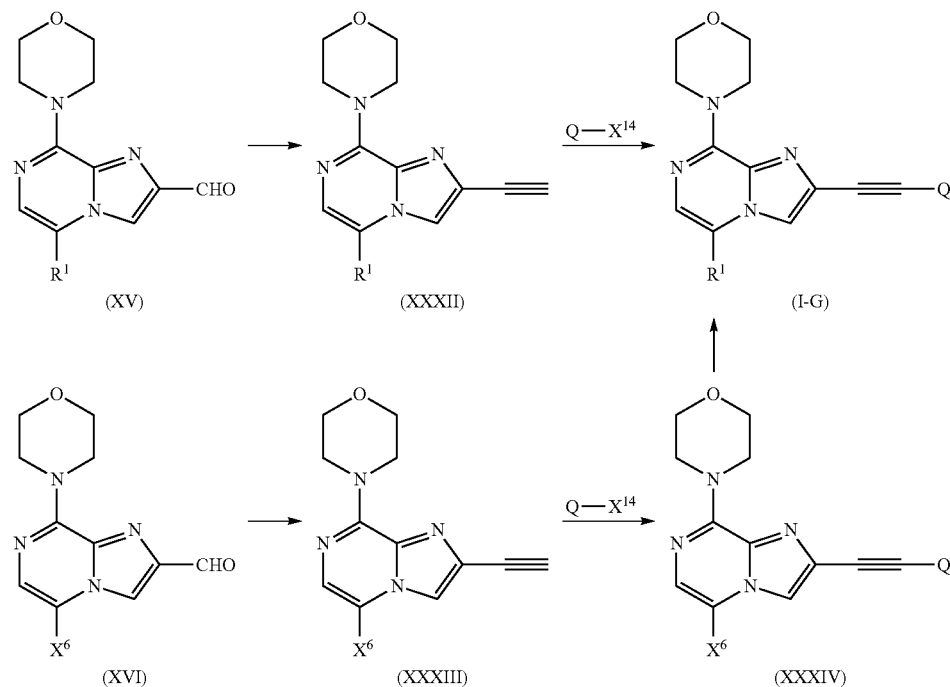

Scheme G

To prepare compounds of formula (I-G), the aldehyde functionality of a compound of formula (XV) may be first converted to a terminal acetylene. For example, an aldehyde of formula (XV) may be reacted with dimethyl-1-diazo-2-oxo-propylphosphonate, in the presence of an inorganic base such as $K_2CO_3$ and the like, in a solvent such as MeOH, at about room temperature, to obtain a compound of formula (XXXII). The compound of formula (XXXII) may then be arylated to obtain a compound of formula (I-G). A preferred synthetic method involves the reaction of a compound of formula (XXXII) with a compound of formula $Q-X^{14}$ (wherein $X^{14}$ is iodide or a bromide, preferably iodide) in the presence of a Pd catalyst, CuI, and an organic base such as $Et_3N$ or DIEA, in a polar aprotic solvent such as DMF or DMA, at a suitable temperature ranging from about 25 to about 120° C. More preferred reaction conditions include, but are not limited to, reacting a compound of formula (XXXII) with a compound of formula Q-X$^{14}$ in DMF, at about 25° C., in the presence of (Ph$_3$P)$_2$PdCl$_2$, CuI, and DIEA, under an argon atmosphere.

Alternatively, a compound of formula (XVI) wherein X$^6$ is a halogen, preferably a bromine can be first alkynylated and the resulting product can then be arylated with a compound of formula Q-X$^{13}$ to obtain a compound of formula (XXXIV) wherein X$^6$ is a halogen, preferably a bromine, which can be used to introduce an R$^1$-substituent as described in Scheme G to obtain a compound of formula (I-G).

Scheme H illustrates another method for the preparation of certain compounds of Formula (I-I) of the present invention wherein L-Q is —CH$_2$O-Q and G is an aromatic substituent.

Scheme H

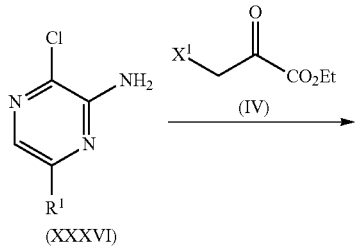

(XXXV)

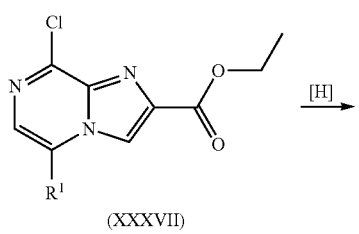

(XXXVI)

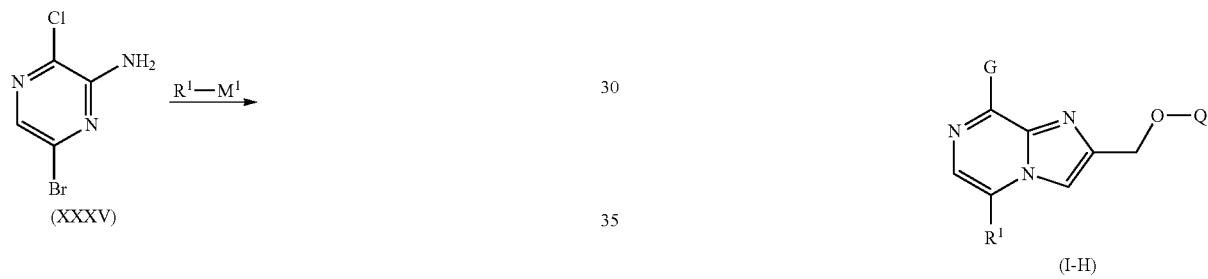

(XXXVII)

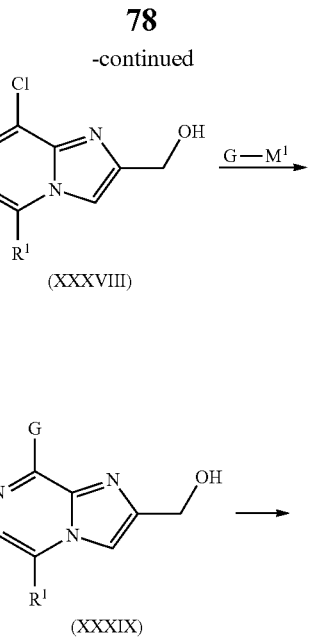

(XXXVIII)

(XXXIX)

(I-H)

A compound of formula (XXXV) may be subjected to transition metal-catalyzed coupling reaction with a compound of formula R$^1$-M$^1$, as described in the Scheme A for the preparation of a compound of formula (I-A) from a compound of formula (VI), to obtain a compound of formula (XXXVI). A compound of formula (XXXVI) may be reacted with a compound of formula (IV) as previously described in Scheme A to obtain a compound of formula (XXXVII). The ester group of a compound of formula (XXXVII) may then be reduced, as previously described, to obtain a compound of formula (XXXVIII) which may then be employed as a substrate in a transition metal-catalyzed coupling reaction with a compound of formula G-M$^1$ to furnish a compound of formula (XXXIX), as described previously.

A compound of formula (XXXIX) may be converted to a compound of formula (I-H) using the methods described in Scheme C for the preparation of a compound of formula (I-C) from a compound of formula (XIV). It is also understood that it may be necessary to remove any protecting group, if present, using appropriate conventional reagents and conditions to obtain the desired compound of formula (I-H).

Scheme I illustrates a methodology for the preparation of certain compounds of formula (I-J) of the present invention wherein L-Q is —CH$_2$O-Q and R$^1$ is a non-aromatic heterocycle.

Scheme I

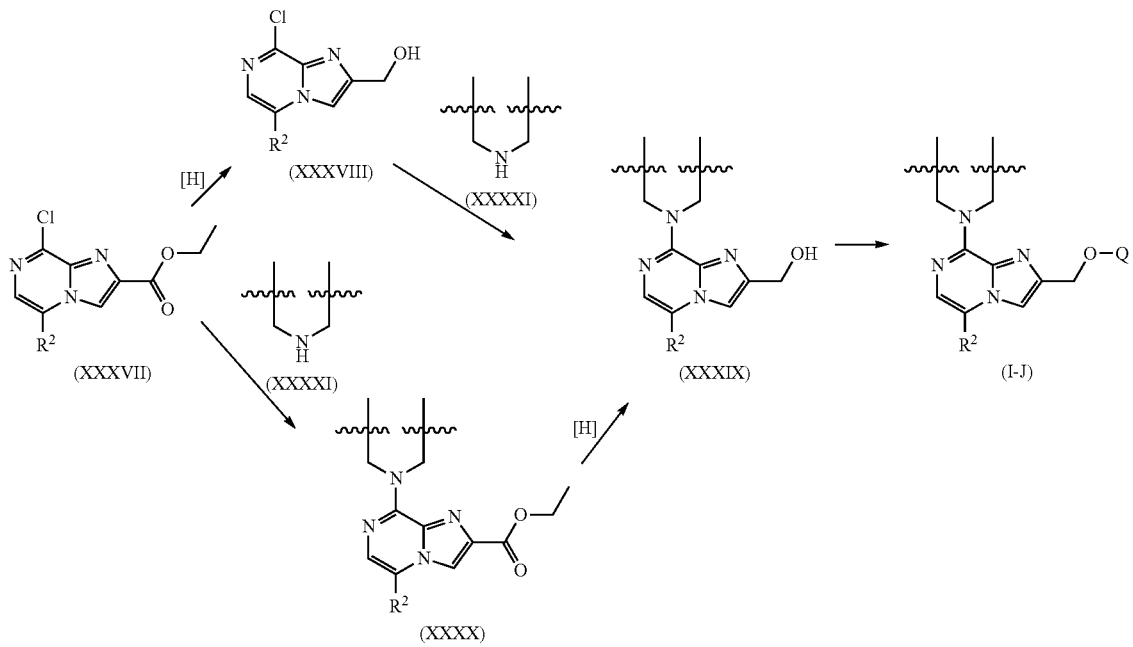

A compound of formula (XXXVII) can be subjected to an aromatic nucleophilic substitution with an secondary cyclic amine of formula (XXXXI) in the presence or absence of a base such as $K_2CO_3$ in a suitable solvent such as DMF at a temperature from about 25 to 200° C. to obtain a compound of formula (XXXX) which may then be reduced to the primary alcohol (XXXIX) as described previously. It is understood that the secondary amine of formula (XXXXI) may contain other heteroatoms and/or protected or non-protected functional groups. Alternately, the ester group may be reduced first to obtain the primary alcohol (XXXVIII) and the amine substituent may then be introduced to yield a compound of formula (XXXIX).

The primary alcohol functionality of a compound of formula (XXXIX) may then be arylated as described previously to obtain a compound of formula (I-J). The Q and/or $R^1$ substituents illustrated herein may be further functionalized. In some instances, when either the Q or $R^1$-substituent contains an ester functionality, the ester may be converted to its corresponding carboxylic acid using conventional methods, and the resultant carboxylic acid may then be further derivatized. For example, a carboxylic acid may be converted to an amide by direct coupling with an amine, in the presence of a suitable coupling agent such as DCC, in the presence or absence of an activating agent such as HOBt.

One of ordinary skill in the art will recognize that this transformation may be achieved following other conventional amide bond formation protocols. The carboxylic acid may also be coupled with a functionalized amine such as an acylated amine or an alkyl-sulfonamide to obtain compounds wherein either $R^1$ or Q is substituted with an acylaminocarbonyl or alkylsulfonylaminocarbonyl groups, respectively. Additionally, the amine employed in the coupling may contain other non-interfering functionalities such as esters, alkyl sulfones and others. It is also understood that the amide product may be further derivatized. For example, an amido-ester may be converted to its corresponding acid to obtain an amido-acid.

An amino group may be sulfonylated or acylated using conventional methods to obtain the corresponding sulfonamides or amides. An amino group may also be alkylated using a suitable alkylating agents under conventional alkylation conditions to obtain the corresponding alkylated amines. Similarly, an amino group may be treated with a suitable acyl halide or sulfonyl halide to afford an amide or sulfonamide, respectively. A nitrile substituent on either a Q or $R^1$ ring may serve as an important intermediate group for the construction of heterocycles. For example, a nitrile can be reacted with an azide, preferably sodium azide in polar aprotic solvents such as DMF, to obtain a tetrazole. The intermediate obtained from the reaction of hydroxylamine with a nitrile (a hydroxyamidine), may be reacted with a carbonyl source such as ethylchloroformate to obtain hydroxyoxadiazole.

Scheme J illustrates another method for the preparation of certain compounds of formula (I-K) of the present invention wherein L-Q is —$CH_2$O-Q or -ethenyl-Q, and G is a non-aromatic cyclic substituent.

Scheme J

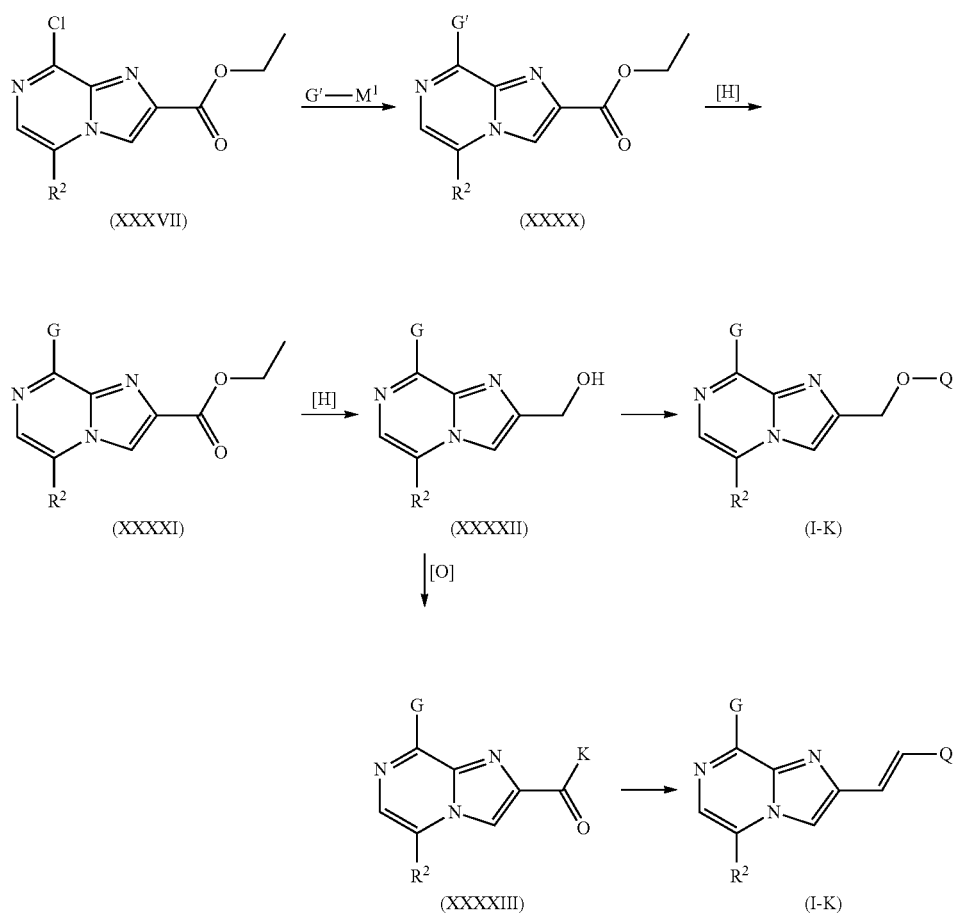

A compound of formula (XXXVII) can be employed as a substrate in a transition metal-catalyzed coupling reaction with a compound of formula G'-M¹ to furnish a compound of formula (XXXX), as described previously wherein G' is an unsaturated carbocyclic or heterocyclic ring. When a saturated ring is desired a compound of formula (XXXX) can be reduced to obtain a compound of formula (XXXXI) wherein G is a saturated carbocyclic or heterocyclic ring. The preferred conditions for this reduction include hydrogenation with Pd/C in an alcoholic solvent such as MeOH. The ester group of a compound of formula (XXXXI) may then be reduced, as previously described, to obtain a compound of formula (XXXXII) which can be converted to a compound of formula (I-K) as described in Scheme H for the preparation of a compound of formula (I-H) from a compound of formula (XXXIX), wherein L-Q is —CH$_2$O-Q.

Additionally a compound of formula (XXXXII) can be oxidized to a compound of formula (XXXXIII) and then converted to a compound of formula (I-K) wherein L is is ethenyl, using the methods described in Scheme D for the preparation of a compound of formula (I-D1) from a compound of formula (XVIII).

SPECIFIC EXAMPLES

Example 1

4-(5-(6-(1H-Tetrazol-5-yl)pyridin-3-yl)-2-((quinolin-2-yloxy)methyl) imidazo[1,2-a]pyrazin-8-yl)morpholine (Cpd 97)

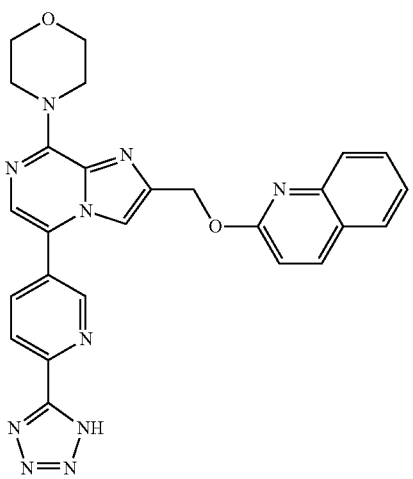 [SMILES: c1ccc2nc(OCc3cn4c(-c5ccc(-c6nnn[nH]6)nc5)cnc(N5CCOCC5)c4n3)ccc2c1]

A. 3-Chloropyrazin-2-amine, 1a

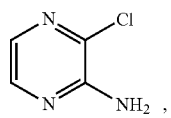

To 2,3-dichloropyrazine (20.0 g, 135 mmol) in a 250 mL sealed tube was added NH$_4$OH (50.0 g, 1.43 mol). The resulting solution was stirred overnight at 100° C. After cooling to rt, the solids were collected by filtration and washed with Et$_2$O to obtain compound 1a as a white solid (15.0 g, 86% yield). Mass Spectrum (LCMS, ESI pos.): Calcd. for C$_4$H$_4$ClN$_3$: 130.0 (M+H). found: 130.2.

B. 3-Morpholinopyrazin-2-amine, 1b

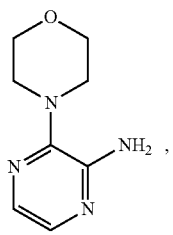

A solution of compound 1a (10.0 g, 76.9 mmol) in morpholine (42.3 g, 486 mmol) was stirred at 120° C. overnight. The mixture was concentrated under reduced pressure. The residue was then treated with DCM (200 mL). The solids were collected by filtration and washed with Et$_2$O. Compound 1b was obtained as a white solid (11.0 g, 74% yield). Mass Spectrum (LCMS, ESI pos.): Calcd. for C$_8$H$_{12}$N$_4$O: 181.1 (M+H). found: 181.2.

C. Ethyl 8-morpholinoimidazo[1,2-a]pyrazine-2-carboxylate, 1c

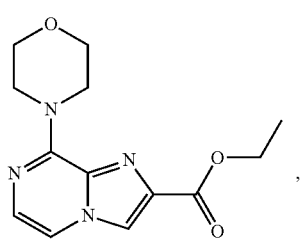

To a solution of compound 1b (6.00 g, 33.3 mmol) in DMF (100 mL) was added ethyl 3-bromo-2-oxopropanoate (8.00 g, 41.0 mmol) dropwise with stirring. The resulting solution was stirred at rt overnight. The reaction mixture was cooled to 0° C. The solids were collected by filtration and washed with Et$_2$O (3×100 mL). Compound 1c was obtained as a white solid (8.40 g, 81% yield). Mass Spectrum (LCMS, ESI pos.): Calcd. for C$_{13}$H$_{16}$N$_4$O$_3$: 276.1 (M+H). found: 276.3.

D. (8-Morpholinoimidazo[1,2-a]pyrazin-2-yl)methanol, 1d

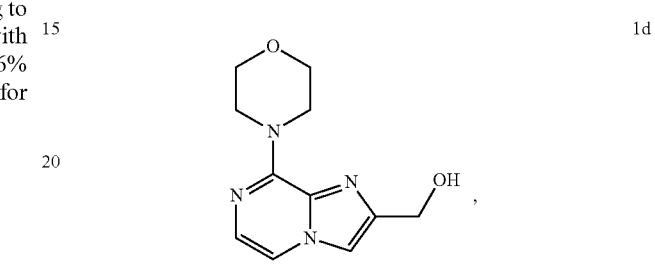

To a solution of compound 1c (8.40 g, 30.4 mmol) in THF (100 mL) was added LiAlH$_4$ (2.55 g, 60.8 mmol) in portions at 0° C. The reaction mixture was stirred at rt for 2 h. The reaction was slowly quenched with H$_2$O (10 mL). The resulting mixture was extracted with DCM (2×100 mL), and the combined organic layers were washed with brine, dried over Na$_2$SO$_4$, filtered and concentrated under reduced pressure to obtain compound 1d as a yellow solid (3.80 g, 53% yield). Mass Spectrum (LCMS, ESI pos.): Calcd. for C$_{11}$H$_{14}$N$_4$O$_2$: 235.1 (M+H). found: 235.2.

E. (5-Bromo-8-morpholinoimidazo[1,2-a]pyrazin-2-yl)methanol, 1e

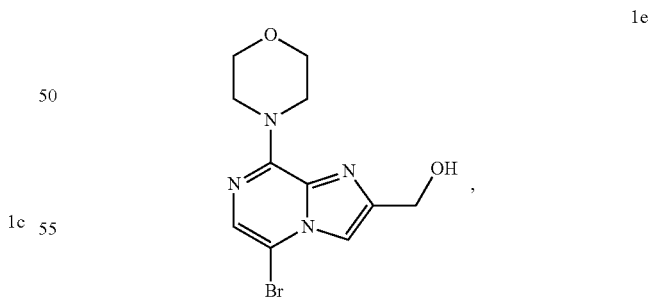

To a solution of compound 1d (2.40 g, 10.3 mmol) in ACN (200 mL) was added NBS (2.40 g, 13.5 mmol) in portions at −20° C. The resulting solution was stirred at −20° C. for 2 h, and was concentrated under reduced pressure. The residue was purified by flash column chromatography on silica gel, eluting with EtOAc/petroleum ether (1:1 v/v) to obtain compound 1e as a yellow solid (1.48 g, 41% yield). Mass Spectrum (LCMS, ESI pos.): Calcd. for $C_{11}H_{13}BrN_4O_2$: 313.0 (M+H). Found 313.2.

F. 5-(4,4,5,5-Tetramethyl-1,3,2-dioxaborolan-2-yl)picolinonitrile, 1f

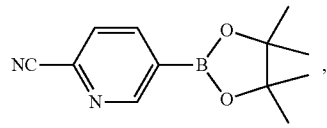

1f

To a solution of 5-bromopicolinonitrile (1.00 g, 5.46 mmol) in DMF (10 mL) was added 4,4,4',4',5,5,5',5'-octamethyl-2,2'-bi(1,3,2-dioxaborolane) (2.77 g, 10.9 mmol), Pd(OAc)$_2$ (61.0 mg, 0.273 mmol), PPh$_3$ (285 mg, 1.09 mmol) and KOAc (1.61 g, 16.4 mol) under a nitrogen atmosphere. The resulting mixture was stirred at 80° C. overnight. The reaction mixture was cooled to rt and the solids were removed by filtration. The filtrate was concentrated under reduced pressure to obtain a residue, which was purified by flash column chromatography on silica gel with EtOAc/petroleum ether (1:50 v/v) to obtain compound 1f as a white solid (300 mg, 24% yield). Mass Spectrum (LCMS, ESI pos.): Calcd. for $C_{12}H_{15}BN_2O_2$: 231.1 (M+H). found: 231.1.

G. 5-(2-(Hydroxymethyl)-8-morpholinoimidazo[1,2-a]pyrazin-5-yl)picolinonitrile, 1g

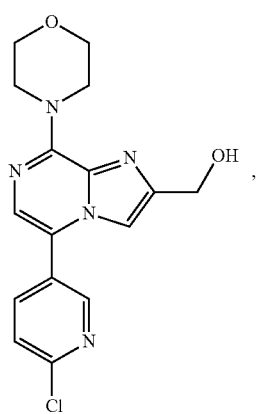

1g

To a solution of compound 1e (600 mg, 1.92 mmol, as prepared in Step E) in 1,4-dioxane/H$_2$O (4:1 v/v, 8 mL) was added compound 1f (560 mg, 2.44 mmol), PdCl$_2$(dppf) (72.1 mg, 0.0960 mmol) and Cs$_2$CO$_3$ (847 mg, 4.99 mmol). The reaction mixture was stirred at 90° C. for 2 h under a nitrogen atmosphere. After cooling to rt, the reaction was quenched with H$_2$O (20 mL). The resulting mixture was extracted with DCM (2×50 mL). The combined organic layers were dried over Na$_2$SO$_4$, filtered, and concentrated under reduced pressure. The resulting residue was purified by flash column chromatography on silica gel with EtOAc/petroleum ether (1:2 v/v) to obtain compound 1g as a yellow solid (350 mg, 51% yield). Mass Spectrum (LCMS, ESI pos.): Calcd. for $C_{17}H_{16}N_6O_2$: 337.1 (M+H). Found 337.2.

H. (5-(6-(1H-Tetrazol-5-yl)pyridin-3-yl)-8-morpholinoimidazo[1,2-a]pyrazin-2-yl)methanol, 1h

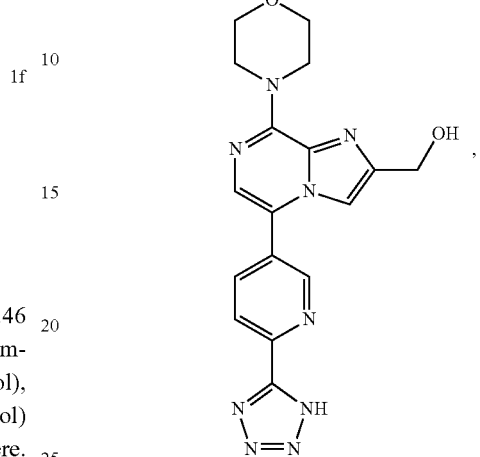

1h

To a solution of compound 1g (220 mg, 0.650 mmol) in DMF (15 mL) was added NaN$_3$ (440 mg, 6.77 mmol) and triethylamine hydrochloride (440 mg, 3.21 mmol). The reaction mixture was stirred at 105° C. for 1 h. The resulting mixture was concentrated, and diluted with H$_2$O (30 mL). The solids were collected by filtration and washed with Et$_2$O to obtain compound 1h as a yellow solid (189 mg, 76% yield). Mass Spectrum (LCMS, ESI pos.): Calcd. for $C_{17}H_{17}N_9O_2$: 380.2 (M+H). Found 380.2.

I. 4-(5-(6-(1H-Tetrazol-5-yl)pyridin-3-yl)-2-((quinolin-2-yloxy)methyl)imidazo[1,2-a]pyrazin-8-yl)morpholine, Cpd 97

To a solution of compound 1h (187 mg, 0.510 mmol) in DMF (2 mL) was added sodium hydride (49.0 mg, 2.04 mmol) in portions at 0° C. The mixture was stirred for 15 min before the addition of 2-chloroquinoline (125 mg, 0.765 mmol). The reaction mixture was stirred at 70° C. overnight. Water was added, and the resulting mixture was extracted with DCM (3×10 mL). The combined organic layers were dried over Na$_2$SO$_4$ and concentrated under reduced pressure. The resulting residue was purified by flash column chromatography on silica gel with EtOAc/petroleum ether (1:3 v/v) to obtain the title compound 97 as a yellow solid (27.6 mg, 11% yield). $^1$H-NMR (300 MHz, DMSO-d$_6$) δ (ppm): 8.23-8.28 (m, 1H), 8.25 (d, J=8.7 Hz, 1H), 8.23-8.15 (m, 1H), 7.89 (d, J=8.1 Hz, 1H), 7.80 (d, J=8.4 Hz, 1H), 7.68 (t, J=7.2 Hz, 1H), 7.63-7.55 (m, 1H), 7.44 (t, J=7.2 Hz, 1H), 7.06 (d, J=8.7 Hz, 1H), 7.03-7.00 (m, 1H), 5.59 (s, 2H), 4.35-4.20 (m, 4H), 3.85-3.69 (m, 4H). Mass Spectrum (LCMS, ESI pos.): Calcd. for $C_{26}H_{22}N_{10}O_2$: 507.2 (M+H). Found 507.2.

Example 2

(E)-4-(5-(6-(1H-Tetrazol-5-yl)pyridin-3-yl)-2-(2-(quinolin-2-yl)vinyl)imidazo[1,2-a]pyrazin-8-yl)morpholine (Cpd 96)

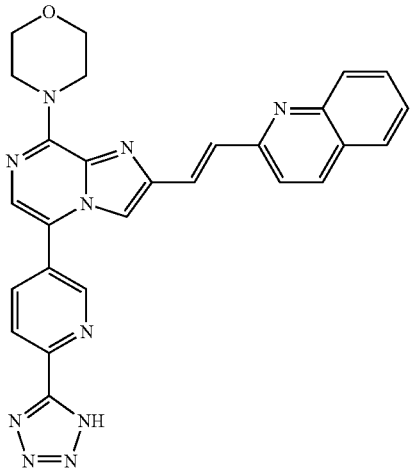 [SMILES: C(=C\c1cn2c(-c3ccc(-c4nnn[nH]4)nc3)cnc(N3CCOCC3)c2n1)/c1ccc2ccccc2n1]

A. 5-Bromo-8-morpholinoimidazo[1,2-a]pyrazine-2-carbaldehyde, 2a

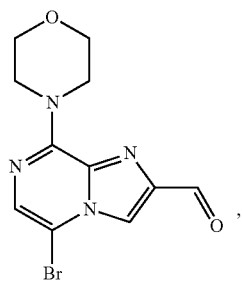

To a solution of compound 1e (10.0 g, 32.1 mmol, as prepared in Example 1, Step E) in DMSO (50 mL) was added IBX (5.54 g, 19.7 mmol) in portions. The reaction mixture was stirred at rt for 3 h, and was quenched with 2N NaOH solution (50 mL). The resulting mixture was extracted with DCM (3×25 mL). The combined organic layers were washed with brine, dried over $Na_2SO_4$, filtered and concentrated under reduced pressure. The residue was purified by flash column chromatography on silica gel with EtOAc/petroleum ether (1:2 v/v) to obtain compound 2a as a yellow solid (6.00 g, 54% yield). Mass Spectrum (LCMS, ESI pos.): Calcd. for $C_{11}H_{11}BrN_4O_2$: 311.0 (M+H). found 311.2.

B. (E)-4-(5-Bromo-2-(2-(quinolin-2-yl)vinyl)imidazo[1,2-a]pyrazin-8-yl)morpholine, 2b

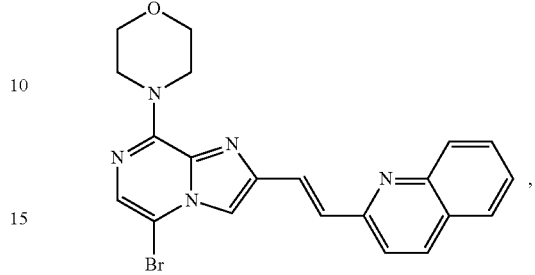

To a solution of compound 2a (800 mg, 2.58 mmol) in DMF (10 mL) was added 2-methylquinoline (600 mg, 4.20 mmol) and bromotrimethylsilane (960 mg, 8.89 mmol). The reaction mixture was stirred in a 20 mL sealed tube at 90° C. for 4 h. After cooling to rt, the reaction was quenched with MeOH (20 mL). The solids were collected by filtration and washed with $Et_2O$ to obtain compound 2b as a red solid (1.05 g, 85% yield). Mass Spectrum (LCMS, ESI pos.): Calcd. for $C_{21}H_{18}BrN_5O$: 436.1 (M+H). found: 436.1.

C. (E)-5-(8-Morpholino-2-(2-(quinolin-2-yl)vinyl)imidazo[1,2-a]pyrazin-5-yl)picolinonitrile, 2c

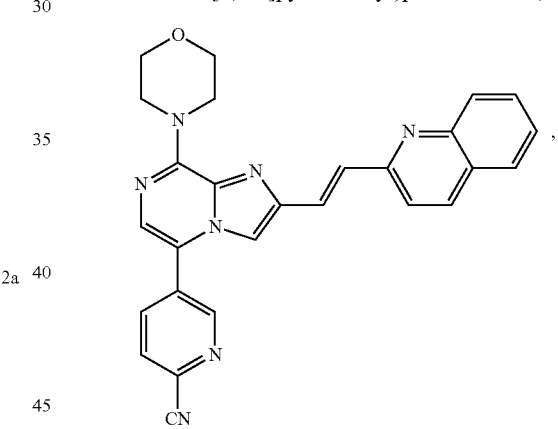

Compound 2b (800 mg, 1.84 mmol) was subjected to Suzuki coupling conditions with compound 1f using the reaction conditions described in Example 1, Step G to obtain compound 2c as a yellow solid (500 mg, 59% yield). Mass Spectrum (LCMS, ESI pos.): Calcd. for $C_{27}H_{21}N_7O$: 460.2 (M+H). found: 460.3.

D. (E)-4-(5-(6-(1H-Tetrazol-5-yl)pyridin-3-yl)-2-(2-(quinolin-2-yl)vinyl)Imidazo[1,2-a]pyrazin-8-yl)morpholine, Cpd 96

Compound 2c (120 mg, 0.260 mmol) was treated with $NaN_3$ as described in Example 1, Step H. This resulted in 150 mg of crude compound 96, which was then purified by Prep-HPLC under the following conditions: XbridgePrep Shield RP 18, 5 μm, 19*150 mm; mobile phase, water with 0.05% $NH_4CO_3$ and $CH_3CN$ (30% $CH_3CN$ up to 50% in 8 min, up to 100% in 1 min, down to 30% in 1 min); Detector, UV 254 nm. The title compound 96 was obtained as a yellow solid (38.4 mg, 29% yield). $^1$H-NMR (300 MHz, DMSO-$d_6$) δ (ppm): 9.09 (s, 1H), 8.41-8.33 (m, 4H), 7.95-7.56 (m, 8H), 4.50-4.28

(m, 4H), 4.00-3.71 (m, 4H). Mass Spectrum (LCMS, ESI pos.): Calcd. for $C_{22}H_{22}N_{10}O$: 503.2 (M+H). Found 503.2.

Example 3

4-(5-(6-(1H-Tetrazol-5-yl)pyridin-3-yl)-2-(2-(quinolin-2-yl)ethyl)imidazo[1,2-a]pyrazin-8-yl)morpholine (Cpd 77)

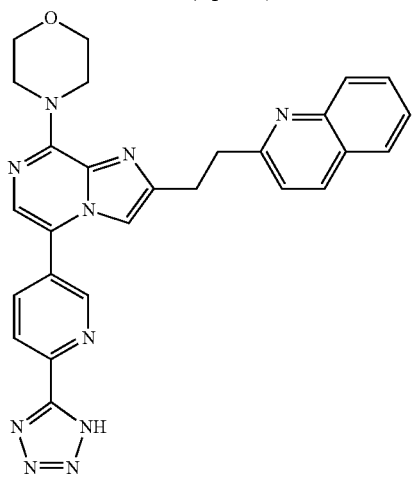

A. 4-(5-Bromo-2-(2-(quinolin-2-yl)ethyl)imidazo[1,2-a]pyrazin-8-yl)morpholine, 3a

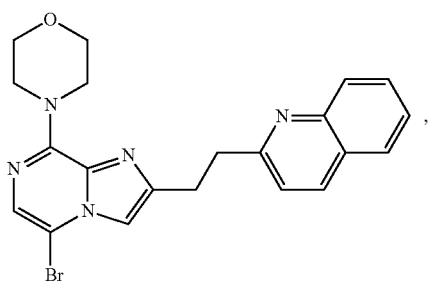

To a solution of compound 2b (5.00 g, 10.9 mmol, as prepared in Example 2, Step B) in DME/H$_2$O (10:1 v/v, 150 mL) was added TosNHNH$_2$ (6.41 g, 34.5 mmol) and NaOAc (4.70 g, 57.3 mmol). The reaction mixture was stirred at 80° C. overnight. After cooling to rt, the reaction was quenched with H$_2$O (200 mL). The solids were collected by filtration and washed with Et$_2$O to obtain compound 3a as a white solid (3.50 g, 67% yield). Mass Spectrum (LCMS, ESI pos.): Calcd. for $C_{21}H_{20}BrN_5O$: 438.1 (M+H). found: 438.1.

B. 5-(8-Morpholino-2-(2-(quinolin-2-yl)ethyl)imidazo[1,2-a]pyrazin-5-yl) picolinonitrile, 3b

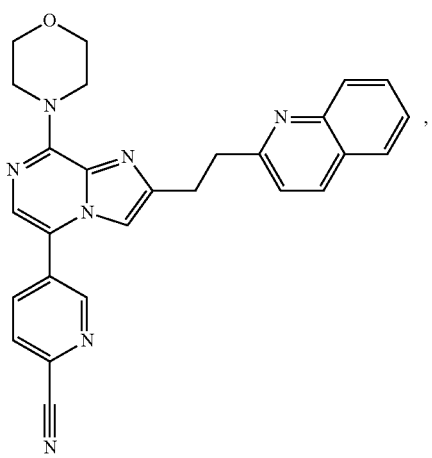

Compound 3a (950 mg, 2.17 mmol) was subjected to Suzuki coupling conditions with compound 1f (prepared in Example 1, Step F) as described in Example 1, Step G to obtain compound 3b as a white solid (820 mg, 82% yield). Mass Spectrum (LCMS, ESI pos.): Calcd. for $C_{27}H_{23}N_7O$: 462.2 (M+H). found: 462.2.

C. 4-(5-(6-(1H-Tetrazol-5-yl)pyridin-3-yl)-2-(2-(quinolin-2-yl)ethyl)imidazo[1,2-a]pyrazin-8-yl)morpholine, Cpd 77

Compound 3b (300 mg, 0.650 mmol) was treated with NaN$_3$ as described in Example 1, Step H to obtain the title compound 77 as a light yellow solid (37.2 mg, 10% yield). $^1$H-NMR (300 MHz, DMSO-d$_6$) δ (ppm): 8.79 (s, 1H), 8.26 (d, J=8.4 Hz, 1H), 8.15 (d, J=8.1 Hz, 1H), 8.04-8.02 (m, 1H), 7.92 (d, J=8.4 Hz, 2H), 7.80 (s, 1H), 7.70 (t, J=7.2 Hz, 1H), 7.56-7.46 (m, 3H), 4.21-4.09 (m, 4H), 3.75-3.65 (m, 4H), 3.35-3.25 (m, 4H). Mass Spectrum (LCMS, ESI pos.): Calcd. for $C_{27}H_{24}N_{10}O$: 505.2 (M+H). Found 505.3.

Example 4

(E)-3-(5-(8-Morpholino-2-(2-(quinolin-2-yl)vinyl)imidazo[1,2-a]pyrazin-5-yl)pyridin-2-yl)-1,2,4-oxadiazol-5-ol (Cpd 95)

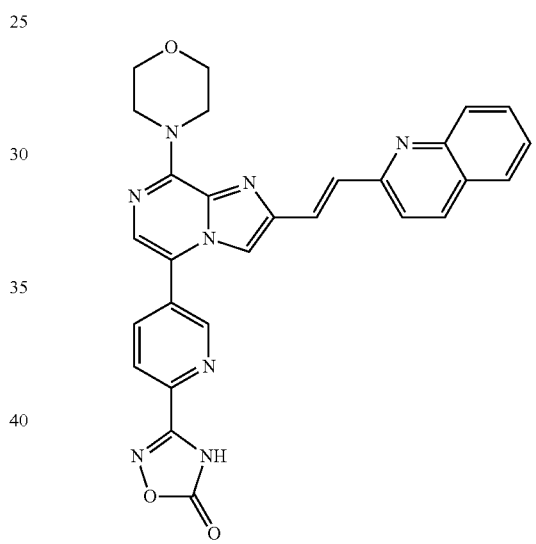

A. (E)-N-Hydroxy-5-(8-morpholino-2-(2-(quinolin-2-yl)vinyl)imidazo[1,2-a]pyrazin-5-yl)picolinimidamide, 4a

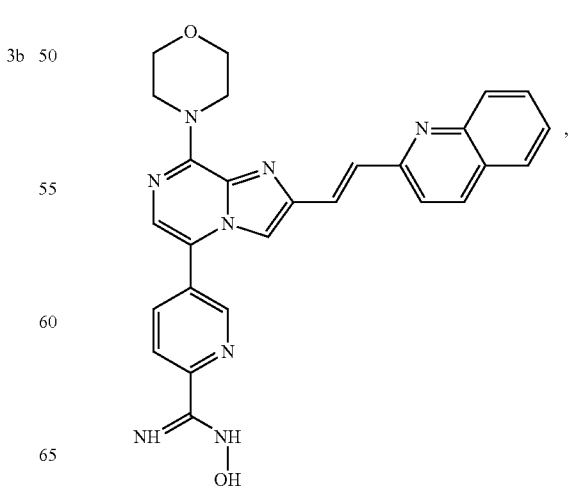

To a solution of compound 77 (150 mg, 0.330 mmol, as prepared in Example 2, Step C) in EtOH (2 mL) was added hydroxylamine hydrochloride (100 mg, 1.45 mmol) and sodium carbonate (100 mg, 0.940 mmol). The reaction mixture was stirred in a 10 mL sealed tube at 80° C. for 2 h. After cooling to rt, the solids were collected by filtration and washed with MeOH to obtain compound 4a as a yellow solid (100 mg, 62% yield). Mass Spectrum (LCMS, ESI pos.): Calcd. for $C_{27}H_{24}N_8O_2$: 493.2 (M+H). found: 493.4.

B. (E)-N-(Ethoxycarbonyloxy)-5-(8-morpholino-2-(2-(quinolin-2-yl)vinyl)imidazo[1,2-a]pyrazin-5-yl)picolinimidamide, 4b

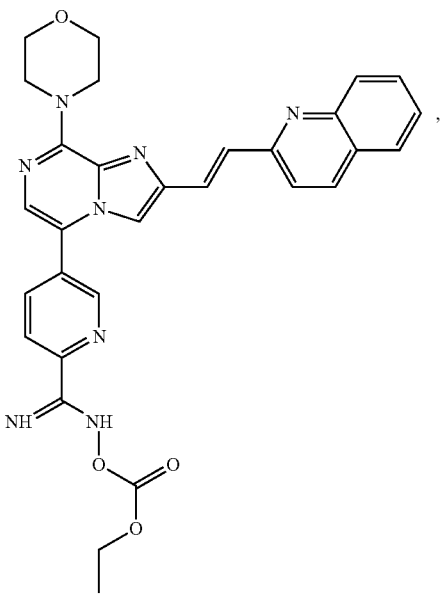

4b

To a solution of compound 4a (100 mg, 0.200 mmol) in THF (1 mL) was added DIPEA (100 mg, 0.800 mmol) and ethyl carbonchloridate (66.0 mg, 0.600 mmol). The reaction mixture was stirred at rt for 3 h. The resulting solids were collected by filtration and washed with Et$_2$O to obtain compound 4b as a yellow solid (100 mg, 89% yield). Mass Spectrum (LCMS, ESI pos.): Calcd. for $C_{30}H_{28}N_8O_4$: 565.2 (M+H). found: 565.4.

C. (E)-3-(5-(8-Morpholino-2-(2-(quinolin-2-yl)vinyl)imidazo[1,2-a]pyrazin-5-yl)pyridin-2-yl)-1,2,4-oxadiazol-5-ol, Cpd 95

To a solution of compound 4b (200 mg, 0.350 mmol) in o-xylene (4 mL) was added DBU (300 mg, 1.97 mmol). The reaction mixture was stirred in a 10 mL sealed tube at 120° C. for 2 h. After cooling to rt, water (20 mL) was added, and the pH of the solution was adjusted to 7 using 1N HCl solution. The solids were collected by filtration and washed with DCM/MeOH (50:1 v/v, 3×10 mL) to obtain the title compound 95 as an orange solid (49.4 mg, 26% yield). $^1$H-NMR (300 MHz, DMSO-d$_6$) δ (ppm): 13.32 (s, 1H), 9.06 (s, 1H), 8.82-8.60 (m, 1H), 8.44-8.40 (m, 2H), 8.30-8.05 (m, 5H), 8.05-7.92 (m, 1H), 7.82 (s, 1H), 7.75 (d, J=9.9 Hz, 1H), 7.65 (s, 1H), 4.55-4.30 (m, 4H), 4.00-3.80 (m, 4H). Mass Spectrum (LCMS, ESI pos.): Calcd. for $C_{28}H_{22}N_8O_3$: 519.2 (M+H). Found 519.2.

Following the procedures described in Example 4 above, and substituting suitably selected and substituted reagents, starting materials and conditions as would be readily apparent to those skilled in the art, the following representative compounds of the present invention were prepared.

| Cpd | Characterization |
|---|---|
| 68 | 3-(5-(8-Morpholino-2-((quinolin-2-yloxy)methyl)imidazo[1,2-a]pyrazin-5-yl)pyridin-2-yl)-1,2,4-oxadiazol-5-ol<br>$^1$H-NMR (300 MHz, DMSO-d$_6$) δ (ppm): 8.88 (s, 1H), 8.28 (d, J = 8.7 Hz, 1H), 8.22 (d, J = 7.5 Hz, 1H), 8.17 (s, 1H), 8.02 (d, J = 8.1 Hz, 1H), 7.92 (d, J = 7.8 Hz, 1H), 7.83 (d, J = 8.4 Hz, 1H), 7.74-7.69 (m, 1H), 7.58 (s, 1H), 7.51-7.46 (m, 1H), 7.09 (d, J = 9.0 Hz, 1H), 5.61 (s, 2H), 4.35-4.20 (m, 4H), 3.90-3.80 (m, 4H).<br>Mass Spectrum (LCMS, ESI pos.): Calcd. for $C_{27}H_{22}N_8O_4$: 523.2 (M + H), Found 523.3. |
| 74 | 3-[5-[8-(Morpholin-4-yl)-2-[2-(quinolin-2-yl)ethyl]imidazo[1,2-a]pyrazin-5-yl]pyridin-2-yl]-4,5-dihydro-1,2,4-oxadiazol-5-one<br>$^1$H-NMR (300 MHz, DMSO-d$_6$) δ (ppm): 8.97 (s, 1H), 8.29-8.23 (m, 2H), 8.09 (d, J = 8.7 Hz, 1H), 7.95-7.92 (m, 2H), 7.85 (s, 1H), 7.75-7.70 (m, 1H), 7.58-7.49 (m, 3H), 4.25-4.15 (m, 4H), 3.80-3.60 (m, 4H), 3.30-3.20 (m, 4H).<br>Mass Spectrum (LCMS, ESI pos.): Calcd. for $C_{28}H_{24}N_8O_3$: 521.2 (M + H), Found 521.2. |

Example 5

(E)-4-(5-(6-(2H-1,2,4-Triazol-3-yl)pyridin-3-yl)-2-(2-(quinolin-2-yl)vinyl)imidazo[1,2-a]pyrazin-8-yl)morpholine (Cpd 91)

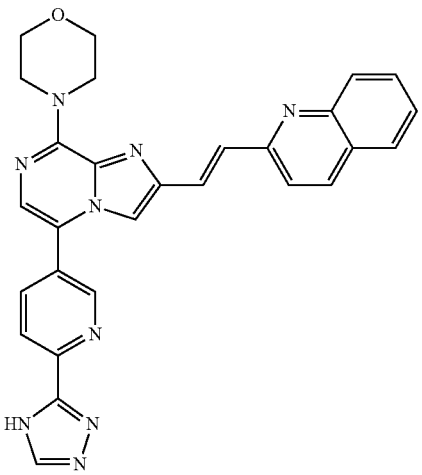 [SMILES: C(=C\c1cn2c(-c3ccc(-c4nnc[nH]4)nc3)cnc(N3CCOCC3)c2n1)/c1ccc2ccccc2n1]

A. (E)-5-(8-Morpholino-2-(2-(quinolin-2-yl)vinyl)imidazo[1,2-a]pyrazin-5-yl)picolinimidohydrazide, 5a

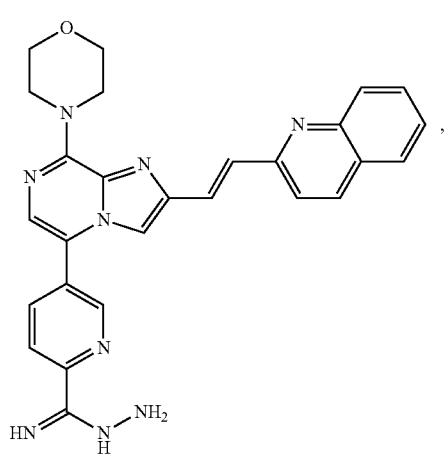

5a

To a solution of compound 2c (210 mg, 0.460 mmol, as prepared in Example 2, Step C) in EtOH (3 mL) was added $N_2H_4 \cdot H_2O$ (3 mL). The reaction mixture was stirred in a 10 mL sealed tube at 80° C. for 6 h. After cooling to rt, the reaction was quenched with MeOH (10 mL). The resulting solids were collected by filtration and washed with $Et_2O$ to obtain compound 5a as a yellow solid (170 mg, 72% yield). Mass Spectrum (LCMS, ESI pos.): Calcd. for $C_{27}H_{25}N_9O$: 492.2 (M+H). Found 592.3.

B. (E)-4-(5-(6-(2H-1,2,4-Triazol-3-yl)pyridin-3-yl)-2-(2-(quinolin-2-yl)vinyl)imidazo[1,2-a]pyrazin-8-yl)morpholine, Cpd 91

A solution of compound 5a (180 mg, 0.370 mmol) in formic acid (3 mL) was stirred in a 10 mL sealed tube at 100° C. for 2 h. After cooling to rt, water (20 mL) was added, and the pH of the solution was adjusted to 7 with saturated $NaHCO_3$ solution. The resulting solids were collected by filtration and washed with $Et_2O$ to obtain the title compound 91 as a yellow solid (37 mg, 19% yield). $^1$H-NMR (300 MHz, DMSO-$d_6$+$D_2O$) δ (ppm): 8.96 (s, 1H), 8.72 (d, J=8.4 Hz, 1H), 8.38-8.32 (m, 4H), 8.19-8.06 (m, 4H), 8.01-7.91 (m, 1H), 7.74-7.68 (m, 2H), 7.58 (s, 1H), 4.45-4.25 (m, 4H), 3.90-3.70 (m, 4H). Mass Spectrum (LCMS, ESI pos.): Calcd. for $C_{28}H_{23}N_9O$: 502.2 (M+H). Found 502.3.

Following the procedures described in Example 5 above, and substituting suitably selected and substituted reagents, starting materials and conditions as would be readily apparent to those skilled in the art, the following representative compound of the present invention was prepared.

| Cpd | Characterization |
|---|---|
| 67 | 4-(5-(6-(4H-1,2,4-Triazol-3-yl)pyridin-3-yl)-2-(2-(quinolin-2-yl)ethyl)imidazo[1,2-a]pyrazin-8-yl)morpholine<br>$^1$H-NMR (300 MHz, DMSO-$d_6$ + $D_2O$) δ (ppm): 8.93 (s, 1H), 8.87 (d, J = 8.1 Hz, 1H), 8.42 (s, 1H), 8.30-8.16 (m, 3H), 8.14 (d, J = 8.4 Hz, 1H), 8.10-8.05 (m, 1H), 7.96-7.91 (m, 2H), 7.90-7.84 (m, 1H), 7.55 (s, 1H), 4.10-3.90 (m, 4H), 3.65-3.50 (m, 6H), 3.45-3.30 (m, 2H).<br>Mass Spectrum (LCMS, ESI pos.): Calcd. for $C_{28}H_{25}N_9O$: 504.2 (M + H), Found 504.2. |

Example 6

(E)-6-(8-Morpholino-2-(2-(quinolin-2-yl)vinyl)imidazo[1,2-a]pyrazin-5-yl)-3H-imidazo[4,5-b]pyridin-2-ol (Cpd 94)

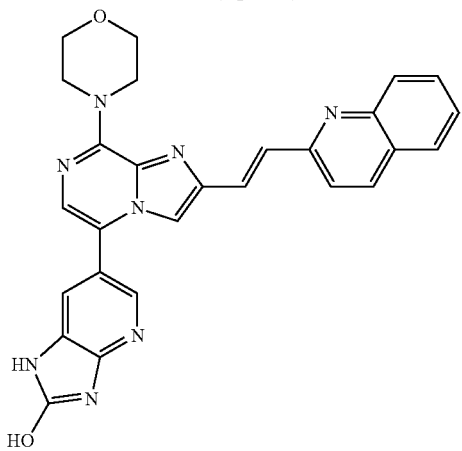 [SMILES: Oc1nc2ncc(-c3cnc(N4CCOCC4)c4nc(/C=C/c5ccc6ccccc6n5)cn34)cc2[nH]1]

A. 4-(4,4,5,5-Tetramethyl-1,3,2-dioxaborolan-2-yl)benzene-1,2-diamine, 6a

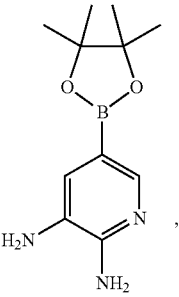

To a solution of 4-bromobenzene-1,2-diamine (5.00 g, 26.7 mmol) in DMSO (50 mL) was added 4,4,4',4',5,5,5',5'-octamethyl-2,2'-bi(1,3,2-dioxaborolane) (12.0 g, 47.2 mmol), $PdCl_2(dppf)$ (1.25 g, 1.53 mmol) and $Cs_2CO_3$ (22.0 g, 67.5 mmol) under a nitrogen atmosphere. The reaction mixture was stirred at 80° C. overnight. After cooling to rt, the reaction was quenched with $H_2O$ (100 mL). The resulting mixture was extracted with DCM (5×150 mL). The combined organic layers were concentrated under reduced pressure to obtain compound 6a as a brown solid (4.10 g, 61% yield). Mass Spectrum (LCMS, ESI pos.): Calcd. for $C_{11}H_{18}BN_3O_2$: 236.1 (M+H). Found 236.3.

B. (E)-5-(8-Morpholino-2-(2-(quinolin-2-yl)vinyl)imidazo[1,2-a]pyrazin-5-yl)pyridine-2,3-diamine, 6b

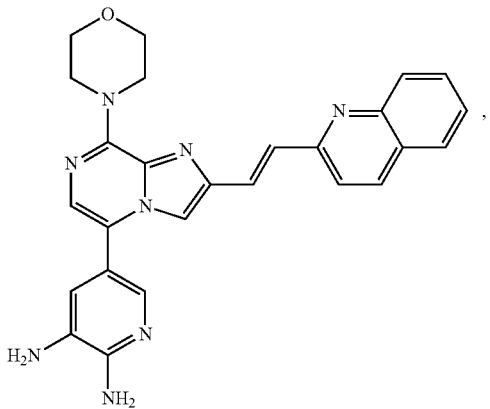

Compound 2b (1.00 g, 2.30 mmol, as prepared in Example 2, Step B) was subjected to Suzuki coupling conditions with 5-(4,4,5,5-tetramethyl-1,3,2-dioxaborolan-2-yl)pyridine-2,3-diamine (1.62 g, 6.91 mmol) using the reaction conditions described in Example 1, Step G to obtain compound 6b (580 mg, 51% yield). Mass Spectrum (LCMS, ESI pos.): Calcd. for $C_{26}H_{24}N_8O$: 465.2 (M+H). Found 465.3.

C. (E)-6-(8-Morpholino-2-(2-(quinolin-2-yl)vinyl)imidazo[1,2-a]pyrazin-5-yl)-3H-imidazo[4,5-b]pyridin-2-ol, Cpd 94

A solution of compound 6b (220 mg, 0.470 mmol) and CDI (200 mg, 1.23 mmol) in THF (8 mL) was stirred at rt for 18 h. The reaction was quenched with $H_2O$ (10 mL). The resulting solids were collected by filtration and washed with $Et_2O$ to obtain the title compound 94 as a light yellow solid (57.6 mg, 25% yield). $^1$H-NMR (300 MHz, DMSO-$d_6$) δ (ppm): 11.62 (s, 1H), 11.08 (s, 1H), 8.33 (d, J=8.4 Hz, 1H), 8.21 (s, 1H), 8.11 (s, 1H), 7.97-7.92 (m, 2H), 7.86-7.80 (m, 2H), 7.74 (t, J=7.8 Hz, 1H), 7.66 (s, 1H), 7.60-7.51 (m, 2H), 7.39 (s, 1H), 4.40-4.25 (m, 4H), 3.95-3.75 (m, 4H). Mass Spectrum (LCMS, ESI pos.): Calcd. for $C_{27}H_{22}N_8O_2$: 491.2 (M+H). Found 491.0.

Following the procedures described in Example 6 above, and substituting suitably selected and substituted reagents, starting materials and conditions as would be readily apparent to those skilled in the art, the following representative compound of the present invention was prepared.

| Cpd | Characterization |
|---|---|
| 79 | 6-(8-Morpholino-2-(2-(quinolin-2-yl)ethyl)imidazo[1,2-a]pyrazin-5-yl)-1H-imidazo[4,5-b]pyridin-2-ol<br>$^1$H-NMR (400 MHz, DMSO-d$_6$) δ (ppm): 11.61 (s, 1H), 11.07 (s, 1H), 8.82 (d, J = 8.8 Hz, 1H), 8.21 (d, J = 7.2 Hz, 1H), 8.10 (d, J = 8.4 Hz, 1H), 8.04 (s, 1H), 8.02-7.93 (m, 1H), 7.89 (d, J = 7.2 Hz, 1H), 7.86-7.80 (m, 1H), 7.74 (s, 1H), 7.41 (s, 1H), 7.33 (s, 1H), 4.00-3.85 (m, 4H), 3.70-3.45 (m, 6H), 3.40-3.28 (m, 2H).<br>Mass Spectrum (LCMS, ESI pos.): Calcd. for C$_{27}$H$_{24}$N$_8$O$_2$: 493.2 (M + H), Found 493.1. |

Example 7

(E)-4-(5-(3H-Imidazo[4,5-b]pyridin-6-yl)-2-(2-(quinolin-2-yl)vinyl)imidazo[1,2-a]pyrazin-8-yl)morpholine (Cpd 93)

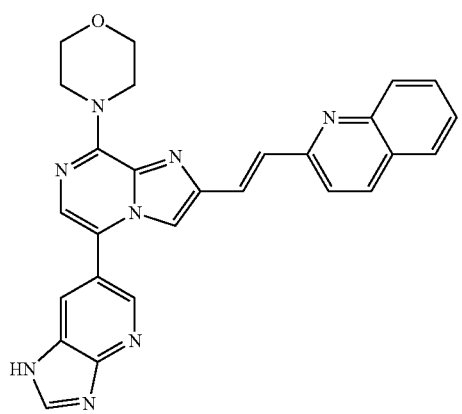 [SMILES: C(=C\c1cn2c(-c3cnc4nc[nH]c4c3)cnc(N3CCOCC3)c2n1)/c1ccc2ccccc2n1]

Compound 6b (380 mg, 0.820 mmol) was treated with formic acid using the reaction conditions described in Example 5, Step B to obtain the title compound 93 as a green solid (136 mg, 34% yield). $^1$H-NMR (300 MHz, DMSO-d$_6$) δ (ppm): 13.37 (s, 1H), 8.75-8.55 (m, 2H), 8.34-8.31 (m, 2H), 8.24 (s, 1H), 7.96-7.46 (m, 8H), 4.40-4.20 (m, 4H), 3.90-3.70 (m, 4H). Mass Spectrum (LCMS, ESI pos.): Calcd. for C$_{27}$H$_{22}$N$_8$O$_2$: 475.2 (M+H). Found 475.2.

Example 8

(E)-N-(5-(8-Morpholino-2-(2-(quinolin-2-yl)vinyl)imidazo[1,2-a]pyrazin-5-yl)pyridin-2-yl)methanesulfonamide (Cpd 89)

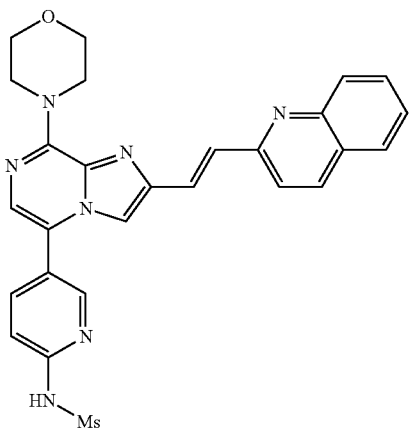 [SMILES: CS(=O)(=O)Nc1ccc(-c2cnc(N3CCOCC3)c3nc(/C=C/c4ccc5ccccc5n4)cn23)cn1]

A. (E)-5-(8-Morpholino-2-(2-(quinolin-2-yl)vinyl)imidazo[1,2-a]pyrazin-5-yl)pyridin-2-amine, 8a

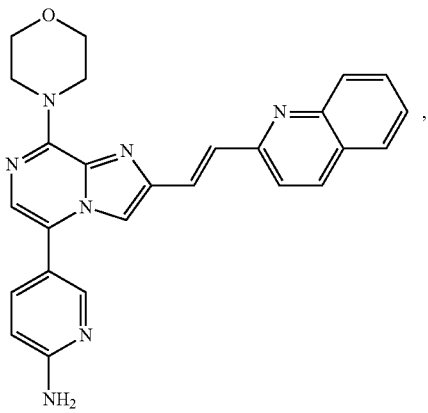

Compound 2b (1.00 g, 2.29 mmol) was subjected to Suzuki coupling conditions with 5-(4,4,5,5-tetramethyl-1,3,2-dioxaborolan-2-yl)pyridin-2-amine 5-(4,4,5,5-tetramethyl-1,3,2-dioxaborolan-2-yl)pyridin-2-amine using the reaction conditions described in Example 1, Step G to obtain compound 8a (620 mg, 52% yield). Mass Spectrum (LCMS, ESI pos.): Calcd. for C$_{26}$H$_{23}$N$_7$O: 450.2 (M+H). Found 450.3.

B. (E)-N-(5-(8-Morpholino-2-(2-(quinolin-2-yl)vinyl)imidazo[1,2-a]pyrazin-5-yl)pyridin-2-yl)methanesulfonamide, 8b To a solution of compound 8a (200 mg, 0.450 mmol) in pyridine (4 mL) was added methanesulfonyl chloride (150 mg, 1.32 mmol). The resulting solution was stirred in a 10 mL sealed tube at 30° C. for 8 h. The reaction was quenched with H₂O (10 mL). The resulting solids were collected by filtration. The crude material was purified by flash column chromatography on silica gel, eluting with DCM/MeOH (100:1 v/v) to obtain compound 8b as a light yellow solid (26.8 mg, 11% yield). ¹H-NMR (300 MHz, DMSO-d₆) δ (ppm): 10.91 (s, 1H), 8.55 (s, 1H), 8.35 (d, J=8.4 Hz, 1H), 8.23 (s, 1H), 8.12 (d, J=2.4 Hz, 1H), 8.10-7.93 (m, 2H), 7.87 (d, J=4.8 Hz, 1H), 7.83 (d, J=2.7 Hz, 1H), 7.78-7.73 (m, 1H), 7.68-7.54 (m, 2H), 7.44 (s, 1H), 7.17 (d, J=8.7 Hz, 1H), 4.40-4.20 (m, 4H), 3.85-3.75 (m, 4H), 3.39 (s, 3H). Mass Spectrum (LCMS, ESI pos.): Calcd. for C₂₇H₂₅N₇O₃S: 528.2 (M+H). Found 528.0.

Following the procedures described in Example 8 above, and substituting suitably selected and substituted reagents, starting materials and conditions as would be readily apparent to those skilled in the art, the following representative compound of the present invention was prepared.

| Cpd | Characterization |
|-----|------------------|
| 78 | N-(5-(8-Morpholino-2-(2-(quinolin-2-yl)ethyl)imidazo[1,2-a]pyrazin-5-yl)pyridin-2-yl)methanesulfonamide <br> ¹H-NMR (300 MHz, DMSO-d₆ + D₂O) δ (ppm): 8.77 (d, J = 8.7 Hz, 1H), 8.45 (s, 1H), 8.20 (d, J = 8.1 Hz, 1H), 8.08 (d, J = 8.4 Hz, 1H), 8.00-7.94 (m, 2H), 7.87-7.79 (m, 2H), 7.71 (s, 1H), 7.35 (s, 1H), 7.11 (d, J = 8.7 Hz, 1H), 4.00-3.85 (m, 4H), 3.65-3.45 (m, 6H), 3.40-3.25 (m, 6H). <br> Mass Spectrum (LCMS, ESI pos.): Calcd. for C₂₇H₂₇N₇O₃S: 530.2 (M + H), Found 530.1. |

Example 9

5-(4-(8-Morpholino-2-(2-(quinolin-2-yl)ethyl)imidazo[1,2-a]pyrazin-5-yl)phenyl)oxazolidine-2,4-dione trifluoroacetic acid salt (Cpd 26)

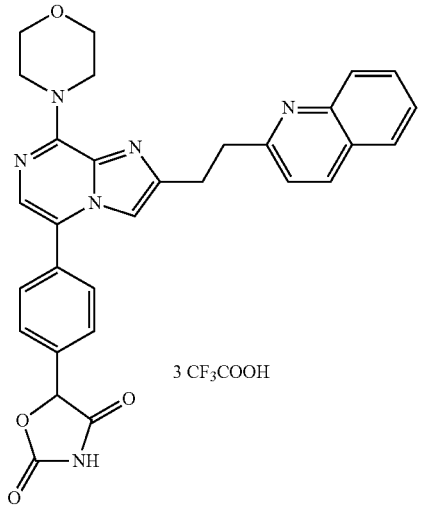 [SMILES: O=C1NC(=O)C(c2ccc(-c3cnc(N4CCOCC4)c4nc(CCc5ccc6ccccc6n5)cn34)cc2)O1]

A. Methyl 2-(4-bromophenyl)-2-hydroxyacetate, 9a

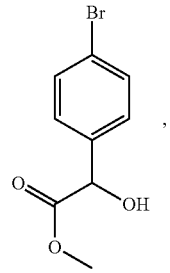

To a solution of 2-(4-bromophenyl)-2-hydroxyacetic acid (5.00 g, 21.6 mmol) in MeOH (10 mL) was added 2,2-dimethoxypropane (3.39 g, 32.6 mmol) and 4-methylbenzene-1-sulfonic acid (2.00 mg, 0.0100 mmol). The resulting solution was stirred at 55° C. overnight. The reaction mixture was concentrated under reduced pressure, and H₂O (100 mL) was added. The resulting solids were collected by filtration and washed with hexane to obtain compound 9a as a gray solid (4.00 g, 72% yield). ¹H-NMR (300 MHz, CDCl₃) δ (ppm): 7.54-7.51 (m, 2H), 7.35-7.28 (m, 2H), 5.18-5.16 (m, 1H), 3.793 (s, 3H), 3.51-3.49 (m, 1H).

B. Methyl 2-hydroxy-2-[4-(tetramethyl-1,3,2-dioxaborolan-2-yl)phenyl]acetate, 9b

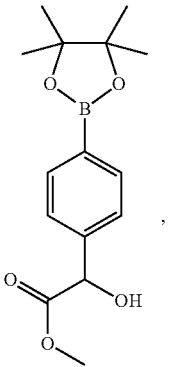

Compound 9b was prepared from compound 9a (3.00 g, 12.2 mmol) using the reaction conditions described in Example 1, Step F. A yellow solid was obtained (1.5 g, 42% yield). Mass Spectrum (LCMS, ESI pos.): Calcd. for C₁₅H₂₁BO₅: 292.1 (M+H). Found 292.1.

C. Methyl 2-hydroxy-2-[4-[8-(morpholin-4-yl)-2-[2-(quinolin-2-yl)ethyl]imidazo[1,2-a]pyrazin-5-yl]phenyl]acetate, 9c

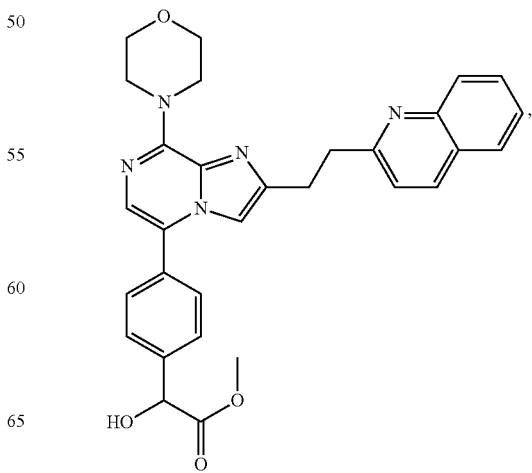

Compound 3a (350 mg, 0.760 mmol) was subjected to Suzuki coupling conditions with methyl 2-hydroxy-2-[4-(tetramethyl-1,3,2-dioxaborolan-2-yl)phenyl]acetate (666 mg, 2.28 mmol) using the reaction conditions described in Example 1, Step G to obtain compound 9c (300 mg, 72% yield). Mass Spectrum (LCMS, ESI pos.): Calcd. for $C_{30}H_{29}N_5O_4$: 524.2 (M+H). Found 524.2.

D. 5-(4-(8-Morpholino-2-(2-(quinolin-2-yl)ethyl)imidazo[1,2-a]pyrazin-5-yl)phenyl)oxazolidine-2,4-dione trifluoroacetic acid salt, Cpd 26

To a solution of compound 9c (300 mg, 0.540 mmol) in DCM (20 mL) was added a solution of trichloroethanecarbonyl isocyanate (161 mg, 0.860 mmol) in DCM (1 mL) dropwise with stirring at 0° C. The reaction mixture was stirred at rt for 30 min and then concentrated under reduced pressure. To the residue was added a solution of TEA (116 mg, 1.14 mmol) in EtOH (20 mL). The resulting solution was stirred at 70° C. for 2 h, and was concentrated under reduced pressure. The resulting residue was purified by Prep-HPLC with the following conditions (1#-Waters 2767-1): Column, SunFire Prep C18, 5 μm, 19*150 mm; mobile phase: water in $NH_4HCO_3$ and $CH_3CN$ (20% $CH_3CN$ up to 35% in 8 min, up to 100% in 2 min, down to 20% in 2 min); Detector, UV 254 nm. The title compound 26 was obtained as a light yellow solid (58.6 mg, 20% yield). $^1$H-NMR (300 MHz, DMSO-d$_6$+ D$_2$O) δ (ppm): 9.01 (d, J=8.4 Hz, 1H), 8.31 (d, J=8.1 Hz, 1H), 8.15-8.08 (m, 2H), 8.02 (d, J=8.7 Hz, 1H), 7.97-7.89 (m, 1H), 7.76 (s, 1H), 7.68 (d, J=8.4 Hz, 2H), 7.56 (d, J=8.1 Hz, 2H), 7.32 (s, 1H), 6.13 (s, 1H), 3.90-3.75 (m, 8H), 3.62-3.50 (m, 2H), 3.45-3.35 (m, 2H). Mass Spectrum (LCMS, ESI pos.): Calcd. for $C_{30}H_{26}N_6O_4$: 535.2 (M+H). Found 535.3. Following the procedures described in Example 9 above, and substituting suitably selected and substituted reagents, starting materials and conditions as would be readily apparent to those skilled in the art, the following representative compound of the present invention was prepared.

| Cpd | Characterization |
| --- | --- |
| 48 | (E)-5-(4-(8-Morpholino-2-(2-(quinolin-2-yl)vinyl)imidazo[1,2-a]pyrazin-5-yl)phenyl)oxazolidine-2,4-dione<br>$^1$H-NMR (300 MHz, DMSO-d$_6$) δ (ppm): 12.29 (br, 1H), 8.37 (d, J = 8.7 Hz, 2H), 8.29 (s, 1H), 8.01-7.56 (m, 11H), 7.48 (s, 1H), 6.21 (s, 1H), 4.35-4.29 (m, 4H), 3.89-3.76 (m, 4H).<br>Mass Spectrum (LCMS, ESI pos.): Calcd. for $C_{30}H_{24}N_6O_4$: 533.2 (M + H), Found 533.3. |

Example 10

1-Methyl-3-[4-[8-(morpholin-4-yl)-2-[2-(quinolin-2-yl)ethyl]imidazo[1,2-a]pyrazin-5-yl]phenyl]-4,5-dihydro-1H-1,2,4-triazol-5-one (Cpd 33)

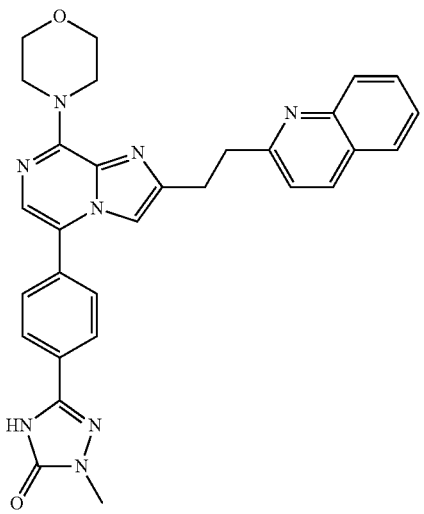 [SMILES: Cn1nc(-c2ccc(-c3cnc(N4CCOCC4)c4nc(CCc5ccc6ccccc6n5)cn34)cc2)[nH]c1=O]

A. 1-[(E)-[(4-Bromophenyl)methylidene]amino]-1-methylurea, 10a

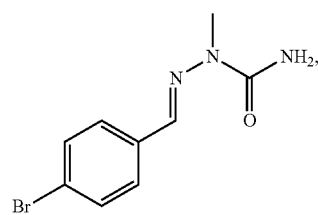

To a solution of 4-bromobenzaldehyde (4.30 g, 23.2 mmol) in EtOH (40 mL) was added 1-amino-1-methylurea (2.50 g, 28.1 mmol), AcOH (2.5 mL) and H$_2$O (4.5 mL). The resulting solution was stirred at 80° C. overnight. After cooling to rt, Et$_2$O (200 mL) was added. The resulting solids were collected by filtration to obtain compound 10a as a white solid (5.80 g, 97% yield). Mass Spectrum (LCMS, ESI pos.): Calcd. for $C_9H_{10}BrN_3O$: 256.0 (M+H). Found 256.1.

B. 3-(4-Bromophenyl)-1-methyl-4,5-dihydro-1H-1,2,4-triazol-5-one, 10b

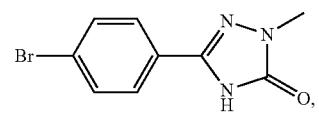

To a solution of compound 10a (5.80 g, 22.6 mmol) in AcOH (20 mL), was added Br$_2$ (7.30 g, 45.7 mmol) dropwise. The reaction mixture was stirred at 95° C. for 30 min. After cooling to rt, the product was precipitated by addition of Et$_2$O and collected by filtration and washed with Et$_2$O to obtain compound 10b as a yellow solid (5.50 g, 96% yield). Mass Spectrum (LCMS, ESI pos.): Calcd. for $C_9H_8BrN_3O$: 254.0 (M+H). Found 254.1.

C. 3-(4-Bromophenyl)-1-methyl-4-[[2-(trimethylsilyl)ethoxy]methyl]-4,5-dihydro-1H-1,2,4-triazol-5-one, 10c

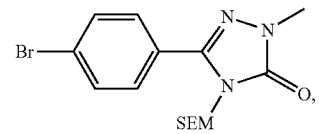

To a solution of compound 10b (1.00 g, 3.94 mmol) in DMF (5 mL) was added sodium hydride (200 mg, 5.00 mmol) in portions at 0° C., and the mixture was stirred for 20 min before 2-(trimethylsilyl)ethoxymethyl chloride (730 mg, 4.37 mmol) was added. The reaction mixture was stirred at rt overnight, and was quenched with H$_2$O (50 mL). The resulting mixture was extracted with DCM (2×50 mL). The combined organic layers were dried over Na$_2$SO$_4$, filtered concentrated under reduced pressure. The residue was purified by flash column chromatography on silica gel, eluting with EtOAc/petroleum ether (1:5 v/v) to obtain compound 10c as a yellow solid (600 mg, 40% yield). Mass Spectrum (LCMS, ESI pos.): Calcd. for $C_{15}H_{22}BrN_3O_2Si$: 383.1 (M+H). Found 383.1.

D. 1-Methyl-3-[4-(tetramethyl-1,3,2-dioxaborolan-2-yl)phenyl]-4-[[2-(trimethylsilyl)ethoxy]methyl]-4,5-dihydro-1H-1,2,4-triazol-5-one, 10d

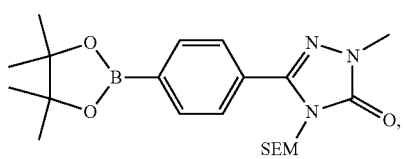

10d

Compound 10d was prepared from compound 10c (495 mg, 1.29 mmol) using the reaction conditions described in Example 1, Step F. A white solid was obtained (200 mg, 36% yield). Mass Spectrum (LCMS, ESI pos.): Calcd. for $C_{21}H_{34}BN_3O_4Si$: 431.2 (M+H). Found 431.4.

E. 1-Methyl-3-[4-[8-(morpholin-4-yl)-2-[2-(quinolin-2-yl)ethyl]imidazo[1,2-a]pyrazin-5-yl]phenyl]-4-[[2-(trimethylsilyl)ethoxy]methyl]-4,5-dihydro-1H-1,2,4-triazol-5-one, 10e

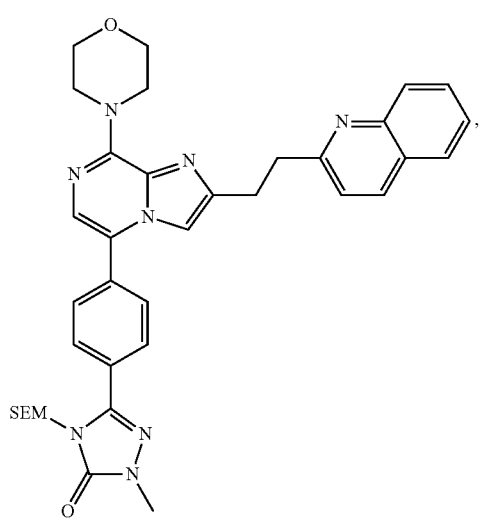

10e

Compound 3a (350 mg, 0.760 mmol) was subjected to Suzuki coupling conditions with 1-methyl-3-[4-(tetramethyl-1,3,2-dioxaborolan-2-yl)phenyl]-4-[[2-(trimethylsilyl)ethoxy]methyl]-4,5-dihydro-1H-1,2,4-triazol-5-one (983 mg, 2.28 mmol) using the reaction conditions described in Example 1, Step G to obtain compound 10e as a yellow solid (230 mg, 43% yield). Mass Spectrum (LCMS, ESI pos.): Calcd. for $C_{36}H_{42}N_8O_3S$: 633.3 (M+H). Found 633.5.

F. 1-Methyl-3-[4-[8-(morpholin-4-yl)-2-[2-(quinolin-2-yl)ethyl]imidazo[1,2-a]pyrazin-5-yl]phenyl]-4,5-dihydro-1H-1,2,4-triazol-5-one, Cpd 33

To a solution of compound 10e (200 mg, 0.290 mmol) in DCM (6 mL) was added TFA (2 mL) dropwise with stirring at 0° C. The resulting solution was stirred at rt overnight. The reaction was quenched with MeOH (10 mL). The resulting solids were collected by filtration and washed with $Et_2O$, and then suspended in MeOH (10 mL) and DIPEA (0.5 mL). The mixture was stirred at 70° C. for 30 min. After cooling to rt, the solids were collected by filtration and washed with $Et_2O$ to obtain the title compound 33 as a light yellow solid (39.4 mg, 24% yield). $^1$H-NMR (300 MHz, DMSO-$d_6$) δ (ppm): 12.36 (s, 1H), 8.28 (d, J=8.4 Hz, 1H), 7.95-7.88 (m, 4H), 7.75-7.68 (m, 4H), 7.58-7.49 (m, 2H), 7.41 (s, 1H), 4.20-4.08 (m, 4H), 3.75-3.65 (m, 4H), 3.41 (s, 3H), 3.40-3.25 (m, 4H). Mass Spectrum (LCMS, ESI pos.): Calcd. for $C_{30}H_{28}N_8O_2$: 533.2 (M+H). Found 533.2.

Following the procedures described in Example 10 above, and substituting suitably selected and substituted reagents, starting materials and conditions as would be readily apparent to those skilled in the art, the following representative compound of the present invention was prepared.

| Cpd | Characterization |
|---|---|
| 47 | (E)-2-Methyl-5-(4-(8-morpholino-2-(2-(quinolin-2-yl)vinyl)imidazo[1,2-a]pyrazin-5-yl)phenyl)-2H-1,2,4-triazol-3(4H)-one<br>$^1$H-NMR (300 MHz, DMSO-$d_6$) δ (ppm): 12.38 (br, 1H), 8.37 (d, J = 8.4 Hz, 1H), 8.29 (s, 1H), 7.99-7.91 (m, 4H), 7.89-7.85 (m, 4H), 7.82-7.74 (m, 1H), 7.68-7.63 (m, 1H), 7.60-7.55 (m, 1H), 7.49 (s, 1H), 4.33-4.28 (m, 4H), 3.92-3.78 (m, 4H), 3.41 (s, 3H). Mass Spectrum (LCMS, ESI pos.): Calcd. for $C_{30}H_{26}N_8O_2$: 531.2 (M + H), Found 531.1. |

Example 11

1-(4-(8-Morpholino-2-(2-(quinolin-2-yl)ethyl)imidazo[1,2-a]pyrazin-5-yl)phenyl)-1H-1,2,4-triazol-3-ol (Cpd 51)

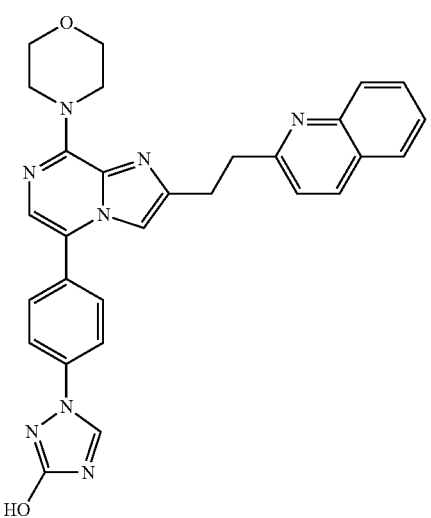 [SMILES: Oc1ncn(-c2ccc(-c3cnc(N4CCOCC4)c4nc(CCc5ccc6ccccc6n5)cn34)cc2)n1]

A. 1-(4-Bromophenyl)semicarbazide, 11a

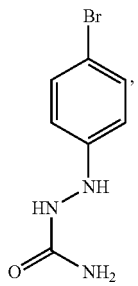

To a solution of 1-(4-bromophenyl)hydrazine hydrochloride (25.0 g, 112 mmol) in $H_2O$ (500 mL) was added KOCN (730 mg, 9.01 mmol). The resulting solution was stirred at 40° C. overnight. After cooling to rt, the resulting solids were collected by filtration to obtain compound 11a as a grey solid (22.0 g, 84% yield). Mass Spectrum (LCMS, ESI pos.): Calcd. for $C_7H_8BrN_3O$: 230.0 (M+H). Found 230.2.

B. 1-(4-Bromophenyl)-1,2-dihydro-1,2,4-triazol-3-one, 11b

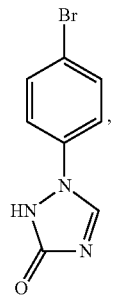

A solution of compound 11a (10.0 g, 43.5 mmol) in triethoxymethane (300 mL) was stirred at 120° C. for 2 h. The reaction mixture was cooled in a water/ice bath. The resulting solids were collected by filtration and washed with $Et_2O$ to obtain compound 11b as a grey solid (7.80 g, 73% yield). Mass Spectrum (LCMS, ESI pos.): Calcd. for $C_8H_6BrN_3O$: 240.0 (M+H). Found 240.2.

C. 1-(4-Bromophenyl)-2-((2-(trimethylsilyl)ethoxy)methyl)-1,2-dihydro-1,2,4-triazol-3-one, 11c

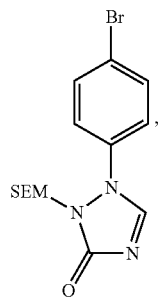

Compound 11b (30.0 g, 125 mmol) was treated with SEMCl using the reaction conditions described in Example 10, Step C to obtain compound 11c as a white solid (30.0 g, 58% yield). Mass Spectrum (LCMS, ESI pos.): Calcd. for $C_{14}H_{20}BrN_3O_2S$: 370.1 (M+H). Found 370.2.

D. 1-(4-(4,4,5,5-Tetramethyl-1,3,2-dioxaborolan-2-yl)phenyl)-2-((2-(trimethylsilyl)ethoxy)methyl)-1,2-dihydro-1,2,4-triazol-3-one, 11d

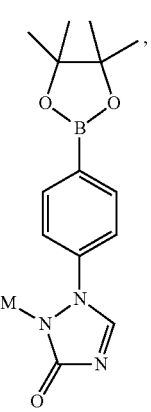

Compound 11d was prepared from compound 11c (30.0 g, 81.3 mmol) using the reaction conditions described in Example 1, Step F. A grey solid was obtained (12.0 g, 34% yield). Mass Spectrum (LCMS, ESI pos.): Calcd. for $C_{20}H_{32}BN_3O_4Si$: 418.2 (M+H). Found 418.4.

E. 1-[4-[8-(Morpholin-4-yl)-2-[2-(quinolin-2-yl)ethyl]imidazo[1,2-a]pyrazin-5-yl]phenyl]-2-[[2-(trimethylsilyl)ethoxy]methyl]-2,3-dihydro-1H-1,2,4-triazol-3-one, 11e

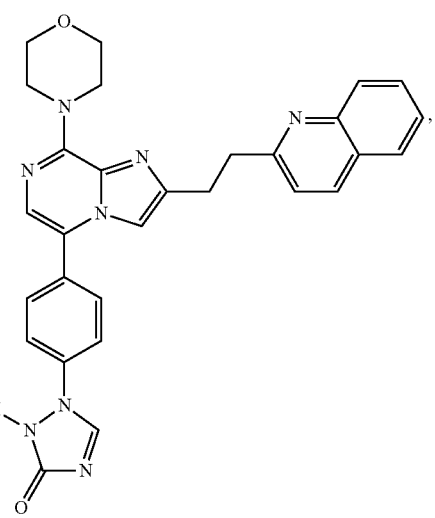

Compound 3a (400 mg, 0.910 mmol) was subjected to Suzuki coupling conditions with 1-[4-(tetramethyl-1,3,2-dioxaborolan-2-yl)phenyl]-2-[[2-(trimethylsilyl)ethoxy]methyl]-2,3-dihydro-1H-1,2,4-triazol-3-one (1.14 g, 2.73 mmol) using the reaction conditions described in Example 1, Step G to obtain compound 11e as a brown solid (148 mg, 25% yield). Mass Spectrum (LCMS, ESI pos.): Calcd. for $C_{35}H_{40}N_8O_3Si$: 649.3 (M+H). Found 649.3.

F. 1-(4-(8-Morpholino-2-(2-(quinolin-2-yl)ethyl) imidazo[1,2-a]pyrazin-5-yl)phenyl)-1H-1,2,4-triazol-3-ol trifluoroacetic acid salt, Cpd 51

The SEM group of compound 11e (148 mg, 0.220 mmol) was removed using the reaction conditions described in Example 10, Step F to obtain the title compound 51 as a yellow solid (30.0 mg, 50% yield). $^1$H-NMR (300 MHz, DMSO-d$_6$+D$_2$O) δ (ppm): 8.98 (s, 1H), 8.63 (d, J=8.1 Hz, 1H), 8.12 (d, J=8.7 Hz, 1H), 8.03 (d, J=8.4 Hz, 1H), 7.93-7.87 (m, 3H), 7.77-7.70 (m, 5H), 7.37 (s, 1H), 4.00-3.94 (m, 4H), 3.60-3.50 (m, 4H), 3.44-3.41 (m, 2H), 3.34-3.31 (m, 2H). Mass Spectrum (LCMS, ESI pos.): Calcd. for C29H26N8O2: 519.2 (M+H). Found 519.1.

Following the procedures described in Example 11 above, and substituting suitably selected and substituted reagents, starting materials and conditions as would be readily apparent to those skilled in the art, the following representative compounds of the present invention were prepared.

| Cpd | Characterization |
|---|---|
| 56 | (E)-1-(4-(8-Morpholino-2-(2-(quinolin-2-yl)vinyl)imidazo[1,2-a]pyrazin-5-yl)phenyl)-1,2-dihydro-1,2,4-triazol-3-one $^1$H-NMR (400 MHz, DMSO-d$_6$) δ (ppm): 9.06 (s, 1H), 8.55-8.48 (m, 1H), 8.28 (s, 1H), 8.03-7.96 (m, 6H), 7.88-7.75 (m, 3H), 7.71-7.62 (m, 2H), 7.49 (s, 1H), 4.35-4.28 (m, 4H), 3.89-3.79 (m, 4H). Mass Spectrum (LCMS, ESI pos.): Calcd. for $C_{29}H_{24}N_8O_2$: 517.2 (M + H), Found 517.2. |
| 52 | (E)-1-(5-(8-Morpholino-2-(2-(quinolin-2-yl)vinyl)imidazo[1,2-a]pyrazin-5-yl)pyridin-2-yl)-1,2-dihydro-1,2,4-triazol-3-one $^1$H-NMR (300 MHz, DMSO-d$_6$) δ (ppm): 9.13 (s, 1H), 8.88-8.78 (m, 1H), 8.69-8.58 (m, 1H), 8.43-8.42 (m, 2H), 8.11-8.02 (m, 4H), 7.93-7.85 (m, 2H), 7.75-7.70 (m, 2H), 7.58 (s, 1H), 4.43-4.32 (m, 4H), 3.89-3.75 (m, 4H). Mass Spectrum (LCMS, ESI pos.): Calcd. for $C_{28}H_{23}N_9O_2$: 518.2 (M + H), Found 518.2. |

Example 12

(E)-4-(5-(6-(2H-1,2,4-Triazol-3-yl)pyridin-3-yl)-2-(2-(quinolin-2-yl)vinyl)imidazo[1,2-a]pyrazin-8-yl) morpholine (Cpd 57)

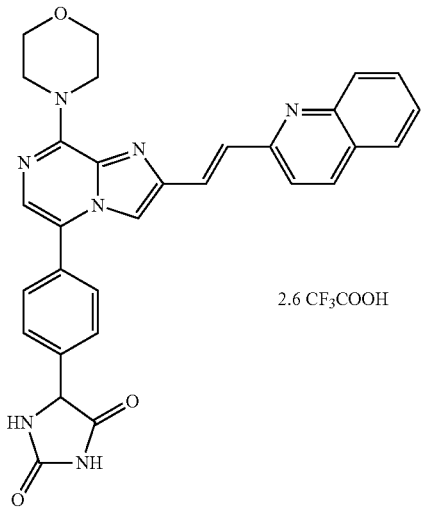 [SMILES: O=C1NC(=O)C(c2ccc(-c3cnc(N4CCOCC4)c4nc(/C=C/c5ccc6ccccc6n5)cn34)cc2)N1]

2.6 CF$_3$COOH

A. (E)-5-(8-Morpholino-2-(2-(quinolin-2-yl)vinyl) imidazo[1,2-a]pyrazin-5-yl)picolinaldehyde, 12a

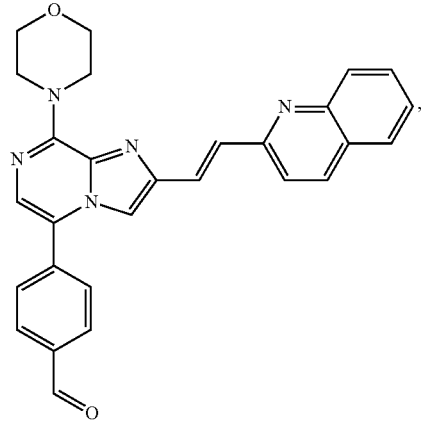

12a

Compound 2b (1.00 g, 2.30 mmol) was subjected to Suzuki coupling conditions with 5-(4,4,5,5-tetramethyl-1,3,2-dioxaborolan-2-yl)benzaldehyde using the reaction conditions described in Example 1, Step G to obtain compound 12a as a yellow solid (570 mg, 51% yield). Mass Spectrum (LCMS, ESI pos.): Calcd. for $C_{28}H_{23}N_5O_2$: 462.2 (M+H). Found 462.2.

B. (E)-5-(4-(8-Morpholino-2-(2-(quinolin-2-yl)vinyl)imidazo[1,2-a]pyrazin-5-yl)phenyl)imidazolidine-2,4-dione 2,2,2-trifluoroacetate, Cpd 57

A mixture of compound 12a (300 mg, 0.650 mmol), KCN (150 mg, 2.30 mmol), (NH$_4$)$_2$CO$_3$ (1.00 g, 10.4 mmol), ethanol (5 mL) and water (5 mL) was stirred in a pressure vessel at 100° C. for 48 h. After cooling to rt, the pH of the solution was adjusted to 7 using 2 N HCl solution. The resulting solids were collected by filtration, which was further purified by Prep-HPLC with the following conditions: (1#water2767-5): Column, SunFire Prep C18, 5 μm, 19*150 mm; mobile phase: water in 0.05% TFA and CH$_3$CN (25% CH$_3$CN up to 60% in 30 min, up to 100% in 2 min, down to 25% in 2 min); Detector, UV 254 nm. The title compound 57 was obtained as a red solid (142 mg, 26% yield). $^1$H-NMR (400 MHz, DMSO-d$_6$) δ (ppm): 8.88 (d, J=8.8 Hz, 1H), 8.30-8.17 (m, 4H), 8.11 (d, J=8.4 Hz, 1H), 8.01 (t, J=8.0 Hz, 1H), 7.82-7.70 (m, 4H), 7.57 (d, J=7.6 Hz, 2H), 7.45 (s, 1H), 5.33 (s, 1H), 4.40-4.25 (m, 4H), 3.90-3.80 (m, 4H). Mass Spectrum (LCMS, ESI pos.): Calcd. for $C_{30}H_{25}N_7O_3$: 532.2 (M+H). Found 532.1.

Example 13

(E)-2-(5-(8-Morpholino-2-(2-(quinolin-2-yl)vinyl)imidazo[1,2-a]pyrazin-5-yl)pyridin-2-ylamino)acetic acid trifluoroacetic acid salt (Cpd 66)

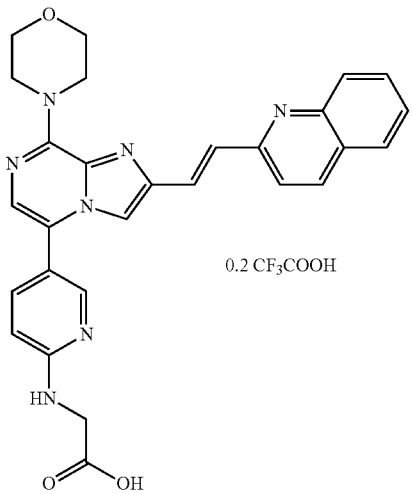 [SMILES: O=C(O)CNc1ccc(-c2cnc(N3CCOCC3)c3nc(/C=C/c4ccc5ccccc5n4)cn23)cn1]

A. (E)-tert-Butyl5-(8-morpholino-2-(2-(quinolin-2-yl)vinyl)imidazo[1,2-a]pyrazin-5-yl)pyridin-2-ylcarbamate, 13a

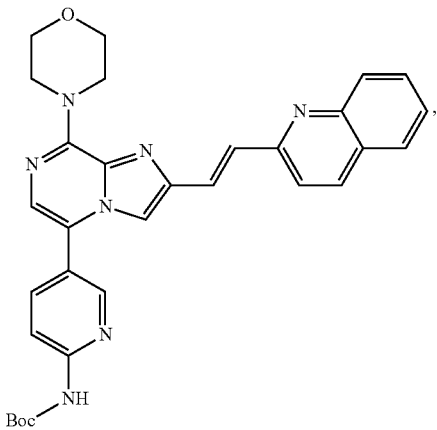

Compound 2b (500 mg, 1.15 mmol) was subjected to Suzuki coupling conditions with tert-butyl 5-(4,4,5,5-tetramethyl-1,3,2-dioxaborolan-2-yl)pyridine-2-ylcarbamate using the reaction conditions described in Example 1, Step G to obtain compound 13a as a yellow solid (300 mg, 48% yield). Mass Spectrum (LCMS, ESI pos.): Calcd. for $C_{31}H_{31}N_7O_3$: 550.2 (M+H). Found 550.2.

B. (E)-tert-Butyl-(tert-butoxycarbonyl(5-(8-morpholino-2-(2-(quinolin-2-yl)vinyl)imidazo[1,2-a]pyrazin-5-yl)pyridin-2-yl)amino)acetate, 13b

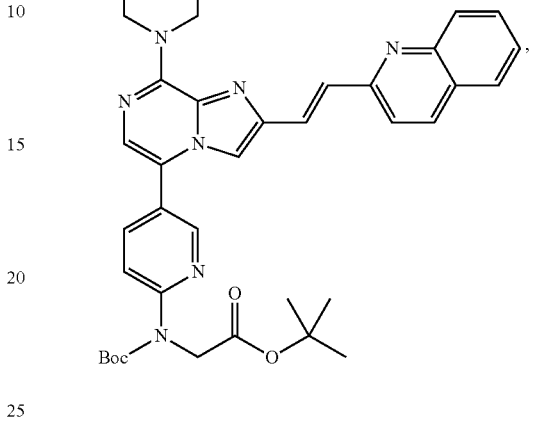

To a solution of compound 13a (300 mg, 0.550 mmol) in DMF (4 mL) was added sodium hydride (60%, 32.7 mg, 0.820 mmol) in portions at 0° C. The resulting mixture was stirred at rt for 30 min before tert-butyl 2-bromoacetate (159 mg, 0.820 mmol) was added. The resulting mixture was stirred at rt for 1 h, and was concentrated under reduced pressure. The residue was purified by flash column chromatography on silica gel, eluting with EtOAc/petroleum ether (1:10 v/v) to obtain compound 13b as a yellow solid (200 mg, 55% yield). Mass Spectrum (LCMS, ESI pos.): Calcd. for $C_{37}H_{41}N_7O_5$: 664.3 (M+H). Found 664.3.

C. (E)-2-(5-(8-Morpholino-2-(2-(quinolin-2-yl)vinyl)imidazo[1,2-a]pyrazin-5-yl)pyridin-2-ylamino) acetic acid trifluoroacetic acid salt, Cpd 66

A solution of compound 13b (200 mg, 0.300 mmol) in DCM/TFA (4:1 v/v, 10 mL) was stirred at rt for 30 min. Solvent was evaporated, and water (5 mL) was added. The resulting solids were collected by filtration and washed with Et$_2$O to obtain the title compound as a yellow solid (40.2 mg, 25% yield). $^1$H-NMR (300 MHz, DMSO-d$_6$) δ (ppm): 8.44 (d, J=8.7 Hz, 1H), 8.29-8.23 (m, 1H), 8.18 (s, 1H), 8.03-7.91 (m, 4H), 7.85-7.73 (m, 2H), 7.71 (s, 1H), 7.65-7.52 (m, 2H), 7.51-7.40 (m, 1H), 7.38 (s, 1H), 6.85 (d, J=8.4 Hz, 1H), 4.40-4.20 (m, 4H), 4.18-4.01 (m, 2H), 3.93-3.77 (m, 4H). Mass Spectrum (LCMS, ESI pos.): Calcd. for $C_{28}H_{25}N_7O_3$: 508.2 (M+H). Found 508.3.

Following the procedures described in Example 13 above, and substituting suitably selected and substituted reagents, starting materials and conditions as would be readily apparent to those skilled in the art, the following representative compounds of the present invention were prepared.

| Cpd | Characterization |
|---|---|
| 22 | (E)-3-(4-(8-Morpholino-2-(2-(quinolin-2-yl)vinyl)imidazo[1,2-a]pyrazin-5-yl)phenylamino)propanoic acid trifluoroacetic acid salt<br>$^1$H-NMR (300 MHz, DMSO-$d_6$) δ (ppm): 8.68-8.64 (m, 1H), 8.21 (s, 1H), 8.11-8.05 (m, 4H), 7.91 (t, J = 7.5 Hz, 1H), 7.70 (m, 2H), 7.40 (d, J = 8.7, 2H), 7.31 (s, 1H), 6.77 (d, J = 8.7 Hz, 2H), 4.35-4.15 (m, 4H), 3.90-3.74 (m, 4H), 3.35 (t, J = 6.6 Hz, 2H), 2.55 (t, J = 6.6 Hz, 2H). Mass Spectrum (LCMS, ESI pos.): Calcd. for $C_{32}H_{28}N_6O_3$: 521.2 (M + H), Found 521.1. |
| 23 | 3-(4-(8-Morpholino-2-(2-(quinolin-2-yl)ethyl)imidazo[1,2-a]pyrazin-5-yl)phenylamino)propanoic acid trifluoroacetic acid salt<br>$^1$H-NMR (400 MHz, DMSO-$d_6$ + $D_2O$) δ (ppm): 9.01 (d, J = 8.7 Hz, 2H), 8.31 (d, J = 8.4 Hz, 1H), 8.17-8.08 (m, 2H), 8.02 (d, J = 8.7 Hz, 1H), 7.94-7.89 (m, 1H), 7.77 (s, 1H), 7.28 (d, J = 8.4 Hz, 2H), 7.15 (s, 1H), 6.72 (d, J = 8.4 Hz, 2H), 3.94-3.85 (m, 4H), 3.58-3.54 (m, 2H), 3.52-3.45 (m, 4H), 3.40-3.30 (m, 4H), 2.55-2.50 (m, 2H). Mass Spectrum (LCMS, ESI pos.): Calcd. for $C_{30}H_{30}N_6O_3$: 523.2 (M + H), Found 523.3. |
| 29 | (E)-2-(4-(8-Morpholino-2-(2-(quinolin-2-yl)vinyl)imidazo[1,2-a]pyrazin-5-yl)phenylamino)acetic acid trifluoroacetic acid salt<br>$^1$H-NMR (300 MHz, DMSO-$d_6$) δ (ppm): 8.72 (d, J = 8.4 Hz, 1H), 8.21-8.06 (m, 5H), 7.96-7.91 (m, 1H), 7.75-7.68 (m, 2H), 7.41 (d, J = 8.4 Hz, 2H), 7.32 (s, 1H), 6.76 (d, J = 8.1 Hz, 2H), 4.35-4.22 (m, 4H), 3.91 (s, 2H), 3.84-3.75 (m, 4H). Mass Spectrum (LCMS, ESI pos.): Calcd. for $C_{29}H_{26}N_6O_3$: 507.2 (M + H), Found 507.0. |
| 30 | 2-(4-(8-Morpholino-2-(2-(quinolin-2-yl)ethyl)imidazo[1,2-a]pyrazin-5-yl)phenylamino)acetic acid trifluoroacetic acid salt<br>$^1$H-NMR (300 MHz, DMSO-$d_6$) δ (ppm): 8.72 (d, J = 8.4 Hz, 1H), 8.21-8.06 (m, 5H), 7.96-7.91 (m, 1H), 7.75-7.68 (m, 2H), 7.41 (d, J = 8.4 Hz, 2H), 7.32 (s, 1H), 6.76 (d, J = 8.1 Hz, 2H), 4.35-4.22 (m, 4H), 3.91 (s, 2H), 3.84-3.75 (m, 4H). Mass Spectrum (LCMS, ESI pos.): Calcd. for $C_{29}H_{26}N_6O_3$: 507.2 (M + H), Found 507.0. |

Example 14

1-(4-(8-Morpholino-2-(2-(quinolin-2-yl)ethyl)imidazo[1,2-a]pyrazin-5-yl)phenyl)-1H-tetrazol-5-ol (Cpd 53)

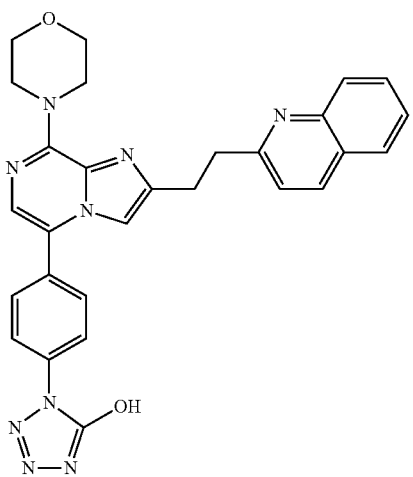 [SMILES: Oc1nnnn1-c1ccc(-c2cnc(N3CCOCC3)c3nc(CCc4ccc5ccccc5n4)cn23)cc1]

A. 1-(4-Bromophenyl)-1H-tetrazol-5(4H)-one, 14a

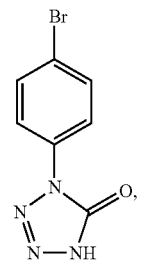

14a

To a solution of 1-bromo-4-isocyanatobenzene (5.00 g, 25.4 mmol) in THF (30 mL) was added sodium azide (5.00 g, 76.9 mmol) followed by the addition of a solution of aluminum trichloride (4.00 g, 30.3 mmol) in THF (18 mL) slowly. The reaction mixture was heated to reflux overnight. After cooling to rt, the reaction was quenched with $H_2O$ (50 mL). The organic solvent was removed under reduced pressure. The solids were collected by filtration to obtain compound 14a as a white solid (4.50 g, 71% yield). Mass Spectrum (LCMS, ESI pos.): Calcd. for $C_2H_5BrN_4O$: 241.0 (M+H). Found 241.1.

B. 1-(4-Bromophenyl)-4-((2-(trimethylsilyl)ethoxy)methyl)-1H-tetrazol-5(4H)-one, 14b

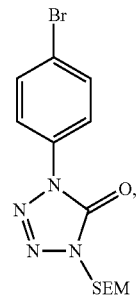

14b

Compound 14a (5.00 g, 20.7 mmol) was treated with SEMCl using the reaction conditions described in Example 10, Step C to obtain compound 14b as a white solid (6.90 g, 81% yield). Mass Spectrum (LCMS, ESI pos.): Calcd. for $C_{13}H_{19}BrN_4O_2Si$: 371.0 (M+H). Found 371.1.

C. 1-(4-(4,4,5,5-Tetramethyl-1,3,2-dioxaborolan-2-yl)phenyl)-4-((2-(trimethylsilyl)ethoxy)methyl)-1H-tetrazol-5(4H)-one, 14c

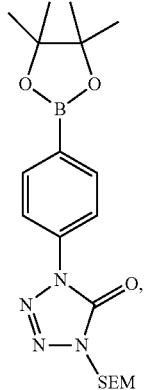

14c

Compound 14c was prepared from compound 14b (6.90 g, 18.6 mmol) using the reaction conditions described in Example 1, Step F. A white solid (6.89 g, 74% yield) was obtained. Mass Spectrum (LCMS, ESI pos.): Calcd. for $C_{19}H_{31}BN_4O_4Si$: 419.2 (M+H). Found 419.2.

D. 1-(4-(8-Morpholino-2-(2-(quinolin-2-yl)ethyl) imidazo[1,2-a]pyrazin-5-yl)phenyl)-4-((2-(trimethyl-silyl)ethoxy)methyl)-1H-tetrazol-5(4H)-one, 14d

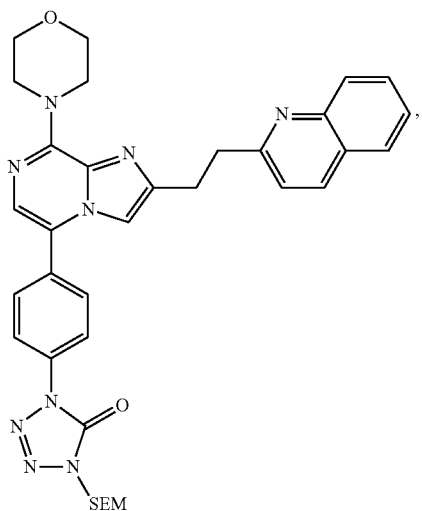

14d

Compound 3a (500 mg, 1.15 mmol) was subjected to Suzuki coupling conditions with 1-[4-(tetramethyl-1,3,2-dioxaborolan-2-yl)phenyl]-4-[[2-(trimethylsilyl)ethoxy]methyl]-1,2,3,4-tetrazolidin-5-one (1.44 g, 3.45 mmol) using the reaction conditions described in Example 1, Step G to obtain compound 14d as a white solid (236 mg, 31% yield). Mass Spectrum (LCMS, ESI pos.): Calcd. for $C_{34}H_{39}N_9O_3Si$: 650.3 (M+H). Found 650.4.

E. 1-(4-(8-Morpholino-2-(2-(quinolin-2-yl)ethyl) imidazo[1,2-a]pyrazin-5-yl)phenyl)-1H-tetrazol-5 (4H)-one, 14e The SEM group of compound 14d (236 mg, 0.360 mmol) was removed according to the procedures described in Example 10, Step F to obtain compound 14e as a white solid (110 mg, 63% yield). $^1$H-NMR (300 MHz, DMSO-d$_6$) δ (ppm): 8.35 (d, J=8.4 Hz, 1H), 8.08-7.99 (m, 4H), 7.84-7.77 (m, 4H), 7.64-7.56 (m, 2H), 7.47 (s, 1H), 4.23-4.11 (m, 4H), 3.81-3.69 (m, 4H), 3.31-3.25 (m, 4H). Mass Spectrum (LCMS, ESI pos.): Calcd. for $C_{28}H_{25}N_9O_2$: 520.2 (M+H). Found 520.1.

Following the procedures described in Example 14 above, and substituting suitably selected and substituted reagents, starting materials and conditions as would be readily apparent to those skilled in the art, the following representative compound of the present invention was prepared.

| Cpd | Characterization |
|---|---|
| 55 | (E)-1-(4-(8-Morpholino-2-(2-(quinolin-2-yl)vinyl)imidazo[1,2-a]pyrazin-5-yl)phenyl)-1H-tetrazol-5(4H)-one<br>$^1$H-NMR (300 MHz, DMSO-d$_6$) δ (ppm): 14.87 (br, 1H), 8.36 (d, J = 8.7 Hz, 2H), 8.31 (s, 1H) 8.15-8.11 (m, 2H), 8.00-7.87 (m, 6H), 7.80-7.65 (m, 2H), 7.60-7.52 (m, 1H), 7.51 (s, 1H), 4.39-4.21 (m, 4H), 3.89-3.76 (m, 4H).<br>Mass Spectrum (LCMS, ESI pos.): Calcd. for $C_{28}H_{23}N_9O_2$: 518.2 (M + H), Found 518.1. |

Example 15

N-Methanesulfonyl-5-[8-(morpholin-4-yl)-2-[(quinolin-2-yloxy)methyl]imidazo[1,2-a]pyrazin-5-yl]pyridine-2-carboxamide (Cpd 76)

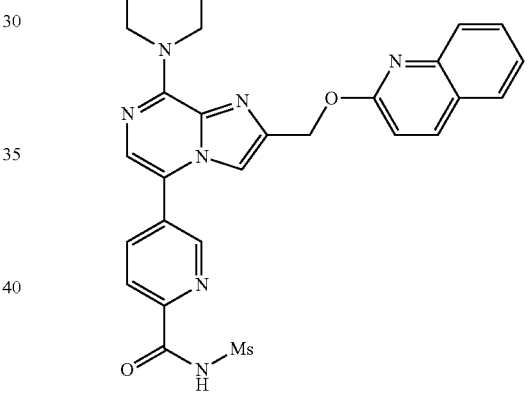

A. 4-(5-Bromo-2-((quinolin-2-yloxy)methyl)imidazo [1,2-a]pyrazin-8-yl)morpholine, 15a

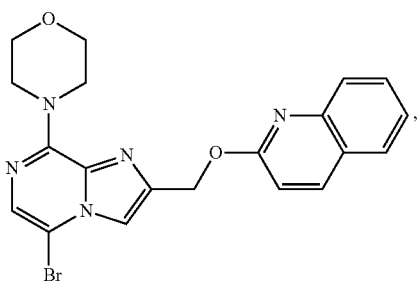

15a

Compound 1e (10.0 g, 30.4 mmol) was treated with 2-chloroquinoline using the reaction conditions described in Example 1, Step I to obtain compound 15a as a white solid

B. Methyl 5-[8-(morpholin-4-yl)-2-[(quinolin-2-yloxy)methyl]imidazo[1,2-a]pyrazin-5-yl]pyridine-2-carboxylate, 15b

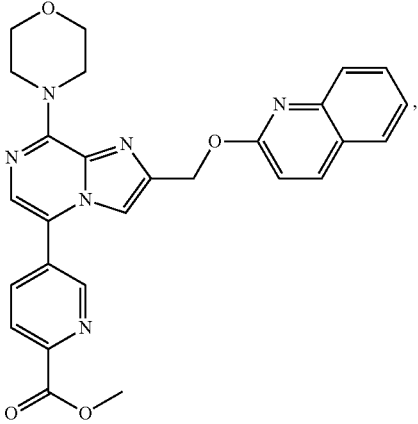

Compound 15a (1.50 g, 3.24 mmol) was subjected to Suzuki coupling conditions with methyl 5-(4,4,5,5-tetramethyl-1,3,2-dioxaborolan-2-yl)picolinate using the reaction conditions described in Example 1, Step G to obtain compound 15b as a yellow solid (600 mg, 35% yield). Mass Spectrum (LCMS, ESI pos.): Calcd. for $C_{27}H_{24}N_6O_4$: 497.2 (M+H). Found 497.2.

C. 5-[8-(Morpholin-4-yl)-2-[(quinolin-2-yloxy)methyl]imidazo[1,2-a]pyrazin-5-yl]pyridine-2-carboxylic acid, 15c

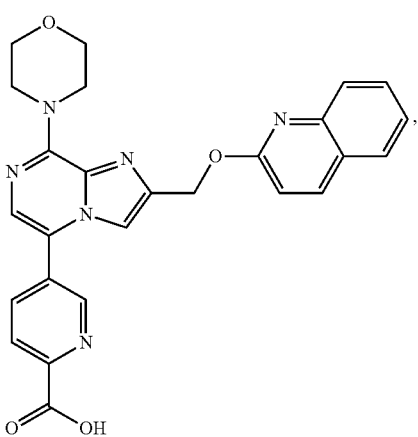

To a solution of compound 15b (500 mg, 0.960 mmol) in THF (20 mL) was added a solution of LiOH (100 mg, 4.18 mmol) in $H_2O$ (5 mL). The resulting solution was stirred at rt overnight, and then diluted with $H_2O$ (20 mL). The pH of the solution was adjusted to 3 with 2 N HCl solution. The resulting solids were collected by filtration and washed with $Et_2O$ to obtain compound 15c as a yellow solid (350 mg, 72% yield). Mass Spectrum (LCMS, ESI pos.): Calcd. for $C_{28}H_{23}N_9O_2$: 482.2 (M+H). Found 482.0.

D. N-Methanesulfonyl-5-[8-(morpholin-4-yl)-2-[(quinolin-2-yloxy)methyl]imidazo[1,2-a]pyrazin-5-yl]pyridine-2-carboxamide, Cpd 76

To a solution of compound 15c (400 mg, 0.790 mmol) in DCM (20 mL) was added methanesulfonamide (78.8 mg, 0.830 mmol), DCC (256 mg, 1.24 mmol) and 4-dimethylaminopyridine (152 mg, 1.24 mmol). The reaction mixture was stirred at rt overnight, and was quenched with $H_2O$ (40 mL). The resulting mixture was extracted with DCM (3×40 mL). The combined organic layers were washed with brine, dried over $Na_2SO_4$ and concentrated under reduced pressure. The resulting residue was purified by flash column chromatography on silica gel, eluting with DCM/MeOH (10:1 v/v). The title compound 76 was obtained as a yellow solid (307 mg, 69% yield). $^1$H-NMR (300 MHz, DMSO-$d_6$) δ (ppm): 8.99 (s, 1H), 8.27-8.19 (m, 3H), 8.08 (s, 1H), 7.89 (d, J=7.8 Hz, 1H), 7.79 (d, J=8.4 Hz, 1H), 7.68 (t, J=6.9 Hz, 1H), 7.56 (s, 1H), 7.47 (t, J=6.9 Hz, 1H), 7.05 (d, J=8.7 Hz, 1H), 5.58 (s, 2H), 4.41-4.20 (m, 4H), 3.88-3.71 (m, 4H), 3.05 (s, 3H). Mass Spectrum (LCMS, ESI pos.): Calcd. for $C_{27}H_{25}N_7O_5S$: 560.2 (M+H). Found 560.0.

Example 16

(E)-N-(4-(8-Morpholino-2-(2-(quinolin-2-yl)vinyl)imidazo[1,2-a]pyrazin-5-yl)phenylsulfonyl)acetamide trifluoroacetic acid salt (Cpd 69)

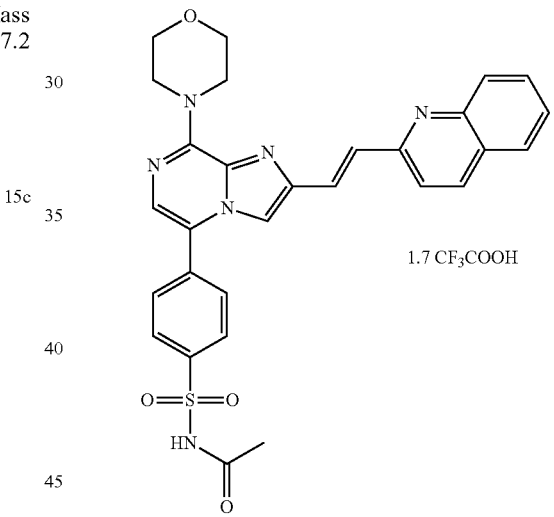

Compound 2b (800 mg, 1.83 mmol) was treated with 4-(N-acetylsulfamoyl)phenylboronic acid using the reaction conditions described in Example 1, Step G. The crude product was purified by Prep-HPLC with the following conditions (1#-Waters 2767-1): Column, SunFire Prep C18, 5 μm, 19*150 mm; mobile phase: water in 0.05% TFA and $CH_3CN$ (20% $CH_3CN$ up to 54% in 10 min, up to 100% in 2 min, down to 20% in 2 min); Detector, UV 254 nm. The title compound 69 was obtained as a light yellow solid (304 mg, 21% yield). $^1$H-NMR (300 MHz, DMSO-$d_6$) δ (ppm): 12.26 (s, 1H), 8.63 (d, J=9.0 Hz, 1H), 8.38 (s, 1H), 8.11-8.03 (m, 8H), 7.89 (t, J=7.2 Hz, 1H), 7.74-7.68 (m, 2H), 7.57 (s, 1H), 4.38-4.25 (m, 4H), 3.86-3.72 (m, 4H), 1.99 (s, 3H). Mass Spectrum (LCMS, ESI pos.): Calcd. for $C_{29}H_{26}N_6O_4S$: 555.2 (M+H). Found 555.0.

Example 17

(S)-1-(4-(8-Morpholino-2-(2-(quinolin-2-yl)ethyl)imidazo[1,2-a]pyrazin-5-yl)benzoyl)pyrrolidine-2-carboxylic acid trifluoroacetic acid salt (Cpd 35)

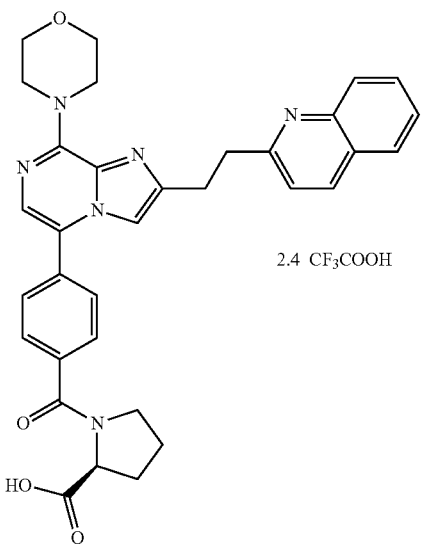 [SMILES: O=C(O)[C@@H]1CCCN1C(=O)c1ccc(-c2cnc(N3CCOCC3)c3nc(CCc4ccc5ccccc5n4)cn23)cc1]

2.4 CF₃COOH

A. (S)-tert-Butyl 1-(4-(4,4,5,5-tetramethyl-1,3,2-dioxaborolan-2-yl)benzoyl)pyrrolidine-2-carboxylate, 17a

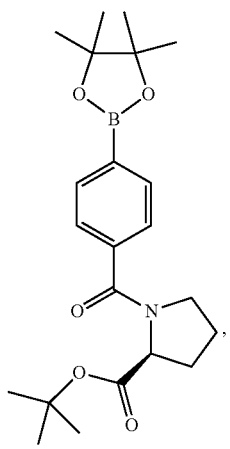
17a

To a solution of 4-(tetramethyl-1,3,2-dioxaborolan-2-yl)benzoic acid (2.00 g, 8.06 mmol) in DMF (20 mL) was added HATU (6.20 g, 16.3 mmol), (S)-tert-butyl pyrrolidine-2-carboxylate (2.00 g, 11.7 mmol) and DIPEA (4.20 g, 32.5 mmol). The reaction mixture was stirred at rt overnight, and was quenched with H₂O (20 mL). The resulting solution was extracted with DCM (3×100 mL). The combined organic layers were washed with brine, dried over Na₂SO₄ and concentrated under reduced pressure. The residue was purified by flash column chromatography on silica gel, eluting with EtOAc/petroleum ether (1:20-1:10 v/v) to obtain compound 17a as a yellow solid (1.40 g, 37% yield). Mass Spectrum (LCMS, ESI pos.): Calcd. for $C_{22}H_{32}BNO_5$: 402.2 (M+H). Found 402.1.

B. (S)-tert-Butyl 1-(4-(8-morpholino-2-(2-(quinolin-2-yl)ethyl)imidazo[1,2-a]pyrazin-5-yl)benzoyl)pyrrolidine-2-carboxylate, 17b

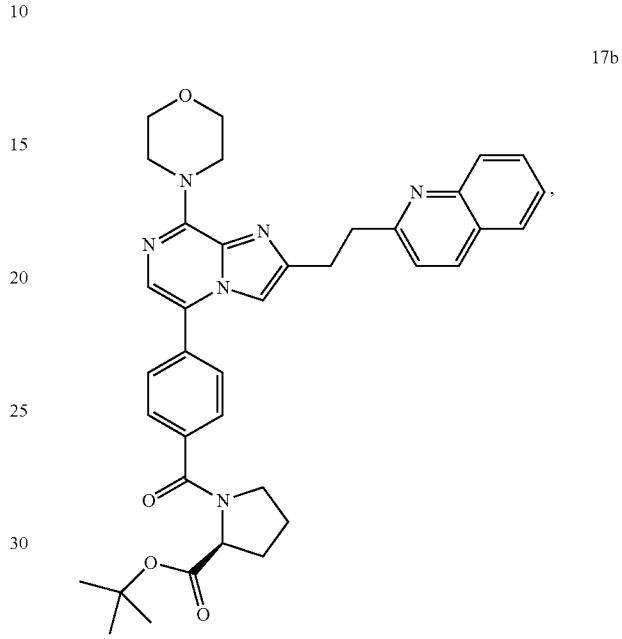
17b

Compound 3a (250 mg, 0.570 mmol) was subjected to Suzuki coupling conditions with (S)-tert-butyl 1-(4-(3,3,4,4-tetramethylborolan-1-yl)benzoyl)pyrrolidine-2-carboxylate (686 mg, 1.71 mmol) using the reaction conditions described in Example 1, Step G to obtain compound 17b as a brown solid (320 mg, 81% yield). Mass Spectrum (LCMS, ESI pos.): Calcd. for $C_{37}H_{40}N_6O_4$: 633.3 (M+H). Found 633.2.

C. (S)-1-(4-(8-Morpholino-2-(2-(quinolin-2-yl)ethyl)imidazo[1,2-a]pyrazin-5-yl)benzoyl)pyrrolidine-2-carboxylic acid trifluoroacetic acid salt, Cpd 35

A solution of compound 17b (350 mg, 0.550 mmol) in TFA/DCM (10 mL, 1:4 v/v) was stirred at rt for 3 h. Solvent was evaporated and Et₂O (30 mL) was added. The resulting solids were collected by filtration and washed with Et₂O to obtain the title compound 35 as a yellow solid (142 mg, 30% yield). ¹H-NMR (400 MHz, DMSO-d₆) δ (ppm): 9.01 (d, J=8.8 Hz, 1H), 8.31 (d, J=8.0 Hz, 1H), 8.16-8.09 (m, 2H), 8.02 (d, J=8.8 Hz, 1H), 7.94-7.90 (m, 1H), 7.80 (s, 1H), 7.72-7.53 (m, 4H), 7.38-7.34 (m, 1H), 4.44-4.35 (m, 1H), 3.81-3.73 (m, 4H), 3.61-3.50 (m, 4H), 3.45-3.31 (m, 6H), 2.43-2.28 (m, 1H), 1.90-1.78 (s, 3H). Mass Spectrum (LCMS, ESI pos.): Calcd. for $C_{33}H_{32}N_6O_4$: 577.2 (M+H). Found 577.1.

Following the procedures described in Example 17 above, and substituting suitably selected and substituted reagents, starting materials and conditions as would be readily apparent to those skilled in the art, the following representative compounds of the present invention were prepared.

| Cpd | Characterization |
|---|---|
| 34 | (S)-3-Methyl-2-(4-(8-morpholino-2-(2-(quinolin-2-yl)ethyl)imidazo[1,2-a]pyrazin-5-yl)benzamido)butanoic acid trifluoroacetic acid salt<br>$^1$H-NMR (300 MHz, DMSO-$d_6$ + $D_2O$) δ (ppm): 8.98 (d, J = 8.7 Hz, 1H), 8.58 (d, J = 7.8 Hz, 1H), 8.30 (d, J = 8.4 Hz, 1H), 8.16-8.12 (m, 2H), 8.09-8.04 (m, 3H), 8.03-7.80 (m, 1H), 7.92 (s, 1H), 7.89 (d, J = 6.9 Hz, 2H), 7.39 (s, 1H), 4.33-4.26 (m, 1H), 3.89-379 (m, 4H), 3.59-3.52 (m, 2H), 3.50-3.38 (m, 4H), 3.38-3.30 (m, 2H), 2.28-2.18 (m, 1H), 1.05-0.95 (m, 6H). Mass Spectrum (LCMS, ESI pos.): Calcd. for $C_{33}H_{34}N_6O_4$: 579.3 (M + H), Found 579.1. |
| 44 | (S,E)-3-Methyl-2-(4-(8-morpholino-2-(2-(quinolin-2-yl)vinyl)imidazo[1,2-a]pyrazin-5-yl)benzamido)butanoic acid trifluoroacetic acid salt<br>$^1$H-NMR (300 MHz, DMSO-$d_6$) δ (ppm): 8.58 (d, J = 8.1 Hz, 2H), 8.30 (s, 1H), 8.13-7.99 (m, 6H), 7.89-7.81 (m, 3H), 7.72-7.67 (m, 2H), 7.52 (s, 1H), 4.41-4.30 (m, 5H), 3.90-3.80 (m, 4H), 2.27-2.21 (m, 1H), 1.05-0.96 (m, 6H). Mass Spectrum (LCMS, ESI pos.): Calcd. for $C_{33}H_{32}N_6O_4$: 577.2 (M + H), Found 577.1. |
| 45 | (S,E)-1-(4-(8-Morpholino-2-(2-(quinolin-2-yl)vinyl)imidazo[1,2-a]pyrazin-5-yl) benzoyl)pyrrolidine-2-carboxylic acid trifluoroacetic acid salt<br>$^1$H-NMR (400 MHz, DMSO-$d_6$ + $D_2O$) δ (ppm): 8.66 (d, J = 8.8 Hz, 1H), 8.30 (s, 1H), 8.13-8.04 (m, 4H), 7.96-7.87 (m, 1H), 7.80-7.67 (m, 6H), 7.50-7.45 (m, 1H), 4.50-4.40 (m, 1H), 4.35-4.27 (m, 4H), 3.87-3.78 (m, 4H), 3.62-3.58 (m, 2H), 2.36-2.28 (m, 1H), 1.93-1.85 (m, 3H). Mass Spectrum (LCMS, ESI pos.): Calcd. for $C_{33}H_{30}N_6O_4$: 575.2 (M + H), Found 575.0. |
| 46 | 2-(4-(8-Morpholino-2-(2-(quinolin-2-yl)ethyl)imidazo[1,2-a]pyrazin-5-yl)benzamido)acetic acid<br>$^1$H-NMR (400 MHz, DMSO-$d_6$) δ (ppm): 8.26 (d, J = 8.4 Hz, 1H), 8.08-7.82 (m, 4H), 7.74-7.67 (m, 2H), 7.58-7.53 (m, 3H), 7.48 (d, J = 8.4 Hz, 1H), 7.37 (s, 1H), 4.19-4.01 (m, 4H), 3.75-3.62 (m, 4H), 3.62-3.50 (m, 2H), 3.35-3.17 (m, 5H). Mass Spectrum (LCMS, ESI pos.): Calcd. for $C_{30}H_{28}N_6O_4$: 537.2 (M + H), Found 537.1. |
| 50 | (E)-2-(4-(8-Morpholino-2-(2-(quinolin-2-yl)vinyl)imidazo[1,2-a]pyrazin-5-yl)benzamido)acetic acid<br>$^1$H-NMR (300 MHz, DMSO-$d_6$) δ (ppm): 8.90 (br, 1H), 8.36 (d, 1H), 8.30 (s, 1H), 8.10 (d, J = 7.8 Hz, 2H), 8.07-7.97 (m, 2H), 7.91-7.84 (m, 4H), 7.77-7.71 (m, 1H), 7.73-7.67 (m, 1H), 7.65-7.55 (m, 1H), 7.51 (s, 1H), 4.40-4.32 (m, 4H), 4.05-3.95 (m, 2H), 3.90-3.81 (m, 4H). Mass Spectrum (LCMS, ESI pos.): Calcd. for $C_{30}H_{26}N_6O_4$: 535.2 (M + H), Found 535.1. |

Example 18

(E)-1-(4-(8-Morpholino-2-(2-(quinolin-2-yl)vinyl)imidazo[1,2-a]pyrazin-5-yl)phenyl)piperidine-4-carboxylic acid trifluoroacetic acid salt (Cpd 14)

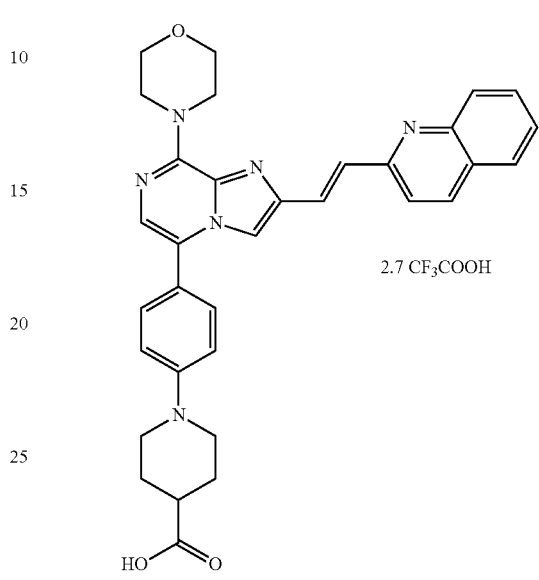

A. Ethyl 1-(4-nitrophenyl)piperidine-4-carboxylate, 18a

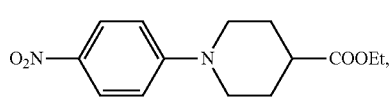

In a solution of 1-fluoro-4-nitro benzene (3.00 g, 21.3 mmol) in DMSO (30 mL) was added ethyl piperidine-4-carboxylate (5.01 g, 31.9 mmol) and $K_2CO_3$ (5.87 g, 42.5 mmol). The resulting mixture was stirred at 100° C. for 8 h. After cooling to rt, the reaction was quenched with $H_2O$ (70 mL). The resulting mixture was extracted with EtOAc (3×100 mL). The combined organic layers were washed with brine, dried over $Na_2SO_4$ and concentrated under reduced pressure. The residue was purified by flash column chromatography on silica gel, eluting with EtOAc/petroleum ether (1:2 v/v) to obtain compound 18a as a yellow solid (5.00 g, 80% yield). Mass Spectrum (LCMS, ESI pos.): Calcd. for $C_{14}H_{18}N_2O_4$: 279.1 (M+H). Found 279.1.

B. Ethyl 1-(4-aminophenyl)piperidine-4-carboxylate, 18b

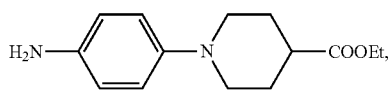

To a solution of compound 18a (15.0 g, 51.2 mmol) in MeOH (100 mL) was added Fe (9.06 g, 162 mmol) and saturated NH$_4$Cl solution (100 mL). The resulting solution was stirred at 80° C. for 5 h. After cooling to rt, the mixture was extracted with EtOAc (200 mL). The organic layer was washed with brine, dried over Na$_2$SO$_4$ and concentrated under reduced pressure. The residue was purified by flash column chromatography on silica gel, eluting with EtOAc/petroleum ether (1:5 v/v) to obtain compound 18b as a black solid (13.0 g, 97% yield). Mass Spectrum (LCMS, ESI pos.): Calcd. for C$_{14}$H$_{20}$N$_2$O$_2$: 249.2 (M+H). Found 249.0.

C. Ethyl 1-[4-(tetramethyl-1,3,2-dioxaborolan-2-yl)phenyl]piperidine-4-carboxylate, 18c

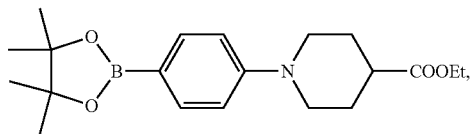

To a solution of 4,4,5,5-tetramethyl-2-(tetramethyl-1,3,2-dioxaborolan-2-yl)-1,3,2-dioxaborolane (6.14 g, 24.2 mmol) in ACN (50 mL) was added BPO (97.6 mg, 0.380 mmol). The resulting solution was stirred at rt for 10 min before the addition of compound 18b (5.00 g, 19.1 mmol) and t-BuONO (3.11 g, 30.2 mmol). The reaction mixture was stirred at rt for 4 h, and was diluted with H$_2$O. The mixture was extracted with EtOAc (200 mL). The organic layer was washed with brine, dried over Na$_2$SO$_4$ and concentrated under reduced pressure. The residue was purified by flash column chromatography on silica gel, eluting with EtOAc/petroleum ether (1:30 v/v) to obtain compound 18b as a yellow solid (3.00 g, 41% yield). Mass Spectrum (LCMS, ESI pos.): Calcd. for C$_{20}$H$_{30}$BNO$_4$: 360.2 (M+H). Found 360.2.

D. (E)-Ethyl 1-(4-(8-morpholino-2-(2-(quinolin-2-yl)vinyl)imidazo[1,2-a]pyrazin-5-yl)phenyl)piperidine-4-carboxylate, 18d

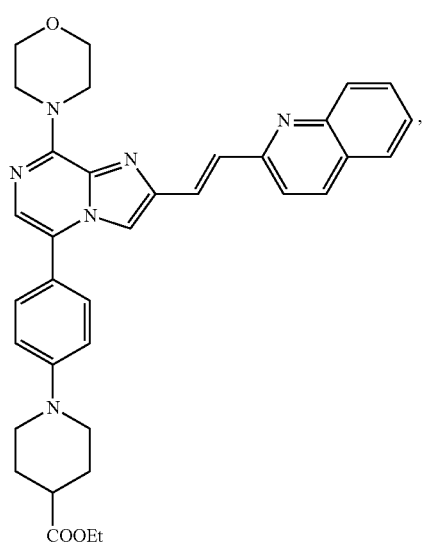

Compound 2b (350 mg, 0.760 mmol) was subjected to Suzuki coupling conditions with ethyl 1-[4-(tetramethyl-1,3, 2-dioxaborolan-2-yl)phenyl]piperidine-4-carboxylate (881 mg, 2.28 mmol) using the reaction conditions described in Example 1, Step G to obtain compound 18d as a brown solid (200 mg, 42% yield). Mass Spectrum (LCMS, ESI pos.): Calcd. for C$_{35}$H$_{36}$N$_6$O$_3$: 589.3 (M+H). Found 589.2.

E. (E)-1-(4-(8-Morpholino-2-(2-(quinolin-2-yl)vinyl)imidazo[1,2-a]pyrazin-5-yl)phenyl)piperidine-4-carboxylic acid trifluoroacetic acid salt, Cpd 14

Compound 18d (200 mg, 0.320 mmol) was hydrolyzed with LiOH using the reaction conditions described in Example 15, Step C to obtain the title compound 14 as an orange solid (48.9 mg, 22% yield). $^1$H-NMR (300 MHz, DMSO-d$_6$+D$_2$O) δ (ppm): 8.84 (d, J=8.7 Hz, 1H), 8.27-8.18 (m, 4H), 8.17-8.09 (m, 1H), 8.07-7.94 (m, 1H), 7.82-7.71 (m, 2H), 7.55 (d, J=8.7 Hz, 2H), 7.36 (s, 1H), 7.20 (d, J=8.7 Hz, 2H), 4.35-4.28 (m, 4H), 3.92-3.78 (m, 6H), 3.65 (m, 2H), 3.05-2.94 (m, 2H), 2.02-1.93 (m, 2H), 1.80-1.64 (m, 2H). Mass Spectrum (LCMS, ESI pos.): Calcd. for C$_{33}$H$_{32}$N$_6$O$_3$: 561.3 (M+H). Found 561.3.

Following the procedures described in Example 18 above, and substituting suitably selected and substituted reagents, starting materials and conditions as would be readily apparent to those skilled in the art, the following representative compound of the present invention was prepared.

| Cpd | Characterization |
|---|---|
| 15 | (S,E)-3-Methyl-2-(4-(8-morpholino-2-(2-(quinolin-2-yl)vinyl)imidazo[1,2-a]pyrazin-5-yl)phenylamino)butanoic acid trifluoroacetic acid salt<br>$^1$H-NMR (300 MHz, DMSO-d$_6$) δ (ppm): 8.75 (d, J = 8.4 Hz, 1H), 8.23 (s, 1H), 8.18-8.09 (m, 4H), 7.99-7.92 (m, 1H), 7.77-7.70 (m, 2H), 7.41 (d, J = 8.1 Hz, 2H), 7.32 (s, 1H), 6.84 (d, J = 8.1 Hz, 2H), 4.35-4.23 (m, 4H), 3.94-3.83 (m, 4H), 3.82-3.74 (m, 1H), 2.17-2.10 (m, 1H), 1.08-1.02 (m, 6H).<br>Mass Spectrum (LCMS, ESI pos.): Calcd. for C32H32N6O3: 549.3 (M + H), Found 549.1. |

Example 19

(E)-4-(5-(6-(piperazin-1-yl)pyridin-3-yl)-2-(2-(quinolin-2-yl)vinyl)imidazo[1,2-a]pyrazin-8-yl)morpholine trifluoroacetic acid salt (Cpd 105)

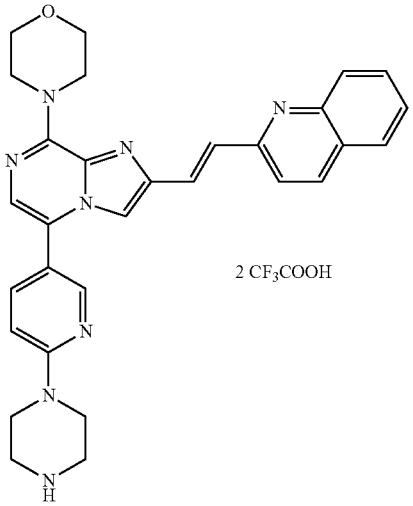 [SMILES: C(=C\c1cn2c(-c3ccc(N4CCNCC4)nc3)cnc(N3CCOCC3)c2n1)/c1ccc2ccccc2n1]

121

A. tert-Butyl 4-(5-(2-formyl-8-morpholinoimidazo[1,2-a]pyrazin-5-yl)pyridin-2-yl)piperazine-1-carboxylate, 19a

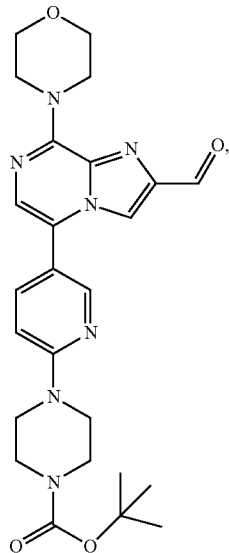

19a

To a suspension of compound 2a (200 mg, 0.643 mmol) and tert-butyl 4-(5-(4,4,5,5-tetramethyl-1,3,2-dioxaborolan-2-yl)pyridin-2-yl)piperazine-1-carboxylate (300 mg, 0.771 mmol) in 1,4-dioxane (10 mL) was added $Na_2CO_3$ solution (2 M, 1.61 mL, 3.21 mmol). The mixture was purged with Argon gas before the addition of $PdCl_2(dppf)$ (47.0 mg, 0.0643 mmol). The reaction mixture was stirred at 80° C. for 2 h. After cooling to rt, water (50 mL) was added and the mixture was extracted with DCM (2×50 mL). The combined organic layers were washed with brine, dried over $Na_2SO_4$, filtered and concentrated. The residue was purified by flash column chromatography on silica gel, eluting with EtOAc/heptane (3:2 v/v) to obtain compound 19a as a yellow solid (276 mg, 87% yield). Mass Spectrum (LCMS, ESI pos.): Calcd. for $C_{25}H_{31}N_7O_4$: 494.2 (M+H). Found 494.2.

B. (E)-tert-Butyl 4-(5-(8-morpholino-2-(2-(quinolin-2-yl)vinyl)imidazo[1,2-a]pyrazin-5-yl)pyridin-2-yl)piperazine-1-carboxylate, 19b

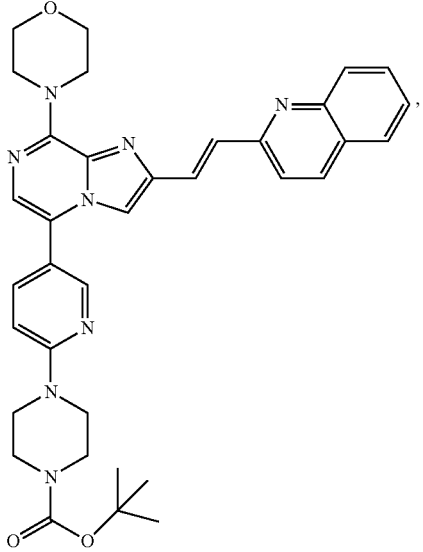

19b

122

To a solution of compound 19a (50.0 mg, 0.101 mmol) in DMF (3 mL) was added 2-methylquinoline (13.2 μL, 0.101 mmol) and chlorotrimethylsilane (38.6 μL, 0.304 mmol). The reaction mixture was stirred in a 10 mL sealed tube for 2 h at 80° C. After cooling to rt, the reaction mixture was poured into water (20 mL). The mixture was adjusted to basic using saturated $NaHCO_3$ solution, and was extracted with DCM (2×20 mL). The combined organic layers were washed with brine, dried over $MgSO_4$, filtered and concentrated. Compound 19b was obtained as a yellow solid (40.0 mg, 64% yield). Mass Spectrum (LCMS, ESI pos.): Calcd. for $C_{35}H_{38}N_8O_3$: 619.3 (M+H). found: 619.3.

C. (E)-4-(5-(6-(piperazin-1-yl)pyridin-3-yl)-2-(2-(quinolin-2-yl)vinyl)imidazo[1,2-a]pyrazin-8-yl)morpholine trifluoroacetic acid salt, Cpd 105

The Boc group of compound 19b (40.0 mg, 0.0646 mmol) was removed using the reaction conditions described in Example 13, Step C. The title compound 105 was obtained as a red solid (28.2 mg, 58% yield). $^1$H-NMR (400 MHz, $CDCl_3$) δ (ppm): 8.37 (d, J=2.0 Hz, 1H), 8.14 (d, J=8.6 Hz, 1H), 8.06 (d, J=8.2 Hz, 1H), 7.79 (d, J=7.4 Hz, 1H), 7.61-7.75 (m, 5H), 7.50 (t, J=7.0 Hz, 1H), 7.28 (d, J=9.8 Hz, 2H), 6.79 (d, J=9.0 Hz, 1H), 4.29-4.42 (m, 4H), 3.90-3.99 (m, 4H), 3.57-3.69 (m, 4H), 2.95-3.11 (m, 4H). Mass Spectrum (LCMS, ESI pos.) Calcd. For $C_{30}H_{30}N_8O$: 519.3 (M+H). Found 519.2.

Following the procedures described in Example 19 above, and substituting suitably selected and substituted reagents, starting materials and conditions as would be readily apparent to those skilled in the art, the following representative compounds of the present invention were prepared.

| Cpd | Characterization |
|---|---|
| 104 | (E)-4-(5-(6-(Piperazin-1-yl)pyridin-3-yl)-2-(2-(quinazolin-2-yl)vinyl)imidazo[1,2-a]pyrazin-8-yl)morpholine <br> $^1$H-NMR (400 MHz, $CDCl_3$) δ (ppm): 9.45 (s, 1H), 8.42 (d, J = 2.0 Hz, 1H), 8.15 (d, J = 15.7 Hz, 1H), 8.05 (s, 1H), 7.94-8.02 (m, 2H), 7.73-7.86 (m, 2H), 7.66-7.74 (m, 1H), 6.94 (d, J = 9.0 Hz, 2H), 6.53 (d, J = 5.9 Hz, 2H), 6.35 (s, 1H), 4.46-4.60 (m, 4H), 3.99-4.21 (m, 8H), 3.32-3.47 (m, 4H). Mass Spectrum (LCMS, ESI pos.) Calcd. For $C_{29}H_{29}N_9O$: 520.3 (M + H), Found 520.3. |
| 103 | (E)-4-(5-(6-(Piperazin-1-yl)pyridin-3-yl)-2-(2-(pyrimidin-2-yl)vinyl)imidazo[1,2-a]pyrazin-8-yl)morpholine <br> $^1$H-NMR (400 MHz, $CDCl_3$) δ (ppm): 8.76 (d, J = 4.7 Hz, 2H), 8.39 (d, J = 2.3 Hz, 1H), 7.95 (d, J = 15.7 Hz, 1H), 7.71-7.77 (m, 1H), 7.59 (d, J = 15.7 Hz, 1H), 7.35 (s, 1H), 7.20 (t, J = 4.9 Hz, 1H), 6.89 (d, J = 8.6 Hz, 1H), 4.42-4.59 (m, 4H), 3.92-4.07 (m, 8H), 3.29-3.39 (m, 4H). Mass Spectrum (LCMS, ESI pos.) Calcd. For $C_{25}H_{27}N_9O$: 470.2 (M + H), Found 470.2. |

Example 20

4-(5-(6-(piperazin-1-yl)pyridin-3-yl)-2-(2-(quinolin-2-yl)ethyl)imidazo[1,2-a]pyrazin-8-yl)morpholine trifluoroacetic acid salt (Cpd 102)

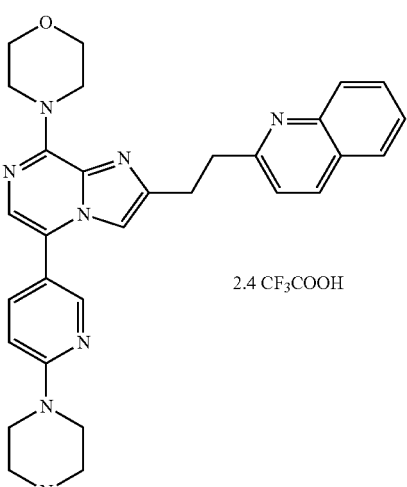

2.4 CF₃COOH

A. tert-Butyl 4-(5-(8-morpholino-2-(2-(quinolin-2-yl)ethyl)imidazo[1,2-a]pyrazin-5-yl)pyridin-2-yl)piperazine-1-carboxylate, 20a

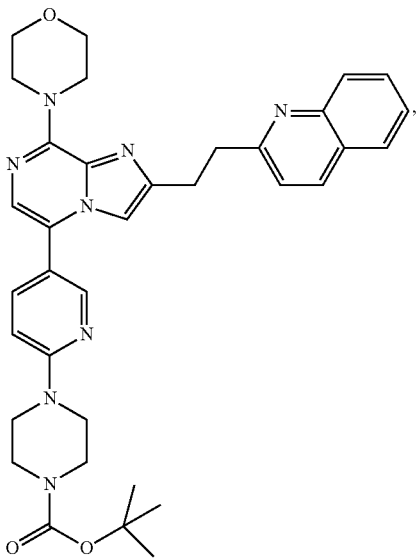

20a

A solution of compound 19b (130 mg, 0.210 mmol) in MeOH (50 mL) was evacuated and back flushed with Argon gas three times before Pd/C (10%, 100 mg) was added. The mixture was evacuated and back flushed with H₂, and was stirred at rt under H₂ (in a balloon) for 3 h. The reaction mixture was filtered through a pad of diatomaceous earth, and the filtrate was concentrated under reduced pressure to leave a brown oil, which was purified by flash column chromatography on silica gel, eluting with EtOAc/heptane (0-100%). Compound 20a was obtained as an off-white solid (69.0 mg, 53% yield). Mass Spectrum (LCMS, ESI pos.): Calcd. for C₃₅H₄₀N₈O₃: 621.3 (M+H). found: 621.4.

B. 4-(5-(6-(piperazin-1-yl)pyridin-3-yl)-2-(2-(quinolin-2-yl)ethyl)imidazo[1,2-a]pyrazin-8-yl)morpholine trifluoroacetic acid salt, Cpd 102

The Boc group of compound 20a (69.0 mg, 0.111 mmol) was removed following the procedures as described in Example 13, Step C. The title compound 102 was obtained as a yellow solid (80.0 mg, 91% yield). ¹H-NMR (400 MHz, CDCl₃) δ (ppm): 8.72 (d, J=8.6 Hz, 1H), 8.46 (d, J=8.6 Hz, 1H), 8.30 (d, J=2.0 Hz, 1H), 8.00-8.14 (m, 2H), 7.82-7.93 (m, 1H), 7.69-7.82 (m, 2H), 7.58 (s, 1H), 7.31 (s, 1H), 6.88 (d, J=9.0 Hz, 1H), 4.12-4.25 (m, 4H), 3.89-4.03 (m, 4H), 3.78-3.86 (m, 4H), 3.75 (t, J=7.6 Hz, 2H), 3.35-3.58 (m, 2H), 3.23-3.35 (m, 4H). Mass Spectrum (LCMS, ESI pos.) Calcd. For C₃₀H₃₂N₈O: 521.3 (M+H). Found 521.3.

Example 21

N-(8-Morpholino-5-(6-(piperazin-1-yl)pyridin-3-yl)imidazo[1,2-a]pyrazin-2-yl)quinoline-2-carboxamide hydrochloric acid salt (Cpd 125)

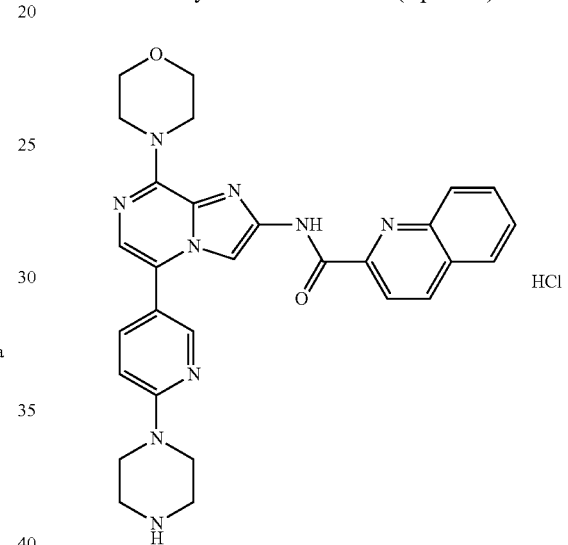

HCl

A. Ethyl 5-bromo-8-morpholinoimidazo[1,2-a]pyrazine-2-carboxylate, 21a

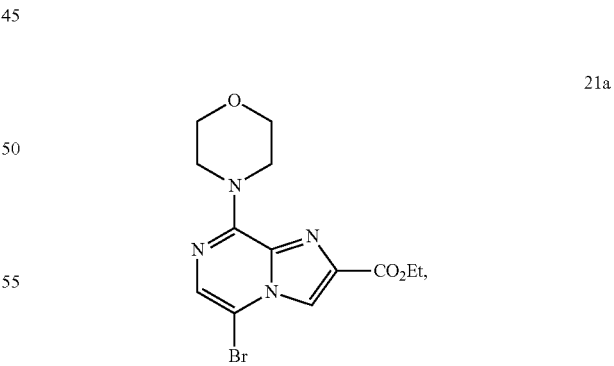

21a

To a solution of compound 1c (3.2 g, 9.0 mmol) in DCM (100 mL) at 0° C. was added NBS (1.6 g, 9.0 mmol) portionwise. The reaction mixture was allowed to stir at rt for 10 min, and subsequently was washed with a saturated aqueous sodium bicarbonate (2×100 mL). The organic layer was separated, dried over Na₂SO₄ and concentrated under reduced pressure to give compound 21a as an off-white solid. Mass Spectrum (LCMS, ESI pos.) Calcd. For C₁₃H₁₅BrN₄O₃: 356.2 (M+H). Found 356.1.

B.
5-Bromo-8-morpholinoimidazo[1,2-a]pyrazin-2-amine, 21b

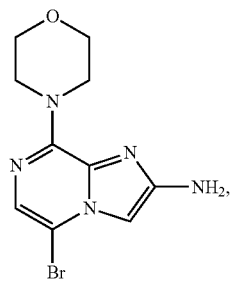

21b

A mixture of compound 21a (1.6 g, 4.5 mmol) and hydrazine monohydrate (2.6 mL, 27 mmol) in EtOH (20 mL) was heated at reflux overnight. An off-white solid formed, the collected by filtration and dried under reduced pressure to give 5-bromo-8-morpholinoimidazo[1,2-a]pyrazine-2-carbohydrazide which was directly used in next step without further purification.

A stirred solution of 5-bromo-8-morpholinoimidazo[1,2-a]pyrazine-2-carbohydrazide (1.5 g, 4.3 mmol, as prepared above) in 2N HCl (5 mL) was diluted with cold $H_2O$ (40 mL). An aqueous solution of $NaNO_2$ (450 mg, 6.5 mmol) in water (2 mL) was then added dropwise while maintaining the temperature below 15° C. The mixture was stirred at rt for 2 h and treated with $NaN_3$ (432 mg, 6.50 mmol) in water (10 mL). The resulting mixture was stirred at rt for 15 min, adjusted to pH 7 with aqueous $Na_2CO_3$ and extracted with DCM (3×20 mL). The combined DCM layers were dried over $Na_2SO_4$ and concentrated under reduced pressure. The crude product obtained was suspended in EtOH (50 mL) and heated at refluxed for 4.5 h. The reaction mixture was allowed to cool to rt, the solvent was removed under reduced pressure, and the residue obtained was purified by flash column chromatography on silica gel (4:1 DCM/EtOAc) to give ethyl (5-bromo-8-morpholinoimidazo[1,2-a]pyrazin-2-yl)carbamate.

A suspension of ethyl (5-bromo-8-morpholinoimidazo[1,2-a]pyrazin-2-yl)carbamate (1.2 g, as prepared above) in 5 N aqueous NaOH was heated at reflux for 18 h. The reaction mixture was allowed to cool to rt, diluted with water (50 mL) and extracted with DCM (3×50 mL). The combined DCM layers were dried over $Na_2SO_4$ and concentrated under reduced pressure to give compound 21b, which was dried under reduced pressure overnight and used in next step without further purification. Mass Spectrum (LCMS, ESI pos.) Calcd. For $C_{10}H_{12}BrN_5O$: 298.0 (M+H). Found 298.1.

C. N-(5-Bromo-8-morpholinoimidazo[1,2-a]pyrazin-2-yl)quinoline-2-carboxamide, 21c

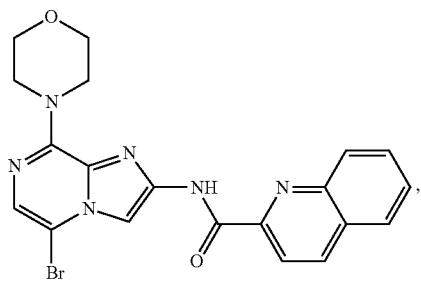

21c

To a solution of quinaldic acid (236 mg, 1.36 mmol) in DCM (10 mL) were added HATU (519 mg, 1.36 mmol) and DIEA (201 μL, 1.15 mmol) at 0° C. The reaction mixture was stirred for 0.5 h at 0° C. and treated with compound 21b (313 mg, 1.04 mmol). The resulting mixture was stirred at rt overnight. The solids formed were collected by filtration, and the organic phase was washed with saturated aqueous $NH_4Cl$ (20 mL). The organic layer was dried over $Na_2SO_4$ and concentrated under reduced pressure. The resulting residue was purified by flash column chromatography on silica gel (9:1 DCM/EtOAc) to give compound 21c. Mass Spectrum (LCMS, ESI pos.) Calcd. for $C_{20}H_{17}BrN_6O_2$: 453.0 (M+H). Found 453.1.

D. tert-Butyl 4-(5-(8-morpholino-2-(quinoline-2-carboxamido)imidazo[1,2-a]pyrazin-5-yl)pyridin-2-yl)piperazine-1-carboxylate, 21d

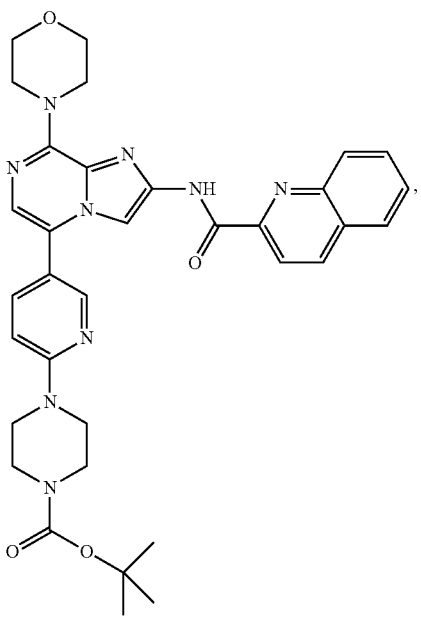

21d

Compound 21d was prepared from compound 21c and tert-butyl 4-(5-(4,4,5,5-tetramethyl-1,3,2-dioxaborolan-2-yl)pyridin-2-yl)piperazine-1-carboxylate using the reaction conditions described in Example 1, Step G, and substituting $K_2CO_3$ as the base. Mass Spectrum (LCMS, ESI pos.) Calcd. For $C_{34}H_{37}N_9O_4$: 636.3 (M+H). Found 636.4.

E. N-(8-Morpholino-5-(6-(piperazin-1-yl)pyridin-3-yl)imidazo[1,2-a]pyrazin-2-yl)quinoline-2-carboxamide hydrochloric acid salt, Cpd 125

To a solution of compound 21d (170 mg, 0.26 mmol) in DCM (6.8 mL), TFA (2.2 mL) was added. The resulting mixture was stirred at rt for 1 h and concentrated under reduced pressure. The residue obtained was dissolved in MeOH (20 mL) and passed through a MeOH pre-washed Bio-Rad AG-2X8 Cl-exchange column (50 g). The eluent was concentrated and dried under reduced pressure to obtain the title compound 125. $^1$H-NMR (400 MHz, DMSO-$d_6$) δ (ppm): 11.11 (s, 1H), 9.19 (br. s., 2H), 8.66 (d, J=8.2 Hz, 1H), 8.43 (d, J=2.3 Hz, 1H), 8.29 (d, J=8.6 Hz, 1H), 8.20 (d, J=8.6 Hz, 1H), 8.10-8.16 (m, 2H), 8.00 (dd, J=8.8, 2.5 Hz, 1H), 7.91-7.97 (m, 1H), 7.78 (t, J=8.0 Hz, 1H), 7.45 (s, 1H), 7.20 (d, J=9.0 Hz, 1H), 4.22 (d, J=3.9 Hz, 4H), 3.87-3.94 (m, 4H), 3.79-3.86 (m, 4H), 3.24 (none, 4H). Mass Spectrum (LCMS, ESI pos.) Calcd. For $C_{29}H_{29}N_9O_2$: 536.2 (M+H). Found 536.3.

Example 22

4-(5-(6-(Piperazin-1-yl)pyridin-3-yl)-2-((quinazolin-2-yloxy)methyl)imidazo[1,2-a]pyrazin-8-yl)morpholine trifluoroacetic acid salt (Cpd 124)

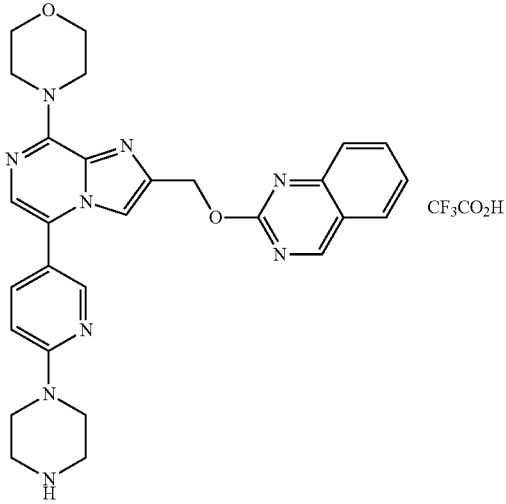

A. 4-(2-((Quinazolin-2-yloxy)methyl)imidazo[1,2-a]pyrazin-8-yl)morpholine, 22a

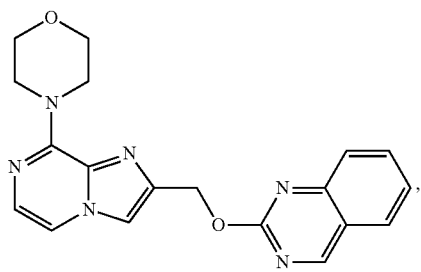

To a solution of compound 1d (600.0 mg, 2.50 mmol) in THF (10 mL) was added 18-crown-6 (677 mg, 2.60 mmol), followed by potassium tert-butoxide (575 mg, 5.12 mmol). The reaction mixture was stirred at rt for 10 min and treated with 2-chloroquinazoline (632 mg, 3.84 mmol). The resulting mixture was stirred for 10 more min at rt and then at 120° C. for 1 h. The reaction mixture was then allowed to cool to rt, diluted with 20 mL of DCM and 20 mL of saturated aqueous NH$_4$Cl. The organic layer was separated, dried over Na$_2$SO$_4$, and concentrated. The residue obtained was purified by flash column chromatography on silica gel (1:0-4:1 DCM/EtOAc) to obtain a white solid. The solid was then suspended in diethyl ether (50 mL) and sonicated for 5 min, before collecting by filtration to yield compound 22a. Mass Spectrum (LCMS, ESI pos.) Calcd. For $C_{19}H_{18}N_6O_2$: 363.1 (M+H). Found 363.1.

B. 4-(5-Bromo-2-((quinazolin-2-yloxy)methyl)imidazo[1,2-a]pyrazin-8-yl)morpholine, 22b

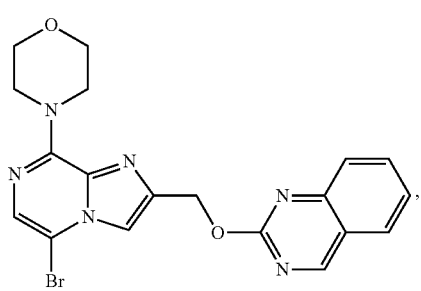

Compound 22a was brominated using the reaction conditions described in Example 1, Step E to obtain compound 22b. Mass Spectrum (LCMS, ESI pos.) Calcd. For $C_{19}H_{17}BrN_6O_2$: 441.0 (M+H). Found 441.1.

C. 4-(5-(6-(piperazin-1-yl)pyridin-3-yl)-2-((quinazolin-2-yloxy)methyl)imidazo[1,2-a]pyrazin-8-yl)morpholine trifluoroacetic acid salt, Cpd 124

Compound 22b was subjected to Suzuki coupling conditions with tert-butyl 4-(5-(4,4,5,5-tetramethyl-1,3,2-dioxaborolan-2-yl)pyridin-2-yl)piperazine-1-carboxylate using the reaction conditions described in Example 1, Step G, and substituting K$_2$CO$_3$ as the base. The resulting product, tert-butyl 4-(5-(8-morpholino-2-((quinazolin-2-yloxy)methyl)imidazo[1,2-a]pyrazin-5-yl)pyridin-2-yl)piperazine-1-carboxylate, was subjected to deprotection of the BOC group as described in Example 13, Step C to obtain the title compound. $^1$H-NMR (400 MHz, CD$_3$OD) δ (ppm): 9.38 (s, 1H), 8.41 (d, J=2.0 Hz, 1H), 8.02-8.08 (m, 2H), 7.93-7.98 (m, 1H), 7.90 (dd, J=8.8, 2.5 Hz, 1H), 7.83 (d, J=8.6 Hz, 1H), 7.59 (t, J=7.0 Hz, 1H), 7.24 (s, 1H), 7.12 (d, J=9.0 Hz, 1H), 5.72 (s, 2H), 4.36-4.41 (m, 4H), 3.94 (dt, J=16.8, 5.1 Hz, 8H), 3.38 (br. s., 4H). Mass Spectrum (LCMS, ESI pos.) Calcd. For $C_{28}H_{29}N_9O_2$: 524.2 (M+H). Found 524.3.

Example 23

4-(5-(6-(piperazin-1-yl)pyridin-3-yl)-2-((pyrimidin-2-yloxy)methyl)imidazo[1,2-a]pyrazin-8-yl)morpholine trifluoroacetic acid salt (Cpd 116)

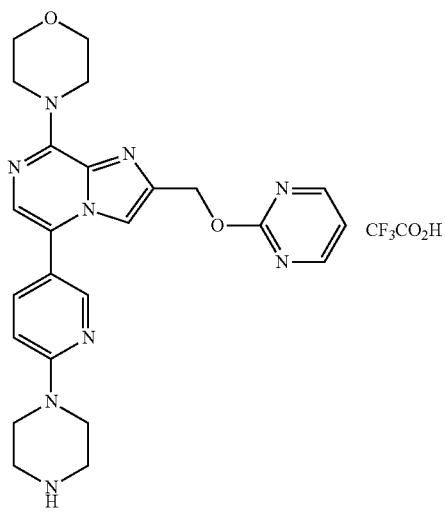 [SMILES: c1cnc(OCc2cn3c(-c4ccc(N5CCNCC5)nc4)cnc(N4CCOCC4)c3n2)nc1 ; "CF3CO2H"]

129

A. tert-Butyl 4-(5-(2-(hydroxymethyl)-8-morpholinoimidazo[1,2-a]pyrazin-5-yl)pyridin-2-yl)piperazine-1-carboxylate, 23a

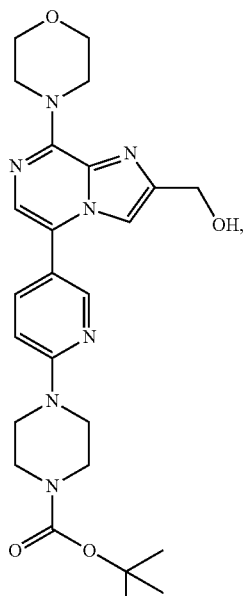
23a

Compound 1e was subjected to Suzuki coupling conditions with tert-butyl 4-(5-(4,4,5,5-tetramethyl-1,3,2-dioxaborolan-2-yl)pyridin-2-yl)piperazine-1-carboxylate using the reaction conditions described in Example 1, Step G, and substituting $K_2CO_3$ as the base to obtain compound 23a. Mass Spectrum (LCMS, ESI pos.) Calcd. for $C_{25}H_{33}N_7O_4$: 496.3 (M+H). Found 496.3.

B. tert-Butyl 4-(5-(8-morpholino-2-((pyrimidin-2-yloxy)methyl)imidazo[1,2-a]pyrazin-5-yl)pyridin-2-yl)piperazine-1-carboxylate, 23b

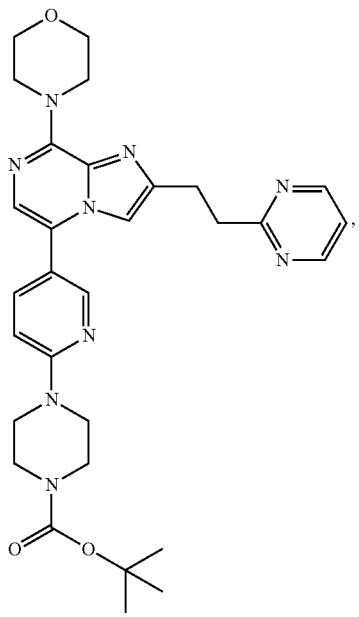
23b

Following the procedures described in Example 22, Step A, the title compound was prepared from compound 23a and 2-chloropyrimidine. Mass Spectrum (LCMS, ESI pos.) Calcd. for $C_{29}H_{35}N_9O_4$: 574.3 (M+H). Found 574.3.

130

C. 4-(5-(6-(piperazin-1-yl)pyridin-3-yl)-2-((pyrimidin-2-yloxy)methyl)imidazo[1,2-a]pyrazin-8-yl) morpholine trifluoroacetic acid salt, Cpd 116

Compound 23b was subjected to BOC deprotection as described in Example 13, Step C to obtain the title compound 116. $^1$H-NMR (400 MHz, CDCl$_3$) δ (ppm): 11.06 (br. s., 2H), 9.83 (br. s., 1H), 8.24-8.65 (m, 1H), 7.80 (s, 1H), 7.27 (s, 1H), 6.81-7.11 (m, 1H), 5.58 (s, 2H), 4.52 (br. s., 4H), 3.82-4.10 (m, 8H), 3.34 (br. s., 4H). Mass Spectrum (LCMS, ESI pos.) Calcd. For $C_{24}H_{27}N_9O_2$: 474.2 (M+H). Found 474.2.

Following the procedure described in Example 23 above, and substituting suitably selected and substituted reagents, starting materials and conditions as would be readily apparent to those skilled in the art, the following representative compounds of the present invention were prepared.

| Cpd | Characterization |
|---|---|
| 130 | 4-(5-(6-(4-Methylpiperazin-1-yl)pyridin-3-yl)-2-((quinolin-2-yloxy)methyl)imidazo[1,2-a]pyrazin-8-yl)morpholine<br>$^1$H-NMR (400 MHz, CDCl$_3$) δ (ppm): 8.26-8.43 (m, 1 H), 7.99 (d, J = 8.8 Hz, 1 H), 7.85 (d, J = 8.3 Hz, 1 H), 7.68-7.79 (m, 2 H), 7.59-7.68 (m, 2 H), 7.39 (t, J = 7.3 Hz, 1 H), 7.21-7.33 (m, 1 H), 6.95 (d, J = 8.8 Hz, 1 H), 6.73 (d, J = 8.8 Hz, 1 H), 5.67 (s, 2 H), 4.17-4.42 (m, 4 H), 3.79-4.02 (m, 4 H), 3.56-3.75 (m, 4 H), 2.47-2.67 (m, 4 H), 2.37 ppm (s, 3 H).<br>Mass Spectrum (LCMS, ESI pos.) Calcd. For $C_{30}H_{32}N_8O_2$: 537.3 (M + H), Found 537.3. |
| 131 | 4-(5-(8-Morpholino-2-((quinolin-2-yloxy)methyl)imidazo[1,2-a]pyrazin-5-yl)pyridin-2-yl)morpholine<br>$^1$H-NMR (400 MHz, CDCl$_3$) δ (ppm): 8.36 (d, J = 2.2 Hz, 1 H), 8.00 (d, J = 8.8 Hz, 1 H), 7.85 (d, J = 8.6 Hz, 1 H), 7.73 (t, J = 3.5 Hz, 2 H), 7.58-7.69 (m, 2 H), 7.34-7.43 (m, 1 H), 7.29 (s, 1 H), 6.95 (d, J = 8.8 Hz, 1 H), 6.73 (d, J = 8.8 Hz, 1 H), 5.67 (s, 2H), 4.21-4.40 (m, 4 H), 3.87 (dt, J = 15.1, 4.9 Hz, 8 H), 3.56-3.68 ppm (m, 4 H).<br>Mass Spectrum (LCMS, ESI pos.) Calcd. For $C_{29}H_{29}N_7O_3$: 524.2 (M + H), Found 524.1. |

Example 24

4-(5-(6-(piperazin-1-yl)pyridin-3-yl)-2-(3-(quinolin-2-yl)azetidin-1-yl)imidazo[1,2-a]pyrazin-8-yl)morpholine trifluoroacetic acid salt (Cpd 114)

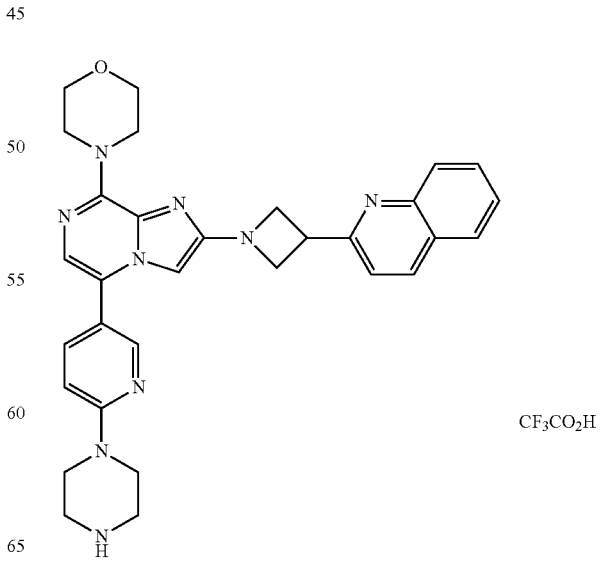

A. 4-(2-Chloroimidazo[1,2-a]pyrazin-8-yl)morpholine, 24a

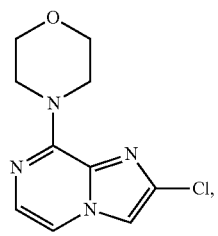

Compound 1b (6.0 g, 33 mmol) and bromoacetic acid (5.3 g, 38 mmol) in isopropanol (100 mL) were heated at 90° C. overnight. The reaction mixture was allowed to cool to rt and the solids formed were collected by suction filtration to obtain 8-morpholinoimidazo[1,2-a]pyrazin-2-ol as its HBr salt. This compound was used in next step without further purifications.

To a suspension of 8-morpholinoimidazo[1,2-a]pyrazin-2-ol. HBr (5.4 g, 18 mmol, as prepared above) in DCE (100 mL), POCl$_3$ (30 mL) was added. The resulting mixture was stirred at 110° C. for 12 h to obtain a clear solution. The reaction mixture was allowed to cool to rt and concentrated to obtain a white residue. DCM (30 mL) and 1N NaOH (20 mL) were then added to the residue and the resulting mixture was stirred at rt for 15 min. The DCM layer was separated. The aqueous layer was extracted with DCM (2×20 mL). The combined organic layers were combined, dried over Na$_2$SO$_4$ and concentrated to obtain compound 24a as a white solid. Mass Spectrum (LCMS, ESI pos.) Calcd. for C$_{10}$H$_{11}$ClN$_4$O: 239.0 (M+H). Found 239.1.

B. 4-(5-Bromo-2-chloroimidazo[1,2-a]pyrazin-8-yl)morpholine. HBr, 24b

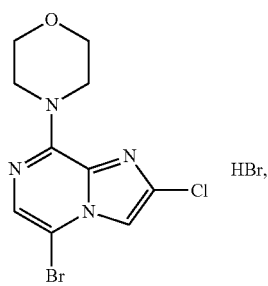

Compound 24a was brominated using NBS under the reaction conditions described in Example 1, Step E to obtain compound 24b. Mass Spectrum (LCMS, ESI pos.) Calcd. for C$_{10}$H$_{10}$BrClN$_4$O: 317.0 (M+H). Found 317.0.

C. tert-Butyl 4-(5-(2-chloro-8-morpholinoimidazo[1,2-a]pyrazin-5-yl)pyridin-2-yl)piperazine-1-carboxylate, 24c

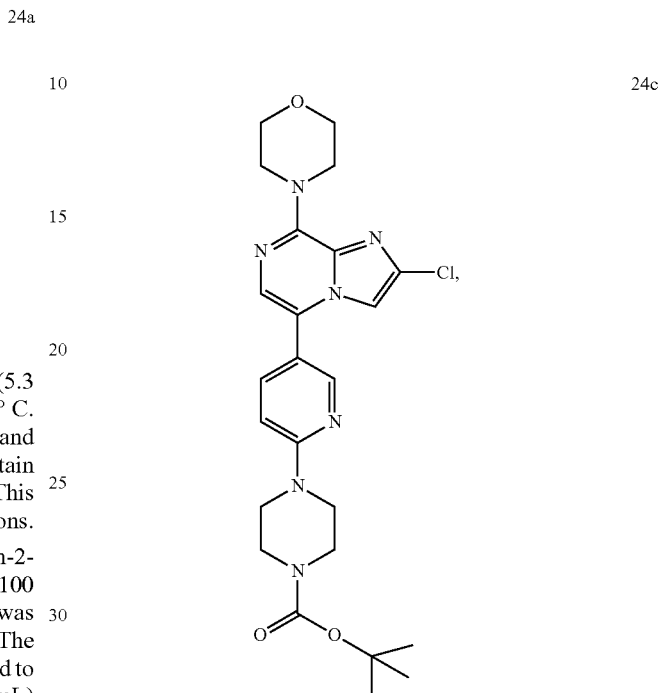

Compound 24b was subjected to Suzuki coupling conditions with tert-butyl 4-(5-(4,4,5,5-tetramethyl-1,3,2-dioxaborolan-2-yl)pyridin-2-yl)piperazine-1-carboxylate using the reaction conditions described in Example 1, Step G, and substituting K$_2$CO$_3$ as the base, to obtain compound 24c. Mass Spectrum (LCMS, ESI pos.) Calcd. for C$_{24}$H$_{30}$ClN$_7$O$_3$: 500.2 (M+H). Found 500.2.

D. 2-(Azetidin-3-yl)quinoline, 24d

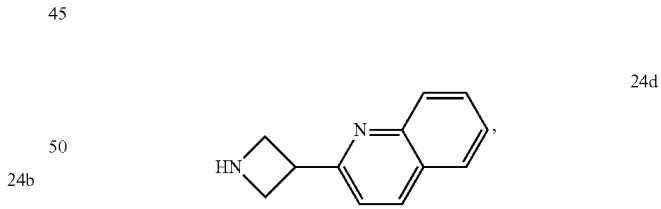

To a stirred suspension of Zn dust (1.70 g, 26.0 mmol) in THF (5 mL) under an Argon atmosphere, 1,2-dibromoethane (250 µl) was added at rt. The resulting mixture was heated at 65° C. for 3 min and allowed to cool to rt. TMSCl (350 µl) was then added and the mixture was stirred at rt for 30 min. tert-Butyl 3-iodoazetidine-1-carboxylate (5.70 g, 20.0 mmol) in THF (15 mL) was then added slowly and the resulting mixture was allowed to stir at rt for 45 min. A solution of Pd$_2$(dba)$_3$ (183 mg, 0.200 mmol) and trifurylphosphine (186 mg, 0.801 mmol) in THF (5 mL) were stirred at rt for 10 min under an Argon atmosphere and the resulting mixture was added to the organozinc reagent prepared, followed by addition of 2-bromoquinoline (5.00 g, 24.0 mmol). The mixture was then heated at 65° C. for 48 h under Argon. The reaction mixture was allowed to cool to rt and filtered through a pad of diatomaceous earth. The filtrate was concentrated and the residue obtained was purified by flash column chromatography on silica gel (0:1-1:0% EtOA/heptanes) to obtain tert-butyl 3-(quinolin-2-yl)azetidine-1-carboxylate.

To a solution of tert-butyl 3-(quinolin-2-yl)azetidine-1-carboxylate (2.8 g, 9.8 mmol, as prepared above) in DCM (10 mL), TFA (10 mL) was added. The resulting mixture was stirred at rt for 2 h and concentrated to obtain a viscous oil which was dried under reduced pressure. The residue obtained was dissolved in DCM (50 mL) and stirred with saturated NaHCO$_3$ (50 mL). The DCM layer was separated and the aqueous layer was concentrated. To the residue obtained, 20% iso-PrOH/DCM (50 mL) was added and stirred for 10 min and filtered. This procedure was repeated three times. The combined filtrates were dried over Na$_2$SO$_4$, filtered, and concentrated to obtain compound 24d as a gummy solid. $^1$H-NMR (400 MHz, CDCl$_3$) δ (ppm): 8.34 (d, J=8.6 Hz, 1H), 7.94-8.01 (m, 2H), 7.76 (s, 1H), 7.59 (d, J=6.7 Hz, 1H), 7.53 (d, J=8.6 Hz, 1H), 3.89-4.30 (m, 4H), 3.72-3.82 (m, 1H).

E. tert-Butyl 4-(5-(8-morpholino-2-(3-(quinolin-2-yl)azetidin-1-yl)imidazo[1,2-a]pyrazin-5-yl)pyridin-2-yl)piperazine-1-carboxylate, 24e

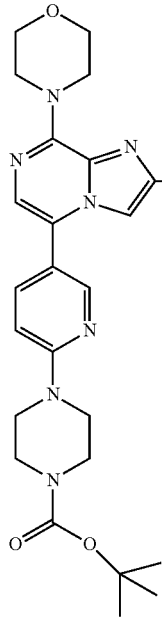

24e

A microwave vial was charged with compound 24d (154 mg, 0.840 mmol), compound 24c (350 mg, 0.700 mmol), sodium tert-butoxide (94.1 mg, 0.980 mmol), Pd$_2$(dba)$_3$ (12.8 mg, 0.0140 mmol), and 2-(dicyclohexylphosphino)-2',4',6'-tri-isopropyl-1,1'-biphenyl (26.6 mg, 0.0560 mmol) and purged with Argon gas. Toluene (3 mL) was then added and the resulting mixture was heated in a microwave at 120° C. for 1 h. The reaction mixture was allowed to cool to rt, diluted with water (20 mL) and EtOAc (20 mL). The organic layer was separated, dried over Na$_2$SO$_4$, filtered, and concentrated. The residue obtained was purified by flash column chromatography on silica gel (1:0-1:4 heptane/EtOAc) to obtain compound 24e. Mass Spectrum (LCMS, ESI pos.) Calcd. for C$_{36}$H$_{41}$N$_9$O$_3$: 648.3 (M+H). Found 648.4.

F. 4-(5-(6-(piperazin-1-yl)pyridin-3-yl)-2-(3-(quinolin-2-yl)azetidin-1-yl)imidazo[1,2-a]pyrazin-8-yl) morpholine trifluoroacetic acid salt, Cpd 114

Compound 24e was subjected to the BOC deprotection as described in the Example 13, Step C to obtain the title compound 114. $^1$H-NMR (400 MHz, CDCl$_3$) δ (ppm): 8.39-8.47 (m, 2H), 8.04 (d, J=8.2 Hz, 1H), 7.97 (d, J=7.8 Hz, 1H), 7.90 (dd, J=8.8, 2.5 Hz, 1H), 7.80 (t, J=7.0 Hz, 1H), 7.73 (d, J=8.6 Hz, 1H), 7.62 (t, J=7.4 Hz, 1H), 7.23 (s, 1H), 7.10 (d, J=9.4 Hz, 1H), 4.42-4.49 (m, 2H), 4.33-4.41 (m, 1H), 4.24-4.30 (m, 2H), 4.15-4.22 (m, 4H), 3.90-3.97 (m, 4H), 3.82-3.90 (m, 4H), 3.38 (m, 4H). Mass Spectrum (LCMS, ESI pos.) Calcd. For C$_{31}$H$_{33}$N$_9$O: 548.3 (M+H). Found 548.3.

Example 25

4-(3-Chloro-5-(6-(piperazin-1-yl)pyridin-3-yl)-2-(3-(quinolin-2-yl)azetidin-1-yl)imidazo[1,2-a]pyrazin-8-yl)morpholine trifluoroacetic acid salt (Cpd 132)

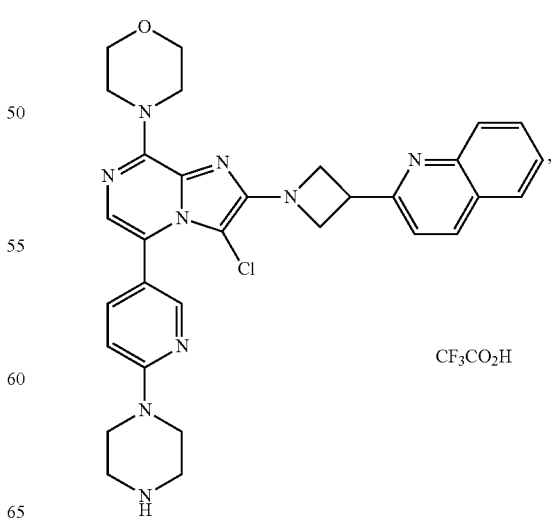

A. 4-(2-(3-(Quinolin-2-yl)azetidin-1-yl)imidazo[1,2-a]pyrazin-8-yl)morpholine, 25a

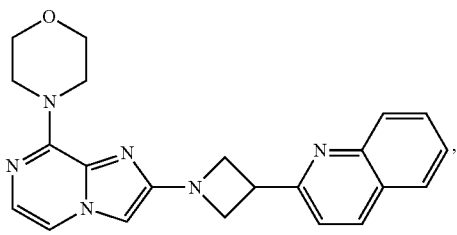

Compound 25a was prepared from compound 24a and compound 24d using the procedure described in Example 24, Step E. Mass Spectrum (LCMS, ESI pos.) Calcd. For $C_{22}H_{22}N_6O$: 387.2 (M+H). Found 387.2.

B. 4-(3-Chloro-2-(3-(quinolin-2-yl)azetidin-1-yl)imidazo[1,2-a]pyrazin-8-yl)morpholine, 25b

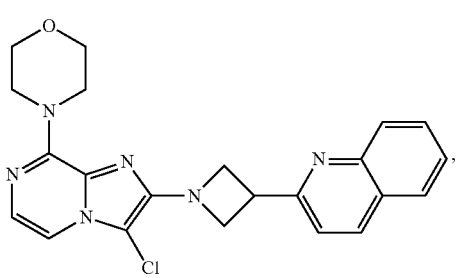

To a solution of compound 25b (74 mg, 0.20 mmol) in DCM (5 mL), $SO_2Cl_2$ (17 μL, 0.21 mmol) was added. The resulting mixture was stirred at rt for 30 min and diluted with DCM (20 mL) and saturated $NaHCO_3$ (20 mL). The DCM layer was separated, dried over $Na_2SO_4$ and concentrated. The residue obtained was purified by flash column chromatography on silica gel (0:1-1:0 EtOA/hexane) to obtain compound 25b. Mass Spectrum (LCMS, ESI pos.) Calcd. For $C_{22}H_{21}ClN_6O$: 421.5 (M+H). Found 421.1.

C. 4-(5-Bromo-3-chloro-2-(3-(quinolin-2-yl)azetidin-1-yl)imidazo[1,2-a]pyrazin-8-yl)morpholine, 25c

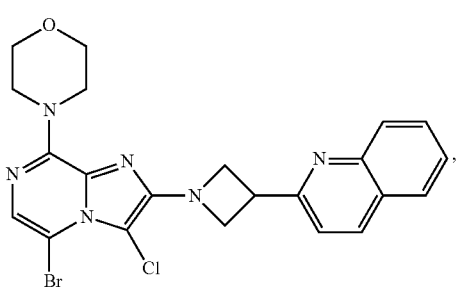

Compound 25b was brominated using the methods described in Example 1, Step E to obtain compound 25c. Mass Spectrum (LCMS, ESI pos.) Calcd. For $C_{22}H_{20}BrClN_6O$: 499.1 (M+H). Found 499.1.

D. tert-Butyl 4-(5-(3-chloro-8-morpholino-2-(3-(quinolin-2-yl)azetidin-1-yl)imidazo[1,2-a]pyrazin-5-yl)pyridin-2-yl)piperazine-1-carboxylate, 25d

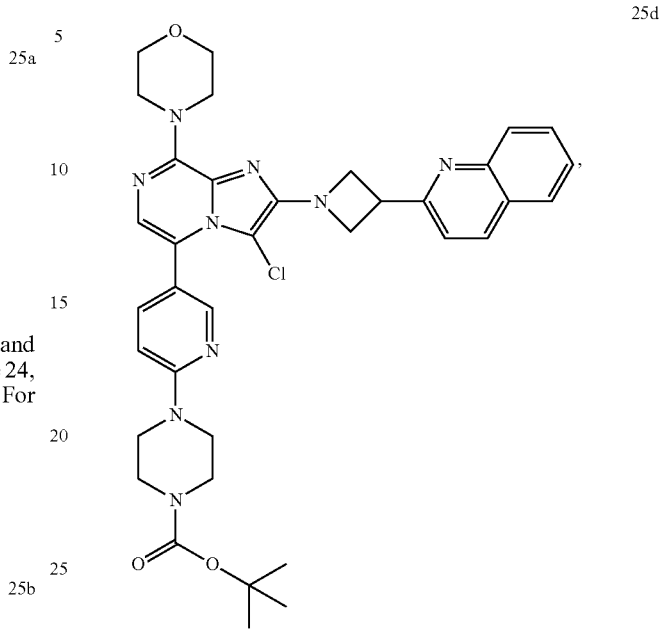

Compound 25c was subjected under Suzuki coupling reaction conditions with tert-butyl 4-(5-(4,4,5,5-tetramethyl-1,3,2-dioxaborolan-2-yl)pyridin-2-yl)piperazine-1-carboxylate using the method described in Example 1, Step G to obtain compound 25c. Mass Spectrum (LCMS, ESI pos.) Calcd. for $C_{36}H_{40}ClN_9O_3$: 682.3 (M+H). Found 682.3.

E. 4-(3-Chloro-5-(6-(piperazin-1-yl)pyridin-3-yl)-2-(3-(quinolin-2-yl)azetidin-1-yl)imidazo[1,2-a]pyrazin-8-yl)morpholine trifluoroacetic acid salt, Cpd 132

Compound 25d was subjected to the BOC deprotection conditions as described in the Example 1, Step E to obtain the title compound 132. $^1$H-NMR (400 MHz, DMSO-$d_6$) δ (ppm): 8.81 (br. s., 2H), 8.47 (d, J=8.2 Hz, 1H), 8.25 (d, J=2.3 Hz, 1H), 8.02 (dd, J=7.6, 4.1 Hz, 2H), 7.72-7.83 (m, 2H), 7.59-7.70 (m, 2H), 7.23 (s, 1H), 7.01 (d, J=9.0 Hz, 1H), 4.44-4.50 (m, 2H), 4.31-4.43 (m, 3H), 4.04-4.11 (m, 4H), 3.71-3.84 (m, 8H), 3.22 (br. s., 4H). Mass Spectrum (LCMS, ESI pos.) Calcd. For $C_{31}H_{32}ClN_9O$: 582.2 (M+H). Found 882.2.

Example 26

4-(5-(Piperidin-4-yl)-2-((quinolin-2-yloxy)methyl)imidazo[1,2-a]pyrazin-8-yl)morpholine trifluoroacetic acid salt (Cpd 111)

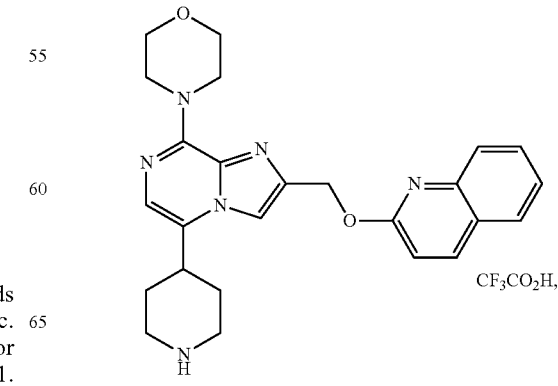

137

A. tert-Butyl 4-(2-(hydroxymethyl)-8-morpholinoimidazo[1,2-a]pyrazin-5-yl)-5,6-dihydropyridine-1(2H)-carboxylate, 26a

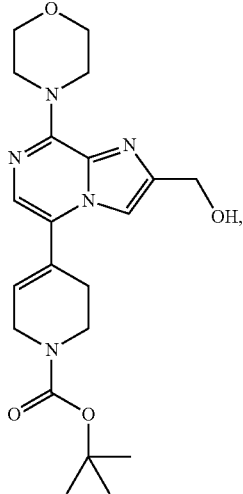

26a

Compound 1e was subjected to Suzuki coupling reaction conditions with N-Boc-1,2,3,6-tetrahydropyridine-4-boronic acid pinacol ester using the method described in Example 1, Step G to obtain compound 26a. Mass Spectrum (LCMS, ESI pos.) Calcd. for $C_{21}H_{29}N_5O_4$: 416.2 (M+H). Found 416.3.

B. tert-Butyl 4-(2-(hydroxymethyl)-8-morpholinoimidazo[1,2-a]pyrazin-5-yl)piperidine-1-carboxylate, 26b

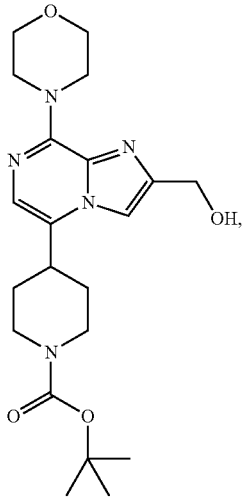

26b

Compound 26a (390 mg, 0.93 mmol) in MeOH (250 mL) was hydrogenated over 10% Pd/C in a continuous-flow hydrogenation reactor. The solvents were removed and the residue was dissolved in DCM, dried over $Na_2SO_4$, filtered, and concentrated to obtain compound 26b. Mass Spectrum (LCMS, ESI pos.) Calcd. for $C_{21}H_{31}N_5O_4$: 418.2 (M+H). Found 418.3.

138

C. tert-Butyl 4-(8-morpholino-2-((quinolin-2-yloxy)methyl)imidazo[1,2-a]pyrazin-5-yl)piperidine-1-carboxylate, 26c

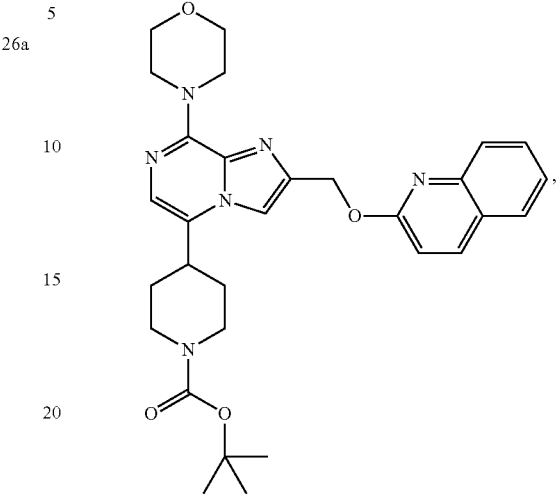

26c

Following the procedures described in Example 22, Step A, compound 26c was prepared from Compound 26b and 2-chloroquinoline. Mass Spectrum (LCMS, ESI pos.) Calcd. for $C_{30}H_{36}N_6O_4$: 545.3 (M+H). Found 545.3.

D. 4-(5-(Piperidin-4-yl)-2-((quinolin-2-yloxy)methyl)imidazo[1,2-a]pyrazin-8-yl)morpholine trifluoroacetic acid salt, Cpd 111

Compound 26c was subjected to the BOC deprotection reaction conditions described in Example 1, Step E to obtain the title compound 111. $^1$H-NMR (400 MHz, CDCl$_3$) δ (ppm): 9.67 (br. s., 1H), 9.22 (br. s., 1H), 8.18 (s, 1H), 8.11 (d, J=9.0 Hz, 1H), 7.88 (d, J=7.8 Hz, 1H), 7.76 (d, J=7.8 Hz, 1H), 7.63-7.72 (m, 1H), 7.44 (t, J=8.0 Hz, 1H), 7.30 (s, 1H), 7.04 (d, J=9.0 Hz, 1H), 5.72 (s, 2H), 4.49 (br. s., 4H), 3.83-3.98 (m, 4H), 3.54 (br. s., 2H), 3.24 (br. s., 3H), 1.98-2.28 (m, 4H). Mass Spectrum (LCMS, ESI pos.) Calcd. for $C_{25}H_{28}N_6O_2$: 445.2 (M+H). Found 445.3.

Example 27

2-(4-(8-Morpholino-2-((quinolin-2-yloxy)methyl)imidazo[1,2-a]pyrazin-5-yl)piperidin-1-yl)acetic acid trifluoroacetic acid salt (Cpd 110)

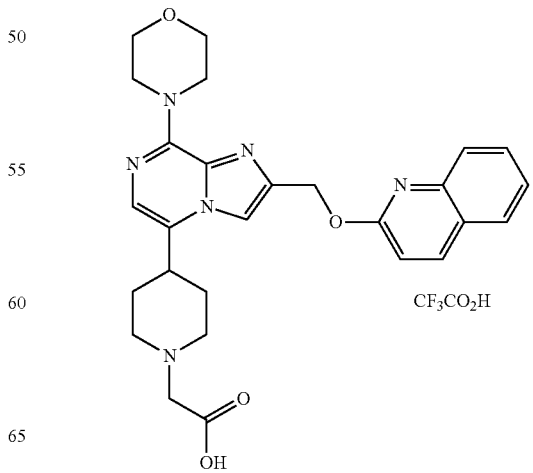

A. tert-Butyl 2-(4-(8-morpholino-2-((quinolin-2-yloxy)methyl)imidazo[1,2-a]pyrazin-5-yl)piperidin-1-yl)acetate, 27a

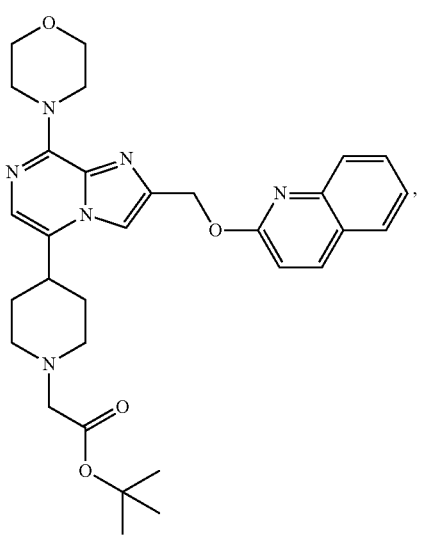

Compound 111 (50 mg, 0.06 mmol, Example 26), DIEA (53 μL, 0.38 mmol) and tert-butyl bromoacetate (12 μL, 0.07 mmol) in THF (1 mL) was heated at 120° C. in a microwave for 10 min. The reaction mixture was allowed to cool to rt and concentrated. The residue obtained was purified by flash column chromatography on silica gel (0:1-1:0 EtOAc/hexanes) to obtain compound 27a. Mass Spectrum (LCMS, ESI pos.) Calcd. For $C_{31}H_{38}N_6O_4$: 559.3 (M+H). Found 559.3.

B. 2-(4-(8-Morpholino-2-((quinolin-2-yloxy)methyl)imidazo[1,2-a]pyrazin-5-yl)piperidin-1-yl)acetic acid trifluoroacetic acid salt, Cpd 110

Compound 27a was subjected to the BOC deprotection conditions described in Example 1, Step E to obtain the title compound 110. $^1$H-NMR (400 MHz, CDCl$_3$) δ (ppm): 8.36-8.39 (m, 1H), 8.14-8.20 (m, 1H), 7.79-7.87 (m, 2H), 7.63-7.70 (m, 1H), 7.40-7.46 (m, 1H), 7.10-7.14 (m, 1H), 6.99-7.03 (m, 1H), 5.72 (s, 2H), 4.32-4.39 (m, 6H), 4.14-4.20 (m, 3H), 3.90 (br. s., 6H), 3.75-3.86 (m, 3H), 3.32-3.42 (m, 4H), 3.05 (s, 2H), 2.31-2.41 (m, 1H), 2.08 (m, 1H). Mass Spectrum (LCMS, ESI pos.) Calcd. for $C_{27}H_{30}N_6O_4$: 503.2 (M+H). Found 503.2.

Example 28

4-(8-Morpholino-2-((quinolin-2-yloxy)methyl)imidazo[1,2-a]pyrazin-5-yl)piperidine-1-sulfonamide trifluoroacetic acid salt (Cpd 109)

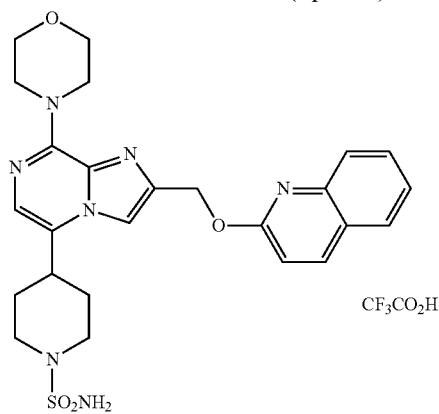

A. tert-Butyl (4-(8-morpholino-2-((quinolin-2-yloxy)methyl)imidazo[1,2-a]pyrazin-5-yl)piperidin-1-yl)sulfonylcarbamate, 28a

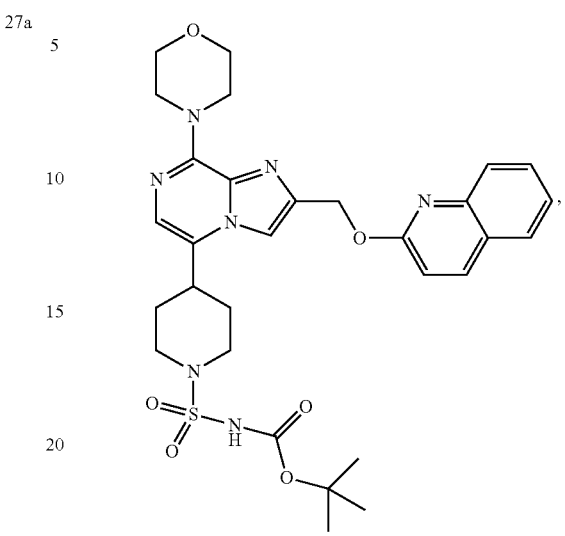

N-(tert-Butoxycarbonyl)-N-[4-(dimethylazaniumylidene)-1,4-dihydropyridin-1-ylsulfonyl]azanide (38 mg, 0.12 mmol, prepared according to the Org. Lett., 2001, 3 (14), pp 2241-2243) was added to a solution of compound 111 (100 mg, 0.12 mmol, Example 26) and DIEA (54 μL, 0.38 mmol) in DCM (1 mL). The resulting mixture was stirred at rt for 3 h and concentrated. The residue obtained was purified by flash column chromatography on silica gel (0:1-1:0 EtAOc/hexane) to obtain compound 28a. Mass Spectrum (LCMS, ESI pos.) Calcd. for $C_{30}H_{37}N_7O_6S$: 624.2 (M+H). Found 624.2.

B. 4-(8-Morpholino-2-((quinolin-2-yloxy)methyl)imidazo[1,2-a]pyrazin-5-yl)piperidine-1-sulfonamide trifluoroacetic acid salt, Cpd 109

Compound 28a was subjected to BOC deprotection methods described in Example 1, Step E to obtain the title compound 109. $^1$H-NMR (400 MHz, CD$_3$OD) δ (ppm): 8.44 (s, 1H), 8.16 (d, J=8.6 Hz, 1H), 7.86 (d, J=8.6 Hz, 1H), 7.81 (d, J=8.2 Hz, 1H), 7.65-7.70 (m, 1H), 7.40-7.46 (m, 1H), 7.00 (d, J=10.2 Hz, 2H), 5.71 (s, 2H), 4.38 (br. s., 4H), 3.89-3.94 (m, 4H), 3.80 (d, J=12.1 Hz, 2H), 3.11 (br. s., 1H), 2.82-2.92 (m, 2H), 2.16 (d, J=12.9 Hz, 2H), 1.71-1.85 (m, 2H). Mass Spectrum (LCMS, ESI pos.) Calcd. for $C_{25}H_{29}N_7O_4S$: 524.2 (M+H). Found 524.2.

Example 29

4-(5-(6-(piperazin-1-yl)pyridin-3-yl)-2-(1-(quinolin-2-yl)azetidin-3-yl)imidazo[1,2-a]pyrazin-8-yl)morpholine (Cpd 99)

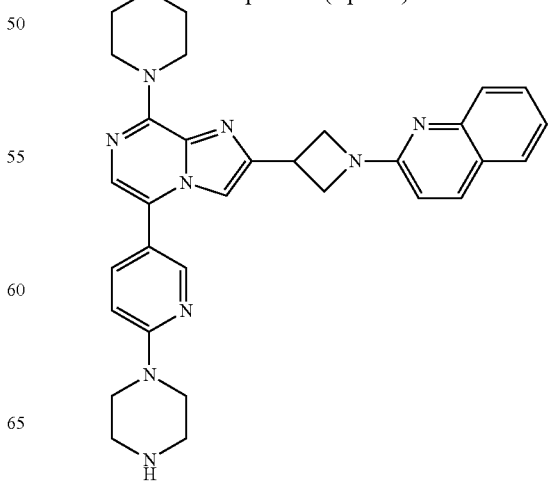

A. tert-Butyl 3-(8-morpholinoimidazo[1,2-a]pyrazin-2-yl)azetidine-1-carboxylate, 29a

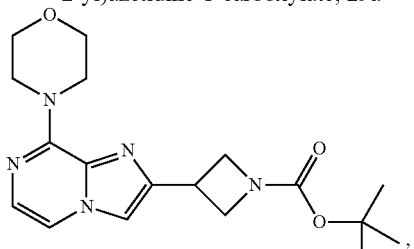

To a solution of compound 1b (2.4 g, 13 mmol) in DMF (20 mL), Na$_2$HPO$_4$ (4.7 g, 33 mmol) was added followed by tert-butyl 3-(2-bromoacetyl)azetidine-1-carboxylate (6.0, 21 mmol). The resulting mixture was stirred at 100° C. for 3 h. The reaction mixture was allowed to cool to rt and water (50 mL) was added. The aqueous layer was extracted with EtOAc (3×25 mL). The combined EtOAc layers were dried over Na$_2$SO$_4$, filtered, and concentrated. The residue obtained was purified by flash column chromatography on silica gel (0:1-1:0 EtOAc/hexanes) to obtain compound 29a. Mass Spectrum (LCMS, ESI pos.): Calcd. for C$_{18}$H$_{25}$N$_5$O$_3$: 360.2 (M+H). found: 360.3.

B. tert-Butyl 3-(5-bromo-8-morpholinoimidazo[1,2-a]pyrazin-2-yl)azetidine-1-carboxylate, 29b

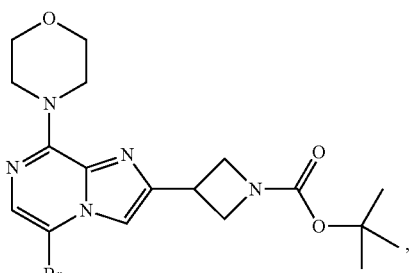

Compound 29a was brominated with NBS using the methods described in Example 1, Step E to obtain compound 29b. Mass Spectrum (LCMS, ESI pos.): Calcd. for C$_{18}$H$_{24}$BrN$_5$O$_3$: 438.1 (M+H). found: 438.2.

C. Benzyl 4-(5-(2-(1-(tert-butoxycarbonyl)azetidin-3-yl)-8-morpholinoimidazo[1,2-a]pyrazin-5-yl)pyridin-2-yl)piperazine-1-carboxylate, 29c

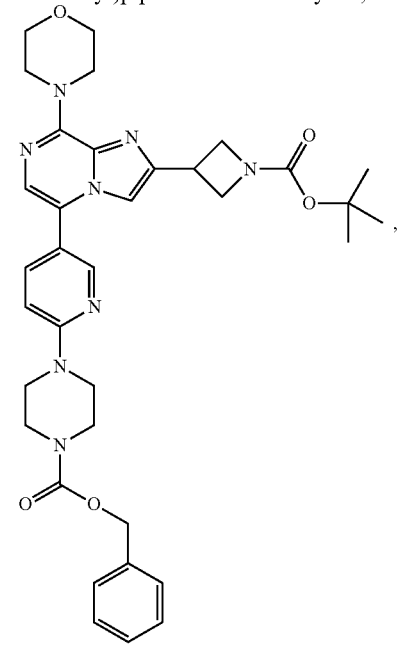

Compound 29b was subjected to Suzuki coupling reaction conditions with benzyl 4-(5-(4,4,5,5-tetramethyl-1,3,2-dioxaborolan-2-yl)pyridin-2-yl)piperazine-1-carboxylate using the methods described in Example 1, Step G to obtain compound 29c. Mass Spectrum (LCMS, ESI pos.) Calcd. for C$_{35}$H$_{42}$N$_8$O$_5$: 655.3 (M+H). Found 655.3.

D. Benzyl 4-(5-(8-morpholino-2-(1-(quinolin-2-yl)azetidin-3-yl)imidazo[1,2-a]pyrazin-5-yl)pyridin-2-yl)piperazine-1-carboxylate, 29d

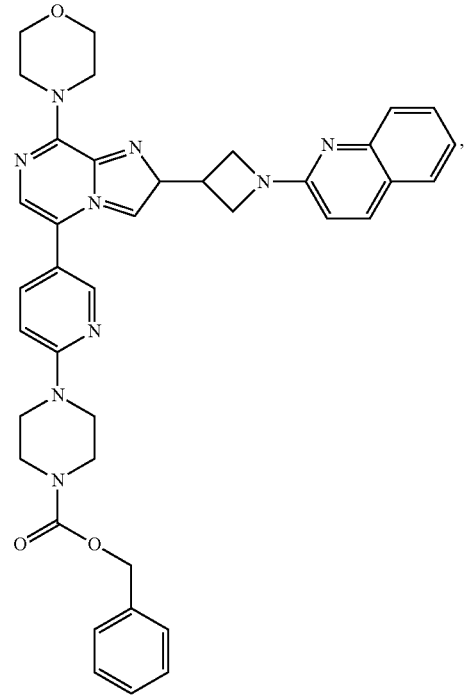

To a solution of compound 29c (275 mg, 0.420 mmol) in DCM (3 mL), TFA (2 mL) was added. The resulting mixture was stirred at rt for 2 h and concentrated. The residue obtained was dried under reduced pressure overnight and re-dissolved in EtOH (5 mL). Na$_2$CO$_3$ (1.00 g, 9.50 mmol) and 2-chloroquinoline (234 mg, 1.43 mmol) were then added and the resulting mixture was heated at reflux for 5 h. The reaction mixture was allowed to cool to rt, diluted with water (20 mL) and extracted with EtOAc (3×20 mL). The combined EtOAc extracts were dried over Na$_2$SO$_4$, filtered, and concentrated. The residue obtained was purified by flash column chromatography on silica gel (0:1-1:0 EtOA/heptane) to obtain compound 29d. Mass Spectrum (LCMS, ESI pos.) Calcd. for C$_{39}$H$_{39}$N$_9$O$_3$: 682.3 (M+H). Found 682.3.

E. 4-(5-(6-(piperazin-1-yl)pyridin-3-yl)-2-(1-(quinolin-2-yl)azetidin-3-yl)imidazo[1,2-a]pyrazin-8-yl)morpholine, Cpd 99

Compound 29d (100 mg, 0.147 mmol) in MeOH (15 mL) and DCM (5 mL) was hydrogenated over 10% Pd/C (20 mg) overnight under balloon pressure. The reaction mixture was filtered through a pad of diatomaceous earth and the filtrate was concentrated and dried under reduced pressure to obtain the title compound 99. $^1$H-NMR (400 MHz, DMSO-d$_6$) δ (ppm): 8.36 (d, J=2.3 Hz, 1H), 8.04 (d, J=9.0 Hz, 1H), 7.84-7.92 (m, 2H), 7.71 (d, J=7.8 Hz, 1H), 7.49-7.60 (m, 2H), 7.33-7.37 (m, 1H), 7.19-7.25 (m, 1H), 7.03 (d, J=8.6 Hz, 1H), 6.77 (d, J=9.0 Hz, 1H), 5.77 (s, 1H), 4.44-4.52 (m, 2H), 4.24 (t, J=6.8 Hz, 2H), 4.10-4.20 (m, 4H), 3.68-3.78 (m, 8H), 3.36 (br. s., 2H), 2.97-3.10 (m, 2H), 2.56 (br. s., 1H). Mass Spectrum (LCMS, ESI pos.) Calcd. for C$_{31}$H$_{33}$N$_9$O: 548.3 (M+H). Found 548.3.

Example 30

4-(5-(6-(piperazin-1-yl)pyridin-3-yl)-2-((quinolin-2-ylthio)methyl)imidazo[1,2-a]pyrazin-8-yl)morpholine trifluoroacetic acid salt (Cpd 98)

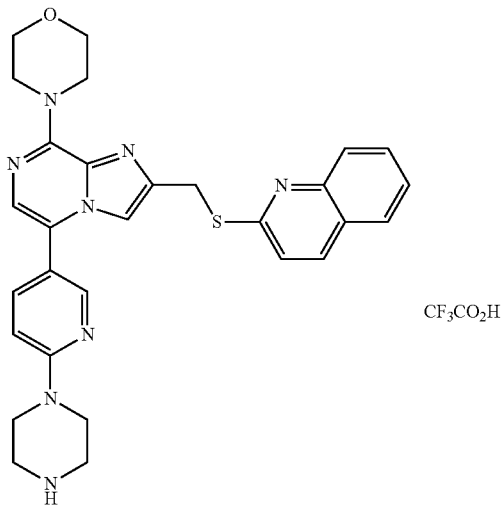 [SMILES: c1ccc2nc(SCc3cn4c(-c5ccc(N6CCNCC6)nc5)cnc(N5CCOCC5)c4n3)ccc2c1 ; "CF3CO2H"]

CF₃CO₂H

A. tert-Butyl 4-(5-(2-(hydroxymethyl)-8-morpholinoimidazo[1,2-a]pyrazin-5-yl)pyridin-2-yl)piperazine-1-carboxylate, 30a

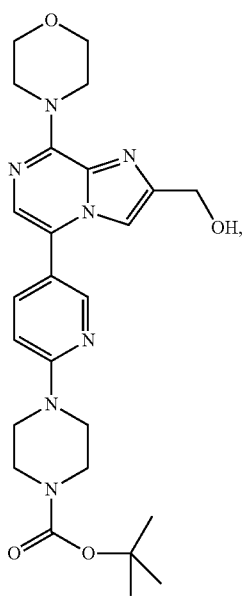

30a

Compound 1d was subjected to Suzuki coupling reaction conditions with tert-butyl 4-(5-(4,4,5,5-tetramethyl-1,3,2-dioxaborolan-2-yl)pyridin-2-yl)piperazine-1-carboxylate using the method described in Example 1, Step G to obtain compound 30a. Mass Spectrum (LCMS, ESI pos.) Calcd. for $C_{25}H_{33}N_7O_4$: 496.2 (M+H). Found 496.3.

B. tert-Butyl 4-(5-(8-morpholino-2-((quinolin-2-ylthio)methyl)imidazo[1,2-a]pyrazin-5-yl)pyridin-2-yl)piperazine-1-carboxylate, 30b

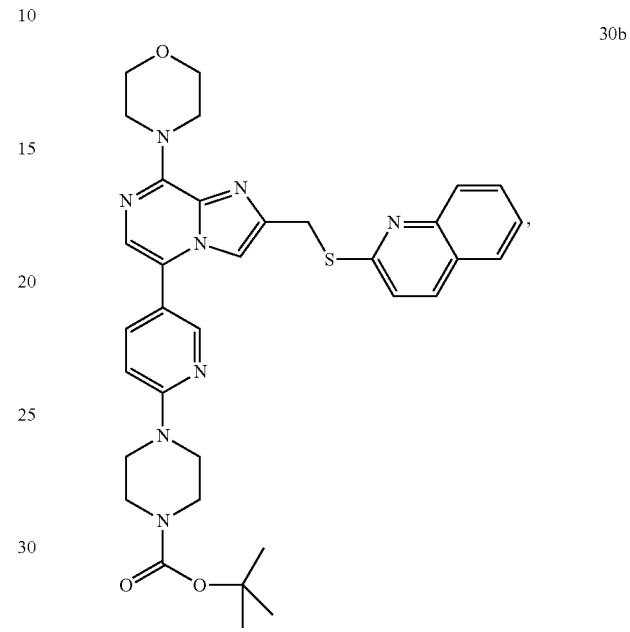

30b

A solution of compound 30a (200 mg, 0.40 mmol) in DCM (2 mL) and DIEA (0.15 mL, 0.80 mmol) was cooled to 0° C. and MsCl (47 µL, 0.60 mmol) was added dropwise. The reaction was stirred at 0° C. for 15 min and the solvents were removed under reduced pressure. The residue obtained was treated with ACN (10 mL), 2-quinolinethiol (74 mg, 0.45 mmol) and K₂CO₃ (84 mg, 0.61 mmol). The resulting mixture was stirred at 60° C. for 20 h. The reaction was diluted with H₂O (20 mL) and extracted with DCM (3×30 mL). The combined organic extracts were washed with brine (20 mL) and dried over MgSO₄ and filtered. The solvent was removed under reduced pressure. The residue was purified by flash column chromatography on silica gel (1:0-0:1 DCM/EtOAc) to obtain compound 30b. Mass Spectrum (LCMS, ESI pos.) Calcd. for $C_{34}H_{38}N_8O_3S$: 639.3 (M+H). Found 639.2.

C. 4-(5-(6-(piperazin-1-yl)pyridin-3-yl)-2-((quinolin-2-ylthio)methyl)imidazo[1,2-a]pyrazin-8-yl)morpholine trifluoroacetic acid salt, Cpd 98

Compound 30b was subjected to the BOC deprotection reaction conditions as described in Example 1, Step E, to obtain the title compound 98. ¹H-NMR (400 MHz, CDCl₃) δ (ppm): 8.30 (d, J=2.3 Hz, 1H), 7.86-7.94 (m, 2H), 7.75 (d, J=7.0 Hz, 1H), 7.72 (s, 1H), 7.64 (t, J=7.0 Hz, 1H), 7.57 (dd, J=8.8, 2.5 Hz, 1H), 7.43-7.49 (m, 1H), 7.29 (s, 1H), 7.23 (d, J=8.6 Hz, 1H), 6.65 (d, J=9.0 Hz, 1H), 4.70 (s, 2H), 4.30-4.37 (m, 4H), 3.92-3.98 (m, 4H), 3.86-3.92 (m, 4H), 3.33 (m, 4H). Mass Spectrum (LCMS, ESI pos.) Calcd. for $C_{29}H_{30}N_8OS$: 539.2 (M+H). Found 539.2.

Example 31

4-(5-(4-(1H-Tetrazol-5-yl)phenyl)-2-((quinolin-2-yloxy)methyl)imidazo[1,2-a]pyrazin-8-yl)morpholine (Cpd 90)

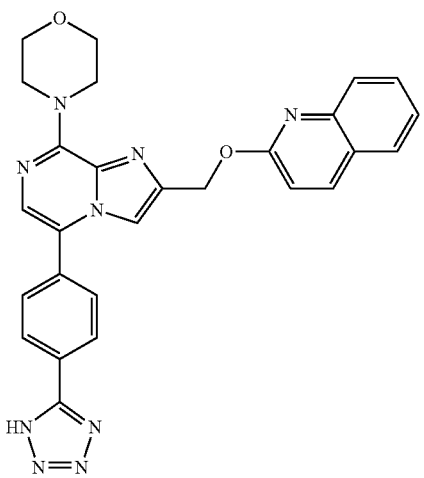 [SMILES: c1ccc2nc(OCc3cn4c(-c5ccc(-c6nnn[nH]6)cc5)cnc(N5CCOCC5)c4n3)ccc2c1]

A. 4-(2-((Quinolin-2-yloxy)methyl)imidazo[1,2-a]pyrazin-8-yl)morpholine, 31a

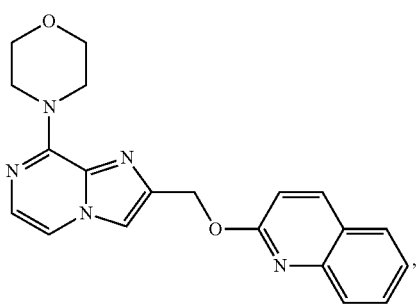

A mixture of compound 1d (5.0 g, 21 mmol) and NaH (2.5 g, 64 mmol) in anhydrous THF (300 mL) was stirred at rt for 10 min. 2-Chloroquinoline (4.2 g, 25 mmol) was then added and the mixture was heated to 70° C. for 5 h. The reaction was quenched with brine (300 mL) and extracted with EtOAc (2×500 mL). The organic layer was washed with brine (300 mL), dried over Na$_2$SO$_4$ and concentrated under reduced pressure. The residue obtained was recrystallized with hot EtOAc-hexanes to give compound 31a. Mass Spectrum (LCMS, ESI pos.): Calcd. for C$_{20}$H$_{19}$N$_5$O$_2$: 362.1 (M+H). found: 362.2.

B. 4-(5-Bromo-2-((quinolin-2-yloxy)methyl)imidazo[1,2-a]pyrazin-8-yl)morpholine, 31b

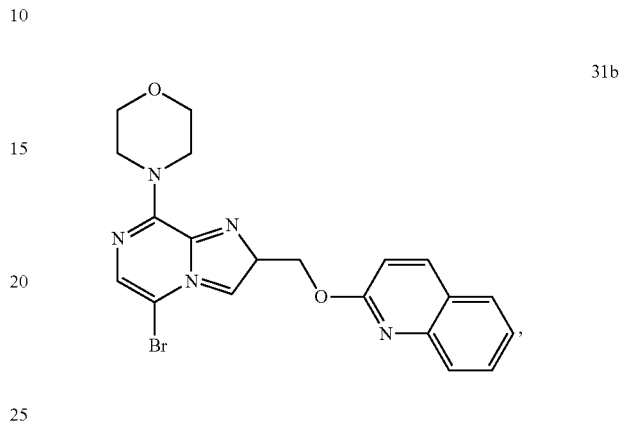

A mixture of compound 31a (5.0 g, 14 mmol) and N-bromosuccinamide (2.5 g, 14 mmol) in DCM (300 mL) at 0° C. was allowed to stir at rt for 10 min. The reaction mixture was diluted with DCM (600 mL) and washed with saturated NaHCO$_3$ (500 mL) and brine (500 mL). The DCM layer was separated, dried over Na$_2$SO$_4$, filtered, and concentrated under reduced pressure. The residue obtained was triturated with EtOAc to give compound 31b as a white solid. Mass Spectrum (LCMS, ESI pos.): Calcd. for C$_{20}$H$_{18}$BrN$_5$O$_2$: 440.1 (M+H). found: 440.0.

C. 4-(5-(4-(1H-Tetrazol-5-yl)phenyl)-2-((quinolin-2-yloxy)methyl)imidazo[1,2-a]pyrazin-8-yl)morpholine, 31c Compound 31b was subjected to Suzuki coupling reaction conditions with (4-(1H-tetrazol-5-yl)phenyl)boronic acid using the methods described in Example 1, Step G to obtain compound 31c. $^1$H-NMR (400 MHz, DMSO-d$_6$) 8.26 (d, J=8.6 Hz, 1H), 8.21 (d, J=8.6 Hz, 2H), 8.17 (s, 1H), 7.88-7.93 (m, 3H), 7.80 (d, J=8.6 Hz, 1H), 7.65-7.71 (m, 1H), 7.55 (s, 1H), 7.45 (t, J=7.0 Hz, 1H), 7.06 (d, J=9.0 Hz, 1H), 5.58 (s, 2H), 4.21-4.28 (m, 4H), 3.75-3.80 (m, 4H). Mass Spectrum (LCMS, ESI pos.) Calcd. for C$_{27}$H$_{23}$N$_9$O$_2$: 506.2 (M+H) .Found 506.2.

Following the procedure described in Example 31 above, and substituting suitably selected and substituted reagents, starting materials and conditions as would be readily apparent to those skilled in the art, the following representative compounds of the present invention were prepared.

| Cpd | Characterization |
|---|---|
| 87 | 4-(8-Morpholino-2-((quinolin-2-yloxy)methyl)imidazo[1,2-a]pyrazin-5-yl)benzenesulfonamide<br>¹H-NMR (400 MHz, CDCl₃) δ (ppm): 8.01 (d, J = 7.8 Hz, 3H), 7.85 (s, 1H), 7.80 (d, J = 8.2 Hz, 1H), 7.66-7.74 (m, 3H), 7.59-7.65 (m, 1H), 7.35-7.40 (m, 1H), 7.33 (s, 1H), 6.93 (d, J = 9.0 Hz, 1H), 5.62 (s, 2H), 4.22-4.28 (m, 4H), 3.84-3.90 (m, 4H). Mass Spectrum (LCMS, ESI pos.) Calcd. For C₂₆H₂₄N₆O₄S: 517.1 (M + H), Found 517.2. |
| 88 | N-((4-(8-Morpholino-2-((quinolin-2-yloxy)methyl)imidazo[1,2-a]pyrazin-5-yl)phenyl)sulfonyl)acetamide<br>¹H-NMR (400 MHz, CDCl₃) δ (ppm): 8.17 (d, J = 8.2 Hz, 2H), 8.01 (d, J = 9.0 Hz, 1H), 7.88 (s, 1H), 7.84 (d, J = 8.2 Hz, 1H), 7.71-7.78 (m, 3H), 7.63-7.70 (m, 1H), 7.40-7.44 (m, 1H), 7.39 (s, 1H), 6.96 (d, J = 8.6 Hz, 1H), 5.68 (s, 2H), 4.35-4.40 (m, 4H), 3.86-3.93 (m, 4H), 2.12 (s, 3H). Mass Spectrum (LCMS, ESI pos.) Calcd. For C₂₈H₂₆N₆O₅S: 559.2 (M + H), Found 559.2. |

Example 32

5-(8-Morpholino-2-((quinolin-2-yloxy)methyl)imidazo[1,2-a]pyrazin-5-yl)pyridine-2-sulfonamide trifluoroacetic acid salt (Cpd 86)

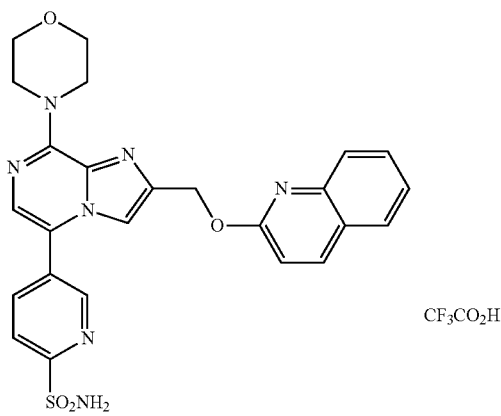 [SMILES: NS(=O)(=O)c1ccc(-c2cnc(N3CCOCC3)c3nc(COc4ccc5ccccc5n4)cn23)cn1 ; "CF3CO2H"]

A. 5-Bromo-N-(tert-butyl)pyridine-2-sulfonamide, 32a

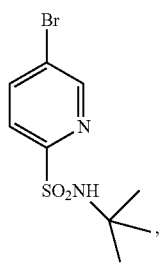

A solution of 5-bromopyridine-2-sulfonyl chloride (2.7 g, 10 mmol) in DCM (100 mL) was cooled to 0° C. and treated with tert-BuNH₂ (5.5 mL, 52 mmol). The resulting mixture was stirred at rt for 48 h. Water (50 mL) was added and the DCM layer were separated, dried and concentrated to obtain compound 32a. ¹H-NMR (400 MHz, CDCl₃) δ (ppm): 8.75 (d, J=2.3 Hz, 1H), 8.03 (dd, J=8.2, 2.3 Hz, 1H), 7.90-7.94 (m, 1H), 5.02-5.07 (m, 1H), 1.23 (s, 9H).

B. N-(tert-Butyl)-5-(4,4,5,5-tetramethyl-1,3,2-dioxaborolan-2-yl)pyridine-2-sulfonamide, 32b

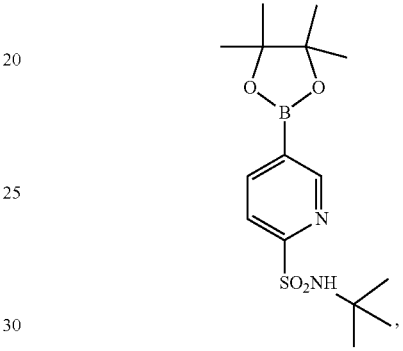

A mixture of compound 32a (500 mg, 1.70 mmol), KOAc (501 mg, 5.11 mmol), bispinacolatodiboron (520 mg, 2.04mmol), PdCl₂(dppf)₂ (49 mg, 0.05 mmol) in DMSO (5 mL) was stirred at 90° C. under an Argon atmosphere for 12 h. After cooling to rt the reaction mixture was diluted with H₂O (10 mL) and extracted with DCM (3×20 mL). The combined DCM layers were dried over Na₂SO₄, filtered, and concentrated to obtain a residue which was purified by flash column chromatography on silica gel (1:0-1:1 DCM/EtOAC) to obtain compound 32b. ¹H-NMR (400 MHz, CDCl₃) δ (ppm): 9.00 (m, 1H), 8.26 (dd, J=7.8, 1.6 Hz, 1H), 8.00 (d, J=8.6 Hz, 1H), 5.01 (s, 1H), 1.35-1.39 (m, 12H), 1.20 (s, 9H).

C. 5-(8-Morpholino-2-((quinolin-2-yloxy)methyl)imidazo[1,2-a]pyrazin-5-yl)pyridine-2-sulfonamide trifluoroacetic acid salt, Cpd 86

Compound 31b was subjected to Suzuki coupling reaction conditions with compound 32b using the methods described in Example 1, Step G, and the resulting product was subjected to TFA deprotection using the methods described in Example 1, Step E, to obtain title compound 86. ¹H-NMR (400 MHz, CD₃OD) δ (ppm): 8.85 (s, 1H), 8.08-8.15 (m, 2H), 8.03 (d, J=9.0 Hz, 1H), 7.84 (s, 1H), 7.79 (d, J=8.6 Hz, 1H), 7.72 (d, J=7.4 Hz, 1H), 7.59-7.65 (m, 1H), 7.43 (s, 1H), 7.35-7.41 (m, 2H), 6.95 (d, J=9.0 Hz, 1H), 5.64 (s, 2H), 4.32 (br. s., 4H), 3.88 (m, 4H). Mass Spectrum (LCMS, ESI pos.) Calcd. for C₂₅H₂₃N₇O₄S: 518.1 (M+H). Found 518.2.

Example 33

(E)-N-(2-Hydroxyethyl)-4-(8-morpholino-2-(2-(quinolin-2-yl)vinyl)imidazo[1,2-a]pyrazin-5-yl)benzenesulfonamide (Cpd 73)

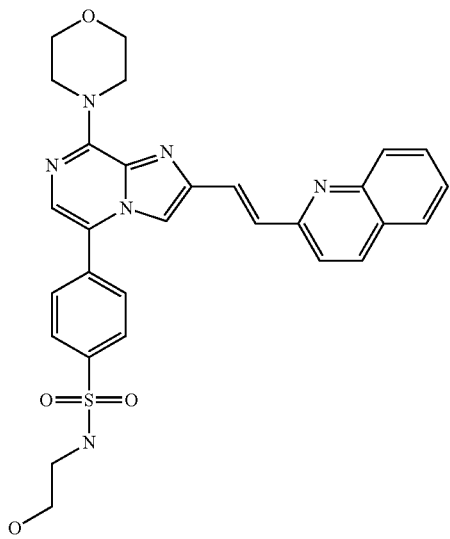 [SMILES: O=S(=O)(NCCO)c1ccc(-c2cnc(N3CCOCC3)c3nc(/C=C/c4ccc5ccccc5n4)cn23)cc1]

A. (E)-N-(2-((tert-Butyldimethylsilyl)oxy)ethyl)-4-(8-morpholino-2-(2-(quinolin-2-yl)vinyl)imidazo[1,2-a]pyrazin-5-yl)benzenesulfonamide, 33a

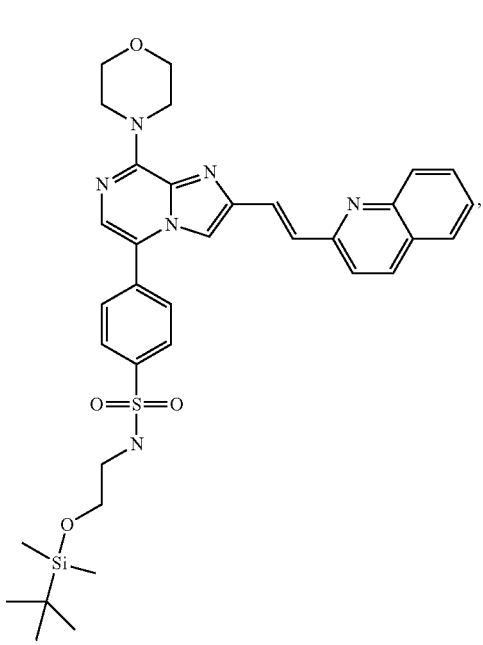

Compound 2b was subjected to Suzuki coupling reaction conditions as described in Example 1, Step G, with (4-(N-(2-((tert-butyldimethylsilyl)oxy)ethyl)sulfamoyl)phenyl)boronic acid to obtain compound 33a. Mass Spectrum (LCMS, ESI pos.) Calcd. For $C_{35}H_{42}N_6O_4SSi$: 671.3 (M+H). Found 671.3.

B. (E)-N-(2-Hydroxyethyl)-4-(8-morpholino-2-(2-(quinolin-2-yl)vinyl)imidazo[1,2-a]pyrazin-5-yl)benzenesulfonamide, Cpd 73

To a solution of compound 33a (135 mg, 0.201 mmol) in THF (5 mL), TBAF (112 mg, 0.402 mmol) was added. The resulting mixture was stirred at rt for 2 h and concentrated. The residue was purified by flash column chromatography on silica gel (EtOAc/hexanes, 0-100%). The solid obtained was suspended in 50% diethyl ether/hexanes, sonicated, and collected by filtration to obtain the title compound 73. $^1$H-NMR (400 MHz, DMSO-$d_6$) δ (ppm): 7.48-7.52 (m, 2H), 7.06-7.13 (m, 6H), 6.99-7.04 (m, 2H), 6.87-6.92 (m, 1H), 6.78-6.84 (m, 1H), 6.67-6.73 (m, 2H), 3.90-3.95 (m, 1H), 3.44-3.50 (m, 4H), 2.94-2.99 (m, 4H), 2.54-2.61 (m, 4H). Mass Spectrum (LCMS, ESI pos.) Calcd. For $C_{29}H_{28}N_6O_4S$: 557.2 (M+H). Found 557.2.

Example 34

(E)-1-(2-Hydroxyethyl)-3-(4-(8-morpholino-2-(2-(quinolin-2-yl)vinyl)imidazo[1,2-a]pyrazin-5-yl)phenyl)urea (Cpd 72)

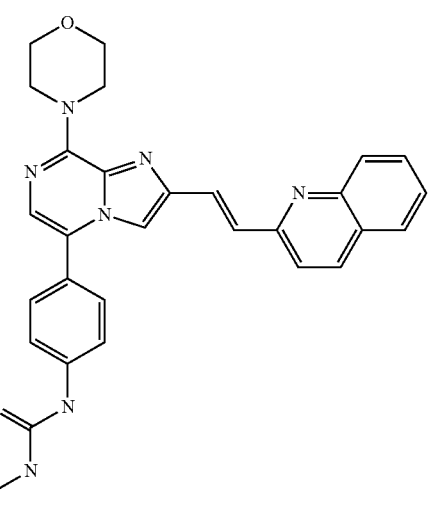

To a solution of 2-((tert-Butyldimethylsilyl)oxy)ethanamine (357 mmol, 2.04 mmol) in DME (5 mL), 4-isocyanatophenylboronic acid pinacol ester (500 mg, 2.04 mmol)

was added. The resulting mixture was stirred at rt overnight and concentrated. The residue obtained was used directly in a Suzuki coupling reaction with compound 2b using the reaction conditions described in Example 1, Step G, and substituting K$_2$CO$_3$ as the base. The resulting product was deprotected using the methods described in Example 33, Step B to obtain the title compound 72. $^1$H-NMR (400 MHz, CD$_3$OD) δ (ppm): 8.25 (d, J=8.8 Hz, 1H), 8.03 (d, J=8.6 Hz, 1H), 7.93 (s, 1H), 7.84 (dd, J=13.7, 8.3 Hz, 2H), 7.68-7.77 (m, 3H), 7.58-7.64 (m, 2H), 7.49-7.56 (m, 3H), 7.30 (s, 1H), 4.28-4.32 (m, 4H), 3.92-4.00 (m, 4H), 3.66-3.74 (m, 2H), 3.40 (m, 2H) Mass Spectrum (LCMS, ESI pos.) Calcd. For C$_{30}$H$_{29}$N$_7$O$_3$: 536.2 (M+H). Found 536.3.

Example 35

(E)-1,1-bis(2-hydroxyethyl)-3-(4-(8-morpholino-2-(2-(quinolin-2-yl)vinyl)imidazo[1,2-a]pyrazin-5-yl) phenyl)urea (Cpd 71)

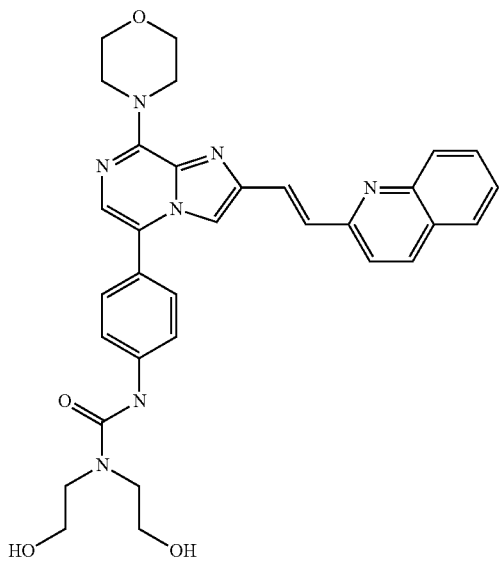 [SMILES: O=C(Nc1ccc(-c2cnc(N3CCOCC3)c3nc(/C=C/c4ccc5ccccc5n4)cn23)cc1)N(CCO)CCO]

To a solution of bis(2-((tert-butyldimethylsilyl)oxy)ethyl) amine (680 mmol, 2.04 mmol) in DME (5 mL), 4-isocyanatophenylboronic acid pinacol ester (500 mg, 2.04 mmol) was added. The resulting mixture was stirred at rt overnight and concentrated. The residue obtained was used directly in a Suzuki coupling reaction with compound 2b using the reaction conditions described in Example 1, Step G, and substituting K$_2$CO$_3$ as the base and the resulting product was deprotected using the methods described in Example 33, Step B to obtain the title compound 71. $^1$H-NMR (400 MHz, DMSO-d$_6$) δ (ppm): 8.97 (s, 1H), 8.35 (d, J=8.6 Hz, 1H), 8.19 (s, 1H), 7.92-8.01 (m, 2H), 7.83-7.91 (m, 2H), 7.75 (t, J=7.6 Hz, 1H), 7.52-7.69 (m, 6H), 7.37 (s, 1H), 5.15 (m, 2H), 4.26 (m., 4H), 3.82 (m, J=4.2 Hz, 4H), 3.62 (m, 4H), 3.42-3.52 (m, 4H). Mass Spectrum (LCMS, ESI pos.) Calcd. For C$_{32}$H$_{33}$N$_7$O$_4$: 580.2 (M+H). Found 580.3.
Following the procedure described in Example 35 above, and substituting suitably selected and substituted reagents, starting materials and conditions as would be readily apparent to those skilled in the art, the following representative compound of the present invention was prepared.

| Cpd | Characterization |
|---|---|
| 49 | (E)-N-isopropyl-3-methyl-4-(8-morpholino-2-(2-(quinolin-2-yl)vinyl)imidazo[1,2-a]pyrazin-5-yl)benzenesulfonamide<br>$^1$H-NMR (400 MHz, CDCl$_3$) δ (ppm): 8.13 (d, J = 8.6 Hz, 1H), 8.05 (d, J = 8.3 Hz, 1H), 7.92 (s, 1H), 7.86 (dd, J = 7.9, 1.6 Hz, 1H), 7.78 (d, J = 8.3 Hz, 1H), 7.69-7.73 (m, 1H), 7.65-7.69 (m, 3H), 7.51 (d, J = 8.1 Hz, 2H), 7.26 (s, 2H), 7.17 (s, 1H), 4.41 (d, J = 7.6 Hz, 4H), 3.95 (t, J = 4.8 Hz, 4H), 3.62 (dd, J = 13.9, 6.6 Hz, 1H), 2.27 (s, 3H), 1.21 (d, 6H).<br>Mass Spectrum (LCMS, ESI pos.) Calcd. For C$_{31}$H$_{32}$N$_6$O$_3$S: 569.2 (M + H), Found 569.5. |

Example 36

6-(8-morpholino-2-(2-(quinolin-2-yl)ethyl)imidazo [1,2-a]pyrazin-5-yl)benzo[d]oxazol-2(3H)-one trifluoroacetic acid salt (Cpd 64)

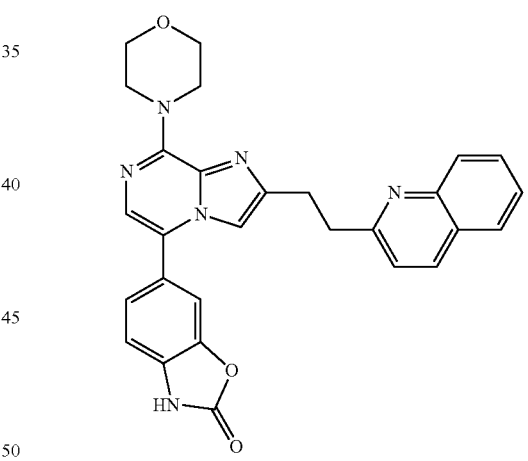

Compound 3a was subjected to Suzuki coupling reaction conditions with 6-(4,4,5,5-tetramethyl-1,3,2-dioxaborolan-2-yl)-3-tritylbenzo[d]oxazol-2(3H)-one (prepared following the procedure in Patent Application Publication WO 2007024600A2, 20070301) and the resulting product was deprotected using TFA as described in Example 13, Step C to obtain the title compound 64. $^1$H-NMR (400 MHz, CD$_3$OD) δ (ppm): 8.90-8.96 (m, 1H), 8.22-8.29 (m, 1H), 8.07-8.20 (m, 2H), 7.89-7.98 (m, 2H), 7.73 (s, 1H), 7.62 (s, 1H), 7.39 (s, 1H), 7.31-7.37 (m, 1H), 7.24 (s, 2H), 3.97-4.05 (m, 4H), 3.62-3.71 (m, 6H), 3.44 (s, 2H). Mass Spectrum (LCMS, ESI pos.) Calcd. For $C_{28}H_{24}N_6O_3$: 493.2 (M+H). Found 493.5.

Example 37

Potassium 3,3-difluoro-5-(8-morpholino-2-(2-(quinolin-2-yl)ethyl)imidazo[1,2-a]pyrazin-5-yl)-2-oxoindolin-1-ide (Cpd 59)

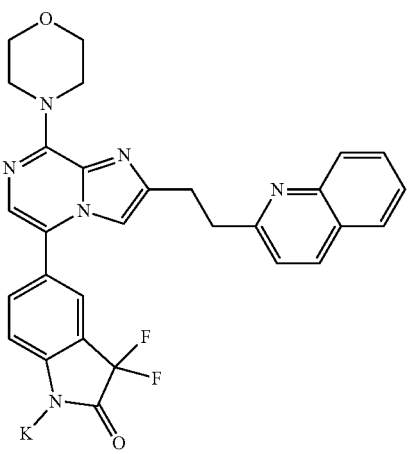

A. 3,3-Difluoro-5-(4,4,5,5-tetramethyl-1,3,2-dioxaborolan-2-yl)-1-((2-(trimethylsilyl)ethoxy)methyl)indolin-2-one, 37a

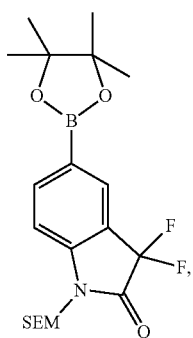

To a solution of 5-bromo-3,3-difluoroindolin-2-one (600 mg, 2.42 mmol) in DMF (5 mL), 60% NaH (69.6 mg, 2.90 mmol) was added. The resulting mixture was stirred at rt for 20 min and SEM-Cl (472 µL, 2.66 mmol) was added. The reaction mixture was stirred at rt overnight, poured into saturated NH₄Cl (40 mL) and extracted with DCM (3×20 mL). The combined DCM layers were dried over Na₂SO₄, filtered, and concentrated. The residue obtained was purified by flash column chromatography on silica gel (0-100% EtOAc/hexanes) to obtain 5-bromo-3,3-difluoro-1-((2-(trimethylsilyl)ethoxy)methyl)indolin-2-one, which was subjected to borylation using the methods described in Example 32, Step B to obtain compound 37a. ¹H-NMR (CDCl₃, 400 MHz) δ (ppm): 8.33 (s, 1H), 8.04 (d, J=9.6 Hz, 1H), 7.57 (d, J=8.6 Hz, 1H), 5.46 (s, 2H), 3.75 (m, 2H), 1.27 (s, 12H), 0.95 (m, 2H).

B. 3,3-Difluoro-5-(8-morpholino-2-(2-(quinolin-2-yl)ethyl)imidazo[1,2-a]pyrazin-5-yl)-1-((2-(trimethylsilyl)ethoxy)methyl)indolin-2-one, 37b Compound 3a was subjected to Suzuki coupling conditions with 3,3-difluoro-5-(4,4,5,5-tetramethyl-1,3,2-dioxaborolan-2-yl)-1-((2(trimethylsilyl)ethoxy)methyl)indolin-2-one to obtain compound 37b using the method described in the Example 21, Step D. Mass Spectrum (LCMS, ESI pos.) Calcd. For $C_{35}H_{38}F_2N_6O_3Si$: 657.2 (M+H). Found 657.5.

C. 3,3-Difluoro-5-(8-morpholino-2-(2-(quinolin-2-yl)ethyl)imidazo[1,2-a]pyrazin-5-yl)indolin-2-one, 37c

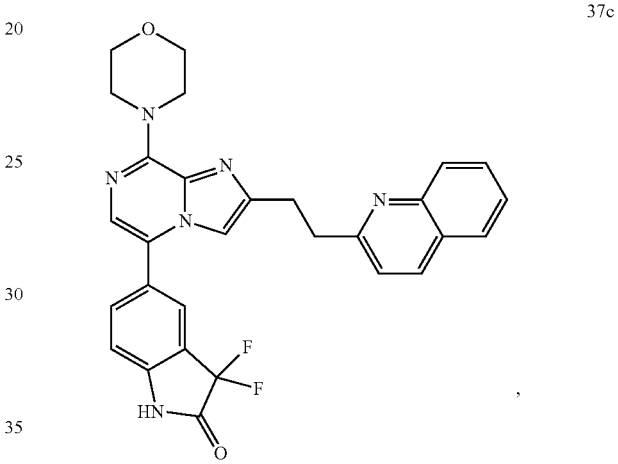

A solution of compound 37c (220 mg, 0.33 mmol) in TFA (10 mL) was stirred at rt for 1 h and concentrated. The resulting residue was dried under reduced pressure, suspended in diethyl ether (10 mL) and sonicated. The solids were collected by filtration and suspended in MeOH (10 mL) containing DIEA (1 mL). The resulting suspension was heated at reflux for 1 h and concentrated. The solid obtained was dried under reduced pressure, suspended in diethyl ether (20 mL) and EtOAc (5 mL) and sonicated for 10 min. The resulting mixture was allowed to stand for 30 min. The solid thus obtained was collected by filtration, dried under reduced pressure, to obtain compound 37c. Mass Spectrum (LCMS, ESI pos.) Calcd. For $C_{29}H_{24}F_2N_6O_2$: 527.2 (M+H). Found 527.5.

D. Potassium 3,3-difluoro-5-(8-morpholino-2-(2-(quinolin-2-yl)ethyl)imidazo[1,2-a]pyrazin-5-yl)-2-oxoindolin-1-ide, Cpd 59

Compound 37c (65.3 mg, 0.124 mmol) was added to a MeOH solution of KOMe (8.69 mg, 0.124 mmol) at 0° C. The resulting mixture was stirred at 0° C. for 15 min, allowed to warm to rt, and stirred for another 30 min. The resulting mixture was concentrated and the resulting residue was dried under reduced pressure to obtain the title compound 59. ¹H-NMR (400 MHz, DMSO-d₆) δ (ppm): 8.25 (d, J=8.6 Hz, 1H), 7.92 (d, J=8.3 Hz, 2H), 7.71 (t, J=7.7 Hz, 1H), 7.45-7.59 (m, 4H), 7.40 (br. s., 1H), 7.26 (s, 1H), 6.84 (d, J=7.6 Hz, 1H), 4.06 (m, 4H), 3.68 (m, 4H) 3.27-3.35 (m, 2H), 3.19-3.27 (m, 2H). Mass Spectrum (LCMS, ESI pos.) Calcd. For C$_{29}$H$_{24}$F$_2$N$_6$O$_2$: 527.2 (M+H). Found 527.5.

Example 38

6-(8-Morpholino-2-(2-(quinolin-2-yl)ethyl)imidazo[1,2-a]pyrazin-5-yl)benzo[d]isothiazol-3(2H)-one 1,1-dioxide trifluoroacetic acid salt (Cpd 54)

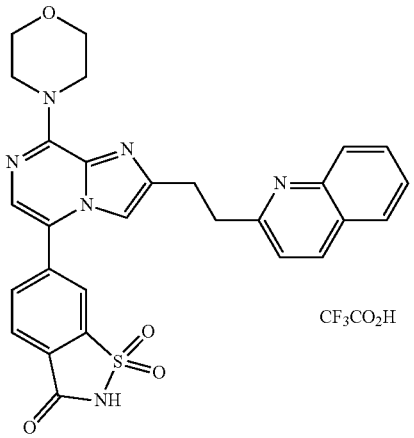 [SMILES: O=C1NS(=O)(=O)c2cc(-c3cnc(N4CCOCC4)c4nc(CCc5ccc6ccccc6n5)cn34)ccc21 ; "CF3CO2H"]

A. 6-Bromo-2-(4-methoxybenzyl)benzo[d]isothiazol-3(2H)-one 1,1-dioxide, 38a

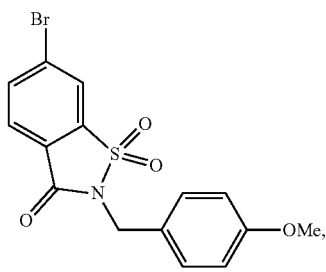

To a suspension of 60% NaH (10.1 mg, 0.254 mmol) in DMF (1 mL), 6-bromobenzo[d]isothiazol-3(2H)-one 1,1-dioxide (55.4 mg, 0.212 mmol) was added portionwise at 0° C. The resulting mixture was stirred at rt for 15 min and p-methoxy benzyl chloride (27.6 μL, 0.212 mmol) was added dropwise. The reaction mixture was heated to 70° C. overnight, allowed to cool to rt, and treated with water (20 mL). The aqueous layer was extracted with EtOAc (3×50 mL) and the combined organic layers were dried over Na$_2$SO$_4$, filtered, and concentrated. The resulting solid was recrystallized from hexane/DCM to obtain compound 38a. $^1$H-NMR (400 MHz, CDCl$_3$) δ (ppm): 8.08 (d, J=1.5 Hz, 1H), 7.89 (dd, J=8.2, 1.6 Hz, 1H), 7.69 (d, J=8.3 Hz, 1H), 7.35 (d, J=8.6 Hz, 2H), 6.79 (d, J=8.6 Hz, 2H), 4.76 (s, 2H), 3.71 (s, 3H).

B. 2-(4-Methoxybenzyl)-6-(4,4,5,5-tetramethyl-1,3,2-dioxaborolan-2-yl)benzo[d]isothiazol-3(2H)-one 1,1-dioxide, 38b

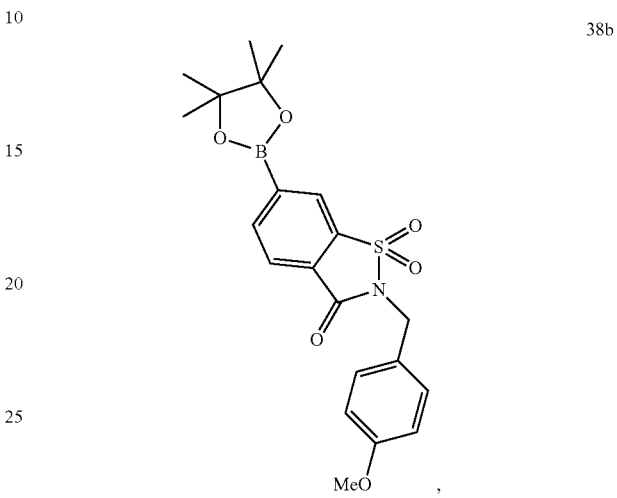

Compound 38a was subjected to borylation using the methods described in the Example 32, Step B to obtain compound 38b. $^1$H-NMR (400 MHz, CDCl$_3$) δ (ppm): 8.38 (s, 1H), 8.16 (d, J=7.6 Hz, 1H), 7.80 (d, J=7.6 Hz, 1H), 7.36 (d, J=8.8 Hz, 2H), 6.76-6.82 (m, 2H), 4.77 (s, 2H), 3.70 (s, 3H), 1.28 (s, 12H).

C. 2-(4-Methoxybenzyl)-5-(8-morpholino-2-(2-(quinolin-2-yl)ethyl)imidazo[1,2-a]pyrazin-5-yl)benzo[d]isothiazol-3(2H)-one 1,1-dioxide, 38c

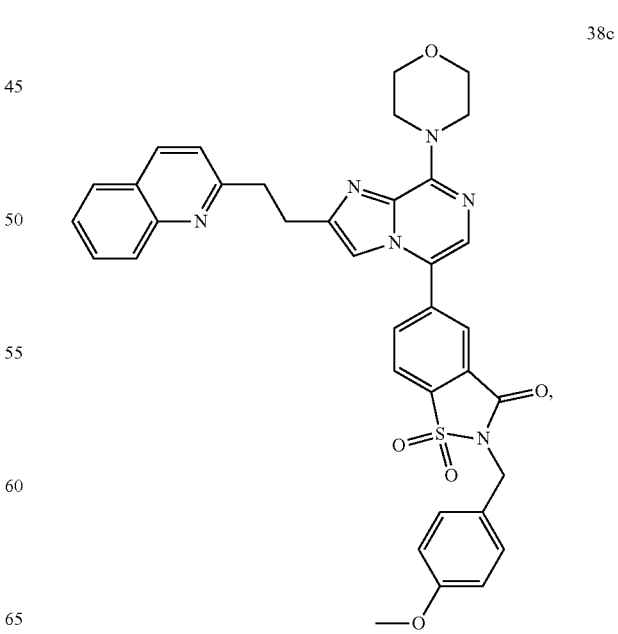

A mixture of compound 3a (200.0 mg, 0.458 mmol), compound 38b (236 mmol, 0.550 mmol), Cl₂Pd(dppf) (33.5 mg, 0.045 mmol), and CsF (209 mg, 1.37 mmol) in dioxane (5 mL) was heated at 100° C. under an Argon atmosphere for 5 h. The reaction mixture was allowed to cool to rt, and then filtered through a pad of diatomaceous earth. The filtrate was concentrated and the residue obtained was purified by flash column chromatography on silica gel (0:1-1:0 EtOAc/heptanes) to obtain compound 38d. Mass Spectrum (LCMS, ESI pos.) Calcd. For $C_{36}H_{32}N_6O_5S$: 661.2 (M+H). Found 661.6.

D. 6-(8-Morpholino-2-(2-(quinolin-2-yl)ethyl)imidazo[1,2-a]pyrazin-5-yl)benzo[d]isothiazol-3(2H)-one 1,1-dioxide trifluoroacetic acid salt, Cpd 54

Compound 38c (90 mg, 0.14 mmol) in TFA (3 mL) was heated at 70° C. overnight. The reaction mixture was allowed to cool to rt and concentrated. The residue obtained was dried under reduced pressure for 4 h, suspended in 1:1 diethyl ether/hexanes (10 mL) and sonicated for 5 min. The solid was collected by suction filtration and dried under reduced pressure overnight to obtain the title compound 54. ¹H-NMR (400 MHz, DMSO-d₆) δ (ppm): 8.92-9.01 (m, 1H), 8.25-8.32 (m, 1H), 8.12-8.21 (m, 2H), 7.98-8.10 (m, 4H), 7.89 (s, 2H), 7.50 (s, 1H), 3.94 (m, 4H), 3.46-3.59 (m, 6H), 3.31-3.42 (m, 4H). Mass Spectrum (LCMS, ESI pos.) Calcd. For $C_{28}H_{24}N_6O_4S$: 541.1 (M+H). Found 541.5.

Example 39

(E)-1-Methyl-6-(8-morpholino-2-(2-(quinolin-2-yl)vinyl)imidazo[1,2-a]pyrazin-5-yl)-1,3-dihydrobenzo[c][1,2,5]thiadiazole 2,2-dioxide trifluoroacetic acid salt (Cpd 43)

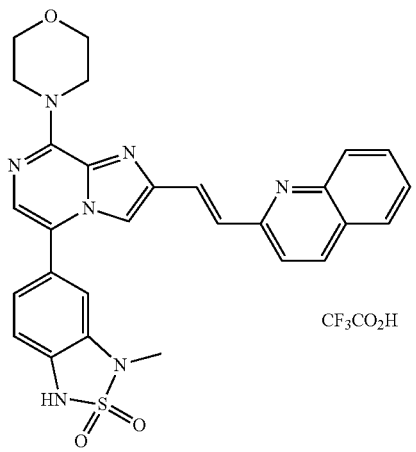 [SMILES: CN1c2cc(-c3cnc(N4CCOCC4)c4nc(/C=C/c5ccc6ccccc6n5)cn34)ccc2NS1(=O)=O ; "CF3CO2H"]

A. 5-Bromo-3-methyl-1-((2-(trimethylsilyl)ethoxy)methyl)-1,3-dihydrobenzo[c][1,2,5]thiadiazole 2,2-dioxide, 39a

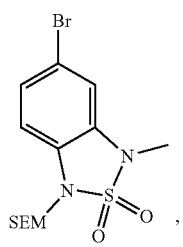

A mixture of 5-bromo-N¹-methylbenzene-1,2-diamine dihydrochloride (800.0 mg, 3.00 mmol) and sulfamide (560 mg, 5.80 mmol) in pyridine (10 mL) was heated at reflux for 2 h. Pyridine was removed under reduced pressure and the residue obtained was dissolved in DCM (20 mL) and washed with 1N HCl (20 mL). The DCM layer was separated, dried over Na₂SO₄, filtered, and concentrated to obtain 6-bromo-1-methyl-1,3-dihydrobenzo[c][1,2,5]thiadiazole 2,2-dioxide. ¹H NMR (400 MHz, DMSO-d₆) δ (ppm): 7.98 (d, J=2.0 Hz, 1H), 7.93 (dd, J=8.8, 2.3 Hz, 1H), 7.46 (d, 1H), 3.41 (s, 3H).

To a solution of 6-bromo-1-methyl-1,3-dihydrobenzo[c][1,2,5]thiadiazole 2,2-dioxide (557 mmol, 2.10 mmol, as prepared above) in DMF (5 mL), K₂CO₃ (1.00 g, 7.23 mmol) and SEM-Cl (0.560 mL, 3.20 mmol) were added. The resulting mixture was stirred at 75° C. for 4 h and allowed to cool to rt. The reaction mixture was diluted with water (50 mL) and extracted with DCM (3×20 mL). The combined DCM layers were dried over Na₂SO₄, filtered, concentrated and the resulting residue was purified by flash column chromatography on silica gel (0-50% hexane/EtOAc) to obtain compound 39a. ¹H-NMR (400 MHz, CDCl₃) δ (ppm): 7.12-7.17 (m, 2H), 6.60 (d, J=8.6 Hz, 1H), 5.14 (s, 2H), 3.68-3.74 (m, 2H), 3.25 (s, 3H), 0.93-0.99 (m, 3H), 0.01 (s, 9H).

B. 3-Methyl-5-(4,4,5,5-tetramethyl-1,3,2-dioxaborolan-2-yl)-1-((2-(trimethylsilyl)ethoxy)methyl)-1,3-dihydrobenzo[c][1,2,5]thiadiazole 2,2-dioxide, 39b

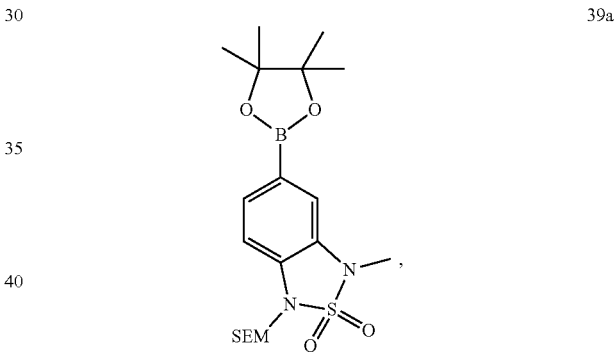

Compound 39a was subjected to borylation using the methods described in the Example 32, Step B to obtain compound 39b. ¹H-NMR (CDCl₃, 400 MHz) δ (ppm): 7.49-7.54 (m, 1H), 7.41 (s, 1H), 6.73 (d, J=7.8 Hz, 1H), 5.20 (s, 2H), 3.72-3.78 (m, 2H), 3.29 (s, 3H), 1.33 (s, 12H), 0.98 (m, 2H), 0.01 (s, 12H).

C. (E)-1-Methyl-6-(8-morpholino-2-(2-(quinolin-2-yl)vinyl)imidazo[1,2-a]pyrazin-5-yl)-1,3-dihydrobenzo[c][1,2,5]thiadiazole 2,2-dioxide trifluoroacetic acid salt, Cpd 43

Compound 2b was subjected to Suzuki coupling conditions with (3-methyl-5-(4,4,5,5-tetramethyl-1,3,2-dioxaborolan-2-yl)-1-((2-(trimethylsilyl)ethoxy)methyl)-1,3-dihydrobenzo[c][1,2,5]thiadiazole 2,2-dioxide and the resulting product was deprotected with TFA using the methods described in Example 37, Steps B and C) to obtain the title compound 43. ¹H NMR (400 MHz, CD₃OD) δ (ppm): 8.79 (d, J=9.0 Hz, 1H), 8.28 (d, J=9.0 Hz, 1H), 8.07-8.18 (m, 4H), 8.02 (td, J=7.8, 1.2 Hz, 1H), 7.78-7.87 (m, 2H), 7.72 (s, 1H), 7.32 (s, 1H), 7.27 (dd, J=8.1, 2.0 Hz, 1H), 7.10 (d, J=1.7 Hz, 1H), 7.02 (d, J=8.1 Hz, 1H), 4.33-4.39 (m, 4H), 3.91-3.99 (m, 4H), 3.34 (s, 3H). Mass Spectrum (LCMS, ESI pos.) Calcd. For $C_{28}H_{25}N_7O_3S$: 540.2 (M+H). Found 540.4.

Example 40

(E)-4-Methyl-7-(8-morpholino-2-(2-(quinolin-2-yl)vinyl)imidazo[1,2-a]pyrazin-5-yl)-2H-benzo[e][1,2,4]thiadiazin-3(4H)-one 1,1-dioxide trifluoroacetic acid salt (Cpd 24)

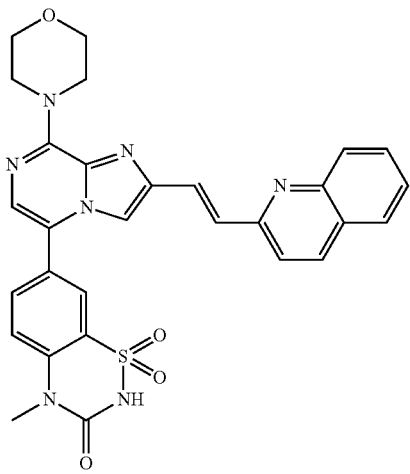 [SMILES: CN1C(=O)NS(=O)(=O)c2cc(-c3cnc(N4CCOCC4)c4nc(/C=C/c5ccc6ccccc6n5)cn34)ccc21]

A. 7-Bromo-2-(4-methoxybenzyl)-4-methyl-2H-benzo[e][1,2,4]thiadiazin-3(4H)-one 1,1-dioxide, 40a

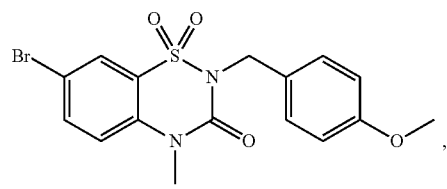

To a solution of 7-bromo-4-methyl-2H-benzo[e][1,2,4]thiadiazin-3(4H)-one 1,1-dioxide (510 mg, 1.7 mmol) in DMF (10 mL), 60% NaH (69 mg, 1.7 mmol) was added in portions at 0° C. The resulting mixture was stirred at rt for 10 min and p-methoxybenzyl chloride (0.25 mL, 1.7 mmol) was added. The resulting mixture was stirred at 70° C. for 5 h, cooled to rt and poured over ice. The resulting compound was extracted with EtOAc (3×20 mL). The combined EtOAc layers were dried over Na$_2$SO$_4$, filtered, and concentrated. The residue obtained was purified by flash column chromatography on silica gel (0-100% EtOAc/heptanes) to obtain compound 40a. $^1$H-NMR (400 MHz, CDCl$_3$) δ (ppm): 8.01 (d, J=2.0 Hz, 1H), 7.74 (dd, J=8.8, 2.3 Hz, 1H), 7.40 (d, J=8.6 Hz, 2H), 7.10 (d, J=8.6 Hz, 1H), 6.83 (d, J=8.6 Hz, 2H), 4.99 (s, 2H), 3.77 (s, 3H).

B. 2-(4-Methoxybenzyl)-4-methyl-7-(4,4,5,5-tetramethyl-1,3,2-dioxaborolan-2-yl)-2H-benzo[e][1,2,4]thiadiazin-3(4H)-one 1,1-dioxide, 40b

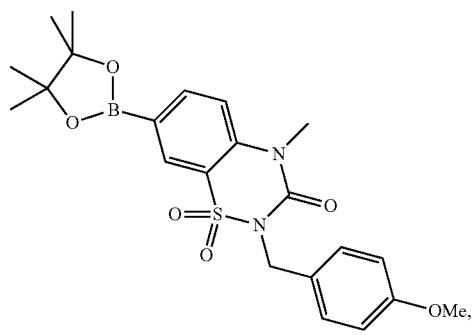

Compound 40a was subjected to borylation using the methods described in Example 32, Step B to obtain compound 40b. $^1$H NMR (400 MHz, CDCl$_3$) δ (ppm): 8.35 (s, 1H), 8.03 (d, J=7.1 Hz, 1H), 7.40 (d, J=9.1 Hz, 2H), 7.18 (d, J=8.6 Hz, 1H), 6.82 (d, J=8.6 Hz, 2H), 5.01 (s, 2H), 3.76 (s, 3H), 3.50 (s, 3H), 1.35 (s, 12H).

C. (E)-4-methyl-7-(8-morpholino-2-(2-(quinolin-2-yl)vinyl)imidazo[1,2-a]pyrazin-5-yl)-2H-benzo[e][1,2,4]thiadiazin-3(4H)-one 1,1-dioxide trifluoroacetic acid salt, Cpd 24

Compound 2b was subjected to Suzuki coupling conditions using the methods described in Example 1, Step G, with compound 40b and the resulting product was deprotected with TFA at 70° C. for 30 min. The reaction mixture was allowed to cool to rt and concentrated. The residue obtained was dried under reduced pressure overnight, suspended in ETOAc (10 mL) and sonicated for 10 min. The solid formed was collected by suction filtration and dried under reduced pressure to obtain the title compound 24. $^1$H NMR (400 MHz, DMSO-d$_6$) δ (ppm): 8.67-8.78 (m, 1H), 8.04-8.23 (m, 7H), 7.88-7.98 (m, 1H), 7.65-7.78 (m, 3H), 7.51 (s, 1H), 4.33 (br. s., 4H), 3.78-3.91 (m, 4H), 3.51 (s, 3H).

Example 41

(E)-2,4-Dimethyl-7-(8-morpholino-2-(2-(quinolin-2-yl)vinyl)imidazo[1,2-a]pyrazin-5-yl)-2H-benzo[e][1,2,4]thiadiazin-3(4H)-one 1,1-dioxide (Cpd 20)

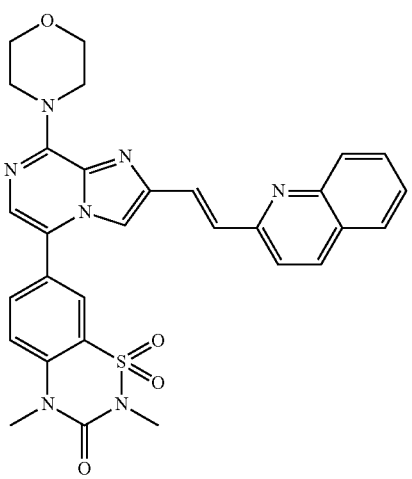 [SMILES: CN1C(=O)N(C)S(=O)(=O)c2cc(-c3cnc(N4CCOCC4)c4nc(/C=C/c5ccc6ccccc6n5)cn34)ccc21]

A. 7-Bromo-2,4-dimethyl-2H-benzo[e][1,2,4]thiadi-azin-3(4H)-one 1,1-dioxide, 41a

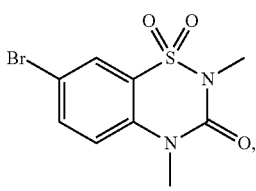

41a

To a solution of 7-bromo-4-methyl-2H-benzo[e][1,2,4]thiadiazin-3(4H)-one 1,1-dioxide (262 mg, 0.902 mmol), in DMF (3 mL), DIEA (233 μL, 1.35 mmol) was added. The resulting mixture was stirred at rt for 10 min and MeI (56.0 μL, 0.902) was added. The reaction mixture was stirred at rt overnight and diluted with 20 mL of water. The solid formed was collected by suction filtration and washed with water (2×20 mL) to obtain compound 41a. Mass Spectrum (LCMS, ESI pos.) Calcd. For $C_9H_9BrN_2O_3S$: 304.9 (M+H). Found 305.0.

B. 2,4-Dimethyl-7-(4,4,5,5-tetramethyl-1,3,2-diox-aborolan-2-yl)-2H-benzo[e][1,2,4]thiadiazin-3(4H)-one 1,1-dioxide, 41b

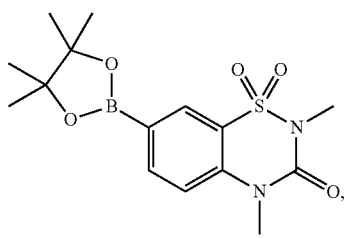

41b

Compound 41a was subjected to borylation using the methods described in the Example 32, Step B to obtain compound 41b. $^1$H NMR (400 MHz, CDCl$_3$) δ (ppm): 8.35 (s, 1H), 8.06 (d, J=8.6 Hz, 1H), 7.23 (d, J=8.6 Hz, 1H), 3.55 (s, 3H), 3.37 (s, 3H), 1.36 (s, 12H).

C. (E)-2,4-Dimethyl-7-(8-morpholino-2-(2-(quino-lin-2-yl)vinyl)imidazo[1,2-a]pyrazin-5-yl)-2H-benzo[e][1,2,4]thiadiazin-3(4H)-one 1,1-dioxide, Cpd 20

Compound 2b was subjected to Suzuki coupling conditions using the methods described in Example 1, Step G, with compound 41b to obtain the title compound 20. $^1$H NMR (400 MHz, DMSO-d$_6$) δ (ppm): 8.35 (d, J=8.6 Hz, 1H), 8.18-8.20 (m, 2H), 8.15 (dd, J=8.6, 2.0 Hz, 1H), 7.96 (t, J=8.6 Hz, 2H), 7.90 (s, 1H), 7.86 (d, J=6.6 Hz, 1H), 7.72-7.80 (m, 2H), 7.64 (d, J=16.2 Hz, 1H), 7.56 (t, J=7.3 Hz, 1H), 7.49 (s, 1H), 4.31 (m, 4H), 3.80-3.86 (m, 4H), 3.58 (s, 3H), 3.28 (s, 3H). Mass Spectrum (LCMS, ESI pos.) Calcd. For $C_{30}H_{27}N_7O_4S$: 582.2 (M+H). Found 582.4.

Following the procedure described in Example 41 above, and substituting suitably selected and substituted reagents, starting materials and conditions as would be readily apparent to those skilled in the art, the following representative compound of the present invention was prepared.

| Cpd | Characterization |
| --- | --- |
| 41 | (E)-4-(5-(4-(methoxymethoxy)-3,5-dimethylphenyl)-2-(2-(quinolin-2-yl)vinyl)imidazo[1,2-a]pyrazin-8-yl)morpholine. <br> $^1$H-NMR (400 MHz, CDCl$_3$) δ (ppm): 8.11-8.16 (m, 1H), 8.03-8.08 (m, 1H), 7.77-7.82 (m, 2H), 7.67-7.72 (m, 4H), 7.47-7.54 (m, 1H), 7.29 (s, 1H), 7.23 (s, 2H), 5.07 (s, 2H), 4.32-4.38 (m, 4H), 3.91-3.98 (m, 4H), 3.68 (s, 3H), 2.39 (s, 6H). <br> Mass Spectrum (LCMS, ESI pos.) Calcd. For $C_{31}H_{31}N_5O_3S$: 522.2 (M + H), Found 522.0. |
| 42 | (E)-5-(8-Morpholino-2-(2-(quinolin-2-yl)vinyl)imidazo[1,2-a]pyrazin-5-yl)benzo[d]isothiazol-3(2H)-one 1,1-dioxide <br> $^1$H NMR (400 MHz, DMSO-d$_6$) δ (ppm): 8.61-8.69 (m, 1H), 8.36-8.39 (m, 1H), 8.01-8.21 (m, 7H), 7.86-7.94 (m, 1H), 7.66-7.74 (m, 2H), 7.58 (s, 1H), 4.31-4.40 (m, 4H), 3.83 (m, 4H) |

| Cpd | Characterization |
|---|---|
| | Mass Spectrum (LCMS, ESI pos.) Calcd. For $C_{28}H_{22}N_6O_4S$: 539.1 (M + H), Found 539.3. |
| 49 | (E)-N-isopropyl-3-methyl-4-(8-morpholino-2-(2-(quinolin-2-yl)vinyl)imidazo[1,2-a]pyrazin-5-yl)benzenesulfonamide<br>$^1$H-NMR (400 MHz, CDCl$_3$) δ (ppm): 8.13 (d, J = 8.6 Hz, 1H), 8.05 (d, J = 8.3 Hz, 1H), 7.92 (s, 1H), 7.86 (dd, J = 7.9, 1.6 Hz, 1H), 7.78 (d, J = 8.3 Hz, 1H), 7.69-7.73 (m, 1H), 7.65-7.69 (m, 3H), 7.51 (d, J = 8.1 Hz, 2H), 7.26 (s, 2H), 7.17 (s, 1H), 4.41 (d, J = 7.6 Hz, 4H), 3.95 (t, J = 4.8 Hz, 4H), 3.62 (dd, J = 13.9, 6.6 Hz, 1H), 2.27 (s, 3H), 1.21 (d, 6H).<br>Mass Spectrum (LCMS, ESI pos.) Calcd. For $C_{31}H_{32}N_6O_3S$: 569.2 (M + H), Found 569.5. |

Example 42

(E)-2-Methyl-7-(8-morpholino-2-(2-(quinolin-2-yl)vinyl)imidazo[1,2-a]pyrazin-5-yl)-2H-benzo[e][1,2,4]thiadiazin-3(4H)-one 1,1-dioxide (Cpd 19)

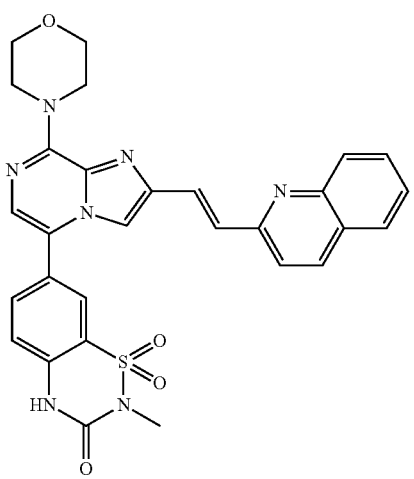 [SMILES: CN1C(=O)Nc2ccc(-c3cnc(N4CCOCC4)c4nc(/C=C/c5ccc6ccccc6n5)cn34)cc2S1(=O)=O]

A. 7-Bromo-2-methyl-2H-benzo[e][1,2,4]thiadiazin-3(4H)-one 1,1-dioxide, 42a

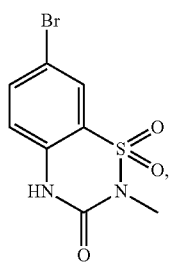

Gaseous ammonia was passed through a suspension of 7-bromo-2H-benzo[e][1,2,4]thiadiazin-3(4H)-one 1,1-dioxide (760 mg, 2.7 mmol) in MeOH (8 mL) until a clear solution was obtained. The solvent was then evaporated and the residue was slurried with MeOH (5 mL) and filtered. The solid obtained was dissolved in DMF (5 mL) and treated with MeI (169 μL, 2.75 mmol). The reaction mixture was stirred at rt for 18 h, poured into water (20 mL) and extracted with EtOAc (3×50 mL). The combined EtOAc layer was dried over Na$_2$SO$_4$, filtered, and concentrated to obtain compound 42a.

$^1$H-NMR (400 MHz, CD$_3$OD) δ (ppm): 7.86 (d, J=2.0 Hz, 1H), 7.60 (dd, J=8.7, 2.1 Hz, 1H), 7.00 (d, J=8.6 Hz, 1H), 3.26 (s, 3H).

B. 7-Bromo-2-methyl-4-((2-(trimethylsilyl)ethoxy)methyl)-2H-benzo[e][1,2,4]thiadiazin-3(4H)-one 1,1-dioxide, 42b

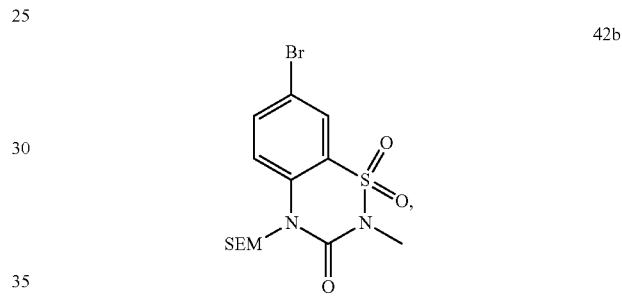

To a solution of compound 42a (616 mg, 2.10 mmol) in DMF (5 mL) was added K$_2$CO$_3$ (1.0 g, 7.2 mmol) and SEM-Cl (563 μL, 3.17 mmol). The resulting mixture was stirred at 75° C. for 4 h, allowed to cool to rt and treated with water (20 mL). The reaction mixture was then extracted with DCM (3×20 mL). The combined DCM layers were dried over Na$_2$SO$_4$, filtered, and concentrated to obtain a residue which was purified by flash column chromatography on silica gel (0-50% EtOAc/hexanes) to obtain compound 42b. $^1$H-NMR (400 MHz, CDCl$_3$) δ (ppm): 7.99 (d, J=2.0 Hz, 1H), 7.74 (dd, J=9.1, 2.5 Hz, 1H), 7.51 (d, J=9.1 Hz, 1H), 5.42 (s, 2H), 3.71-3.77 (m, 2H), 3.35 (s, 3H), 0.91-0.98 (m, 2H), 0.01 (s, 9H).

C. 2-Methyl-7-(4,4,5,5-tetramethyl-1,3,2-dioxaborolan-2-yl)-4-((2-(trimethylsilyl)ethoxy)methyl)-2H-benzo[e][1,2,4]thiadiazin-3(4H)-one dioxide, 42c

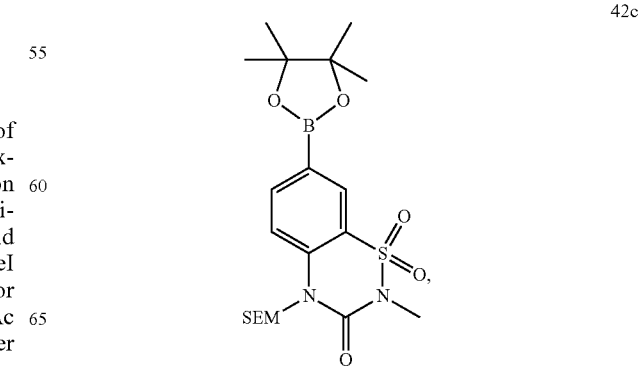

Compound 42b was subjected to borylation using the methods described in Example 32, Step B to obtain compound 42c. $^1$H NMR (400 MHz, CDCl$_3$) δ (ppm): 8.33 (s, 1H), 8.04 (d, J=7.1 Hz, 1H), 7.57 (d, J=8.6 Hz, 1H), 5.46 (s, 2H), 3.72-3.79 (m, 2H), 3.37 (s, 3H), 1.36 (s, 12H), 0.92-0.98 (m, 2H). 0.01 (s, 9H).

D. (E)-2-Methyl-7-(8-morpholino-2-(2-(quinolin-2-yl)vinyl)imidazo[1,2-a]pyrazin-5-yl)-2H-benzo[e][1,2,4]thiadiazin-3(4H)-one 1,1-dioxide, Cpd 19

Compound 2b was subjected to Suzuki coupling conditions using the methods described in Example 1, Step G, with compound 42c and the resulting product was deprotected with TFA using the methods described Example 37, Steps B and C to obtain the title compound 19. $^1$H NMR (400 MHz, DMSO-d$_6$) δ (ppm): 11.71 (s, 1H), 8.35 (d, J=8.6 Hz, 1H), 8.19 (s, 1H), 8.12 (s, 1H), 8.05 (d, J=8.6 Hz, 1H), 7.96 (t, J=8.6 Hz, 2H), 7.83-7.90 (m, 2H), 7.75 (t, J=7.6 Hz, 1H), 7.64 (d, J=16.2 Hz, 1H), 7.53-7.60 (m, 1H), 7.43-7.51 (m, 2H), 4.31 (br. s., 4H), 3.82 (br. s., 4H), 3.25 (s, 3H). Mass Spectrum (LCMS, ESI pos.) Calcd. For C$_{29}$H$_{25}$N$_7$O$_4$S: 568.2 (M+H). Found 568.5.

Example 43

4-(8-Morpholino-2-((1r,3r)-3-(quinolin-2-yl)cyclobutyl)imidazo[1,2-a]pyrazin-3-yl)benzoic acid trifluoroacetic acid salt (Cpd 5)

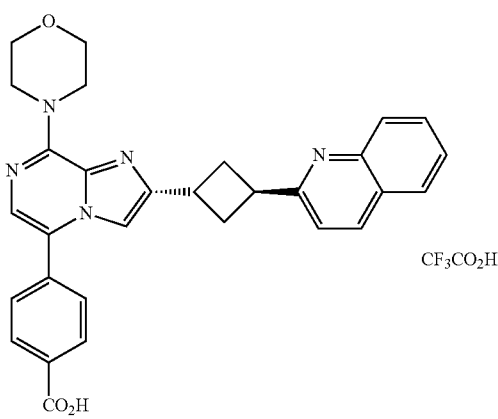

A. Ethyl 3-iodocyclobutanecarboxylate

43a

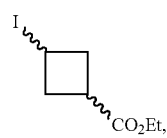

43a

To a solution of ethyl 3-hydroxycyclobutanecarboxylate (10.2 g, 78.4 mmol) in dry pyridine (56.5 mL) at 0° C., TsCl (14.9 g, 78.4 mmol) was added portionwise. The resulting mixture was stirred at rt overnight. The reaction mixture was concentrated under reduced pressure and the residue obtained was dissolved in EtOAc (100 mL) and sequentially washed with 2 N HCl (100 mL), saturated NaHCO$_3$ (100 mL) and water (100 mL). The EtOAc layer was dried over Na$_2$SO$_4$, filtered, and concentrated to obtain ethyl 3-(tosyloxy)cyclobutanecarboxylate as a pale yellow oil, which was used in the next step without further purification.

To a solution ethyl 3-(tosyloxy)cyclobutanecarboxylate (6.0 g, 20 mmol, as prepared above) in anhydrous MEK (20 mL), NaI (7.5 g, 50 mmol) was added. The resulting mixture was heated at 120° C. for 4 h in a microwave reactor. The reaction mixture was concentrated and water (50 mL) was added. The resultant mixture was extracted with ether (100 mL) and washed with 10% Na$_2$S$_2$O$_3$ (50 mL) and water (50 mL). The ether layer was separated, dried over Na$_2$SO$_4$, filtered, and concentrated. The residue was distilled under reduced pressure to obtain the title compound 43a as a cis and trans mixture. $^1$H-NMR (400 MHz, CDCl$_3$) δ (ppm): 4.66 (quin, J=7.2 Hz, 1H), 4.30-4.48 (m, 2H), 4.02-4.24 (m, 6H), 3.30-3.49 (m, 1H), 3.03-3.21 (m, 2H), 2.64-3.02 (m, 12H), 1.18-1.34 (m, 9H).

B. (1r,3r)-Ethyl 3-(quinolin-2-yl)cyclobutanecarboxylate (43b) and (1s,3s)-ethyl 3-(quinolin-2-yl) cyclobutanecarboxylate (43c)

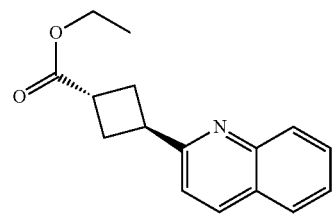

(43b)

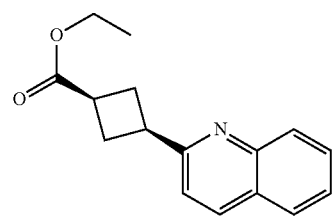

(43c)

To a solution of naphthalene (1.9 g, 15 mmol) in dry THF (10 mL) under an Argon atmosphere, finely cut Li metal (104 mg, 15.0 mmol) was added in portions and the resulting green mixture was stirred for 2 h. A solution of 0.5 M ZnCl$_2$ in THF (16 mL, 8.0 mmol) was then added dropwise and the resulting mixture was stirred at rt for 3 h. The stirring was stopped and the supernatant was removed and replaced with compound 43a (762 mg, 3.00 mmol) in THF (10 mL). The reaction mixture was stirred for 20 h and the stirring was stopped to let the remaining Zn metal settle. The resulting solution was then transferred to a dry flask via 1μ PTFE filter and treated with a mixture of 2-iodo-quinoline (382 mg, 1.53 mmol), Pd$_2$(dba)$_3$ (27.0 mg, 0.030 mmol) and trifurylphosphine (56.0 mg, 0.24 mmol). The mixture obtained was stirred at rt for 16 h and diluted with EtOAc (50 mL) and filtered through a pad of diatomaceous earth. The filtrate was concentrated and the residue obtained was purified by flash column chromatography on silica gel (0-100% EtOAc-heptane) to obtain the desired products.

Cpd 43b: Mass Spectrum (LCMS, ESI pos.): Calcd. for $C_{16}H_{17}NO_2$: 256.1 (M+H). found: 256.3.

Cpd 43c: Mass Spectrum (LCMS, ESI pos.): Calcd. for $C_{16}H_{17}NO_2$: 256.1 (M+H). found: 256.3.

D. 4-(2-((1r,3r)-3-(Quinolin-2-yl)cyclobutyl)imidazo[1,2-a]pyrazin-8-yl)morpholine (43d) and 4-(2-((1s,3s)-3-(Quinolin-2-yl)cyclobutyl)imidazo[1,2-a]pyrazin-8-yl)morpholine (43e)

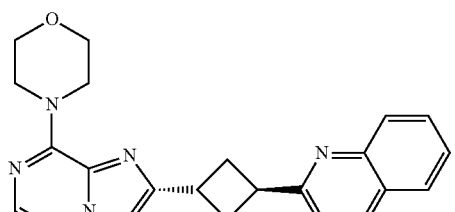

(43d)

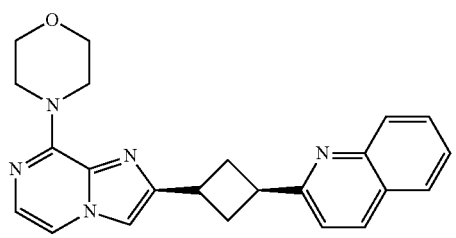

(43e)

To a solution of compound 43b (863 mg, 3.38 mmol) in EtOH (21.6 mL) was added 1 M NaOH (6.76 mL, 6.76 mmol). The reaction mixture was stirred at rt overnight and treated with 1 N HCl (6.76 mL, 6.76 mmol) and concentrated under reduced pressure. To the residue obtained, water (10 mL) and DCM (10 mL) were added. The DCM layer was separated, dried over $Na_2SO_4$, filtered, and concentrated to obtain 3-(quinolin-2-yl)cyclobutanecarboxylic acid which was used in the next step without further purification.

A solution of 3-(quinolin-2-yl)cyclobutanecarboxylic acid (200 mg, 0.800 mmol, as prepared above) in DCM was cooled to 0° C. and treated with 10 μL of DMF followed by oxalyl chloride (154 μL, 1.76 mmol). The resulting mixture was stirred at rt for 30 min and concentrated. The residue obtained was dried under reduced pressure for 15 min before being dissolved in $CH_3CN$ (5 mL) and treated with 2 M solution of $TMSCHN_2$ in hexanes (0.88 mL, 1.76 mmol). The resulting mixture was stirred for 1 h, cooled to 0° C. and treated with 33 wt % HBr in acetic acid (0.35 mL, 1.76 mmol) dropwise. After stirring for 30 min, the reaction mixture was diluted with DCM (25 mL) and washed with saturated $NaHCO_3$ (2×25 mL). The DCM layer was separated, dried over $Na_2SO_4$, filtered, and concentrated. The residue obtained was dried under reduced pressure for 15 min to obtain 2-bromo-1-(3-(quinolin-2-yl)cyclobutyl)ethanone as a viscous oil which was used without further purification in the next step.

A solution of 2-bromo-1-(3-(quinolin-2-yl)cyclobutyl)ethanone (273 mg, 0.900 mmol, as prepared above) in DMF (1 mL) was added to a solution of compound 1b (162 mg, 0.900 mmol) in DMF (1 mL). The resulting mixture was stirred at 90° C. overnight. The reaction mixture was concentrated under reduced pressure and the residue obtained was purified by flash column chromatography on silica gel (0-100% EtOAc/heptanes) to obtain compounds 43d and 43e.

Cpd 43d: Mass Spectrum (LCMS, ESI pos.): Calcd. for $C_{23}H_{23}F_3N_5O$: 386.2 (M+H). found: 386.4.

Cpd 43e: Mass Spectrum (LCMS, ESI pos.): Calcd. for $C_{23}H_{23}F_3N_5O$: 386.2 (M+H). found: 386.4.

E. 4-(5-Bromo-2-((1r,3r)-3-(quinolin-2-yl)cyclobutyl)imidazo[1,2-a]pyrazin-8-yl)morpholine, 43f

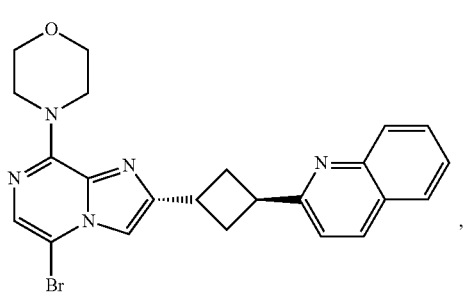

43f

Compound 43d was brominated as described in the Example 21, Step A to obtain compound 43f. Mass Spectrum (LCMS, ESI pos.) Calcd. For $C_{23}H_{22}BrN_5O$: 464.1 (M+H). Found 464.3.

F. 4-(8-Morpholino-2-((1r,3r)-3-(quinolin-2-yl)cyclobutyl)imidazo[1,2-a]pyrazin-3-yl)benzoic acid trifluoroacetic acid salt, Cpd 5

Compound 43f was subjected to Suzuki coupling conditions using the methods described in Example 1, Step G, with tert-butyl 4-(4,4,5,5-tetramethyl-1,3,2-dioxaborolan-2-yl)benzoate and the resulting product was deprotected with TFA (as described in the Example 13, Step C) to obtain the title compound 5. $^1$H-NMR (400 MHz, $CD_3OD$) δ (ppm): 8.78 (d, J=8.6 Hz, 1H), 8.33 (d, J=8.6 Hz, 1H), 8.19 (d, J=8.6 Hz, 2H), 8.08 (d, J=8.1 Hz, 1H), 7.99 (t, J=7.8 Hz, 1H), 7.92 (d, J=8.6 Hz, 1H), 7.75-7.83 (m, 1H), 7.66 (d, J=8.1 Hz, 2H), 7.62 (s, 1H), 7.33-7.39 (s, 1H), 4.46 (m, 1H), 4.31-4.38 (m, 4H), 3.88-3.96 (m, 4H), 3.84 (m, 1H), 2.93 (t, 4H). Mass Spectrum (LCMS, ESI pos.) Calcd. For $C_{30}H_{27}N_5O_3$: 506.2 (M+H). Found 506.5.

Example 44

4-(8-Morpholino-2-((1s,3s)-3-(quinolin-2-yl)cyclobutyl)imidazo[1,2-a]pyrazin-3-yl)benzoic acid trifluoroacetic acid salt (Cpd 1)

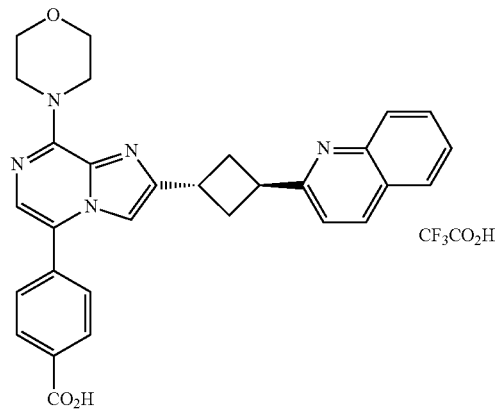

The title compound 1 was prepared from compound 43e following Example 43, Steps E and F, using the methods described in Example 43. $^1$H-NMR (400 MHz, CD$_3$OD) δ (ppm): 8.74 (d, J=8.6 Hz, 1H), 8.32 (d, J=8.6 Hz, 1H), 8.17 (d, J=8.1 Hz, 2H), 8.06 (d, J=8.1 Hz, 1H), 7.94-8.02 (m, 2H), 7.75-7.83 (m, 1H), 7.62 (d, J=8.6 Hz, 2H), 7.52 (s, 1H), 4.16-4.34 (m, 5H), 3.86-3.93 (m, 4H), 3.81 (m, 1H), 2.97-3.08 (m, 2H), 2.67-2.79 (m, 2H). Mass Spectrum (LCMS, ESI pos.) Calcd. For C$_{30}$H$_{27}$N$_5$O$_3$: 506.2 (M+H). Found 506.5.

Example 45

(E)-2-(2-(8-morpholinoimidazo[1,2-a]pyrazin-2-yl)vinyl)quinoline-4-carboxylic acid sodium salt (Cpd 8)

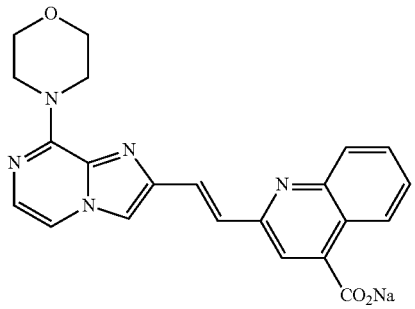

A. Ethyl 2-((diethoxyphosphoryl)methyl)quinoline-4-carboxylate, 45a

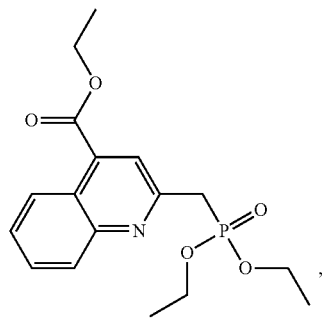

45a

To a refluxing solution of ethyl 2-methylquinoline-4-carboxylate (1.6 g, 7.60 mmol) in CCl$_4$ (150 mL), benzoyl peroxide (186 mg, 0.767 mmol) was added followed by NBS (750 g, 4.23 mmol). After 1 h, a second batch of NBS (750 g, 4.23 mmol) was added and the refluxing was continued overnight. The reaction mixture was allowed to cool to rt and washed with satd. Na$_2$CO$_3$. The organic layer was separated, dried (Na$_2$SO$_4$) and concentrated. The residue obtained was purified by flash column chromatography on silica gel (0:100-2:3 EtOAc/heptanes) to obtain ethyl 2-(bromomethyl)quinoline-4-carboxylate. Mass Spectrum (LCMS, ESI pos.) Calcd. For C$_{13}$H$_{12}$BrNO$_2$: 294.0 (M+H). Found 294.1.

Ethyl 2-(bromomethyl)quinoline-4-carboxylate (1.0 g, 3.4 mmol, as prepared above) was treated with triethyl phosphite (11.3 g, 68.0 mmol) and the resultant slurry was heated to 100° C. overnight. The reaction was concentrated under reduced pressure, diluted with DCM (50 mL), washed with sodium bicarbonate, dried over Na$_2$SO$_4$, filtered, and concentrated under reduced pressure. The residue was purified by flash column chromatography on silica gel (0:100-1:1 EtOAc/heptane) to afford compound 45a. Mass spectrum (LCMS, ESI pos.) Calcd. For C$_{17}$H$_{22}$NO$_5$P: 352.1 (M+H). found 352.2.

B. 8-Morpholinoimidazo[1,2-a]pyrazine-2-carbaldehyde, 45b

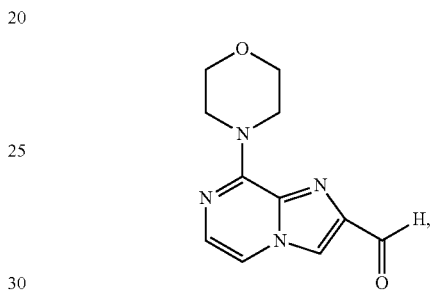

45b

To a solution of 8-morpholinoimidazo[1,2-a]pyrazin-2-yl)methanol (616 mg, 2.63 mmol) in DCM (14 mL), DMP (1.3 g, 3.1 mmol) was added. The resulting mixture was stirred for 2 h and treated with saturated aqueous Na$_2$S$_2$O$_3$. The DCM layer was separated, dried over Na$_2$SO$_4$, filtered, and concentrated. The residue obtained was purified by flash column chromatography on silica gel (0-40% EtOAc/DCM) obtain compound 45b. $^1$H NMR (400 MHz, CDCl$_3$) δ (ppm): 10.08 (s, 1H), 8.05 (s, 1H), 7.50 (d, J=4.4 Hz, 1H), 7.42 (d, J=4.4 Hz, 1H), 4.29-4.40 (m, 4H), 3.88 (m, 4H).

C. (E)-2-(2-(8-morpholinoimidazo[1,2-a]pyrazin-2-yl)vinyl)quinoline-4-carboxylic acid sodium salt, Cpd 8

A solution of compound 45a (124 mg, 0.353 mmol) in DMF (3.5 mmol) was treated with 60% NaH (42.3 mg, 1.05 mmol) at 0° C. The resulting mixture was stirred at rt for 15 min, cooled to 0° C. and treated with compound 45b (90.2 mmol, 0.388 mmol) in THF (2 mL). The resulting mixture was stirred for 30 min, cooled in a dry ice/acetone bath and treated with HOAc (0.060 mL, 1.05 mmol). The reaction mixture was then allowed to warm to rt and the pH was adjusted to about 5 with concentrated HCl. The precipitate formed was collected by filtration and dried under reduced pressure to obtain (E)-2-(2-(8-morpholinoimidazo[1,2-a]pyrazin-2-yl)vinyl)quinoline-4-carboxylic acid.

To a slurry of (E)-2-(2-(8-morpholinoimidazo[1,2-a]pyrazin-2-yl)vinyl)quinoline-4-carboxylic acid (32 mg, 0.08 mmol) in MeOH (0.6 mL), 1.5 M NaOMe in MeOH (0.16mL, 0.08 mmol) was added. The resulting mixture was stirred for 10 min, concentrated, and dried under reduced pressure to obtain the title compound 8. $^1$H NMR (400 MHz, CD$_3$OD) δ (ppm): 8.36 (d, J=8.6 Hz, 1H), 7.92-8.04 (m, 3H), 7.67-7.82 (m, 4H), 7.55 (t, J=7.6 Hz, 1H), 7.32 (d, J=4.4 Hz, 1H), 4.24-4.32 (m, 4H), 3.89 (t, 4H). Mass Spectrum (LCMS, ESI pos.) Calcd. For C$_{22}$H$_{19}$N$_5$O$_3$: 402.2 (M+H). Found 402.4.

Example 46

4-(5-(Pyridin-3-yl)-2-((quinolin-2-yloxy)methyl)imidazo[1,2-a]pyrazin-8-yl)morpholine methane sulfonic acid salt (Cpd 129)

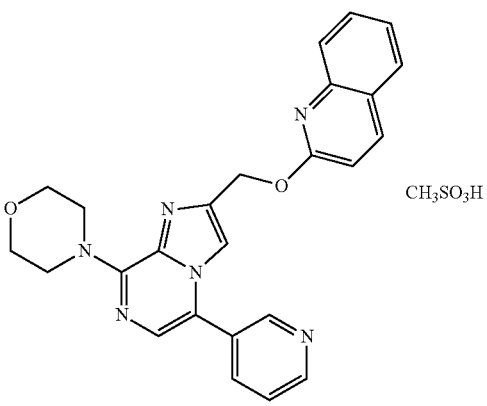

A. 4-(5-(Pyridin-3-yl)-2-((quinolin-2-yloxy)methyl)imidazo[1,2-a]pyrazin-8-yl)morpholine, 46a

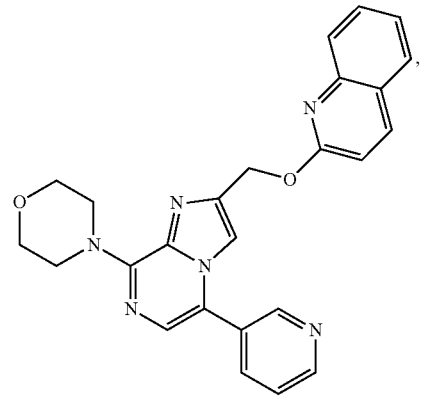

46a

Compound 15a (150.0 mg, 0.34 mmol) was subjected to Suzuki coupling conditions with 3-pyridineboronic acid pinacol ester using the methods described in Example 1, Step G to obtain compound 46a. Mass Spectrum (LCMS, ESI pos.) Calcd. for C$_{25}$H$_{22}$N$_6$O$_2$: 439.1 (M+H). Found 439.1.

B. 4-(5-(Pyridin-3-yl)-2-((quinolin-2-yloxy)methyl)imidazo[1,2-a]pyrazin-8-yl)morpholine methane sulfonic acid salt, Cpd 129

To a solution of compound 46a (90.0 mg, 0.205 mmol) in DCM (2 mL) was added a solution of methanesulfonic acid as a 1 M DCM solution (0.205 mL, 0.205 mmol). The reaction mixture was stirred at rt for 30 min and concentrated under reduced pressure to obtain the title compound 129. $^1$H-NMR (400 MHz, CDCl$_3$) δ (ppm): 2.81 (s, 6H), 3.92-4.03 (m, 4H), 4.57 (br. s., 4H), 5.78 (s, 2H), 7.18 (d, J=9.0 Hz, 1H), 7.47-7.56 (m, 1H), 7.70 (s, 1H), 7.75 (td, J=7.8, 1.3 Hz, 1H), 7.83 (d, J=7.8 Hz, 1H), 7.94 (d, J=8.3 Hz, 1H), 8.01 (dd, J=8.1, 5.6 Hz, 1H), 8.18 (s, 1H), 8.27 (d, J=8.8 Hz, 1H), 8.54-8.62 (m, 1H), 8.90-8.97 (m, 1H), 9.16 (d, J=1.7 Hz, 1H). Mass Spectrum (LCMS, ESI pos.) Calcd. for C$_{25}$H$_{22}$N$_6$O$_2$: 439.1 (M+H). Found 439.1.

Following the procedures described in Example 46 above, and substituting suitably selected and substituted reagents, starting materials and conditions as would be readily apparent to those skilled in the art, the following representative compounds of the present invention were prepared.

| Cpd | Characterization |
|---|---|
| 123 | 4-(5-(2-(4-Methylpiperazin-1-yl)pyrimidin-5-yl)-2-((quinolin-2-yloxy)methyl)imidazo[1,2-a]pyrazin-8-yl)morpholine methane sulfonic acid salt<br>$^1$H-NMR (400 MHz, CDCl$_3$) δ (ppm): 2.73-2.85 (m, 2 H), 2.86 (s, 3 H), 2.94 (s, 3 H), 3.69 (br. s., 4 H), 3.84-3.94 (m, 4 H), 4.35 (br. s., 4 H), 4.99 (d, J = 14.2 Hz, 2 H), 5.68 (s, 2 H), 6.96 (d, J = 8.8 Hz, 1 H), 7.36-7.44 (m, 1 H), 7.60-7.69 (m, 2 H), 7.73 (d, J = 8.1 Hz, 1 H), 7.84 (d, J = 8.3 Hz, 1 H), 8.01 (d, J = 8.8 Hz, 1 H), 8.52 (s, 2 H).<br>Mass Spectrum (LCMS, ESI pos.) Calcd. for C$_{29}$H$_{31}$N$_9$O$_2$: 538.3 (M + H), Found 538.3. |
| 127 | N,N-Dimethyl-5-(8-morpholino-2-((quinolin-2-yloxy)methyl)imidazo[1,2-a]pyrazin-5-yl)pyridin-2-amine methane sulfonic acid salt<br>$^1$H-NMR (400 MHz, CDCl$_3$) δ (ppm): 2.81 (s, 3 H), 3.34 (s, 6 H), 3.89-3.98 (m, 4 H), 4.44 (br. s., 4 H), 5.69 (s, 2 H), 6.99 (d, J = 9.0 Hz, 2 H), 7.39-7.46 (m, 2 H), 7.65 (t, J = 7.7 Hz, 1 H), 7.76 (d, J = 8.1 Hz, 1 H), 7.81-7.92 (m, 3 H), 8.05 (d, J = 8.8 Hz, 1 H), 8.38 (s, 1 H). |

| Cpd | Characterization |
|---|---|
| | Mass Spectrum (LCMS, ESI pos.) Calcd. for $C_{27}H_{27}N_7O_2$: 482.2 (M + H), Found 482.3. |
| 128 | 4-(5-(6-Methylpyridin-3-yl)-2-((quinolin-2-yloxy)methyl)imidazo[1,2-a]pyrazin-8-yl)morpholine methane sulfonic acid salt<br>$^1$H-NMR (400 MHz, CDCl$_3$) δ (ppm): 2.74-2.84 (m, 6 H), 2.92 (s, 3 H), 3.91-4.04 (m, 4 H), 4.55 (br. s., 4 H), 5.76 (s, 2 H), 7.16 (d, J = 9.0 Hz, 1 H), 7.50 (t, J = 7.5 Hz, 1 H), 7.66 (s, 1 H), 7.73 (t, J = 7.7 Hz, 1 H), 7.82 (d, J = 7.8 Hz, 1 H), 7.92 (d, J = 8.3 Hz, 1 H), 7.87 (d, J = 8.3 Hz, 1 H), 8.16 (s, 1 H), 8.23 (d, J = 8.8 Hz, 1 H), 8.55 (d, J = 8.3 Hz, 1 H), 9.10 (s, 1 H).<br>Mass Spectrum (LCMS, ESI pos.) Calcd. for $C_{26}H_{24}N_6O_2$: 453.2 (M + H), Found 453.3. |

Example 47

4-(5-(6-(piperazin-1-yl)pyridin-3-yl)-2-((quinolin-2-yloxy)methyl)imidazo[1,2-a]pyrazin-8-yl)morpholine methane sulfonic acid salt (Cpd 126)

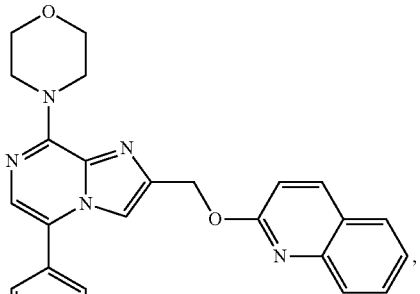

A. tert-Butyl 4-(5-(8-morpholino-2-((quinolin-2-yloxy)methyl)imidazo[1,2-a]pyrazin-5-yl)pyridin-2-yl)piperazine-1-carboxylate, 47a

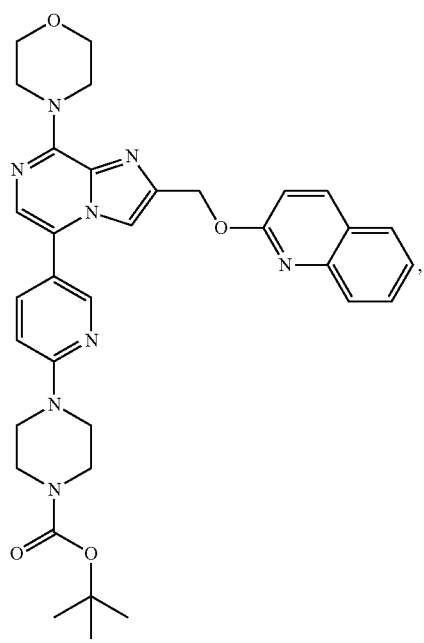

Compound 15a (130 mg. 0.29 mmol) was subjected to Suzuki coupling conditions with 2-(4-BOC-piperazin-1-yl)pyridine-5-boronic acid pinacol ester using the methods described in Example 1, Step G to obtain compound 47a. Mass Spectrum (LCMS, ESI pos.) Calcd. for $C_{34}H_{38}N_8O_4$: 623.2 (M+H). Found 623.3.

B. 4-(5-(6-(piperazin-1-yl)pyridin-3-yl)-2-((quinolin-2-yloxy)methyl)imidazo[1,2-a]pyrazin-8-yl)morpholine, 47b

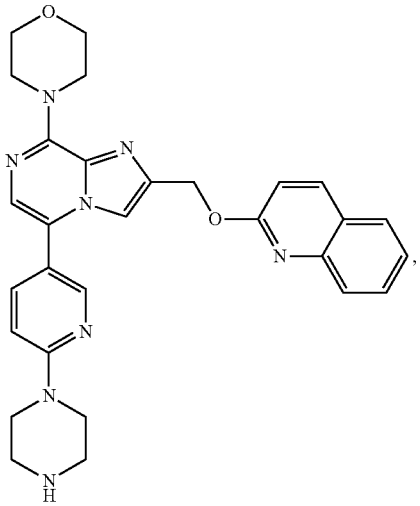

To a solution of compound 47a (144 mg, 0.240 mmol) in DCM (1 mL) was added TFA (0.8 mL). The resulting mixture was stirred at rt for 1 h and concentrated under reduced pressure. The residue obtained was dried under reduced pressure overnight, suspended in 20 mL of diethyl ether, sonicated for 5 min and concentrated. The solid obtained was dried under reduced pressure for 4 h to obtain a residue which was dissolved in 1:1 MeOH/DCM solution (5 mL) and filtered through a sodium bicarbonate cartridge. The filtrate was concentrated under reduced pressure and the resulting residue was triturated in ether to give compound 47b. Mass Spectrum (LCMS, ESI pos.) Calcd. for $C_{29}H_{30}N_8O_2$: 523.2 (M+H). Found 523.3.

C. 4-(5-(6-(piperazin-1-yl)pyridin-3-yl)-2-((quinolin-2-yloxy)methyl)imidazo[1,2-a]pyrazin-8-yl)morpholine methane sulfonic acid salt, Cpd 126

To a solution of compound 47b (90.0 mg, 0.172 mmol) in DCM (2 mL) was added a solution of methanesulfonic acid as a 1 M DCM solution (0.172 mL, 0.172 mmol). The reaction mixture was stirred at rt for 30 min and then concentrated under reduced pressure to obtain the title compound 126. $^1$H-NMR (400 MHz, CD$_3$OD) δ (ppm): 2.71 (s, 6H), 3.19-3.26 (m, 4H), 3.85-3.91 (m, 8H), 4.43 (br. s., 4H), 5.60 (s, 2H), 6.83 (d, J=9.0 Hz, 1H), 6.88 (d, J=8.8 Hz, 1H), 7.32 (s, 1H), 7.33-7.38 (m, 1H), 7.56 (td, J=7.7, 1.5 Hz, 1H), 7.63-7.70 (m, 2H), 7.73 (d, J=8.6 Hz, 1H), 7.79 (s, 1H), 7.98 (d, J=8.8 Hz, 1H), 8.26 (d, J=2.4 Hz, 1H). Mass Spectrum(LCMS, ESI pos.) Calcd. for C$_{29}$H$_{30}$N$_8$O$_2$: 523.2 (M+H). Found 523.3.

Following the procedures described in Example 47 above, and substituting suitably selected and substituted reagents, starting materials and conditions as would be readily apparent to those skilled in the art, the following representative compounds of the present invention were prepared.

| Cpd | Characterization |
|---|---|
| 122 | 5-(8-Morpholino-2-((quinolin-2-yloxy)methyl)imidazo[1,2-a]pyrazin-5-yl)pyridin-2-amine methane sulfonic acid salt<br>$^1$H-NMR (400 MHz, CDCl$_3$) δ (ppm): 2.81 (s, 4 H), 3.94-4.00 (m, 4 H), 4.54 (br. s., 4 H), 5.70-5.75 (m, 2 H), 6.95-7.05 (m, 1 H), 7.33 (d, J = 9.3 Hz, 1 H), 7.44 (t, J = 7.6 Hz, 1 H), 7.51-7.60 (m, 1 H), 7.65-7.72 (m, 1 H), 7.76 (d, J = 7.1 Hz, 1 H), 7.81 (s, 1 H), 7.85 (d, J = 8.8 Hz, 1 H), 7.97 (br. s., 1 H), 8.06-8.14 (m, 1 H). Mass Spectrum (LCMS, ESI pos.) Calcd. For C$_{25}$H$_{23}$N$_7$O$_2$: 454.2 (M + H), Found 454.3. |
| 121 | 4-(5-(2-(Piperazin-1-yl)pyrimidin-5-yl)-2-((quinolin-2-yloxy)methyl)imidazo[1,2-a]pyrazin-8-yl)morpholine methane sulfonic acid salt<br>$^1$H-NMR (400 MHz, CDCl$_3$) δ (ppm): 2.82 (s, 3 H), 3.28-3.32 (m, 4 H), 3.88-3.97 (m, 4 H) 4.18-4.25 (m, 4 H), 4.33-4.41 (m, 4 H), 5.68 (s, 2 H), 6.97 (d, J = 8.8 Hz, 1 H), 7.33 (s, 1 H), 7.38-7.46 (m, 1 H), 7.65 (ddd, J = 8.5, 7.0, 1.3 Hz, 1 H), 7.72 (s, 1 H), 7.75 (d, J = 8.1 Hz, 1 H), 7.85 (d, J = 8.3 Hz, 1 H), 8.04 (d, J = 8.8 Hz, 1 H), 8.54 (s, 2 H). Mass Spectrum (LCMS, ESI pos.) Calcd. For C$_{28}$H$_{29}$N$_9$O$_2$: 524.2 (M + H), Found 524.3. |
| 108 | 4-(2-((quinolin-2-yloxy)methyl)-5-(1',2',3',6'-tetrahydro-[2,4'-bipyridin]-5-yl)imidazo[1,2-a]pyrazin-8-yl)morpholine methane sulfonic acid salt<br>$^1$H-NMR (400 MHz, CDCl$_3$) δ (ppm): 2.92-3.02 (m, 2 H), 3.43-3.49 (m, 2 H), 3.88-3.97 (m, 6 H), 4.28-4.38 (m, 4 H), 5.68 (s, 2 H), 6.69 (t, J = 1.6 Hz, 1 H), 6.97 (d, J = 8.8 Hz, 1 H), 7.39-7.46 (m, 1 H), 7.60-7.69 (m, 2 H), 7.75 (dd, J = 8.1, 1.0 Hz, 1 H), 7.80 (s, 1 H), 7.85 (d, J = 8.3 Hz, 1 H), 7.96 (dd, J = 8.3, 2.2 Hz, 1 H), 8.04 (d, J = 8.8 Hz, 1 H), 8.77 (d, J = 1.7 Hz, 1 H). Mass Spectrum (LCMS, ESI pos.) Calcd. For C$_{30}$H$_{29}$N$_7$O$_2$: 520.2 (M + H), Found 520.2. |

Example 48

2-((5-(8-Morpholino-2-((quinolin-2-yloxy)methyl)imidazo[1,2-a]pyrazin-5-yl)pyridin-2-yl)amino)acetic acid trifluoroacetic acid salt (Cpd 107)

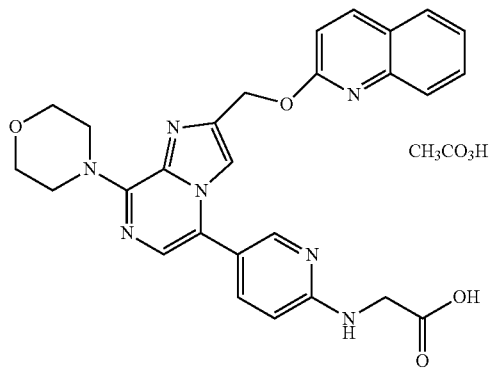

A. tert-Butyl (5-(8-morpholino-2-((quinolin-2-yloxy)methyl)imidazo[1,2-a]pyrazin-5-yl)pyridin-2-yl)carbamate, 48a

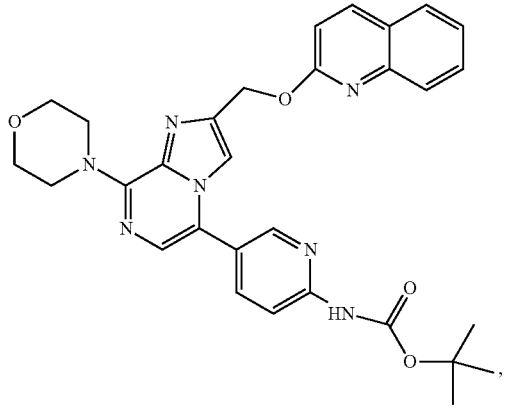

Compound 48a was prepared from compound 15a and 2-(BOC-amino)pyridine-5-boronic acid pinacol ester according to procedure described in Example 13, Step A. Mass Spectrum (LCMS, ESI pos.) Calcd. For $C_{30}H_{31}N_7O_4$: 453.3 (M+H-BOC). Found 554.2.

B. 2-((5-(8-Morpholino-2-((quinolin-2-yloxy)methyl)imidazo[1,2-a]pyrazin-5-yl)pyridin-2-yl)amino)acetic acid, Cpd 107

Compound 48a (200.0 mg, 0.450 mmol) was treated with 60% sodium hydride (19.2 mg, 0.48 mmol) in DMF (5 mL) for 15 min. tert-Butyl bromoacetate (25.6 mg, 0.25 mmol) was then added, and the resulting mixture was stirred for 5 h at rt. The reaction was diluted with EtOAc and washed with water. The organic layer was washed with brine, dried over $Na_2SO_4$, filtered, and concentrated under reduced pressure. The residue was purified by flash column chromatography on silica gel (0-100% EtOAc/heptanes) to give tert-butyl 2-((tert-butoxycarbonyl)(5-(8-morpholino-2-((quinolin-2-yloxy)methyl)imidazo[1,2-a]pyrazin-5-yl)pyridin-2-yl)amino)acetate as an off-white solid, which was subsequently deprotected with TFA following the methods described in the Example 47, Step B to afford the title compound 107 as an off-white solid after trituration with ether. $^1$H-NMR (400 MHz, $CD_3OD$) δ (ppm): 3.84-3.93 (m, 4H), 4.27 (s, 2H), 4.31-4.39 (m, 4H), 5.66 (s, 2H), 6.97 (d, J=8.8 Hz, 1H), 7.11 (d, J=9.0 Hz, 1H), 7.31 (s, 1H), 7.39-7.45 (m, 1H), 7.66 (ddd, J=8.4, 6.9, 1.3 Hz, 1H), 7.80 (d, J=8.3 Hz, 2H), 7.95-8.01 (m, 2H), 8.12-8.18 (m, 2H). Mass Spectrum (LCMS, ESI pos.) Calcd. For $C_{27}H_{25}N_7O_4$: 512.2 [M+H]. found 512.2.

Example 49

4-(5-(6-(Piperidin-4-yl)pyridin-3-yl)-2-((quinolin-2-yloxy)methyl)imidazo[1,2-a]pyrazin-8-yl)morpholine trifluoroacetic acid salt (Cpd 106)

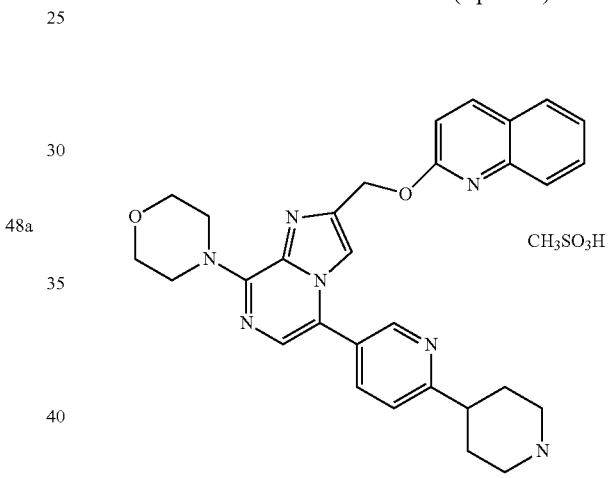

A. 4-(5-(6-Chloropyridin-3-yl)-2-((quinolin-2-yloxy)methyl)imidazo[1,2-a]pyrazin-8-yl)morpholine, 49a

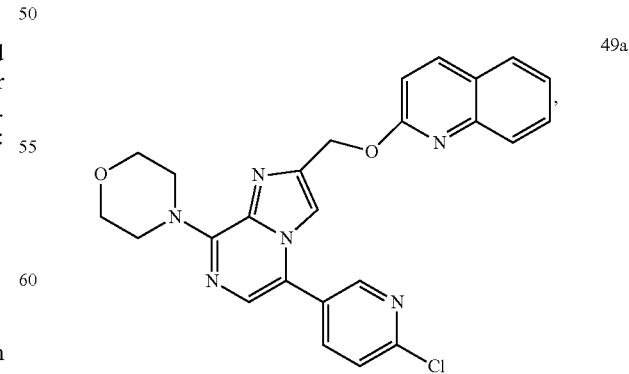

Compound 49a was prepared from compound 15a and 2-chloro-5-pyridineboronic acid using the methods described in Example 1, Step G. Mass Spectrum (LCMS, ESI pos.) Calcd. For $C_{25}H_{21}ClN_6O_2$: 473.1 [M+H]. found 473.2

B. tert-Butyl 5-(8-morpholino-2-((quinolin-2-yloxy) methyl)imidazo[1,2-a]pyrazin-5-yl)-5',6'-dihydro-[2, 4'-bipyridine]-1'(2'H)-carboxylate, 49b

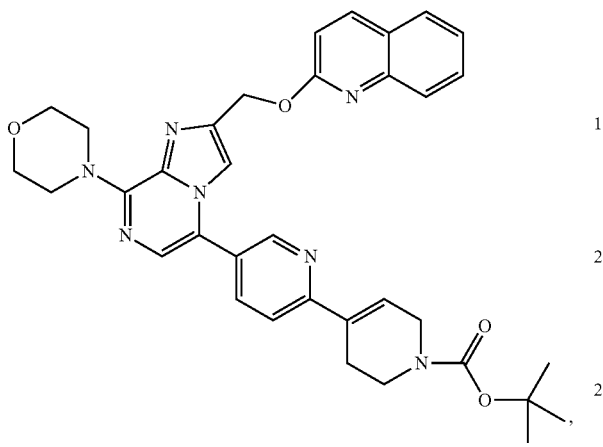

49b

Compound 49b was prepared from compound 49a and N-Boc-1,2,3,6-tetrahydropyridine-4-boronic acid pinacol ester using the methods described in Example 1, Step G. Mass Spectrum (LCMS, ESI pos.) Calcd. For $C_{35}H_{37}N_7O_4$: 620.4 [M+H]. found 620.3.

C. tert-Butyl 4-(5-(8-morpholino-2-((quinolin-2-yloxy)methyl)imidazo[1,2-a]pyrazin-5-yl)pyridin-2-yl)piperidine-1-carboxylate, 49c

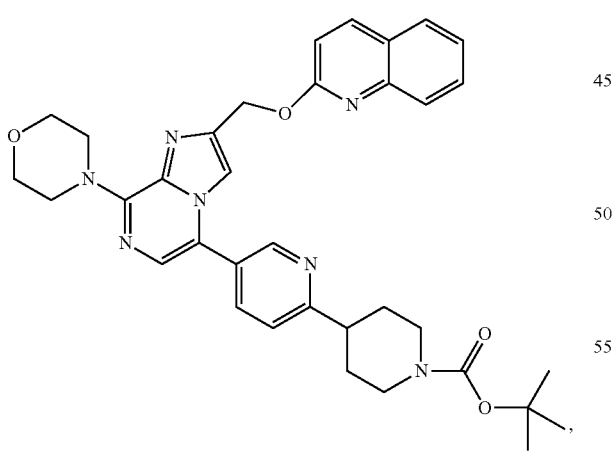

49c

Compound 49b (50 mg, 0.08 mmol) in THF (50 mL) was hydrogenated using 10% Pd/C in a continuous-flow hydrogenation reactor. The solvents were removed and the residue obtained was purified by flash column chromatography on silica gel (0-100% EtOAc/heptanes) to obtain compound 49c. Mass Spectrum (LCMS, ESI pos.) Calcd. For $C_{35}H_{39}N_7O_4$: 622.3 [M+H]. found 622.3.

D. 4-(5-(6-(Piperidin-4-yl)pyridin-3-yl)-2-((quinolin-2-yloxy)methyl)imidazo[1,2-a]pyrazin-8-yl)morpholine trifluoroacetic acid salt, Cpd 106

Compound 49c was deprotected using TFA using the methods described in the Example 48, Step B to obtain the title compound. $^1$H-NMR (400 MHz, CDCl$_3$) δ (ppm): 1.99-2.14 (m, 6H), 2.20-2.32 (m, 4H), 3.02-3.20 (m, 3H), 3.56-3.67 (m, 2H), 3.85-3.95 (m, 4H), 4.32-4.45 (m, 4H), 5.68 (s, 2H), 6.95 (d, J=8.8 Hz, 1H), 7.33-7.45 (m, 3H), 7.63 (td, J=7.7, 1.5 Hz, 1H), 7.69-7.75 (m, 1H), 7.76 (s, 1H), 7.83 (d, J=8.6 Hz, 1H), 7.89 (dd, J=8.1, 2.2 Hz, 1H), 8.00 (d, J=8.8 Hz, 1H), 8.70-8.79 (m, 1H), 9.34 (br. s., 1H), 9.79 (br. s., 1H). Mass Spectrum (LCMS, ESI pos.) Calcd. for $C_{30}H_{31}N_7O_2$: 522.2 [M+H]. found 522.2.

Example 50

2-(5-(8-Morpholino-2-((quinolin-2-yloxy)methyl) imidazo[1,2-a]pyrazin-5-yl)pyridin-2-yl)acetic acid (Cpd 101)

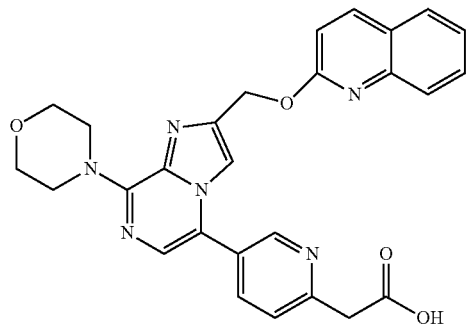 [SMILES: O=C(O)Cc1ccc(-c2cnc(N3CCOCC3)c3nc(COc4ccc5ccccc5n4)cn23)cn1]

The title compound 101 was prepared from compound 15a and 1-ethyl-2-(pyridin-2-yl)acetate-5-boronic acid pinacol ester using the methods described in Example 1, Step G. Saponification of the resulting product using the methods described in Example 15, Step C, and substituting NaOH for LiOH, afforded the title compound 101. $^1$H-NMR (400 MHz, CD$_3$OD) δ (ppm): 3.68-3.83 (m, 6H), 4.12-4.17 (m, 4H), 5.51 (s, 2H), 6.81 (d, J=9.0 Hz, 1H), 7.19 (s, 1H), 7.22-7.26 (m, 1H), 7.37 (d, J=8.1 Hz, 1H), 7.45-7.52 (m, 1H), 7.56-7.61 (m, 1H), 7.64 (s, 1H), 7.68 (d, J=8.1 Hz, 1H), 7.79 (dd, J=8.1, 2.4 Hz, 1H), 7.88 (d, J=8.8 Hz, 1H), 8.55 (d, J=2.0 Hz, 1H). Mass Spectrum (LCMS, ESI pos.) Calcd. for $C_{22}H_{24}N_6O_4$: 497.2 [M+H]. found 497.2.

Example 51

4-(5-(6-((4H-1,2,4-triazol-3-yl)thio)pyridin-3-yl)-2-((quinolin-2-yloxy)methyl)imidazo[1,2-a]pyrazin-8-yl)morpholine (Cpd 100)

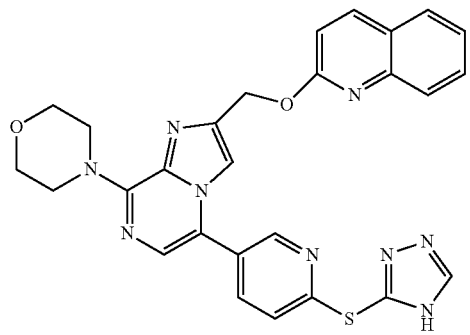 [SMILES: c1ccc2nc(OCc3cn4c(-c5ccc(Sc6nnc[nH]6)nc5)cnc(N5CCOCC5)c4n3)ccc2c1]

A mixture of compound 49a (100.0 mg, 0.210 mmol), 4H-1,2,4-triazole-3-thiol (25.6 mg, 0.250 mmol) and potassium tert-butoxide (35.6 mg, 0.320 mmol) in DMA (2 mL) was heated to 160° C. in a microwave reactor for 2 h. The reaction was cooled to rt, diluted with EtOAc and washed with water. The EtOAc layer was separated, dried over Na₂SO₄, filtered, and concentrated under reduced pressure. The residue was purified by flash column chromatography on silica gel (0-10% MeOH/DCM), then triturated with ether to give the title compound 100 as an off-white solid. ¹H-NMR (400 MHz, CDCl₃) δ (ppm): 3.86-3.92 (m, 4H), 4.27-4.35 (m, 4H), 5.67 (s, 2H), 6.96 (d, J=8.8 Hz, 1H), 7.32 (s, 1H), 7.38-7.43 (m, 2H), 7.64 (td, J=7.7, 1.5 Hz, 1H), 7.71-7.76 (m, 2H), 7.79 (dd, J=8.4, 2.3 Hz, 1H), 7.84 (d, J=8.3 Hz, 1H), 8.02 (d, J=8.6 Hz, 1H), 8.32 (br. s., 1H), 8.63 (d, J=2.0 Hz, 1H). Mass Spectrum (LCMS, ESI pos.) Calcd. for C₂₂H₂₃N₉O₂S: 538.2 [M+H]. found 538.2.

Example 52

4-(5-(6-((1H-1,2,3-Triazol-5-yl)thio)pyridin-3-yl)-2-((quinolin-2-yloxy)methyl)imidazo[1,2-a]pyrazin-8-yl)morpholine (Cpd 92)

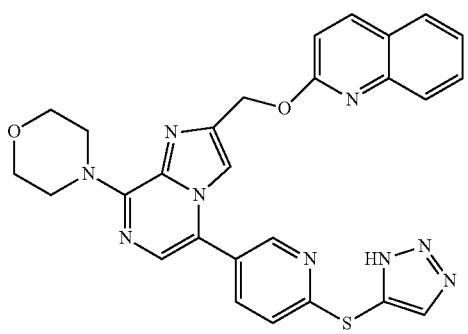 [SMILES: c1ccc2nc(OCc3cn4c(-c5ccc(Sc6cnn[nH]6)nc5)cnc(N5CCOCC5)c4n3)ccc2c1]

The title compound 92 was prepared from compound 49a and 2H-1,2,3-triazole-4-thiol using the methods described in Example 51. ¹H-NMR (400 MHz, CDCl₃) δ (ppm): 3.88-3.92 (m, 4H), 4.28-4.32 (m, 4H), 5.66 (s, 2H), 6.96 (d, J=9.0 Hz, 1H), 7.10 (d, J=8.3 Hz, 1H), 7.30 (s, 1H), 7.38-7.44 (m, 1H), 7.64 (td, J=7.7, 1.5 Hz, 1H), 7.67-7.76 (m, 3H), 7.81-7.86 (m, 1H), 7.97 (s, 1H), 8.02 (d, J=8.8 Hz, 1H), 8.57 (d, J=2.0 Hz, 1H). Mass Spectrum (LCMS, ESI pos.) Calcd. for C₂₇H₂₃N₉O₂S: 538.2 [M+H]. found 538.2.

Example 53

N-(5-(8-Morpholino-2-((quinolin-2-yloxy)methyl)imidazo[1,2-a]pyrazin-5-yl)pyridin-2-yl)methanesulfonamide (Cpd 85)

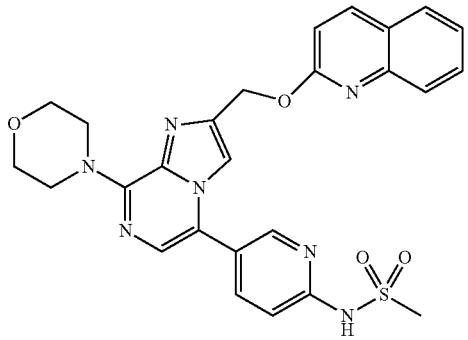 [SMILES: CS(=O)(=O)Nc1ccc(-c2cnc(N3CCOCC3)c3nc(COc4ccc5ccccc5n4)cn23)cn1]

A solution of compound 48a (534 mg, 0.965 mmol) in 1:1 DCM/TFA (2 mL) was stirred at rt for 1 h. The solvents were removed and the gummy solid obtained was dissolved in 1:1 MeOH/EtOAc (10 mL) and concentrated. The semi-solid obtained was dissolved in DCM (5 mL) and diethyl ether (25 mL). The mixture was concentrated and the residue obtained was triturated with DCM/diethyl ether. The solid obtained was collected by filtration and dried. The residue (100.0 mg, 0.147 mmol) in DCM (3 mL) was treated with TEA (61 µL, 0.44 mmol) and MsCl (18 µL, 0.24 mmol) at 0° C. The resulting mixture was stirred at rt for 3 h and treated with TEA (122 µL, 0.88 mmol) and MsCl (36 µL, 0.48 mmol) again. The mixture was stirred at rt for 4 h and concentrated. The resulting N-(methylsulfonyl)-N-(5-(8-morpholino-2-((quinolin-2-yloxy)methyl)imidazo[1,2-a]pyrazin-5-yl)pyridin-2-yl)methanesulfonamide (105 mg, 0.172 mmol) in CH₃CN (5 mL) was treated with K₂CO₃ (238 mg, 1.722 mmol) and the resulting mixture was heated to 80° C. for 2 h. The reaction mixture was allowed to cool to rt and treated with DCM and water. The DCM layer was separated, dried over Na₂SO₄, filtered, and concentrated. The residue obtained was purified by flash column chromatography on silica gel (0-100% EtOA/heptanes) to obtain the title compound 85. ¹H-NMR (400 MHz, CDCl₃) δ (ppm): 3.23 (s, 3H), 3.84-3.95 (m, 4H), 4.29-4.41 (m, 4H), 5.69 (s, 2H), 6.96 (d, J=8.8 Hz, 1H), 7.26 (s, 1H), 7.35-7.48 (m, 2H), 7.59-7.68 (m, 1H), 7.68-7.76 (m, 2H), 7.84 (d, J=8.3 Hz, 1H), 7.91 (dd, J=8.6, 2.2 Hz, 1H), 8.00 (d, J=8.8 Hz, 1H), 8.56 (d, J=1.7 Hz, 1H), 10.08 (br. s., 1H). Mass Spectrum (LCMS, ESI pos.) Calcd. for C26H25N7O4S: 532.2 [M+H]. found 532.2.

Example 54

5-(8-Morpholino-2-((quinolin-2-yloxy)methyl)imidazo[1,2-a]pyrazin-5-yl)picolinamide (Cpd 84)

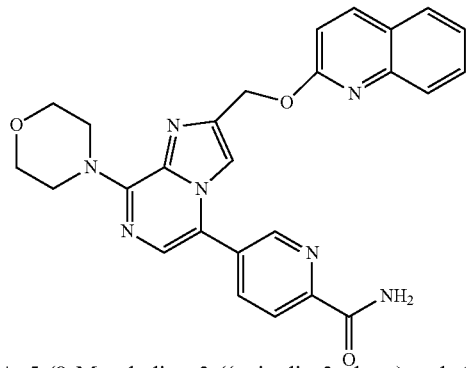

A. 5-(8-Morpholino-2-((quinolin-2-yloxy)methyl)imidazo[1,2-a]pyrazin-5-yl)picolinonitrile, 54a

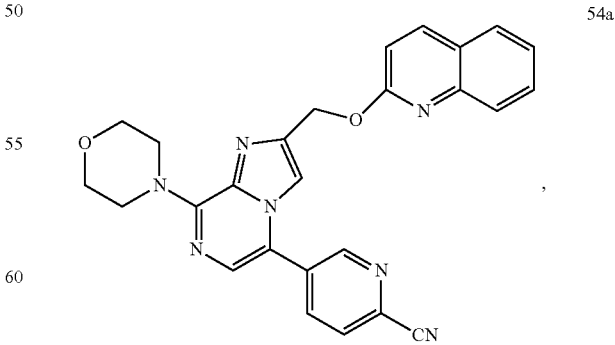

54a

Compound 54a was prepared from compound 31b and 2-cyanopyridine-5-boronic acid pinacol ester using the methods described in Example 1, Step G. Mass Spectrum (LCMS, ESI pos.) Calcd. for C₂₆H₂₁N₇O₂: 464.2 [M+H]. found 464.2.

B. 5-(8-Morpholino-2-((quinolin-2-yloxy)methyl)imidazo[1,2-a]pyrazin-5-yl)picolinamide, Cpd 84

To a solution of compound 54a (60 mg, 0.13 mmol) in EtOH (4 mL) and DMSO (1 mL) was added a 3N aqueous NaOH (0.06 mL, 0.18 mmol) and 30% hydrogen peroxide (0.3 mL). The reaction mixture was refluxed at 60° C. for 12 h. The reaction mixture was allowed to cool to rt and acidified with 2N HCl to pH~2 and extracted with DCM (2×30 mL). The combined DCM layers were dried over $Na_2SO_4$, filtered, and concentrated under reduced pressure. The residue obtained was purified by flash column chromatography on silica gel (0-10% MeOH/DCM) to give the title compound 84. $^1$H-NMR (400 MHz, MeOH) δ (ppm): 3.83-3.87 (m, 4H), 4.27-4.32 (m, 4H), 5.62 (s, 2H), 6.90 (d, J=8.8 Hz, 1H), 7.32-7.38 (m, 2H), 7.59 (ddd, J=8.4, 7.0, 1.5 Hz, 1H), 7.65-7.72 (m, 1H), 7.74-7.81 (m, 2H), 7.97 (d, J=8.8 Hz, 1H), 8.03 (dd, J=8.1, 2.2 Hz, 1H), 8.25 (d, J=8.1 Hz, 1H), 8.73 (d, J=1.5 Hz, 1H). (LCMS, ESI pos.) Calcd. for $C_{26}H_{23}N_7O_3$: 482.2 [M+H]. found 482.2.

Example 55

3-(8-Morpholino-2-((quinolin-2-yloxy)methyl)imidazo[1,2-a]pyrazin-5-yl)-1,2,4-oxadiazol-5-ol (Cpd 75)

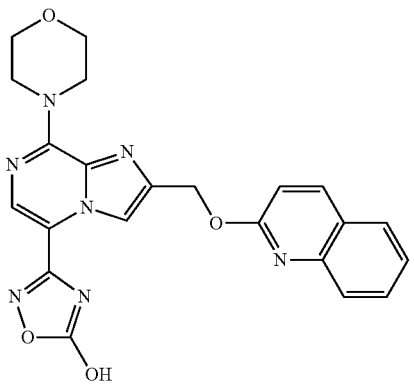 [SMILES: Oc1nc(-c2cnc(N3CCOCC3)c3nc(COc4ccc5ccccc5n4)cn23)no1]

A. 8-Morpholino-2-((quinolin-2-yloxy)methyl)imidazo[1,2-a]pyrazine-5-carbonitrile, 55a

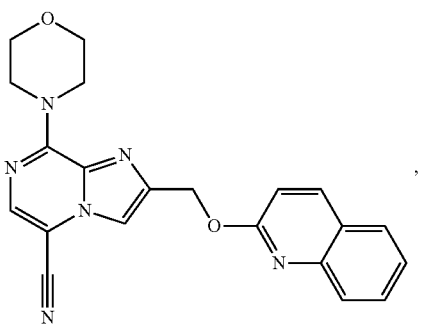

55a

A mixture of compound 31b (200 mg, 0.450 mmol), zinc cyanide (106 mg, 0.910 mmol), Pd(PPh$_3$)$_4$ (105 mg, 0.910 mmol) in DMF (5 mL) was heated to 80° C. for 4 h. The reaction was cooled to rt, filtered through a diatomaceous earth cartridge (2.5 g), and the filter cake was rinsed with EtOAc. The combined organic layers were concentrated under reduced pressure. The residue was recrystallized with hot EtOAc, collected by filtration, and dried to give compound 55a. Mass Spectrum (LCMS, ESI pos.) Calcd. for $C_{21}H_{18}N_6O_2$: 387.2 [M+H]. found 387.2

B. (Z)-N'-hydroxy-8-morpholino-2-((quinolin-2-yloxy)methyl)imidazo[1,2-a]pyrazine-5-carboximidamide, 55b

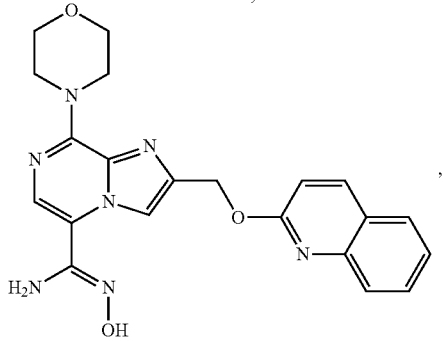

55b

A mixture of compound 55a (100 mg, 0.26 mmol) and hydroxylamine (50% wt, 0.086 mL, 1.4 mmol) in EtOH (2 mL) was heated to 90° C. for 5 h. The precipitate obtained was collected by filtration, washed with EtOH, and dried to give compound 55b. Mass Spectrum (LCMS, ESI pos.) Calcd. for $C_{21}H_{21}N_7O_3$: 420.2 [M+H]. found 420.2

C. 3-(8-Morpholino-2-((quinolin-2-yloxy)methyl)imidazo[1,2-a]pyrazin-5-yl)-1,2,4-oxadiazol-5-ol, Cpd 75

A mixture of compound 55b (70.0 mg, 0.170 mmol), 1,1'-carbonyldiimidazole (40.6 mg, 0.250 mmol), 1,8-diazabicyclo[5.4.0]undec-7-ene (0.099 mL, 0.670 mmol) in acetonitrile (2 mL) was stirred at rt for 12 h. The residue was diluted with EtOAc (2×50 mL) and washed with 1N HCl (30 mL). The organic layer was washed with brine, dried over $Na_2SO_4$, filtered, and concentrated under reduced pressure. The residue was triturated with MeOH, collected by filtration, and dried to give the title compound 75 as a yellow solid. $^1$H-NMR (400 MHz, CDCl$_3$) δ (ppm): 3.79-3.96 (m, 4H), 4.49 (br. s., 4H), 5.66-5.76 (m, 2H), 6.99 (d, J=8.8 Hz, 1H), 7.36-7.47 (m, 1H), 7.66 (td, J=7.7, 1.2 Hz, 1H), 7.74 (d, J=8.1 Hz, 1H), 7.81 (s, 1H), 7.91 (d, J=8.3 Hz, 1H), 8.03 (d, J=8.8 Hz, 1H), 8.76 (s, 1H). Mass Spectrum (LCMS, ESI pos.) Calcd. for $C_{22}H_{19}N_7O_4$: 446.2 [M+H]. found 446.2.

Example 56

N-((4-(8-Morpholino-2-(2-(quinolin-2-yl)ethyl)imidazo[1,2-a]pyrazin-5-yl)phenyl)sulfonyl)acetamide (Cpd 63)

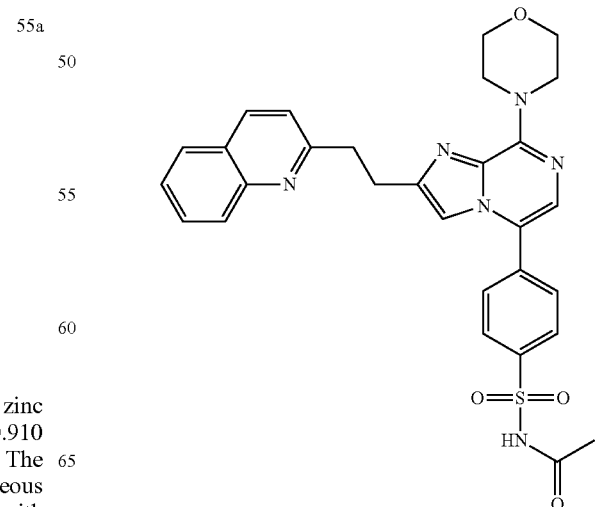

The title compound 63 was prepared from compound 3a and (4-(N-acetylsulfamoyl)phenyl)boronic acid using the methods described in the Example 1, Step G. $^1$H-NMR (400 MHz, CDCl$_3$) δ (ppm): 2.05 (s, 3H), 3.28-3.36 (m, 2H), 3.43-3.45 (m, 2H), 3.77-3.87 (m, 4H), 4.15-4.24 (m, 4H), 7.32-7.33 (m, 1H), 7.41-7.50 (m, 2H), 7.56-7.70 (m, 3H), 7.76-7.85 (m, 1H), 7.88 (d, J=7.8 Hz, 1H), 8.07-8.17 (m, 3H), 8.24 (d, J=8.3 Hz, 1H). Mass Spectrum (LCMS, ESI pos.) Calcd. for C$_{29}$H$_{28}$N$_6$O$_4$S: 557.2 [M+H]. found 557.5.

Example 57

(E)-N-(Methylsulfonyl)-4-(8-morpholino-2-(2-(quinolin-2-yl)vinyl)imidazo[1,2-a]pyrazin-5-yl)benzamide hydrochloric acid salt (Cpd 62)

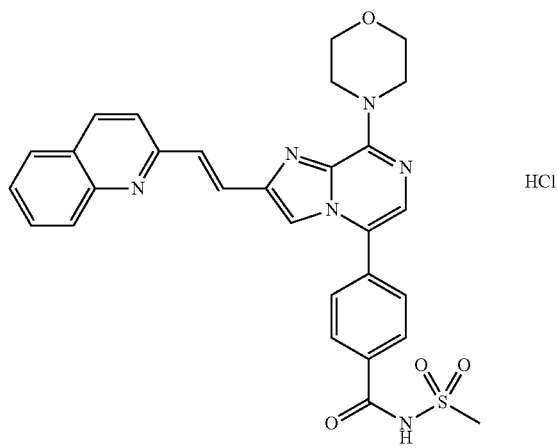 [SMILES: CS(=O)(=O)NC(=O)c1ccc(-c2cnc(N3CCOCC3)c3nc(/C=C/c4ccc5ccccc5n4)cn23)cc1 ; Cl]

A. (E)-4-(8-Morpholino-2-(2-(quinolin-2-yl)vinyl)imidazo[1,2-a]pyrazin-5-yl)benzoic acid trifluoroacetic acid salt, 57a

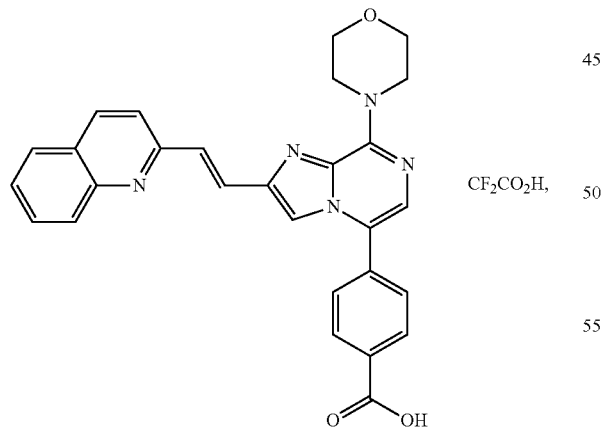

The title compound was prepared from compound 2b and 4-(tert-butoxycarbonyl)phenylboronic acid pinacol ester using the methods described in Example 1, Step G, followed by the deprotection of the resulting product with TFA using the methods described in Example 6, Step B. Mass Spectrum (LCMS, ESI pos.) Calcd. for C$_{28}$H$_{23}$N$_5$O$_3$: 478.2 [M+H]. found 478.1.

B. (E)-N-(Methylsulfonyl)-4-(8-morpholino-2-(2-(quinolin-2-yl)vinyl)imidazo[1,2-a]pyrazin-5-yl)benzamide hydrochloric acid salt, Cpd 62

To the suspension of compound 57a (160 mg, 0.33 mmol) in DCM (20 mL) was added oxalyl chloride (1.67 mL, 3.35 mmol) dropwise followed by a drop of DMF. The mixture was stirred at rt overnight under an Argon atmosphere. The reaction mixture was concentrated and the orange solid obtained was redissolved in DCM (20 mL). To this solution was added methanesulfonamide (63.7 mg, 0.670 mmol), Et$_3$N (139 μL, 1.00 mmol) and DMAP (40.9 mg, 0.335 mmol). The mixture was stirred at rt for 12 h and concentrated. The residue was dissolved in DCM and extracted with 1N HCl, resulting in an emulsion. The emulsion was concentrated to obtain a residue which was then triturated with MeOH, collected by filtration, and dried to give the title compound 62. $^1$H-NMR (400 MHz, DMSO-d$_6$) δ (ppm): 3.43 (s, 3H), 3.80-3.88 (m, 4H), 4.29-4.45 (m, 4H), 7.55 (s, 1H), 7.78-7.95 (m, 4H), 8.04 (t, J=7.6 Hz, 1H), 8.15 (d, J=8.3 Hz, 2H), 8.19-8.30 (m, 3H), 8.30-8.40 (m, 3H), 8.95 (d, J=8.6 Hz, 1H). Mass Spectrum (LCMS, ESI pos.) Calcd. for C$_{29}$H$_{26}$N$_6$O$_4$S: 555.2 [M+H]. found 555.4.

Example 58

N-(Methylsulfonyl)-4-(8-morpholino-2-(2-(quinolin-2-yl)ethyl)imidazo[1,2-a]pyrazin-5-yl)benzamide hydrochloric acid salt (Cpd 61)

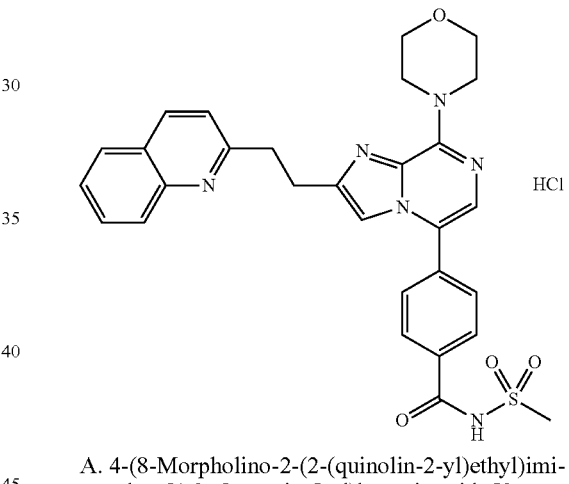

A. 4-(8-Morpholino-2-(2-(quinolin-2-yl)ethyl)imidazo[1,2-a]pyrazin-5-yl)benzoic acid, 58a

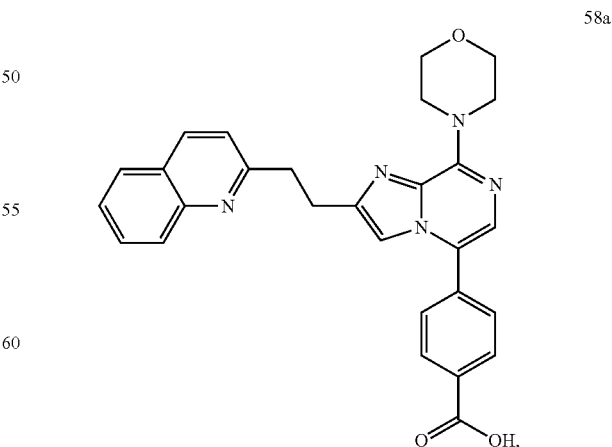

Compound 58a was prepared from compound 3a and 4-(tert-butoxycarbonyl)phenylboronic acid pinacol ester using the methods described in Example 57, Step A.

B. N-(Methylsulfonyl)-4-(8-morpholino-2-(2-(quinolin-2-yl)ethyl)imidazo[1,2-a]pyrazin-5-yl)benzamide hydrochloric acid salt, Cpd 61

Title compound 61 was prepared from compound 58a and methanesulfonamide using the methods described in Example 57, Step B. $^1$H-NMR (400 MHz, CDCl$_3$) δ (ppm): 3.11 (s, 3H), 3.19 (t, J=7.6 Hz, 2H), 3.32 (t, J=7.6 Hz, 2H), 3.71-3.85 (m, 4H), 4.11-4.21 (m, 4H), 7.16 (s, 1H), 7.24-7.30 (m, 2H), 7.30-7.38 (m, 3H), 7.45 (t, J=7.2 Hz, 1H), 7.60-7.67 (m, 1H), 7.73 (d, J=8.1 Hz, 1H), 8.01 (d, J=8.8 Hz, 1H), 7.98 (d, J=8.8 Hz, 1H), 8.13 (d, J=8.1 Hz, 2H). Mass Spectrum (LCMS, ESI pos.) Calcd. for C$_{29}$H$_{28}$N$_6$O$_4$S: 557.2 [M+H]. found 557.8.

Example 59

N-((4-(8-Morpholino-2-(2-(quinolin-2-yl)ethyl)imidazo[1,2-a]pyrazin-5-yl)phenyl)carbamoyl)methanesulfonamide (Cpd 40)

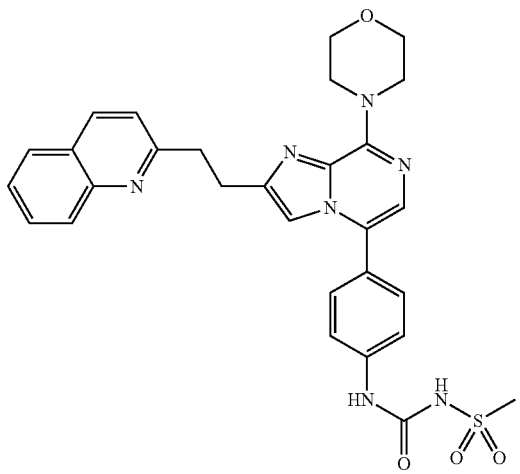 [SMILES: CS(=O)(=O)NC(=O)Nc1ccc(-c2cnc(N3CCOCC3)c3nc(CCc4ccc5ccccc5n4)cn23)cc1]

A. 4-(8-Morpholino-2-(2-(quinolin-2-yl)ethyl)imidazo[1,2-a]pyrazin-5-yl)aniline trifluoroacetic acid salt, 59a

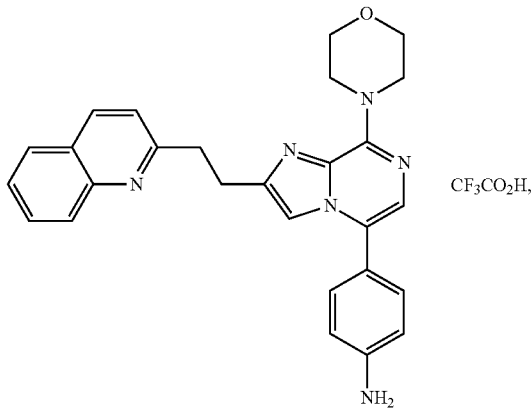

59a

Compound 59a was prepared from compound 3a and 4-(N—BOC-amino)phenylboronic acid using the methods described in the Example 1, Step G, followed by the TFA deprotection of the resulting product. Mass Spectrum LCMS, ESI (pos.) Calcd. for C$_{27}$H$_{26}$N$_6$O: 451.2 [M+H]. found 451.5.

B. N-((4-(8-Morpholino-2-(2-(quinolin-2-yl)ethyl)imidazo[1,2-a]pyrazin-5-yl)phenyl)carbamoyl)methanesulfonamide, Cpd 40

A mixture of compound 59a (100 mg, 0.147 mmol) and ethyl methylsulfonylcarbamate (148 mg, 0.888 mmol) and DIEA (0.191 mL, 1.11 mmol) in DMF (2 mL) was stirred at 100° C. for 2 h. The reaction mixture was allowed to cool to rt and diluted with DCM. The reaction mixture was concentrated and the residue obtained was purified by flash column chromatography on silica gel (0-20% MeOH/EtOAc), recrystallized with EtOAc/heptanes and purified by prep-TLC (1:5:5 MeOH/DCM/EtOAc) to give the title compound 40. $^1$H-NMR (400 MHz, CDCl$_3$) δ (ppm): 3.22-3.30 (m, 2H), 3.33 (s, 3H), 3.37-3.47 (m, 2H), 3.69-3.87 (m, 4H), 4.03-4.21 (m, 4H), 7.16 (s, 1H), 7.31 (s, 1H), 7.28 (s, 1H), 7.39 (d, J=8.3 Hz, 1H), 7.43-7.60 (m, 3H), 7.67-7.76 (m, 1H), 7.82 (d, J=7.6 Hz, 1H), 8.05 (d, J=8.3 Hz, 1H), 8.15 (d, J=8.3 Hz, 1H), 8.81 (br. s., 1H). Mass Spectrum LCMS, ESI (pos.) Calcd. for C$_{29}$H$_{29}$N$_7$O$_4$S: 572.2 [M+H]. found 572.5.

Example 60

(E)-3-(4-(8-Morpholino-2-(2-(quinolin-2-yl)vinyl)imidazo[1,2-a]pyrazin-5-yl)benzamido)propanoic acid (Cpd 39)

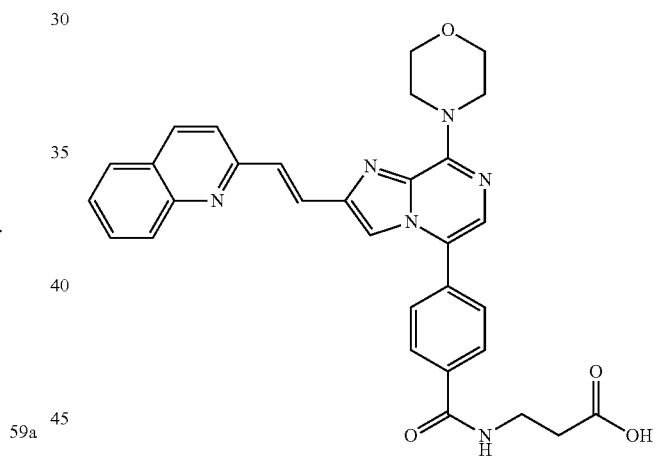

The (E)-4-(8-morpholino-2-(2-(quinolin-2-yl)vinyl)imidazo[1,2-a]pyrazin-5-yl)benzoic acid compound 57a (100.0 mg, 0.170 mmol) was treated with β alanine methyl ester (59.1 mg, 0.420 mmol), HATU (96.4 mg, 0.250 mmol), DIEA (0.175 mL, 1.00 mmol) in DMF (2 mL), and the mixture was stirred at rt for 3 h. The reaction was diluted with DCM and washed with water. The organic layer was dried over Na$_2$SO$_4$, filtered, and concentrated under reduced pressure. The residue was triturated with MeOH, filtered and dried to give (E)-methyl 3-(4-(8-morpholino-2-(2-(quinolin-2-yl)vinyl)imidazo[1,2-a]pyrazin-5-yl)benzamido)propanoate which was subjected to saponification with LiOH, using the methods described in Example 15, Step C, to afford the title compound 39. $^1$H-NMR (400 MHz, DMSO-d$_6$) δ (ppm): 2.54-2.57 (m, 1H), 3.46-3.57 (m, 3H), 3.77-3.88 (m, 4H), 4.26-

4.36 (m, 4H), 7.46-7.51 (m, 1H), 7.56 (t, J=7.5 Hz, 1H), 7.65 (d, J=16.1 Hz, 1H), 7.70-7.91 (m, 5H), 7.96 (t, J=9.3 Hz, 2H), 8.00-8.11 (m, 2H), 8.25-8.30 (m, 1H), 8.35 (d, J=8.6 Hz, 1H), 8.75 (s, 1H). Mass Spectrum LCMS, ESI (pos.) Calcd. for $C_{31}H_{28}N_6O_4$: 572.2 [M+H]. found 572.5.

Example 61

3-(4-(8-Morpholino-2-(2-(quinolin-2-yl)ethyl)imidazo[1,2-a]pyrazin-5-yl)benzamido)propanoic acid (Cpd 38)

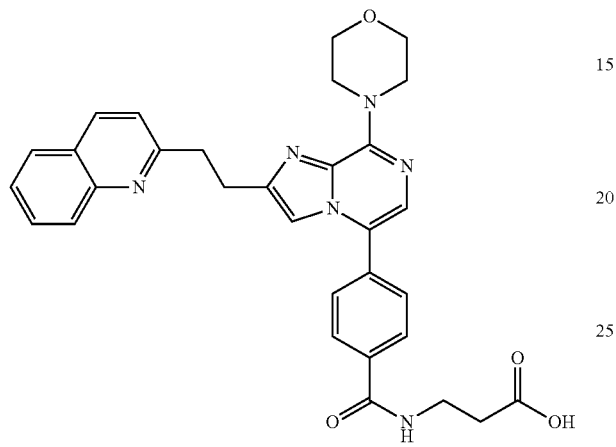

Compound 38 was prepared from 4-(8-morpholino-2-(2-(quinolin-2-yl)ethyl)imidazo[1,2-a]pyrazin-5-yl)benzoic acid trifluoroacetic acid salt, compound 17 (as prepared in Example 65), and β alanine methyl ester using the procedure described in Example 60 followed by the saponification of the ester intermediate using the methods described in Example 15, Step C. $^1$H-NMR (400 MHz, CDCl$_3$) δ (ppm): 2.68 (t, J=6.1 Hz, 2H), 3.25-3.33 (m, 2H), 3.38-3.43 (m, 2H), 3.72 (t, J=6.1 Hz, 2H), 3.80-3.89 (m, 4H), 4.12-4.21 (m, 4H), 7.30 (s, 1H), 7.37-7.41 (m, 2H), 7.51-7.58 (m, 3H), 7.73 (ddd, J=8.4, 7.0, 1.5 Hz, 1H), 7.83 (d, J=8.3 Hz, 1H), 7.87 (d, J=8.6 Hz, 2H), 8.02 (d, J=8.6 Hz, 1H), 8.12 (d, J=8.3 Hz, 1H). Mass Spectrum LCMS, ESI (pos.) Calcd. for $C_{31}H_{30}N_6O_4$: 551.2 [M+H]. found 551.5.

Example 62

4-((4-(8-Morpholino-2-(2-(quinolin-2-yl)ethyl)imidazo[1,2-a]pyrazin-5-yl)phenyl)amino)-4-oxobutanoic acid (Cpd 37)

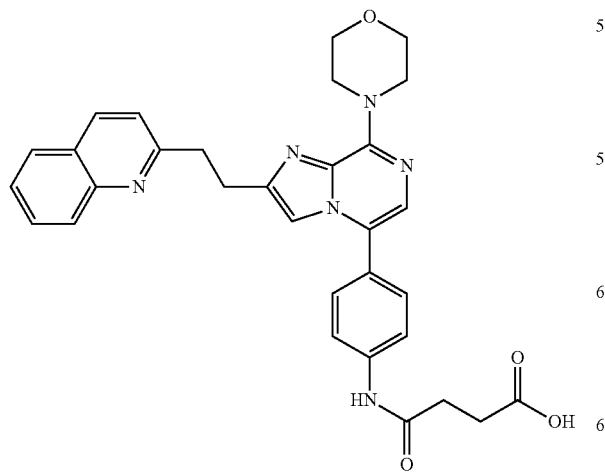

Compound 37 was prepared from compound 59a and mono-methyl succinate followed by saponification of the intermediate ester using the methods described in Example 15, Step C. $^1$H-NMR (400 MHz, CDCl$_3$) d (ppm): 2.67-2.73 (m, 2H), 2.73-2.79 (m, 2H), 3.28 (t, J=7.6 Hz, 2H), 3.41 (d, J=7.3 Hz, 2H), 3.82-3.89 (m, 4H), 4.06-4.16 (m, 4H), 7.24 (s, 1H), 7.33-7.38 (m, 3H), 7.38-7.45 (m, 3H), 7.50-7.58 (m, 1H), 7.67 (d, J=8.6 Hz, 2H), 7.73 (td, J=7.7, 1.2 Hz, 1H), 7.82 (d, J=8.1 Hz, 1H), 8.02 (d, J=8.6 Hz, 1H), 8.12 (d, J=8.3 Hz, 1H). Mass Spectrum LCMS, ESI (pos.) Calcd. for $C_{31}H_{30}N_6O_4$: 551.2 [M+H]. found 551.5.

Example 63

4-(5-(4-((1H-1,2,3-triazol-5-yl)thio)phenyl)-2-(2-(quinolin-2-yl)ethyl)imidazo[1,2-a]pyrazin-8-yl)morpholine (Cpd 36)

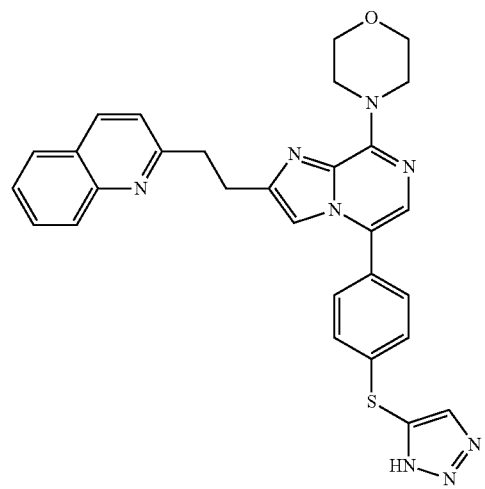 [SMILES: c1ccc2nc(CCc3cn4c(-c5ccc(Sc6cnn[nH]6)cc5)cnc(N5CCOCC5)c4n3)ccc2c1]

A. 5-((4-Bromophenyl)thio)-1H-1,2,3-triazole, 63a

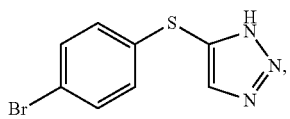

63a

A mixture of 2H-1,2,3-triazole-4-thiol (870 mg, 7.10 mmol), 1-bromo-4-iodobenzene (1.00 g, 3.50 mmol), K$_3$PO$_4$ (1.90 g, 8.80 mmol), CuI (67.0 mg, 0.350 mmol) and glycine (132.7 mg, 1.80 mmol) in DMSO (10 mL) was heated to 110° C. for 3 days. The reaction mixture was cooled to rt, diluted with EtOAc (500 mL) and washed with water (2×400 mL) followed by brine (400 mL). The organic layer was dried over Na$_2$SO$_4$, filtered, and concentrated under reduced pressure to give 360 mg of compound 63a as a white solid. Mass Spectrum LCMS, ESI (pos.) Calcd. for $C_8H_6BrN_3S$: 256.1 [M+H]. found 256.1.

B. 5-((4-Bromophenyl)thio)-1-((2-(trimethylsilyl)ethoxy)methyl)-1H-1,2,3-triazole, 63b

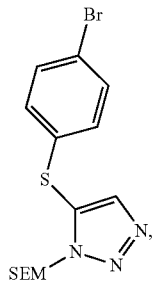

A mixture of compound 63a (360 mg, 1.40 mmol) and 60% NaH (135 mg, 3.40 mmol) in DMF (2 mL) was stirred for 20 min at rt. At that time, 2-(trimethylsilyl) ethoxymethyl chloride (0.558 mL, 3.10 mmol) was added and the resulting mixture was stirred at rt for 12 h. The reaction mixture was diluted with DCM (300 mL) and washed with saturated NH$_4$Cl solution (200 mL), water (200 mL) and brine (200 mL). The organic layer was dried over Na$_2$SO$_4$, filtered, and concentrated under reduced pressure. The residue was purified by flash column chromatography on silica gel (0-50% EtOAc/heptanes) to give compound 63b. Mass Spectrum LCMS, ESI (pos.) Calcd. for C$_{14}$H$_{20}$BrN$_3$OSSi: 386.1 [M+H]. found 386.2.

C. 5-((4-(4,4,5,5-tetramethyl-1,3,2-dioxaborolan-2-yl)phenyl)thio)-1-((2-(trimethylsilyl)ethoxy)methyl)-1H-1,2,3-triazole, 63c

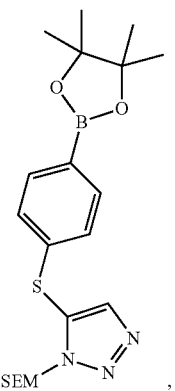

A mixture of compound 63b (400 mg, 1.00 mmol), bis(pinacolato)diboron (289 mg, 1.10 mmol), KOAc (305 mg, 3.10 mmol), PdCl$_2$(dppf) (85.5 mg, 0.104 mmol) in DMSO (5 mL) was heated at 100° C. for 12 h. The reaction mixture was diluted with DCM (500 mL) and washed with water (2×300 mL) and brine (300 mL). The organic layer was dried over Na$_2$SO$_4$, filtered, and concentrated under reduced pressure. The residue was purified by flash column chromatography on silica gel (0-60% EtOAc/heptanes) to give compound 63c. Mass Spectrum LCMS, ESI (pos.) Calcd. for C$_{29}$H$_{26}$N$_8$OS: 535.2 [M+H]. found 535.2.

D. 4-(5-(4-((1H-1,2,3-triazol-5-yl)thio)phenyl)-2-(2-(quinolin-2-yl)ethyl)imidazo[1,2-a]pyrazin-8-yl)morpholine, Cpd 36

The title compound 36 was prepared from compound 3a and compound 63c using the methods described in Example 1, Step G. Subsequently, the SEM group was removed using the methods described in Example 37, Step C. $^1$H-NMR (400 MHz CDCl$_3$) δ (ppm): 3.22-3.32 (m, 2H), 3.35-3.43 (m, 2H), 3.83 (br. s., 4H), 4.14 (br. s., 4H), 7.17-7.30 (m, 3H), 7.31-7.39 (m, 4H), 7.48-7.59 (m, 1H), 7.73 (br. s., 1H), 7.76-7.88 (m, 2H), 8.01 (d, J=8.6 Hz, 1H), 8.10 (d, J=8.6 Hz, 1H). Mass Spectrum LCMS, ESI (pos.) Calcd. for C$_{29}$H$_{26}$N$_8$OS: 535.0 [M+H]. found 535.6.

Example 64

(E)-4-((4-(8-Morpholino-2-(2-(quinolin-2-yl)vinyl)imidazo[1,2-a]pyrazin-5-yl)phenyl)amino)-4-oxobutanoic acid (Cpd 37)

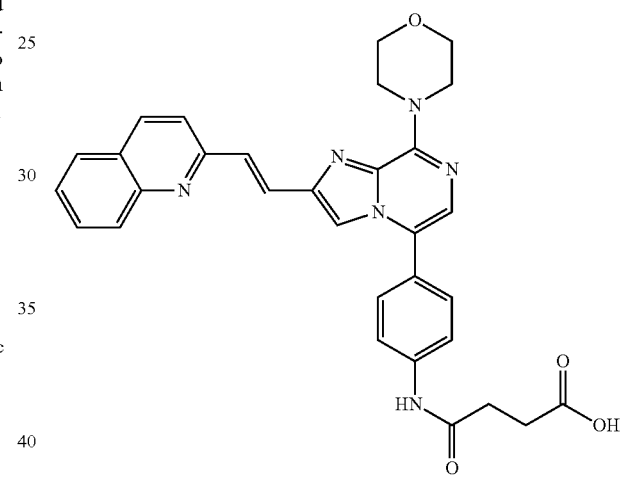

A. (E)-4-(8-Morpholino-2-(2-(quinolin-2-yl)vinyl)imidazo[1,2-a]pyrazin-5-yl)aniline trifluoroacetic acid salt, 64a

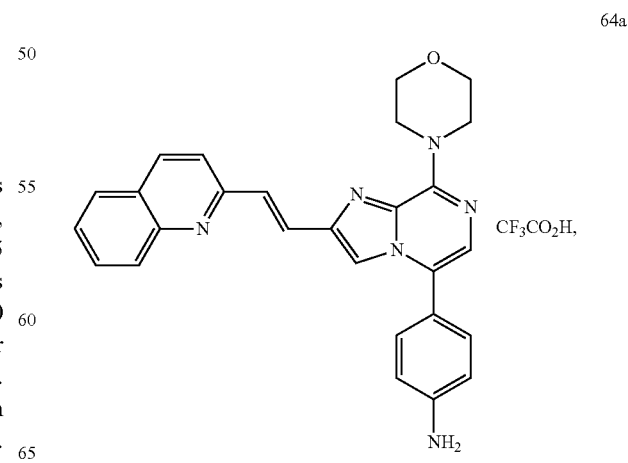

Compound 64a was prepared from compound 2b and 4-(N-BOC-amino)phenylboronic acid using the methods described in Example 59, Step A. Mass Spectrum LCMS, ESI (pos.) Calcd. for $C_{22}H_{24}N_6O$: 449.2 [M+H]. found 449.4.

B. (E)-4-((4-(8-morpholino-2-(2-(quinolin-2-yl)vinyl)imidazo[1,2-a]pyrazin-5-yl)phenyl)amino)-4-oxobutanoic acid The title compound 37 was prepared from compound 64a and mono-methyl succinate followed by saponification of the intermediate ester using the methods described in Example 60. $^1$H-NMR (400 MHz, DMSO-$d_6$) δ (ppm): 2.54-2.69 (m, 4H), 3.82 (br. s., 4H), 4.27 (br. s., 4H), 7.38 (s, 1H), 7.50-7.70 (m, 4H), 7.70-7.90 (m, 5H), 7.90-8.02 (m, 2H), 8.21 (s, 1H), 8.34 (d, J=8.6 Hz, 1H), 10.40 (br. s., 1H). Mass Spectrum LCMS, ESI (pos.) Calcd. for $C_3H_{28}N_6O_4$: 549.2 [M+H]. found 549.5.

Example 65
4-(8-Morpholino-2-(2-(quinolin-2-yl)ethyl)imidazo[1,2-a]pyrazin-5-yl)benzoic acid trifluoroacetic acid salt (Cpd 17)

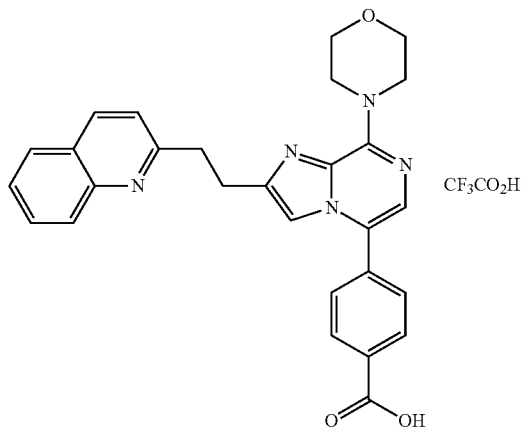 [SMILES: O=C(O)c1ccc(-c2cnc(N3CCOCC3)c3nc(CCc4ccc5ccccc5n4)cn23)cc1 ; "CF3CO2H"]

The title compound 17 was prepared from compound 3a and 4-(t-butoxycarbonyl)phenylboronic acid pinacol ester using the methods described in the Example 1, Step G, followed by deprotection of the resulting product with TFA using the methods described in Example 58, Step A. $^1$H-NMR (400 MHz, CD$_3$OD) δ (ppm): 3.39-3.45 (m, 2H), 3.70-3.76 (m, 2H), 3.76-3.82 (m, 4H), 4.12-4.23 (m, 4H), 7.37 (s, 1H), 7.57-7.67 (m, 3H), 7.77 (d, J=8.6 Hz, 1H), 7.85 (t, 1H), 8.04 (t, J=7.6 Hz, 1H), 8.10 (d, J=8.1 Hz, 1H), 8.18 (d, J=8.1 Hz, 2H), 8.44 (d, J=8.6 Hz, 1H), 8.71 (d, J=8.6 Hz, 1H). Mass Spectrum (LCMS, ESI pos.) Calcd. for $C_{28}H_{25}N_5O_3$: 480.2 [M+H]. found 480.5.

Example 66
(E)-4-(8-morpholino-2-(2-(quinolin-2-yl)vinyl)imidazo[1,2-a]pyrazin-5-yl)benzoic acid trifluoroacetic acid salt (Cpd 16)

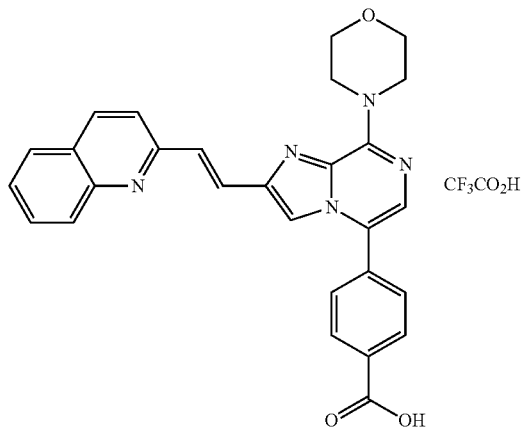 [SMILES: O=C(O)c1ccc(-c2cnc(N3CCOCC3)c3nc(/C=C/c4ccc5ccccc5n4)cn23)cc1 ; "CF3CO2H"]

The title compound 16 was prepared from compound 2b and 4-(tert-butoxycarbonyl)phenylboronic acid pinacol ester using the methods described in Example 1, Step G, followed by deprotection of the resulting intermediate with TFA using the methods described in Example 57, Step A. $^1$H-NMR (400 MHz, CD$_3$OD) δ (ppm): 3.89-4.03 (m, 4H), 4.37-4.47 (m, 4H), 7.65-7.79 (m, 3H), 7.85-8.10 (m, 7H), 8.20-8.32 (m, 3H), 8.60 (d, J=8.8 Hz, 1H). Mass Spectrum (LCMS, ESI pos.) Calcd. for $C_{28}H_{23}N_5O_3$: 478.2 [M+H]. found 478.5.

Example 67
(E)-4-(2-(2-(6-Methoxypyridin-2-yl)vinyl)-8-morpholinoimidazo[1,2-a]pyrazin-5-yl)benzoic acid (Cpd 7)

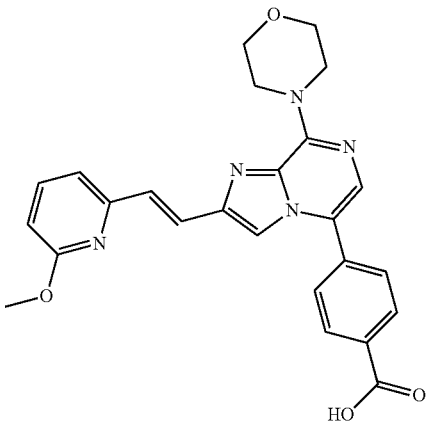 [SMILES: COc1cccc(/C=C/c2cn3c(-c4ccc(C(=O)O)cc4)cnc(N4CCOCC4)c3n2)n1]

A. tert-Butyl 4-(2-formyl-8-morpholinoimidazo[1,2-a]pyrazin-5-yl)benzoate, 67a

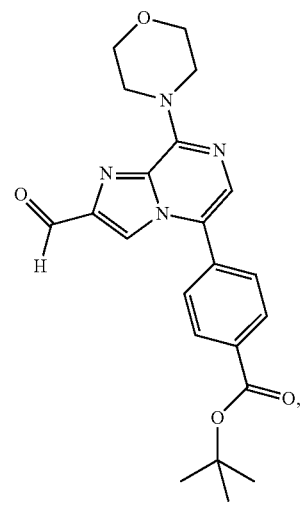

A mixture of compound 2a (1.0 g, 3.2 mmol), 4-(tert-butoxycarbonyl)phenylboronic acid pinacol ester (1.2 g, 3.9 mmol), PdCl$_2$(dppf) (260 mg, 0.30 mmol), 2M Na$_2$CO$_3$ (8.0 mL, 16 mmol) in dioxane (10 mL) was heated to 80° C. for 2 h. The reaction was cooled, filtered through a diatomaceous earth-filled cartridge (2.5 g), and the filter cake was rinsed with EtOAc. The combined filtrates were concentrated under reduced pressure. The residue was diluted with DCM and extracted with water, brine, then dried over Na$_2$SO$_4$, filtered, and concentrated under reduced pressure. The residue was triturated with MeOH, filtered and dried to give compound 67a. Mass Spectrum (LCMS, ESI pos.) Calcd. for C$_{22}$H$_{24}$N$_4$O$_4$: 409.4 [M+H]. found 409.4.

B. (E)-4-(2-(2-(6-Methoxypyridin-2-yl)vinyl)-8-morpholinoimidazo[1,2-a]pyrazin-5-yl)benzoic acid, Cpd 7

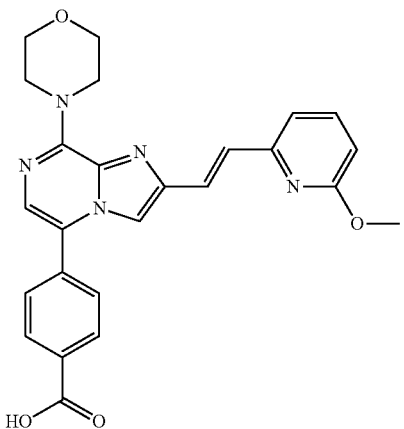 [SMILES: COc1cccc(/C=C/c2cn3c(-c4ccc(C(=O)O)cc4)cnc(N4CCOCC4)c3n2)n1]

To a solution of diethyl ((6-methoxypyridin-2-yl)methyl)phosphonate (76.2 mg, 0.29 mmol, prepared according to literature procedure: *J. Med. Chem.* 2005, 48, 5884-5887), n-BuLi (0.184 mL, 0.29 mmol, 1.6 M in hexanes) was added dropwise. After stirring the resulting mixture for 15 min at rt, it was slowly added to a suspension of compound 67a (100 mg, 0.25 mmol) in THF (5 mL). The resulting mixture was stirred at rt for 30 min and quenched with saturated NH$_4$Cl (2 mL). The reaction mixture was treated with water (20 mL) and extracted with EtOAc (2×40 mL). The combined organic layers were washed with brine (20 mL), dried over Na$_2$SO$_4$, filtered, and concentrated under reduced pressure. The residue obtained was purified by flash column chromatography on silica gel (0-100% EtOAc/heptanes) to give (E)-tert-butyl 4-(2-(2-(6-methoxypyridin-2-yl)vinyl)-8-morpholinoimidazo[1,2-a]pyrazin-5-yl)benzoate, which was subjected to TFA deprotection using the methods described in Example 57, Step A to yield the title compound 7 containing 0.1 eq. of TFA. $^1$H-NMR (400 MHz, DMSO-d$_6$) δ (ppm): 8.25 (s, 1H), 8.11 (m, J=7.8 Hz, 2H), 7.83 (m, J=7.8 Hz, 2H), 7.63-7.69 (m, 1H), 7.69-7.75 (m, 1H), 7.49 (s, 1H), 7.40 (d, J=15.7 Hz, 1H), 7.08 (d, J=7.1 Hz, 1H), 6.70 (d, J=8.1 Hz, 1H), 4.29 (br. s., 4H), 3.92 (s, 3H), 3.80 (br. s., 4H). Mass Spectrum (LCMS, ESI pos.) Calcd. for C$_{25}$H$_{23}$N$_5$O$_4$: 458.2 [M+H]. found 458.4.

Example 68

(E)-5-(8-morpholino-2-(2-(quinolin-2-yl)vinyl)imidazo[1,2-a]pyrazin-5-yl)picolinic acid (Cpd 133)

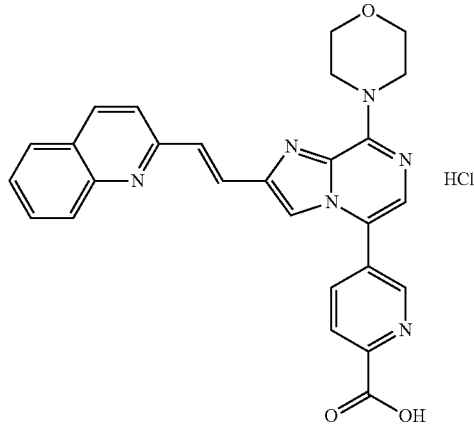 [SMILES: O=C(O)c1ccc(-c2cnc(N3CCOCC3)c3nc(/C=C/c4ccc5ccccc5n4)cn23)cn1 ; Cl]

To a mixture of compound 3a (200.0 mg, 0.458 mmol) and methyl 5-(4,4,5,5-tetramethyl-1,3,2-dioxaborolan-2-yl)picolinate (148 mg, 0.550 mmol) in 1,4-dioxane (3 mL) and 2M Na$_2$CO$_3$ (1.14 mL, 2.29 mmol), PdCl$_2$(dppf)DCM (37.4 mg, 0.045 mmol) was added. The solution was purged with Argon gas and stirred at 120° C. for 2 h. The reaction mixture was cooled to rt, filtered through a cartridge of diatomaceous earth (2.5 g), and the filter cake was washed with EtOAc/DCM. The filter cake was dissolved in water, acidified with 1N HCl and concentrated to half the volume. The solid formed was collected by filtration, washed with water, and dried under reduced pressure to give the title compound 133 as a yellowish-orange solid. $^1$H-NMR (400 MHz, DMSO-d$_6$) δ (ppm): 3.83 (br. s., 4H), 4.36 (br. s., 4H), 7.57-7.75 (m, 3H), 7.78-7.91 (m, 1H), 7.91-8.09 (m, 4H), 8.18-8.27 (m, 1H), 8.34-8.39 (m, 1H), 8.40-8.46 (m, 1H), 8.48-8.58 (m, 1H), 9.02 (br. s., 1H). Mass Spectrum (LCMS, ESI pos.) Calcd. for C$_{27}$H$_{22}$N$_6$O$_3$: 479.2 [M+H]. found 479.4.

Example 69

(E)-6-(8-morpholino-2-(2-(quinolin-2-yl)vinyl)imidazo[1,2-a]pyrazin-5-yl)nicotinic acid hydrochloric acid salt (Cpd 6)

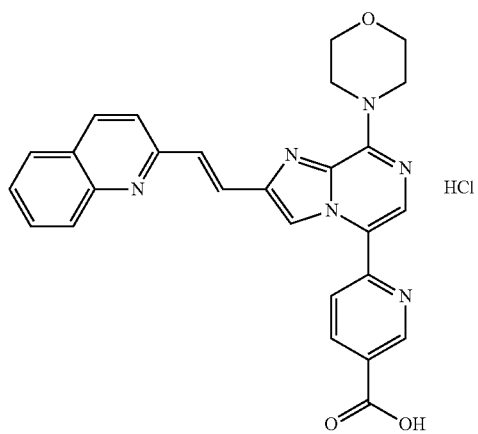 [SMILES: O=C(O)c1ccc(-c2cnc(N3CCOCC3)c3nc(/C=C/c4ccc5ccccc5n4)cn23)nc1 ; Cl]

The title compound was prepared from compound 2b and methyl 6-(4,4,5,5-tetramethyl-1,3,2-dioxaborolan-2-yl)picolinate using the methods described in Example 68. $^1$H-NMR (400 MHz, CDCl$_3$) δ (ppm) 3.95 (br. s., 4H), 4.52 (br. s., 4H), 7.77-7.87 (m, 2H), 7.94-8.17 (m, 6H), 8.20 (br. s., 1H), 8.38 (d, J=8.6 Hz, 2H), 8.71 (d, J=8.6 Hz, 1H), 9.34 (s, 1H), 9.42 (s, 1H). Mass Spectrum (LCMS, ESI pos.): calcd. for C$_{27}$H$_{22}$N$_6$O$_3$: 479.2 [M+H]$^+$. found 479.4

Example 70

(E)-2-methoxy-4-(8-morpholino-2-(2-(quinolin-2-yl)vinyl)imidazo[1,2-a]pyrazin-5-yl)benzoic acid hydrochloric acid salt (Cpd 4)

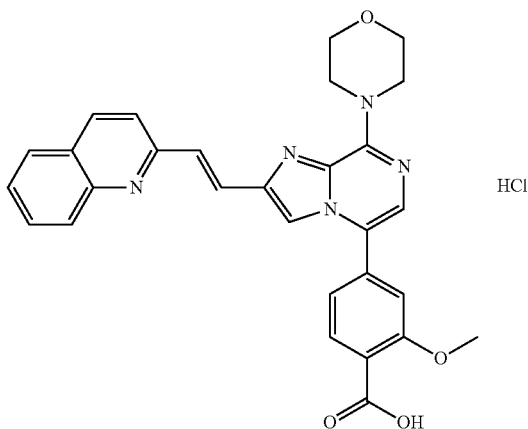 [SMILES: COc1cc(-c2cnc(N3CCOCC3)c3nc(/C=C/c4ccc5ccccc5n4)cn23)ccc1C(=O)O ; Cl]

The title compound 4 was prepared from compound 2b and 3-methoxy-4-methoxycarbonylphenyl-boronic acid pinacol ester using the methods described in Example 1, Step G, followed by saponification of the intermediate ester compound with LiOH using the methods described in Example 15, Step C. $^1$H-NMR (400 MHz, DMSO-d$_6$) δ (ppm): 8.63 (br. s., 1H), 8.40 (s, 1H), 7.96-8.15 (m, 4H), 7.86-7.93 (m, 1H), 7.83 (d, J=7.8 Hz, 1H), 7.64-7.79 (m, 2H), 7.56 (s, 1H), 7.43 (s, 1H), 7.33 (d, J=7.6 Hz, 1H), 4.33 (br. s., 4H), 3.92 (s, 3H), 3.83 (br. s., 4H). Mass Spectrum (LCMS, ESI pos.) Calcd. for C$_{29}$H$_{25}$N$_5$O$_4$: 508.2 [M+H]. found 508.4.

Example 71

(E)-2-Fluoro-4-(8-morpholino-2-(2-(quinolin-2-yl)vinyl)imidazo[1,2-a]pyrazin-5-yl)benzoic acid hydrochloric acid salt (Cpd 3)

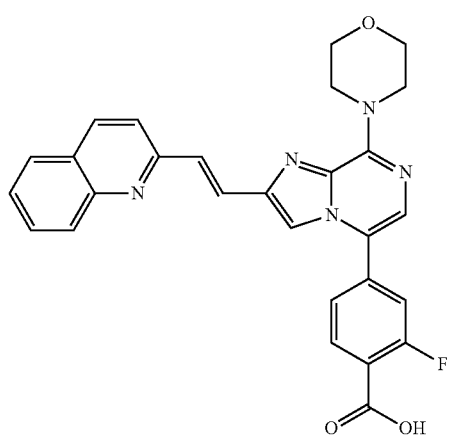 [SMILES: O=C(O)c1ccc(-c2cnc(N3CCOCC3)c3nc(/C=C/c4ccc5ccccc5n4)cn23)cc1F]

The title compound was prepared from compound 2b and 3-fluoro-4-methoxycarbonylphenyl-boronic acid pinacol ester using the methods described in Example 1, Step G, followed by saponification of the ester intermediate compound with LiOH using the methods described in the Example 15, Step C. $^1$H-NMR (400 MHz, DMSO-d$_6$) d (ppm): 8.61 (br. s., 1H), 8.42 (s, 1H), 7.96-8.16 (m, 5H), 7.88 (br. s., 1H), 7.62-7.81 (m, 4H), 7.58 (s, 1H), 4.35 (br. s., 4H), 3.83 (br. s., 4H). Mass Spectrum (LCMS, ESI pos.) Calcd. for C$_{28}$H$_{22}$FN$_5$O$_3$: 496.2 [M+H]. found 496.3.

Example 72

(E)-1,1,1,3,3,3-hexafluoro-2-(4-(8-morpholino-2-(2-(quinolin-2-yl)vinyl)imidazo[1,2-a]pyrazin-5-yl)phenyl)propan-2-ol (Cpd 2)

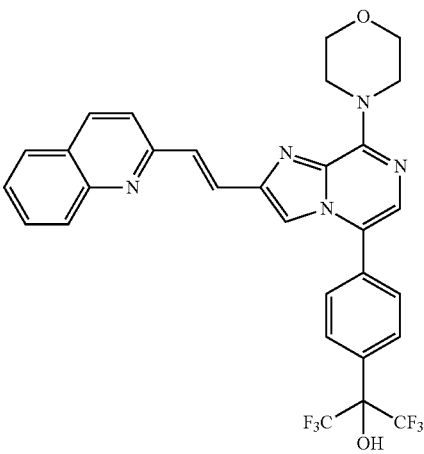 [SMILES: OC(c1ccc(-c2cnc(N3CCOCC3)c3nc(/C=C/c4ccc5ccccc5n4)cn23)cc1)(C(F)(F)F)C(F)(F)F]

The title compound was prepared from compound 2b and 4-(1,1,1,3,3,3-hexafluoro-2-propan-2-ol)phenylboronic acid using the methods described in the Example 1, Step G. $^1$H-NMR (400 MHz, CDCl$_3$) δ (ppm): 8.18 (d, J=8.6 Hz, 1H), 8.05 (d, J=8.6 Hz, 1H), 7.88-7.99 (m, 3H), 7.81 (d, J=8.1 Hz, 1H), 7.66-7.77 (m, 6H), 7.49-7.56 (m, 1H), 7.38 (s, 1H), 4.31-4.42 (m, 4H), 3.91-4.00 (m, 4H). Mass Spectrum (LCMS, ESI pos.) Calcd. for C$_{30}$H$_{23}$F$_6$N$_5$O$_2$: 600.2 [M+H]. found 600.4.

Example 73

(E)-5-(8-Morpholino-2-(2-(quinolin-2-yl)vinyl)imidazo[1,2-a]pyrazin-5-yl)nicotinic acid (Cpd 27)

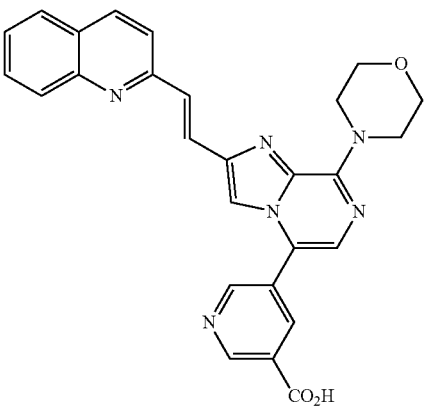 [SMILES: O=C(O)c1cncc(-c2cnc(N3CCOCC3)c3nc(/C=C/c4ccc5ccccc5n4)cn23)c1]

A. (E)-Ethyl 5-(8-morpholino-2-(2-(quinolin-2-yl)vinyl)imidazo[1,2-a]pyrazin-5-yl)nicotinate, 73a

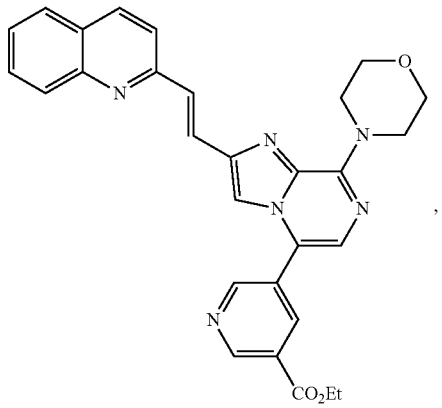

Compound 2b (436 mg, 1.00 mmol), PdCl₂(dppf).DCM (40.8 mg, 0.0500 mmol), and 3-(ethoxycarbonyl)pyridine-5-boronic acid pinacol ester (333 mg, 1.20 mmol) were placed in an 8 mL vial equipped with a stir bar and evacuated/backflushed with Argon gas. Dry dioxane (4 mL) and 2M Na₂CO₃ (2.5 mL) were added and then the reaction was stirred at 80° C. for 2.5 h. The reaction was cooled to rt and diluted with water (20 mL). The precipitate was collected by filtration and then the filter cake was washed with water (2×10 mL). The solid was dried in air and then purified by flash column chromatography on silica gel (40-g SiO₂ pre-packed column, 0-100% EtOAc/DCM) to afford compound 73a. ¹H-NMR (400 MHz, CDCl₃) δ (ppm): 9.32 (d, J=2.2 Hz, 1H), 8.99 (d, J=2.2 Hz, 1H), 8.54 (t, J=2.2 Hz, 1H), 8.12 (d, J=8.6 Hz, 1H), 8.06 (d, J=8.3 Hz, 1H), 7.77 (d, J=8.1 Hz, 1H), 7.63-7.75 (m, 5H), 7.46-7.53 (m, 1H), 7.38 (s, 1H), 4.48 (q, J=7.1 Hz, 2H), 4.39-4.45 (m, 4H), 3.90-3.98 (m, 4H), 1.45 (t, J=7.2 Hz, 3H). Mass Spectrum (LCMS, ESI pos.) Calcd. for C₂₉H₂₆N₆O₃: 507.2 (M+H). found: 507.4.

B. (E)-5-(8-Morpholino-2-(2-(quinolin-2-yl)vinyl)imidazo[1,2-a]pyrazin-5-yl)nicotinic acid, Cpd 27

Compound 73a (297 mg, 0.586 mmol) was placed in a 40 mL vial equipped with a stir bar and then dioxane (10 mL), MeOH (10 mL), and 1 M NaOH solution (10 mL) were added. The reaction was stirred at rt for 3 days and then the solvent was removed under reduced pressure. The residue was suspended in water (50 mL) and adjusted to pH 2 using 2 M HCl. The solid was collected by filtration and then washed with water (2×5 mL). The solid was air dried to afford the title compound 27. ¹H-NMR (400 MHz, DMSO-d₆) δ: 9.11 (d, J=2.0 Hz, 1H), 8.85 (d, J=2.2 Hz, 1H), 8.43 (t, J=2.0 Hz, 1H), 8.34 (d, J=8.6 Hz, 1H), 8.21 (s, 1H), 7.94 (d, J=7.8 Hz, 1H), 7.97 (d, J=8.3 Hz, 1H), 7.87 (d, J=16.1 Hz, 1H), 7.87 (d, J=8.8 Hz, 1H), 7.71-7.79 (m, 1H), 7.64 (d, J=16.1 Hz, 1H), 7.56 (t, J=7.3 Hz, 1H), 7.48 (s, 1H), 4.26-4.37 (m, 4H), 3.78-3.89 (m, 4H). Mass Spectrum (LCMS, ESI pos.) Calcd. for C₂₇H₂₂N₆O₃: 479.2 (M+H). found: 479.5.

Example 74
(E)-N-(Methylsulfonyl)-5-(8-morpholino-2-(2-(quinolin-2-yl)vinyl)imidazo[1,2-a]pyrazin-5-yl)nicotinamide (Cpd 25)

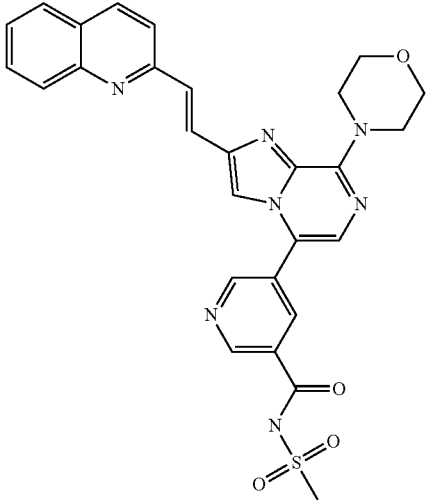 [SMILES: CS(=O)(=O)NC(=O)c1cncc(-c2cnc(N3CCOCC3)c3nc(/C=C/c4ccc5ccccc5n4)cn23)c1]

Compound 27 (109 mg, 0.228 mmol, Example 73) was placed in an 8 mL vial equipped with a stir bar and then dry DMF (2 mL) and DIPEA (0.240 mL, 1.38 mmol) were added. Methanesulfonamide (106 mg, 1.11 mmol) was added followed by HATU (130 mg, 0.342 mmol). The reaction was stirred at rt for 3 h during which time most of the solids dissolved. The solvent was removed under a N₂ purge and then the residue was triturated with water (8 mL). The solid was collected by filtration and allowed to air dry over 3 days. The solid was dissolved in MeOH/DCM (1:1, 100 mL) and the solution was filtered. The filtrate was concentrated under reduced pressure. The residue was triturated with MeOH and then the solid was collected by filtration to give the title compound 25. ¹H-NMR (400 MHz, d₆-DMSO) δ: 9.16 (d, J=2.0 Hz, 1H), 9.08 (d, J=1.5 Hz, 1H), 8.64 (t, J=2.0 Hz, 1H), 8.39 (s, 1H), 8.36 (d, J=8.6 Hz, 1H), 7.96 (t, J=7.8 Hz, 2H), 7.84-7.92 (m, 2H), 7.72-7.80 (m, 1H), 7.67 (d, J=16.2 Hz, 1H), 7.52-7.61 (m, 2H), 4.29-4.40 (m, 4H), 3.78-3.88 (m, 4H), 3.38 (s, 3H). Mass Spectrum (LCMS, ESI pos.) Calcd. for C₂₈H₂₅N₇O₄S: 556.2 (M+H). found: 556.5.

Example 75
4-(5-(6-(1H-Tetrazol-5-yl)pyridin-3-yl)-2-((quinolin-2-ylthio)methyl)imidazo[1,2-a]pyrazin-8-yl)morpholine (Cpd 70)

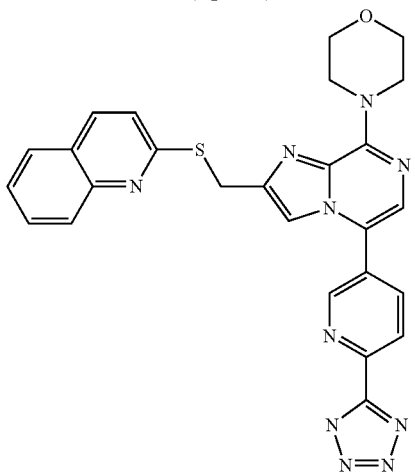

A. 5-(2-Formyl-8-morpholinoimidazo[1,2-a]pyrazin-5-yl)picolinonitrile, 75a

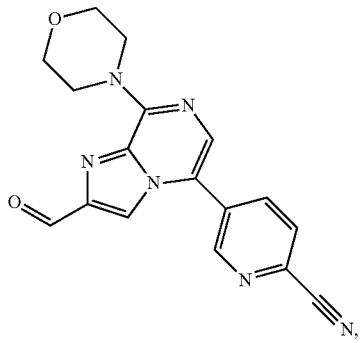

75a

Compound 2a (156 mg, 0.500 mmol), 2-cyanopyridine-5-boronic acid pinacol ester (230 mg, 1.00 mmol), and PdCl$_2$(dppf).DCM (40.8 mg, 0.0500 mmol), were placed in an 8 mL vial equipped with a stir bar and then the vial was evacuated and backflushed with Argon gas. Dry DME (4 mL) and 2M Na$_2$CO$_3$ (2 mL) were added sequentially and then the reaction was stirred at 90° C. for 3 h. The reaction was cooled to rt and diluted with DCM (10 mL). The mixture was dried through a Na$_2$SO$_4$ pre-packed cartridge and then the solvent was removed under reduced pressure. The crude product was purified by flash column chromatography on silica gel (40-g SiO$_2$ pre-packed column, 0-100% EtOAc/DCM) to afford compound 75a. $^1$H-NMR (400 MHz, CDCl$_3$) δ (ppm): 10.08 (s, 1H), 8.93 (s, 1H), 8.17 (s, 1H), 8.02-8.10 (m, 1H), 7.88 (d, J=8.1 Hz, 1H), 7.49 (s, 1H), 4.47 (br. s., 4H), 3.90 (t, J=4.6 Hz, 4H). LCMS calcd for C$_{17}$H$_{14}$N$_6$O$_2$: 335.1 (M+H). found: 335.1.

B. 5-(2-(Hydroxymethyl)-8-morpholinoimidazo[1,2-a]pyrazin-5-yl)picolinonitrile, 75b

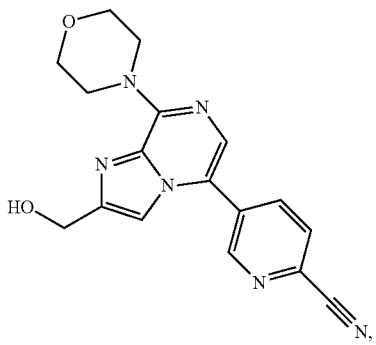

75b

Compound 75a (74.5 mg, 0.223 mmol) was suspended in MeOH (10 mL) and then NaBH$_4$ (26.3 mg, 0.695 mmol) was added. The reaction was stirred at rt for 18 h and then diluted with water (10 mL) and filtered. The solid was collected by filtration and the filter cake was washed with water (2×10 mL). The solid was dissolved in a mixture of DCM (100 mL) and MeOH (50 mL), dried over Na$_2$SO$_4$, and filtered. The solvent was removed under reduced pressure to afford compound 75b. $^1$H-NMR (400 MHz, CD$_3$OD+CDCl$_3$) δ (ppm): 8.96 (d, J=2.2 Hz, 1H), 8.20 (dd, J=8.1, 2.2 Hz, 1H), 7.95 (d, J=8.1 Hz, 1H), 7.70 (s, 1H), 7.43 (s, 1H), 4.79 (s, 2H), 4.29-4.36 (m, 4H), 3.85-3.94 (m, 4H). LCMS calcd for C$_{17}$H$_{16}$N$_6$O$_2$: 337.1 (M+H). found: 337.1.

C. 5-(8-Morpholino-2-((quinolin-2-ylthio)methyl)imidazo[1,2-a]pyrazin-5-yl)picolinonitrile, 75c

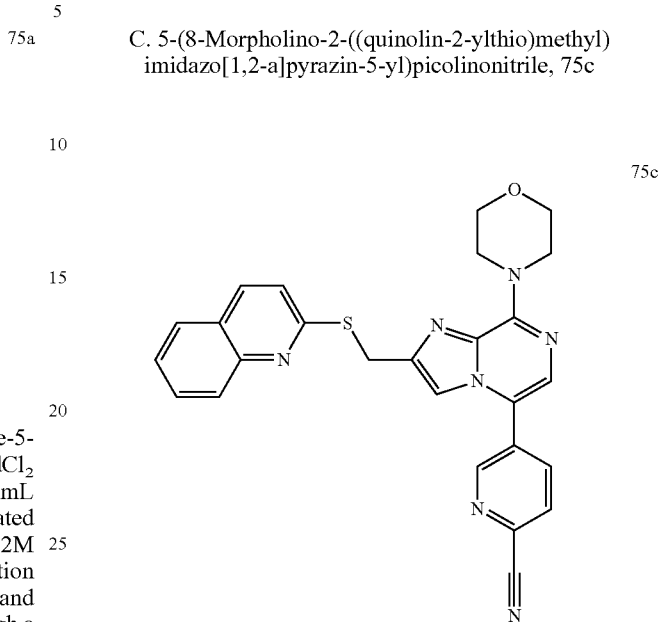

75c

Compound 75b (70.2 mg, 0.209 mmol) was placed in an 8 mL vial equipped with a stir bar and then DCM (10 mL) and DIEA (72.7 μL, 0.417 mmol) were added. MsCl (24.3 μL, 0.313 mmol) was added, and then the reaction was stirred at rt for 3 days. Additional MsCl (24.3 μL, 0.313 mmol) and DIEA (72.7 μL, 0.417 mmol) were added and the reaction was stirred for 2 h. The solvent was removed under reduced pressure. The crude material was placed in a 50 mL round bottom flask equipped with a stir bar, followed by addition of ACN (25 mL). 2-Quinolinethiol (38.2 mg, 0.230 mmol) and K$_2$CO$_3$ (43.3 mg, 0.313 mmol) were added and then the reaction was stirred at rt for 1 h. The temperature was increased to 80° C. and the reaction was stirred for 18 h. The reaction was cooled to rt, diluted with DCM (20 mL), and filtered. The solvent was removed under reduced pressure. The crude produced was purified by flash column chromatography on silica gel (25-g SiO$_2$ pre-packed column, 0-100% EtOAc/heptanes) to afford compound 75c. $^1$H-NMR (400 MHz, CDCl$_3$) δ (ppm): 8.84 (s, 1H), 7.91 (d, J=8.6 Hz, 1H), 7.81-7.89 (m, 2H), 7.78 (s, 1H), 7.76 (d, J=8.1 Hz, 1H), 7.70 (t, J=7.7 Hz, 1H), 7.60 (d, J=8.1 Hz, 1H), 7.46-7.53 (m, 1H), 7.35 (s, 1H), 7.21 (d, J=8.6 Hz, 1H), 4.69 (s, 2H), 4.30-4.43 (m, 4H), 3.82-3.91 (m, J=4.5, 4.5 Hz, 4H). Mass Spectrum (LCMS, ESI pos.) Calcd. for C$_{26}$H$_{21}$N$_7$OS: 480.2 (M+H). found: 480.1.

D. 4-(5-(6-(1H-Tetrazol-5-yl)pyridin-3-yl)-2-((quinolin-2-ylthio)methyl)imidazo[1,2-a]pyrazin-8-yl)morpholine, Cpd 70

Compound 75c (54.9 mg, 0.114 mmol) NH$_4$Cl (9.20 mg, 0.172 mmol), and NaN$_3$ (11.2 mg, 0.172 mmol) were placed in an 8 mL vial equipped with a stir bar and then the vial was evacuated and backflushed with Argon gas. Dry DMF (1 mL) was added via syringe and then the mixture was stirred at 120° C. for 2 h. The reaction was cooled to rt, diluted with water (5 mL), and adjusted to pH 2 with 2M HCl. The precipitate was collected by filtration and then the solid was washed with water (2×5 mL). The solid was dissolved in a mixture of DCM (20 mL) and MeOH (10 mL), dried over Na$_2$SO$_4$, and filtered. The solvent was removed under reduced pressure. The residue was triturated with MeOH (5 mL) and the solid was collected by filtration. The residual solvent was removed under reduced pressure to afford the title compound 70. $^1$H-NMR (400 MHz, DMSO-d$_6$) δ (ppm): 8.98 (s, 1H), 8.30 (s, 2H), 8.17 (d, J=8.6 Hz, 1H), 8.07 (s, 1H), 7.89 (d, J=7.8 Hz, 1H), 7.86 (d, J=8.3 Hz, 1H), 7.66 (t, J=7.6 Hz, 1H), 7.59 (s, 1H), 7.48 (t, J=7.5 Hz, 1H), 7.43 (d, J=8.6 Hz, 1H), 4.68 (s, 2H), 4.15-4.27 (m, 4H), 3.69-3.75 (m, 4H). Mass Spectrum (LCMS, ESI pos.) Calcd. for C$_{26}$H$_{22}$N$_{10}$OS: 523.2 (M+H). found: 523.3.

Example 76

(E)-4-(5-(5-(1H-Tetrazol-5-yl)pyridin-3-yl)-2-(2-(quinolin-2-yl)vinyl)imidazo[1,2-a]pyrazin-8-yl) morpholine hydrochloric acid salt (Cpd 60)

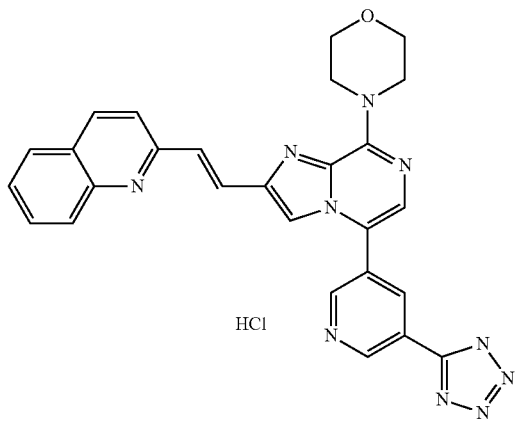 [SMILES: C(=C\c1cn2c(-c3cncc(-c4nnn[nH]4)c3)cnc(N3CCOCC3)c2n1)/c1ccc2ccccc2n1 ; Cl]

HCl

A. (E)-5-(8-Morpholino-2-(2-(quinolin-2-yl)vinyl) imidazo[1,2-a]pyrazin-5-yl)nicotinonitrile, 76a

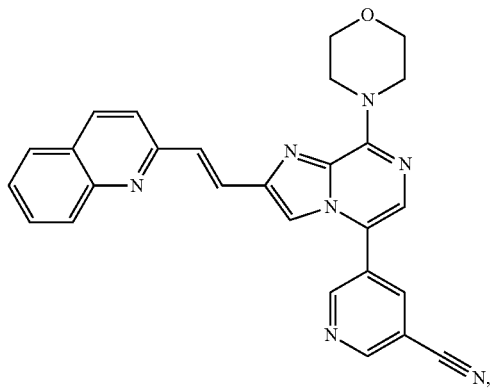

76a

Compound 2b (436 mg, 1.00 mmol), PdCl$_2$(dppf).DCM (40.8 mg, 0.0500 mmol), and 3-cyanopyridine-5-boronic acid (178 mg, 1.20 mmol) were placed in an 8 mL vial equipped with a stir bar and evacuated/backflushed with Argon gas. Dry dioxane (4 mL) and 2M Na$_2$CO$_3$ (2.5 mL) were added and then the reaction was stirred at 80° C. for 2.5 h. The reaction was cooled to rt and diluted with water (20 mL). The precipitate was collected by filtration and then the filter cake was washed with water (2×10 mL). The solid was dried in air and then was purified by flash column chromatography on silica gel (40-g SiO$_2$ pre-packed column, 0-100% EtOAc/DCM) to afford compound 76a. $^1$H-NMR (400 MHz, CDCl$_3$) δ (ppm): 9.06 (d, J=2.2 Hz, 1H), 8.98 (d, J=2.0 Hz, 1H), 8.19 (t, J=2.1 Hz, 1H), 8.15 (d, J=8.6 Hz, 1H), 8.07 (d, J=8.6 Hz, 1H), 7.80 (d, J=8.3 Hz, 1H), 7.65-7.77 (m, 5H), 7.48-7.54 (m, 1H), 7.38 (s, 1H), 4.44-4.52 (m, 4H), 3.89-3.97 (m, 4H). Mass Spectrum (LCMS, ESI pos.) Calcd. for C$_{27}$H$_{21}$N$_7$O: 460.2 (M+H). found: 460.5.

B. (E)-4-(5-(5-(1H-Tetrazol-5-yl)pyridin-3-yl)-2-(2-(quinolin-2-yl)vinyl)imidazo[1,2-a]pyrazin-8-yl) morpholine hydrochloric acid salt, Cpd 60

Compound 76a (90.0 mg, 0.196 mmol), NH$_4$Cl (15.7 mg, 0.294 mmol), and NaN$_3$ (19.1 mg, 0.294 mmol) were placed in an 8 mL vial equipped with a stir bar and then the vial was evacuated and backflushed with Argon gas. Dry DMF (1 mL) was added via syringe and then the mixture was stirred at 120° C. for 2 h. The reaction was cooled to rt, diluted with water (5 mL), and adjusted to pH 2 with 2M HCl. The precipitate was collected by filtration and then the solid was washed with water (2×5 mL). The solid was air-dried to afford the title compound 60 as a red solid. $^1$H-NMR (400 MHz, DMSO-d$_6$+TFA) δ (ppm): 9.40 (d, J=2.2 Hz, 1H), 9.10 (d, J=2.0 Hz, 1H), 9.04 (d, J=9.0 Hz, 1H), 8.79 (t, J=2.1 Hz, 1H), 8.48 (s, 1H), 8.42 (d, J=9.0 Hz, 1H), 8.31 (d, J=15.9 Hz, 1H), 8.28 (d, J=8.6 Hz, 1H), 8.22 (d, J=8.6 Hz, 1H), 8.10 (t, J=7.8 Hz, 1H), 7.81-7.92 (m, 2H), 7.68 (s, 1H), 4.35-4.51 (m, 4H), 3.83-3.94 (m, 4H). Mass Spectrum (LCMS, ESI pos.) Calcd. for C$_{22}$H$_{22}$N$_{10}$O: 503.2 (M+H). found: 503.5.

Example 77

(E)-3-(5-(8-Morpholino-2-(2-(quinolin-2-yl)vinyl) imidazo[1,2-a]pyrazin-5-yl)pyridin-3-yl)-1,2,4-oxadiazol-5-ol (Cpd 28)

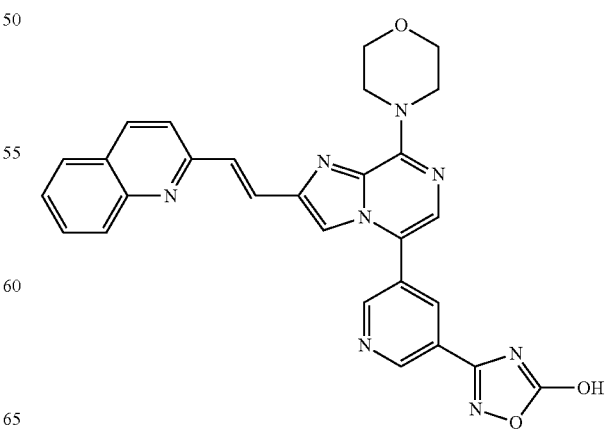

A. (E)-N'-((ethoxycarbonyl)oxy)-5-(8-morpholino-2-((E)-2-(quinolin-2-yl)vinyl)imidazo[1,2-a]pyrazin-5-yl)nicotinimidamide, 77a

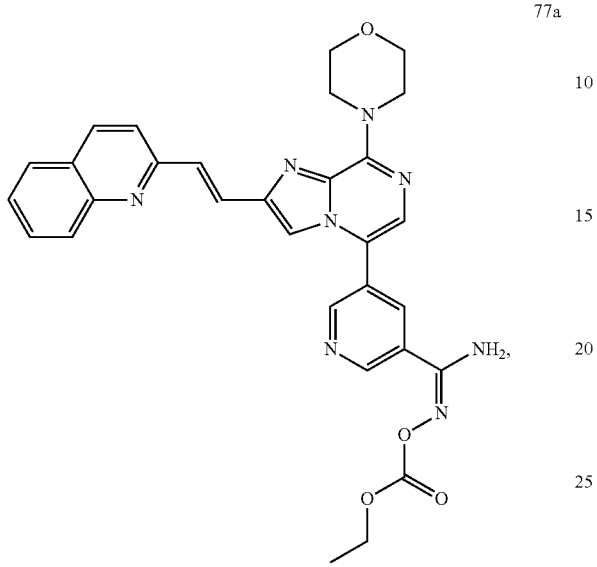

Compound 76a (82.2 mg, 0.179 mmol) was placed in an 8 mL vial equipped with a stir bar, then EtOH (1 mL) was added. NH₂OH (16.4 μL, 0.268 mmol) was added via syringe and the reaction was stirred at 80° C. for 1 h. The reaction was cooled to rt and diluted with water (4 mL). The solid was collected by filtration, and then washed with water (2×4 mL). The solid was dried under reduced pressure. The crude residue was dissolved in THF (25 mL) and then DIEA (125 μL, 0.716 mmol) was added. Ethyl chloroformate (51.2 μL, 0.537 mmol) was added dropwise via syringe and the reaction was stirred at rt for 48 h. The solvent was removed under reduced pressure. The residue was purified by PREP TLC (2×1000μ SiO₂ plates, developed with a mixture of ACN (100 mL), DCM (100 mL) and MeOH (10 mL)) to afford compound 77a. ¹H-NMR (400 MHz, CDCl₃) δ (ppm): 9.00 (d, J=2.0 Hz, 1H), 8.92 (d, J=2.0 Hz, 1H), 8.27 (t, J=2.1 Hz, 1H), 8.13 (d, J=8.6 Hz, 1H), 8.05 (d, J=8.3 Hz, 1H), 7.78 (d, J=8.1 Hz, 1H), 7.65-7.71 (m, 5H), 7.46-7.53 (m, 1H), 7.35 (s, 1H), 5.38 (br. s., 2H), 4.38-4.48 (m, 4H), 4.35 (q, J=7.2 Hz, 2H), 3.87-3.98 (m, 4H), 1.38 (t, J=7.1 Hz, 3H). Mass Spectrum (LCMS, ESI pos.) Calcd. for C₃₀H₂₈N₈O₄: 565.2 (M+H). found: 565.5.

B. (E)-3-(5-(8-Morpholino-2-(2-(quinolin-2-yl)vinyl)imidazo[1,2-a]pyrazin-5-yl)pyridin-3-yl)-1,2,4-oxadiazol-5-ol, Cpd 28

Compound 77a (26.5 mg, 0.469 mmol) was placed in an 8 mL vial equipped with a stir bar. ACN (1 mL) and DBU (0.358 μL, 0.00235 mmol) were added. The reaction was stirred at 100° C. for 18 h and then cooled to rt. The precipitate was collected by filtration and then the solid was washed with ACN (2×5 mL). The residual solvent was removed under reduced pressure to afford the title compound 28. ¹H-NMR (400 MHz, DMSO-d₆) δ (ppm): 9.06 (d, J=2.0 Hz, 1H), 8.85 (d, J=2.0 Hz, 1H), 8.32-8.37 (m, 2H), 8.27 (s, 1H), 7.97 (d, J=8.6 Hz, 1H), 7.94 (d, J=7.6 Hz, 1H), 7.87 (d, J=3.5 Hz, 1H), 7.90 (d, J=4.0 Hz, 1H), 7.75 (t, J=7.1 Hz, 1H), 7.66 (d, J=16.2 Hz, 1H), 7.56 (t, J=7.3 Hz, 1H), 7.52 (s, 1H), 4.29-4.39 (m, 4H), 3.81-3.87 (m, 4H). Mass Spectrum (LCMS, ESI pos.) Calcd. for C₂₈H₂₂N₈O₃: 519.2 (M+H). found: 519.3.

Example 78

4-(8-Morpholino-2-((quinolin-2-ylthio)methyl)imidazo[1,2-a]pyrazin-5-yl)benzoic acid (Cpd 13)

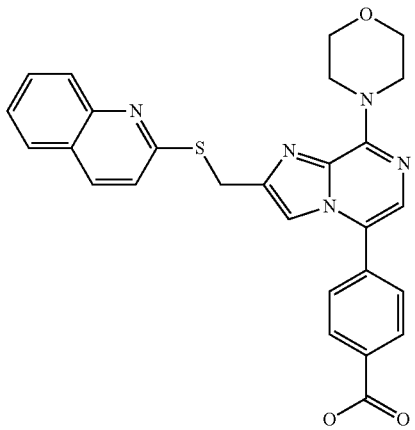 [SMILES: O=C(O)c1ccc(-c2cnc(N3CCOCC3)c3nc(CSc4ccc5ccccc5n4)cn23)cc1]

A. 4-(5-Bromo-2-((quinolin-2-ylthio)methyl)imidazo[1,2-a]pyrazin-8-yl)morpholine, 78a

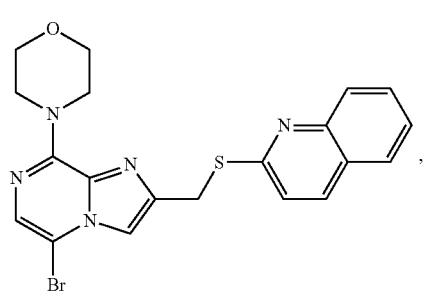

A stirred solution of compound 1e (10 g, 30.45 mmol) and DIPEA (10.23 g, 79.30 mmol) in dichloromethane (200 mL) was cooled in an ice bath and MsCl (7.3 g, 63.48 mmol) was added dropwise. Upon complete addition, the reaction mixture was stirred for 3 h at room temperature and concentrated under reduced pressure. To the residue was added CH₃CN (150 mL), followed by potassium carbonate (6.57 g, 47.6 mmol) and quinoline-2-thiol (5.62 g, 34.9 mmol). The resulting mixture was stirred overnight at 60° C. and allowed to cool to rt. Water (300 mL) was then added. The solids were collected by filtration. The crude product was recrystallized from DCM/ethyl ether (1:2 v/v) to obtain compound 78a as a white solid. Mass Spectrum (LCMS, ESI pos.): Calcd. for $C_{20}H_{18}BrN_5OS$: 457.1 (M+H). found: 457.0

B. tert-Butyl 4-(8-morpholino-2-((quinolin-2-ylthio)methyl)imidazo[1,2-a]pyrazin-5-yl)benzoate, 78b

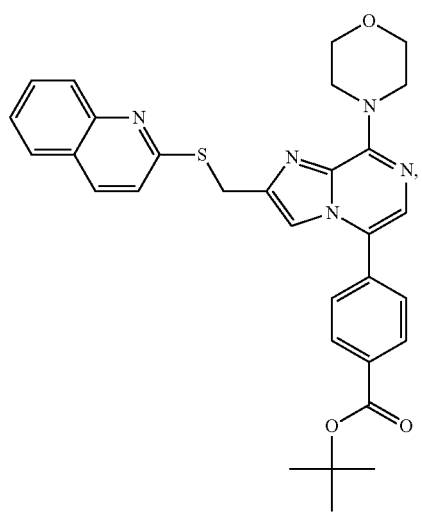

Compound 78a (456 mg, 1.00 mmol), $PdCl_2(dppf)$.DCM (81.7 mg, 0.100 mmol), and 4-tert-butoxycarbonylphenyl boronic acid (444 mg, 2.00 mmol) were placed in an 8 mL vial equipped with a stir bar and evacuated/backflushed with Argon gas. Dry diglyme (8 mL) and 2M $Na_2CO_3$ (4 mL) were added and then the reaction was stirred at 90° C. for 18 h. The organic layer was separated, and the aqueous phase was extracted with DCM (3×30 mL). The organic extracts were combined, dried over $MgSO_4$, and filtered. The solvent was removed under reduced pressure. The crude product was purified by flash column chromatography on silica gel (80-g $SiO_2$ pre-packed column, 0-100% EtOAc/heptanes) to afford compound 78b. $^1$H-NMR (400 MHz, $CDCl_3$) δ (ppm): 7.99 (d, J=8.1 Hz, 2H), 7.87-7.92 (m, 2H), 7.86 (s, 1H), 7.74 (d, J=8.1 Hz, 1H), 7.67 (t, J=7.6 Hz, 1H), 7.41-7.51 (m, 3H), 7.32 (s, 1H), 7.21 (d, J=8.6 Hz, 1H), 4.68 (s, 2H), 4.23-4.34 (m, 4H), 3.82-3.92 (m, 4H), 1.64 (s, 9H). Mass Spectrum (LCMS, ESI pos.) Calcd. for $C_{31}H_{31}N_5O_3S$: 554.2 (M+H). found: 554.5.

C. 4-(8-Morpholino-2-((quinolin-2-ylthio)methyl)imidazo[1,2-a]pyrazin-5-yl)benzoic acid, Cpd 13

Compound 78b (443 mg, 0.800 mmol) was placed in an 8 mL vial equipped with a stir bar and then DCM (4 mL) was added. After the solid had completely dissolved, TFA (2 mL) was added dropwise and the reaction was stirred at rt for 4 h. The solvent was removed under reduced pressure and then the residue was dissolved in MeOH (10 mL). The solvent was removed under reduced pressure. The residue was triturated with $Et_2O$ (15 mL) and then the residual solvent was removed under reduced pressure to afford the title compound 13. $^1$H-NMR (400 MHz, DMSO-$d_6$) δ (ppm): 13.16 (br. s., 1H), 8.17 (d, J=8.6 Hz, 1H), 7.99-8.05 (m, 3H), 7.91 (d, J=7.6 Hz, 1H), 7.86 (d, J=8.6 Hz, 1H), 7.63-7.73 (m, 3H), 7.52 (t, J=6.8 Hz, 1H), 7.46 (s, 1H), 7.42 (d, J=9.1 Hz, 1H), 4.66 (s, 2H), 4.13-4.23 (m, 4H), 3.67-3.76 (m, 4H). Mass Spectrum (LCMS, ESI pos.) Calcd. for $C_{27}H_{23}N_5O_3S$: 498.2 (M+H). found: 498.4.

Example 79

N-(Methylsulfonyl)-4-(8-morpholino-2-((quinolin-2-ylthio)methyl)imidazo[1,2-a]pyrazin-5-yl)benzamide (Cpd 12)

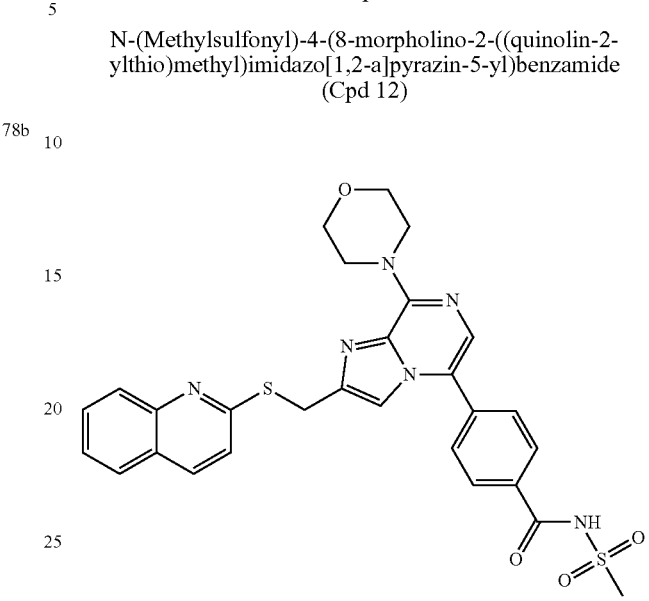

Compound 78b (181 mg, 0.295 mmol) was placed in an 8 mL vial equipped with a stir bar and then dry DMF (1 mL) and DIEA (257 µL, 1.48 mmol) were added. Methanesulfonamide (281 mg, 2.95 mmol) and HATU (168 mg, 0.443 mmol) were sequentially added as solids. The reaction was stirred at rt for 18 h. The mixture was diluted with water (20 mL) and then the precipitate was collected by filtration. The resulting solid was purified by RP HPLC and concentrated. The resultant residue was triturated with MeOH (10 mL) to afford the title compound 12 as a pale yellow solid. $^1$H-NMR (400 MHz, DMSO-$d_6$) δ (ppm): 12.29 (br. s., 1H), 8.17 (d, J=8.6 Hz, 1H), 8.01-8.07 (m, 2H), 7.99 (s, 1H), 7.91 (d, J=8.1 Hz, 1H), 7.85 (d, J=8.1 Hz, 1H), 7.64-7.75 (m, 3H), 7.52 (t, J=7.6 Hz, 1H), 7.46-7.49 (m, 1H), 7.42 (d, J=8.6 Hz, 1H), 4.66 (s, 2H), 4.12-4.25 (m, 4H), 3.67-3.76 (m, J=4.5, 4.5 Hz, 4H), 3.42 (s, 3H). Mass Spectrum (LCMS, ESI pos.) Calcd. for $C_{28}H_{26}N_6O_4S_2$: 575.2 (M+H). found: 575.5.

Example 80

2-(4-(8-Morpholino-2-(quinolin-2-ylethynyl)imidazo[1,2-a]pyrazin-5-yl)-1H-pyrazol-1-yl)acetic acid (Cpd 9)

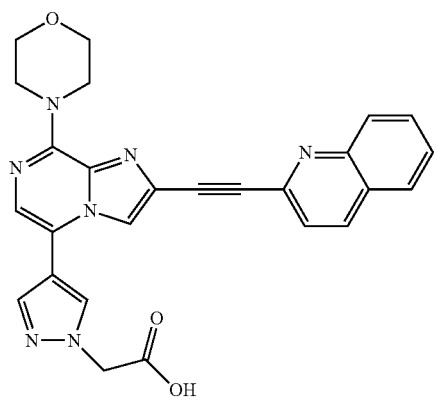 [SMILES: O=C(O)Cn1cc(-c2cnc(N3CCOCC3)c3nc(C#Cc4ccc5ccccc5n4)cn23)cn1]

A. 4-(5-Bromo-2-ethynylimidazo[1,2-a]pyrazin-8-yl)morpholine, 80a

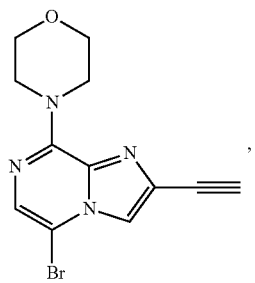

80a

To a stirred suspension of compound 2a (562 mg, 1.80 mmol) in MeOH (10 mL), solid K$_2$CO$_3$ (0.749 g, 5.41 mmol) was added followed by dimethyl(1-diazo-2-oxopropyl)phosphonate (382 mg, 1.98 mmol) in MeOH (5 mL). The reaction was stirred at rt for 12 h and concentrated. The residue was dissolved in DCM (40 mL) and washed with water (25 mL). The aqueous layer was extracted with DCM (3×20 mL). The combined organic extracts were washed with brine (25 mL), dried over Na$_2$SO$_4$, filtered and concentrated under reduced pressure. The residue was triturated with 1:1 EtOAc/heptane, filtered and dried to give compound 80a as an off-white solid. Mass Spectrum (LCMS, ESI pos.): Calcd. for C$_{12}$H$_{11}$BrN$_4$O: 307.0 (M+H). found: 307.1.

B. 4-(5-Bromo-2-(quinolin-2-ylethynyl)imidazo[1,2-a]pyrazin-8-yl)morpholine 80b

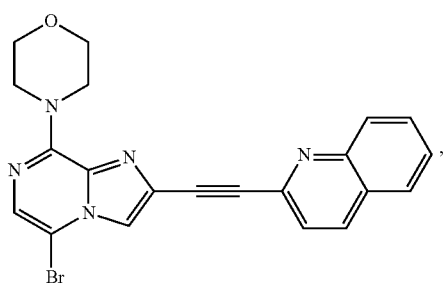

80b

To a stirred solution of compound 80a (200 mg, 0.7 mmol) and 2-bromoquinoline (0.800 mg, 4 mmol) in dry DMF (5 mL) and DIEA (0.7 mL, 4 mmol) under an Argon gas atmosphere, CuI (12 mg, 0.06 mmol) and (Ph$_3$P)$_2$PdCl$_2$ (46 mg, 0.06 mmol) were added. The reaction was stirred at rt overnight, poured into water (50 mL) and extracted with DCM (3×30 mL). The combined organic extracts were washed with water (20 mL), brine (2×20 mL), dried over Na$_2$SO$_4$, filtered and concentrated under reduced pressure. The residue was purified by flash column chromatography on silica gel (0-50% EtOAc/heptanes) to give compound 80b as an off-white solid. Mass Spectrum (LCMS, ESI pos.): Calcd. for C$_{21}$H$_{16}$BrN$_5$O: 434.0 (M+H). found: 434.2.

C. Ethyl 2-(4-(8-morpholino-2-(quinolin-2-ylethynyl)imidazo[1,2-a]pyrazin-5-yl)-1H-pyrazol-1-yl)acetate, 80c

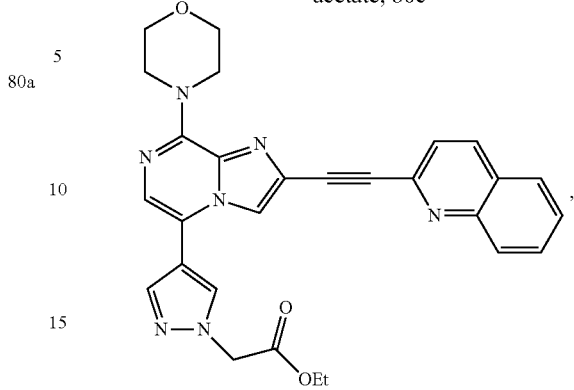

80c

A mixture of compound 80b (100 mg, 0.230 mmol), 4-(4,4,5,5-tetramethyl-1,3,2-dioxaborolan-2-yl)-1H-Pyrazole-1-acetic acid ethyl ester (129 mg, 0.460 mmol), dichloro(1,1'-bis(diphenylphosphino)ferrocene)palladium(II) dichloromethane adduct (17.0 mg, 0.0230 mmol), and 1M sodium carbonate (1.15 mL, 1.15 mmol) in dioxane (4 mL) under and Argon gas atmosphere was heated to 80° C. for 1 h. After cooling, the reaction mixture was filtered through a pad of diatomaceous earth and concentrated under reduced pressure. The resulting residue was purified by preparative TLC (EtOAc/CH$_2$Cl$_2$; 7:3, v/v) to give compound 80c. Mass Spectrum (LCMS, ESI pos.): Calcd. for C$_{28}$H$_{25}$N$_7$O$_3$: 508.2 (M+H). found: 508.5.

D. 2-(4-(8-Morpholino-2-(quinolin-2-ylethynyl)imidazo[1,2-a]pyrazin-5-yl)-1H-pyrazol-1-yl)acetic acid, Cpd 9

To a solution of compound 80c (43.4 mg, 0.0860 mmol) in THF (2 mL) and EtOH (2 mL) was added 1N NaOH (1.00 mL, 1.00 mmol) and the resulting mixture was stirred at rt for 3.5 h. The solvents were removed under reduced pressure. The residue obtained was treated with EtOAc (20 mL) and water (20 mL). The resulting mixture was neutralized with 2N hydrochloric acid. The EtOAc layer was separated and the aqueous layer was extracted with EtOAc (20 mL). The combined organic layers were dried over Na$_2$SO$_4$, filtered, and concentrated under reduced pressure to yield the title compound 9. $^1$H-NMR (DMSO-d$_6$) δ (ppm): 13.24 (br s, 1H), 8.49 (m, 3H), 8.05 (m, 3H), 7.86 (t, J=7.6 Hz, 1H), 7.79 (d, J=8.4 Hz, 1H), 7.74-7.61 (m, 2H), 5.08 (s, 2H), 4.22 (m, 4H), 3.82 (m, 4H). Mass Spectrum (LCMS, ESI pos.) Calcd. For C$_{26}$H$_{21}$N$_7$O$_3$ (M+H) 480.2. Found 480.4.

Example 81
4-(2-(Benzo[d]thiazol-2-ylethynyl)-8-morpholinoimidazo[1,2-a]pyrazin-5-yl)benzoic acid (Cpd 11)

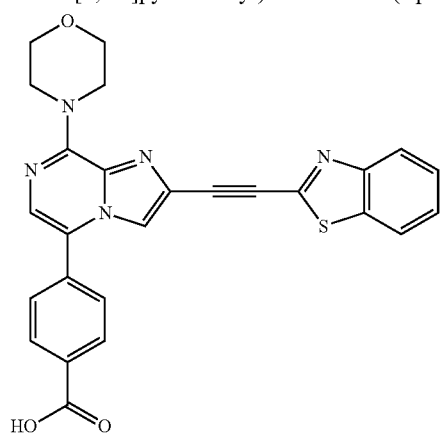

A. tert-Butyl 4-(2-formyl-8-morpholinoimidazo[1,2-a]pyrazin-5-yl)benzoate, 81a

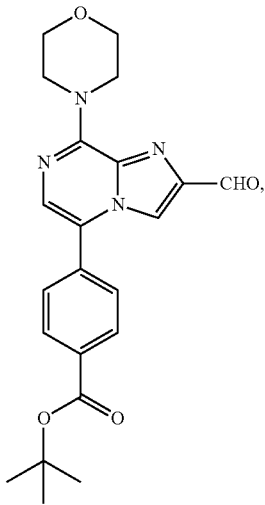

A mixture of compound 2a (100.0 mg, 0.320 mmol), 4-(tert-butoxycarbonyl)benzeneboronic acid pinacol ester (117 mg, 0.390 mmol), dichloro(1,1'-bis(diphenylphosphino)ferrocene)palladium(II) dichloromethane adduct (24.0 mg, 0.0320 mmol), and 1M sodium carbonate (1.61 mL, 1.61 mmol) in dioxane (6 mL) was purged with Argon gas. The resulting mixture was heated to 80° C. for 18 h. After the mixture was cooled, it was filtered through a pad of diatomaceous earth. The filtrate was concentrated under reduced pressure and the resulting residue was purified by Preparative TLC (EtOAc/CH$_2$Cl$_2$; 2:3, v/v) to give compound 81a. Mass Spectrum (LCMS, ESI pos.): Calcd. for C$_{22}$H$_{25}$N$_4$O$_4$: 409.2 (M+H). found: 409.3.

B. tert-Butyl 4-(2-ethynyl-8-morpholinoimidazo[1,2-a]pyrazin-5-yl)benzoate, 81b

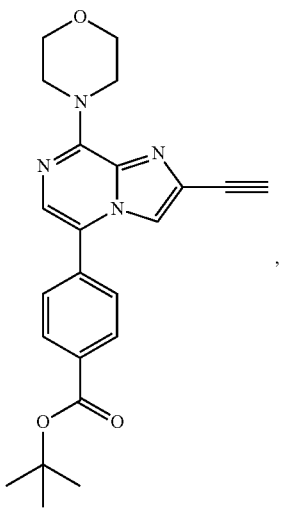

To a suspension of compound 81a (239 mg, 0.580 mmol) in anhydrous THF (8 mL) and anhydrous MeOH (3 mL), dimethyl (1-diazo-2-oxopropyl)phosphonate (164 mg, 0.850 mmol) in MeOH (2 mL) was added followed by potassium carbonate (252 mg, 1.82 mmol). The resulting yellow suspension was stirred at rt for 18 h. The mixture was filtered through a pad of diatomaceous earth. The filter cake was washed CH$_2$Cl$_2$. The combined filtrates were concentrated under reduced pressure. The residue was dissolved in DCM and washed with diluted NaHCO$_3$, brine, dried over Na$_2$SO$_4$, filtered, and concentrated under reduced pressure. The residue was purified on preparative TLC (EtOAc/CH$_2$Cl$_2$; 2:3, v/v) to afford compound 81b. Mass Spectrum (LCMS, ESI pos.): Calcd. for C$_{23}$H$_{25}$N$_4$O$_3$: 405.2 (M+H). found: 405.4.

C. tert-Butyl 4-(2-(benzo[d]thiazol-2-ylethynyl)-8-morpholinoimidazo[1,2-a]pyrazin-5-yl)benzoate, 81c

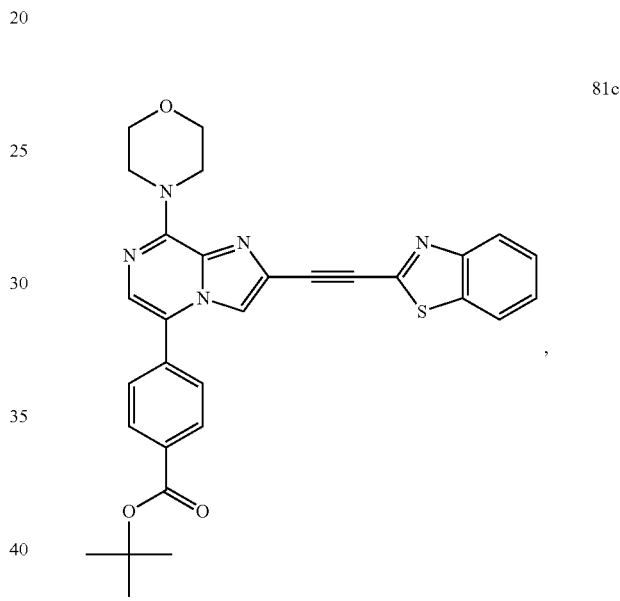

Compound 81b (95.0 mg, 0.230 mmol) and 2-bromothiazole (430 mg, 2.00 mmol) were placed in a vial and purged with Argon. Anhydrous DMF (2 mL) and DIEA (0.410 mL, 2.35 mmol) were added. The mixture was degassed and purged with Argon. CuI (2.24 mg, 0.0120 mmol) and dichloro(1,1'-bis(diphenylphosphino)ferrocene)palladium(II) dichloromethane adduct (16.5 mg, 0.0230 mmol) were added. The reaction was stirred at rt for 4 h. The reaction was filtered through a pad of diatomaceous earth and the filter cake was rinsed with EtOAc. The combined filtrates were washed with brine and water, dried, and concentrated. The residue was purified with preparative TLC (EtOAc/dichloromethane; 3:7) to obtain compound 81c. Mass Spectrum (LCMS, ESI pos.): Calcd. for C$_{30}$H$_{28}$N$_5$O$_3$S: 538.2 (M+H). found: 538.5.

D. 4-(2-(Benzo[d]thiazol-2-ylethynyl)-8-morpholinoimidazo[1,2-a]pyrazin-5-yl)benzoic acid, Cpd 11

To a solution of compound 81c (49 mg, 0.09 mmol) in dichloromethane (4 mL), TFA (1 mL, 13 mmol) was added. The mixture was stirred at rt for 18 h and concentrated under reduced pressure. The oil obtained was dissolved in dichloromethane and water was added. The resultant precipitate was collected by filtration to afford the title compound 11.

$^1$H-NMR (400 MHz, DMSO-d$_6$) δ (ppm): 13.18 (s, 1H), 8.60 (s, 1H), 8.20 (d, J=8.2 Hz, 1H), 8.13-8.11 (m, 3H), 7.85 (d, J=8.3 Hz, 2H), 7.66-7.57 (m, 3H), 4.29 (m, 4H), 3.82 (m, 4H). Mass Spectrum (LCMS, ESI pos.) Calcd. For C$_{26}$H$_{20}$N$_5$O$_3$S: (M+H) 482.1. Found 482.4.

Following the procedures described in Example 81 above, and substituting suitably selected and substituted reagents, starting materials and conditions as would be readily apparent to those skilled in the art, the following representative compound of the present invention was prepared.

| Cpd | Characterization |
|---|---|
| 10 | 4-(8-Morpholino-2-(pyridin-2-ylethynyl)imidazo[1,2-a]pyrazin-5-yl)benzoic acid<br>$^1$H-NMR (400 MHz, DMSO-d$_6$) δ (ppm): 13.17 (br s, 1H), 8.64 (d, J = 5.0 Hz, 1H), 8.39 (s, 1H), 8.11 (d, J = 8.3 Hz, 2H), 7.89 (td, J = 7.7, 1.7 Hz, 1H), 7.85 (d, J = 8.3 Hz, 2H), 7.69 (d, J = 7.9 Hz, 1H), 7.59 (s, 1H), 7.46 (ddd, J = 7.6, 5.0, 0.9 Hz, 1H), 4.28 (m, 4H), 3.81 (m, 4H).<br>Mass Spectrum (LCMS, ESI pos.) Calcd. For C$_{24}$H$_{20}$N$_5$O$_3$: (M + H) 426.2, Found 426.4. |

Example 82

4-(4-(8-Morpholino-2-(2-(quinolin-2-yl)ethyl)imidazo[1,2-a]pyrazin-5-yl)phenyl)-1H-1,2,4-triazol-5(4H)-one (Cpd 65)

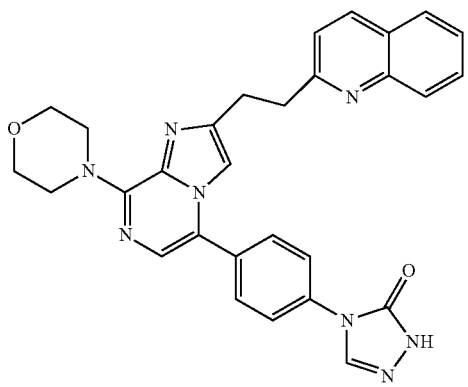 [SMILES: O=c1[nH]ncn1-c1ccc(-c2cnc(N3CCOCC3)c3nc(CCc4ccc5ccccc5n4)cn23)cc1]

A. 4-(4-Bromophenyl)-4H-1,2,4-triazol-3-ol, 82a

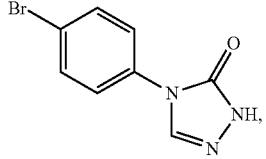

A mixture of methyl carbazate (1.40 g, 15.3 mmol), triethyl orthoformate (2.26 g, 15.3 mmol), and p-toluenesulfonic acid monohydrate (82.9 mg, 0.436 mmol) in methanol (30 mL) was stirred at 60° C. under an Argon atmosphere for 3 h. NaOMe (1.26 g, 23.3 mmol) was added and the mixture was stirred at 60° C. for 4.5 h. After cooling to room temperature, the mixture was concentrated under reduced pressure to a red solid. Water (30 mL) was added and the stirred mixture was adjusted to pH 1 with 1M HCl. The purple suspension was filtered, and the solid was washed with water (3×10 mL) and dried under suction and high vacuum to afford compound 82a as a grayish white powder, which was used in the following reaction without further purification (purity 85% by LCMS). Mass spectrum (LCMS, ESI pos.): Calcd. for C$_8$H$_6$BrN$_3$O, 240.0/242.0 (M+H). found 240.1/242.2.

B. 4-(4-Bromophenyl)-1-((2-(trimethylsilyl)ethoxy)methyl)-1H-1,2,4-triazol-5(4H)-one, 82b

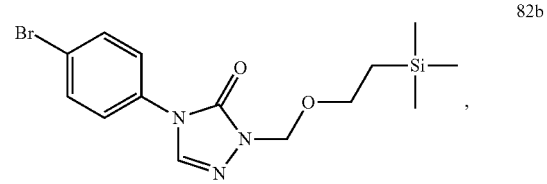 [SMILES: C[Si](C)(C)CCOCn1ncn(-c2ccc(Br)cc2)c1=O]

To dry NaH (360 mg, 15.0 mmol) under an Argon atmosphere was added dropwise a solution of compound 82a (1.92 g, 6.80 mmol; based on 85% purity) in anhydrous DMF (20 mL). After stirring at room temperature for 1 h, the mixture was cooled to 0° C. and 2-(trimethylsilyl)ethoxymethyl chloride (3.07 mL, 17.0 mmol) was added dropwise over 2 min. The mixture was stirred at room temperature for 1.5 h. The mixture was quenched carefully with 1 mL of saturated aqueous NH$_4$Cl and poured into water (150 mL). After saturating the aqueous mixture with solid NaCl, the mixture was extracted with EtOAc (3×25 mL). The combined extracts were washed with brine (50 mL), dried over Na$_2$SO$_4$, filtered, and concentrated under reduced pressure to give a pale brown solid which was purified by flash column chromatography on silica gel (0-40% EtOAc-heptane) to afford compound 82b as a white solid. Mass spectrum (LCMS, ESI pos.): Calcd. for C$_{14}$H$_{20}$BrN$_3$O$_2$Si, 392.1/3.94.1 (M+Na). found 392.2/3.94.1.

C. 4-(4-(4,4,5,5-Tetramethyl-1,3,2-dioxaborolan-2-yl)phenyl)-1-((2-(trimethylsilyl)ethoxy)methyl)-1H-1,2,4-triazol-5(4H)-one, 82c

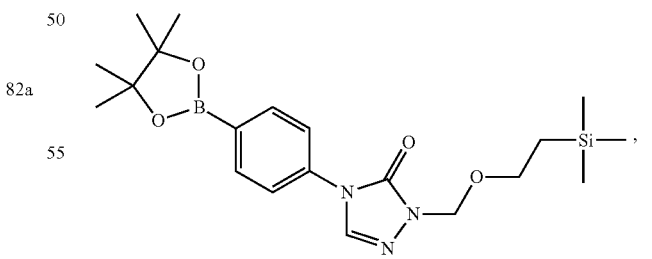

Under an Argon atmosphere, a mixture of compound 82b (1.00 g, 2.70 mmol), bis(pinacolato)diboron (840 mg, 3.24 mmol), KOAc (795 mg, 8.10 mmol), and PdCl$_2$(dppf)-DCM (78.0 mg, 0.09 mmol) in Argon-degassed DMSO (10 mL) was stirred at 90° C. for 12 h. After cooling to room temperature, the reaction mixture was diluted with water (100 mL) and extracted with EtOAc (3×25 mL). The combined extracts were washed with water (25 mL) and brine (25 mL), dried over Na₂SO₄, filtered, and concentrated under reduced pressure to give a dark purple solid which was purified by flash column chromatography on silica gel (0-100% EtOAc-DCM) to afford compound 82c as a white solid. Mass spectrum (LCMS, ESI pos.): Calcd. for C₂₀H₃₂BN₃O₄Si, 440.2 (M+Na). found 440.4.

D. 4-(4-(8-Morpholino-2-(2-(quinolin-2-yl)ethyl) imidazo[1,2-a]pyrazin-5-yl)phenyl)-1-((2-(trimethyl-silyl)ethoxy)methyl)-1H-1,2,4-triazol-5(4H)-one, 82d

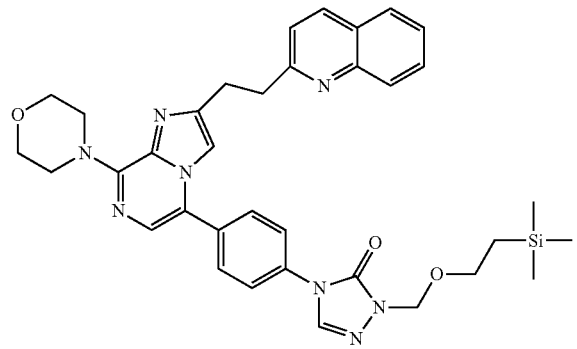

82d

A mixture of compound 3a (108 mg, 0.246 mmol), compound 82c (206 mg, 0.246 mmol), PdCl₂(dppf)-DCM (6.0 mg, 0.0074 mmol), and Argon-degassed aqueous 2M Na₂CO₃ (0.616 mL, 1.23 mmol) in Argon-degassed 1,4-dioxane (4 mL) was further degassed with Argon for 3 min and then stirred at 90° C. for 5 h. After cooling to room temperature, the reaction mixture was concentrated under reduced pressure to a brown residue, which was purified by flash column chromatography on silica gel (40-100% EtOAc-DCM, followed by 100% EtOAc) to afford compound 82d as a hard white foam. Mass spectrum (LCMS, ESI pos.): Calcd. for C₃₅H₄₀N₈O₃Si, 649.3 (M+H). found 649.6.

E. 4-(4-(8-Morpholino-2-(2-(quinolin-2-yl)ethyl) imidazo[1,2-a]pyrazin-5-yl)phenyl)-1H-1,2,4-triazol-5(4H)-one, Cpd 65

Compound 82d (108 mg, 0.246 mmol) was treated with 5 mL of DCM-TFA-water (30:10:1) and stirred at room temperature for 1 h. EtOH (1 mL) was added and the mixture was concentrated to a pale yellow resin. The resulting material in DCM (10 mL) was treated with solid NaHCO₃ (2 g), stirred 20 min, filtered, and concentrated to give a white solid which was purified by flash column chromatography on silica gel (0-25% MeOH-EtOAc) to afford a white solid. A portion (68.1 mg) of this material in MeOH (70 mL) and CHCl₃ (20 mL) was treated with DIEA (229 µL, 1.32 mmol), refluxed for 2.5 h, and then concentrated to give a white solid which was purified by flash column chromatography on silica gel (0-25% MeOH-EtOAc) to afford the title compound 65 as a white solid. ¹H-NMR (CDCl₃-MeOH (3:1), 400 MHz): δ 8.15 (d, J=8.6 Hz, 1H), 8.02 (d, J=8.6 Hz, 1H), 7.92 (s, 1H), 7.84 (d, J=8.3 Hz, 1H), 7.73 (ddd, J=8.4, 7.0, 1.5 Hz, 1H), 7.67-7.70 (m, 2H), 7.58-7.63 (m, 2H), 7.52-7.58 (m, 1H), 7.36-7.40 (m, 2H), 7.29 (s, 1H), 4.12-4.17 (m, 4H), 3.81-3.86 (m, 4H), 3.38-3.44 (m, 2H), 3.27-3.33 ppm (m, 2H). Mass spectrum (LCMS, ESI pos.): Calcd. for C₂₉H₂₆N₈O₂, 519.2 (M+H). found 519.0.

Example 83

(E)-4-(4-(8-morpholino-2-(2-(quinolin-2-yl)vinyl) imidazo[1,2-a]pyrazin-5-yl)phenyl)-1H-1,2,4-triazol-5(4H)-one (Cpd 58)

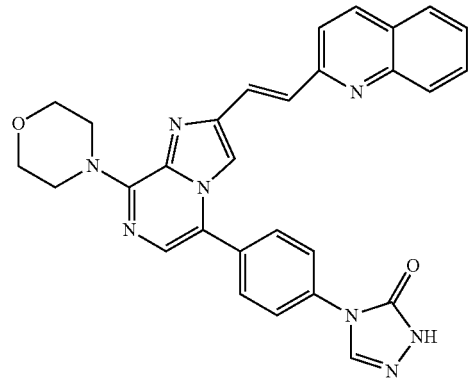 [SMILES: O=c1[nH]ncn1-c1ccc(-c2cnc(N3CCOCC3)c3nc(/C=C/c4ccc5ccccc5n4)cn23)cc1]

A. (E)-4-(4-(8-morpholino-2-(2-(quinolin-2-yl)vinyl) imidazo[1,2-a]pyrazin-5-yl)phenyl)-1-((2-(trimethyl-silyl)ethoxy)methyl)-1H-1,2,4-triazol-5(4H)-one, 83a

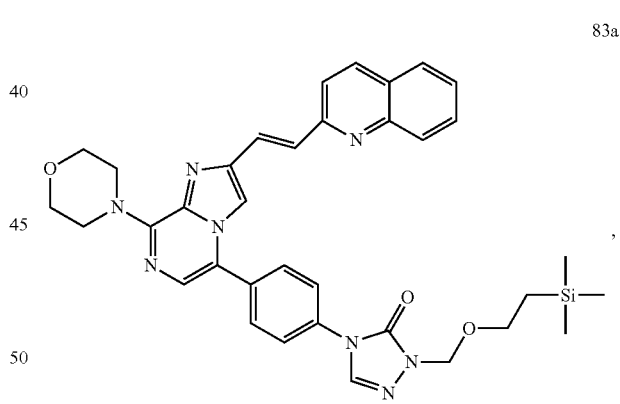

83a

A mixture of compound 2b (100 mg, 0.229 mmol), compound 82c (115 mg, 0.275 mmol), PdCl₂(dppf)-DCM (5.6 mg, 0.0069 mmol), and Argon-degassed aqueous 2M Na₂CO₃ (0.573 mL, 1.15 mmol) in Argon-degassed 1,4-dioxane (4 mL) was further degassed with Argon for 3 min and then stirred at 90° C. for 5 h. After cooling to room temperature, the reaction mixture was concentrated under reduced pressure to a brown oil which was purified by flash column chromatography on silica gel (20-100% EtOAc-DCM), followed by a second purification by flash column chromography for mixed fractions (0-80% EtOAc-DCM), to afford compound 83a as a pale yellow solid. Mass spectrum (LCMS, ESI pos.): Calcd. for C₃₅H₃₈N₈O₃Si, 647.3 (M+H). found 647.7.

B. (E)-4-(4-(8-morpholino-2-(2-(quinolin-2-yl)vinyl)imidazo[1,2-a]pyrazin-5-yl)phenyl)-1-((2-(trimethylsilyl)ethoxy)methyl)-1H-1,2,4-triazol-5(4H)-one, Cpd 58

Compound 83a (70.3 mg, 0.109 mmol) was treated with 5 mL of DCM-TFA-water (30:10:1) and stirred at rt for 1 h. EtOH (1 mL) was added and the mixture was concentrated. The resultant residue was treated with MeOH (70 mL) and CHCl$_3$ (25 mL) and DIEA (189 µL, 1.09 mmol), and the resulting mixture was refluxed for 2.5 h. The mixture was then concentrated to obtain an orange solid which was washed with CHCl$_3$, EtOAc, and MeOH (ca. 3 mL each) and dried under reduced pressure to afford the title compound 58 as a light yellow solid. $^1$H-NMR (DMSO-d$_6$, 400 MHz): δ (ppm): 11.7-12.8 (v br s, 1H), 8.52 (s, 1H), 8.35 (d, J=8.6 Hz, 1H), 8.24 (s, 1H), 7.92-8.02 (m, 4H), 7.82-7.92 (m, 4H), 7.75 (t, J=7.6 Hz, 1H), 7.65 (d, J=16.1 Hz, 1H), 7.53-7.61 (m, 1H), 7.46 (s, 1H), 4.25-4.38 (m, 4H), 3.79-3.91 (m, 4H). Mass spectrum (LCMS, ESI pos.): Calcd. for C$_{29}$H$_{24}$N$_8$O$_2$, 517.2 (M+H). found 517.5.

Example 84

1-(4-(8-Morpholino-2-(2-(quinolin-2-yl)ethyl)imidazo[1,2-a]pyrazin-5-yl)phenyl)-1H-1,2,4-triazol-5(4H)-one (Cpd 21)

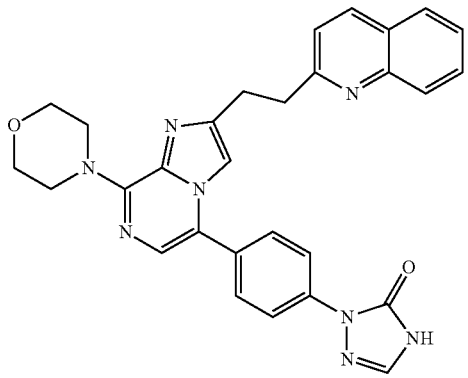 [SMILES: O=c1[nH]cnn1-c1ccc(-c2cnc(N3CCOCC3)c3nc(CCc4ccc5ccccc5n4)cn23)cc1]

A. ((E)-2-(2-(4-Bromophenyl)hydrazono)acetic acid, 84a

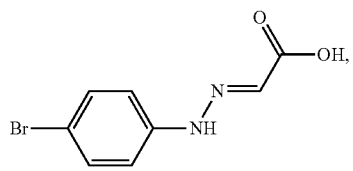

To a stirred suspension of (4-bromophenyl)hydrazine HCl (2.01 g, 8.81 mmol) in water (20 mL) was added conc. HCl (1 mL) followed by glyoxylic acid monohydrate (811 mg, 8.81 mmol). The mixture was stirred vigorously at rt for 30 min and the light yellow suspension was filtered, washed with water (3×15 mL), and dried under suction followed by high vacuum to afford compound 84a as a light yellow solid, used without further purification in the following step. Mass spectrum (LCMS, ESI pos.): Calcd. for C$_8$H$_7$BrN$_2$O$_2$, 243.0/245.0 (M+H). found 243.2/245.1.

B. 1-(4-Bromophenyl)-1H-1,2,4-triazol-5(4H)-one, 84b

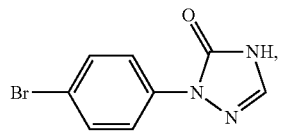

To a stirred suspension of compound 84a (1.14 g, 4.69 mmol) in toluene (25 mL) was added Et$_3$N (0.913 mL, 6.57 mmol) and (PhO)$_2$PON$_3$ (1.012 g, 4.69 mmol) and the mixture was heated slowly over 20 min to reflux. Gas evolution began at 75° C. and became more vigorous at 100° C. After 1 h at reflux, an additional portion of (PhO)$_2$PON$_3$ (0.304 mL, 1.41 mmol) was added and the reaction was refluxed for an additional 30 min. The mixture was cooled to rt and extracted with 1M NaOH (3×75 mL). The combined aqueous extracts were washed with Et$_2$O (2×25 mL) and adjusted to pH 1 with 3M HCl. The resultant precipitate was collected by filtration, washed with water (3×20 mL), and dried under suction and then high vacuum to afford a beige solid which was recrystallized from EtOAc-heptanes to afford compound 84b as a granular light yellow solid. Mass spectrum (LCMS, ESI pos.): Calcd. for C$_8$H$_6$BrN$_3$O, 240.0/242.0 (M+H). found 240.1/242.1

C. 1-(4-Bromophenyl)-4-((2-(trimethylsilyl)ethoxy)methyl)-1H-1,2,4-triazol-5(4H)-one, 84c

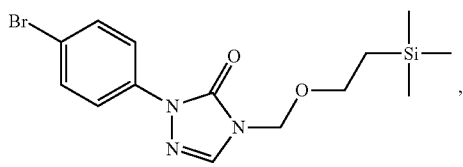

To dry NaH (67.8 mg, 2.83 mmol) under an Argon atmosphere was added a solution of compound 84b (532 mg, 1.88 mmol) in anhydrous DMF (5 mL) slowly over 2 min. The mixture was stirred at rt for 1 h and then cooled to 0° C. 2-(Trimethylsilyl)ethoxymethyl chloride (0.612 mL, 3.391 mmol) was added dropwise over 2 min. After stirring at rt for 1 h, the mixture was quenched carefully with 1 mL of saturated aqueous NH$_4$Cl and poured into brine (75 mL). The mixture was extracted with EtOAc (3×25 mL) and the combined extracts were washed with water (2×25 mL) and brine (25 mL), dried over Na$_2$SO$_4$, filtered, and concentrated under reduced pressure to give a faintly yellow crystalline solid. The solid was purified by flash column chromatography on silica gel (0-40% EtOAc-heptane) to give compound 84c as a white solid. Mass spectrum (LCMS, ESI pos.): Calcd. for C$_{14}$H$_{20}$BrN$_3$O$_2$Si, 392.1/394.1 (M+Na). found 392.2/394.1.

D. 1-(4-(4,4,5,5-Tetramethyl-1,3,2-dioxaborolan-2-yl)phenyl)-4-((2-(trimethylsilyl)ethoxy)methyl)-1H-1,2,4-triazol-5(4H)-one, 84d

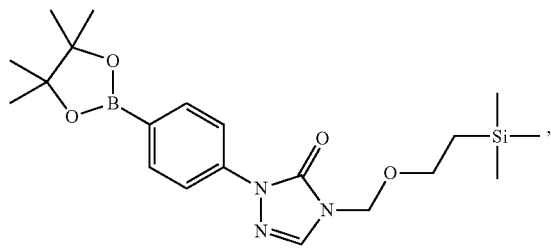

84d

A mixture of compound 84c (702 mg, 1.90 mmol), KOAc (558 mg, 5.69 mmol), bis(pinacolato)diboron (589 mg, 2.28 mmol), and PdCl$_2$(dppf)-DCM (54.8 mg, 0.0663 mmol) in Argon-degassed DMSO (7 mL) was stirred at 90° C. under an Argon atmosphere for 12 h. After cooling to rt, the reaction mixture was diluted with water (100 mL) and extracted with EtOAc (3×25 mL). The combined extracts were washed with water (25 mL) and brine (25 mL), dried over Na$_2$SO$_4$, filtered, and concentrated to give a dark purple solid, which was purified by flash column chromatography on silica gel (0-60% EtOAc-heptane) to afford compound 84d as a white solid. Mass spectrum (LCMS, ESI pos.): Calcd. For C$_{20}$H$_{32}$BN$_3$O$_4$Si, 440.2 (M+Na). found 440.4.

E. 1-(4-(8-Morpholino-2-(2-(quinolin-2-yl)ethyl) imidazo[1,2-a]pyrazin-5-yl)phenyl)-4-((2-(trimethylsilyl)ethoxy)methyl)-1H-1,2,4-triazol-5(4H)-one, 84e

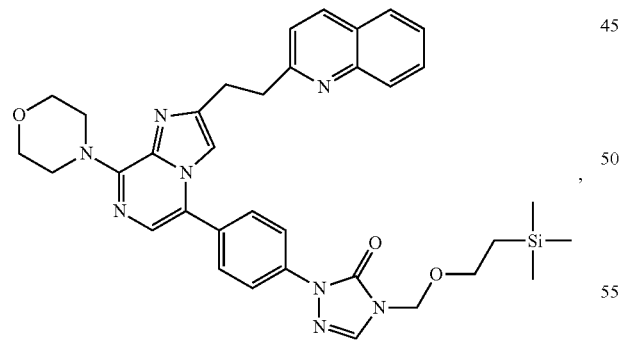

84e

A mixture of compound 3a (102 mg, 0.233 mmol), compound 84d (97.1 mg, 0.233 mmol, PdCl$_2$(dppf)-DCM (5.7 mg, 0.0070 mmol), and Ar-degassed aqueous 2M Na$_2$CO$_3$ (0.582 mL, 1.16 mmol) in Argon-degassed 1,4-dioxane (4 mL) was further degassed with Argon for 3 min and then stirred at 90° C. for 5 h. After cooling to rt, the reaction mixture was concentrated under reduced pressure to a brown oil which was purified by flash column chromatography on silica gel (40-100% EtOAc-DCM, followed by 100% EtOAc)

to afford compound 84e as a crystalline white solid. Mass spectrum (LCMS, ESI pos.): Calcd. for C$_{35}$H$_{40}$N$_8$O$_3$Si, 649.3 (M+H). found 649.6.

F. 1-(4-(8-Morpholino-2-(2-(quinolin-2-yl)ethyl) imidazo[1,2-a]pyrazin-5-yl)phenyl)-1H-1,2,4-triazol-5(4H)-one, Cpd 21

Compound 84e (89.8 mg, 0.138 mmol) was treated with 5 mL of DCM-TFA-water (30:10:1) and stirred at rt for 14 h. EtOH (1 mL) was added and the mixture was concentrated to a yellow resin (112 mg). The resulting material was taken up in MeOH (20 mL) and CHCl$_3$ (10 mL), treated with DIEA (241 µL, 1.38 mmol), refluxed for 2 h, and then concentrated to give a beige solid. The solid was then purified by flash column chromatography on silica gel (100% EtOAc, followed by 0-30% MeOH-EtOAc) to afford a beige solid that was washed with MeOH (1.5 mL) and dried to give compound 21 as an off-white solid. $^1$H-NMR (CDCl$_3$—CD$_3$OD (1:1), 400 MHz): δ 8.19 (d, J=8.6 Hz, 1H), 8.05 (d, J=8.6 Hz, 2H), 8.00 (d, J=8.1 Hz, 1H), 7.87 (d, J=9.1 Hz, 1H), 7.81 (s, 1H), 7.72-7.77 (m, 1H), 7.54-7.59 (m, 1H), 7.52 (d, J=9.1 Hz, 2H), 7.38-7.42 (m, 2H), 7.28 (s, 1H), 4.06-4.10 (m, 4H), 3.81-3.85 (m, 4H), 3.38-3.44 (m, 2H), 3.29-3.33 (m, 2H); Mass spectrum (LCMS, ESI pos.): Calcd. for C$_{29}$H$_{26}$N$_8$O$_2$, 519.2 (M+H). found 519.4.

Example 85

4-(5-(4-(2-(2-Methoxyethoxy)ethoxy)phenyl)-2-(2-(quinolin-2-yl)ethyl)imidazo[1,2-a]pyrazin-8-yl) morpholine (Cpd 31)

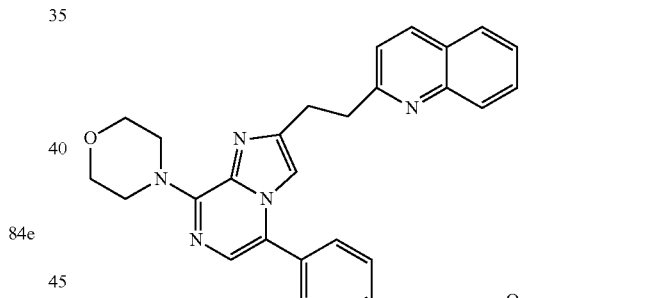

A. 1-Bromo-4-(2-(2-methoxyethoxy)ethoxy)benzene, 85a

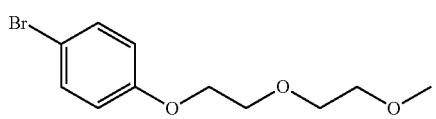

85a

To a cooled (0° C.) suspension of dry NaH (0.512 g, 21.4 mmol) in anhydrous DMF (10 mL) under an Argon atmosphere, a solution of 4-bromophenol (3.11 g, 17.8 mmol) in anhydrous DMF (20 mL) was added dropwise over 2-3 min. The mixture was stirred at 0° C. for 10 min and then allowed to warm to rt over 30 min. To the resulting white suspension was added 1-bromo-2-(2-methoxyethoxy)ethane (2.66 mL, 19.6 mmol) dropwise over 2 min and the mixture was stirred at rt for 30 min and then at 65° C. for 1.5 h. After cooling to rt, the mixture was concentrated under reduced pressure to an oily suspension, diluted with brine (80 mL), and the mixture was extracted with EtOAc (3×60 mL). The combined extracts were washed with brine (2×25 mL), dried over $Na_2SO_4$, filtered, and concentrated to give compound 85a as a mobile, pale amber-colored oil, used in the following reaction without further purification. Mass spectrum (LCMS, ESI pos.): Calcd. for $C_{11}H_{15}BrO_3$, 275.0/277.0 (M+H). found 275.2/277.1

B. 2-(4-(2-(2-Methoxyethoxy)ethoxy)phenyl)-4,4,5,5-tetramethyl-1,3,2-dioxaborolane, 85b

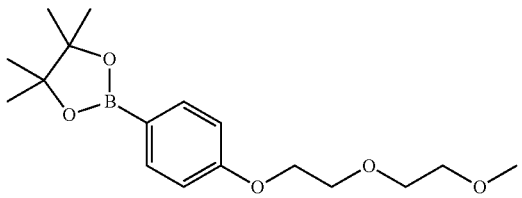
85b

A mixture of compound 85a (2.00 g, 8.00 mmol), bis(pinacolato)diboron (2.49 g, 9.60 mmol), KOAc (2.35 g, 24.0 mmol), and $PdCl_2$(dppf)-DCM (0.231 g, 0.280 mmol) in Argon-degassed DMSO (20 mL) was stirred at 90° C. under an Argon atmosphere for 16 h. After cooling to rt, the reaction mixture was diluted with brine (200 mL) and extracted with EtOAc (3×50 mL). The combined extracts were washed with brine (3×50 mL), dried over $Na_2SO_4$, filtered, and concentrated to give a dark brown oil which was purified by flash column chromatography on silica gel (25-100% EtOAc-heptane) to afford compound 85b as a colorless oil. Mass spectrum (LCMS, ESI pos.): Calcd. for $C_{17}H_{27}BO_5$, 345.2 (M+Na). found 345.2.

C. 4-(5-(4-(2-(2-methoxyethoxy)ethoxy)phenyl)-2-(2-(quinolin-2-yl)ethyl)imidazo[1,2-a]pyrazin-8-yl)morpholine, Cpd 31

A mixture of compound 3a (100 mg, 0.228 mmol), compound 85b (88.2 mg, 0.274 mmol), $PdCl_2$(dppf)-DCM (5.6 mg, 0.0068 mmol), and Argon-degassed aqueous 2M $Na_2CO_3$ (0.570 mL, 1.14 mmol) in Argon-degassed 1,4-dioxane (4 mL) was further degassed with Argon for 2 min and then stirred at 90° C. for 5 h. After cooling to room temperature, the reaction mixture was concentrated under reduced pressure to a brown oil which was purified by flash column chromatography on silica gel (0-100% EtOAc-heptane, followed by 100% EtOAc) to afford a colorless resin. The residue obtained was further purified by flash column chromatography (100% EtOAc, followed by 0-10% MeOH-EtOAc) to afford a colorless oil, which was triturated with EtOAc-heptane (1:3) and concentrated under reduced pressure to give the title compound 31 as an off-white crystalline solid. $^1$H-NMR (CDCl$_3$; 400 MHz): δ (ppm) 8.01-8.08 (m, 2H), 7.79 (d, J=8.1 Hz, 1H), 7.67-7.73 (m, 1H), 7.48-7.54 (m, 1H), 7.30-7.38 (m, 4H), 7.24 (s, 1H), 6.98 (d, J=8.6 Hz, 2H), 4.16-4.23 (m, 6H), 3.91 (t, J=4.8 Hz, 2H), 3.82-3.86 (m, 4H), 3.73-3.78 (m, 2H), 3.59-3.63 (m, 2H), 3.41-3.42 (m, 3H), 3.38-3.44 (m, 2H), 3.27-3.33 (m, 2H); Mass spectrum (LCMS, ESI pos.): Calcd. for $C_{32}H_{35}N_5O_4$, 554.3 (M+H). found 554.5.

Example 86

(E)-4-(5-(4-(2-(2-Methoxyethoxy)ethoxy)phenyl)-2-(2-(quinolin-2-yl)vinyl)imidazo[1,2-a]pyrazin-8-yl)morpholine (Cpd 18)

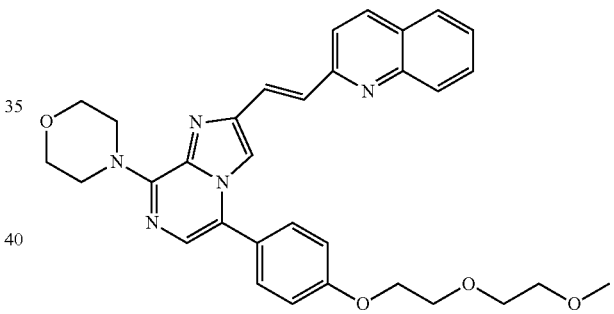

A mixture of compound 2b (117 mg, 0.268 mmol), compound 85b (104 mg, 0.322 mmol), $PdCl_2$(dppf)-DCM (6.6 mg, 0.0081 mmol), and Argon-degassed aqueous 2M $Na_2CO_3$ (0.670 mL, 1.34 mmol) in Argon-degassed 1,4-dioxane (4 mL) was further degassed with Argon for 2 min and then stirred at 90° C. for 6 h. After cooling to room temperature, the reaction mixture was concentrated under reduced pressure to a brown oil which was purified by flash column chromatography on silica gel (0-100% EtOAc-heptane, followed by 100% EtOAc) to afford a greenish-yellow resin. The residue obtained was further purified by flash column chromatography (20-100% EtOAc, followed by 0-30% MeOH/EtOAc) to afford a yellow residue. A solution of the residue in $Et_2O$-heptane (20:1) was allowed to evaporate slowly to afford a light yellow solid which was triturated with MeOH, cooled to −20° C., filtered, and placed under reduced pressure to give the title compound 18 as a light yellow solid. Mass spectrum (LCMS, ESI pos.): Calcd. for $C_{32}H_{33}N_5O_4$, 552.3

(M+H). found 552.5.

Example 87

2-((5-(6-(Piperazin-1-yl)pyridin-3-yl)-8-(pyridin-4-yl)imidazo[1,2-a]pyrazin-2-yl)methoxy)quinoline trifluoroacetic acid salt (Cpd 120)

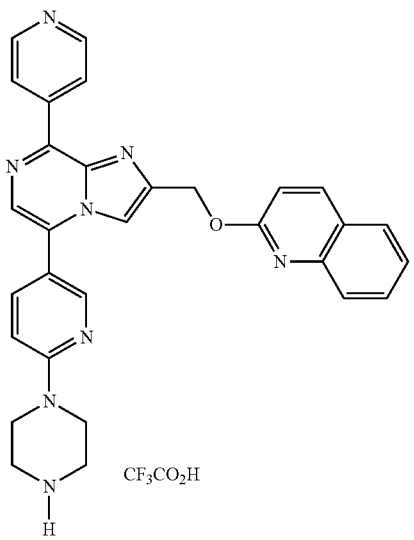

A. tert-Butyl 4-(5-(6-amino-5-chloropyrazin-2-yl)pyridin-2-yl)piperazine-1-carboxylate, 87a

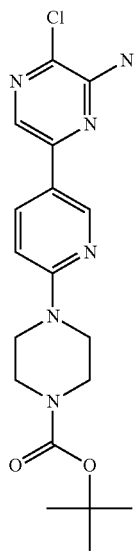 [SMILES: CC(C)(C)OC(=O)N1CCN(c2ccc(-c3cnc(Cl)c(N)n3)cn2)CC1]

To a mixture of 6-bromo-3-chloropyrazin-2-amine (2.00 g, 9.60 mmol), tert-butyl 4-(5-(4,4,5,5-tetramethyl-1,3,2-dioxaborolan-2-yl)pyridin-2-yl)piperazine-1-carboxylate (3.74 g, 9.60 mmol), $Cs_2CO_3$ (7.82 g, 24.0 mmol), and $Pd(dppf)_2 \cdot CH_2Cl_2$ (786 mg, 0.959 mmol) in 1,4-dioxane (40 mL) was added water (20 mL). The resulting mixture was stirred at 90° C. for 16 h and then cooled to rt. The reaction mixture was diluted with EtOAc (300 mL), then washed with water (2×50 mL) and brine (50 mL). Removal of the solvent under reduced pressure followed by purification by flash column chromatography on silica gel (0-3% MeOH/DCM) gave compound 87a as a yellow solid. $^1$H-NMR (CDCl$_3$; 400 MHz) δ 8.75 (d, J=2.2 Hz, 1H), 8.01-8.09 (m, 2H), 6.70 (d, J=9.0 Hz, 1H), 5.02 (br. s., 2H), 3.60-3.69 (m, 4H), 3.57 (br. s., 4H), 1.49 (s, 9H). Mass spectrum (LCMS, ESI pos.): Calcd. for $C_{18}H_{23}ClN_6O_2$, 391.1 (M+H). found 391.1.

B. Ethyl 5-(6-(4-(tert-butoxycarbonyl)piperazin-1-yl)pyridin-3-yl)-8-chloroimidazo[1,2-a]pyrazine-2-carboxylate, 87b

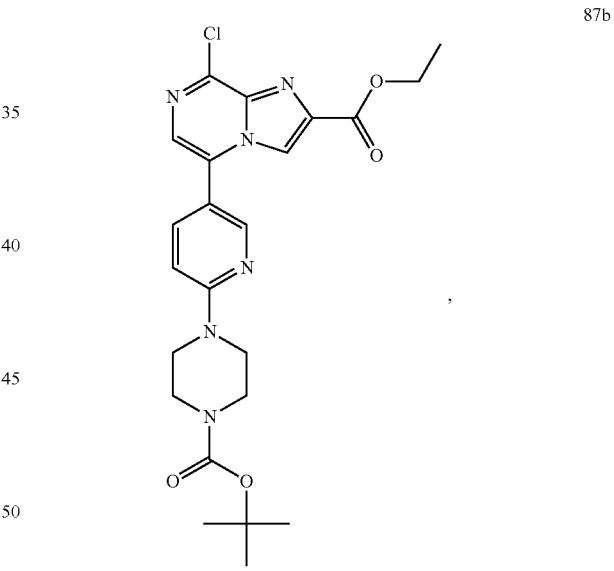

A mixture of compound 87a (1.60 g, 4.09 mmol), and ethyl 3-bromo-2-oxopropanoate (1.72 mL, 12.3 mmol) in DME (25 mL) was stirred at 80° C. under Argon for 3 days. After cooling to rt, the mixture was concentrated under reduced pressure and the residue was purified by flash chromatography on silica gel (20-60% EtOAc/heptane) to give compound 87b as a light brown solid. $^1$H-NMR (CDCl$_3$; 400 MHz) δ 8.43 (d, J=2.2 Hz, 1H), 8.38 (d, J=9.0 Hz, 1H), 7.74 (dd, J=8.8, 2.4 Hz, 1H), 7.66 (d, J=2.7 Hz, 1H), 6.81 (d, J=8.8 Hz, 1H), 4.44-4.52 (m, 2H), 3.68-3.75 (m, 4H), 3.60 (d, J=5.1 Hz, 4H), 1.51 (s, 9H), 1.43 (t, J=7.1 Hz, 3H).

C. tert-Butyl 4-(5-(8-chloro-2-(hydroxymethyl)imidazo[1,2-a]pyrazin-5-yl)pyridin-2-yl)piperazine-1-carboxylate, 87c

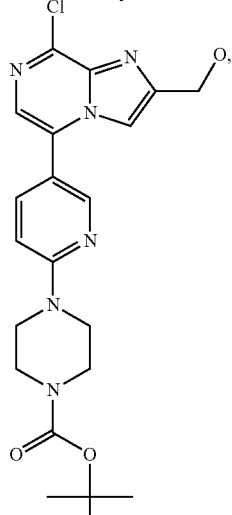

To a solution of compound 87c (450 mg, 0.924 mmol) in THF (18 mL) at 0° C. was added LiAlH$_4$ (0.693 mL, 0.693 mmol, 1.0 M in THF). The reaction was stirred at 0° C. for 30 min. The mixture was treated with 40 mL of saturated NH$_4$Cl solution and then extracted with EtOAc (3×30 mL). The combined organic layers were washed with brine (30 mL) and then dried over Na$_2$SO$_4$. The solvent was evaporated under reduced pressure and the residue was purified by flash chromatography on silica gel (0-5% MeOH/DCM) to give compound 87c (298 mg, 72%) as a light yellow solid. $^1$H-NMR (CDCl$_3$; 400 MHz) δ: 8.42 (d, J=2.4 Hz, 1H), 7.81-7.88 (m, 3H), 7.74 (dd, J=8.8, 2.4 Hz, 1H), 7.60 (s, 1H), 6.79 (d, J=8.8 Hz, 1H), 4.93 (s, 2H), 3.65-3.74 (m, 4H), 3.55-3.63 (m, 4H), 1.50 (s, 9H). Mass spectrum (LCMS, ESI pos.): Calcd. for C$_{21}$H$_{25}$ClN$_6$O$_3$, 445.2 (M+H). found 445.1.

D. tert-Butyl 4-(5-(2-(hydroxymethyl)-8-(pyridin-4-yl)imidazo[1,2-a]pyrazin-5-yl)pyridin-2-yl)piperazine-1-carboxylate, 87d

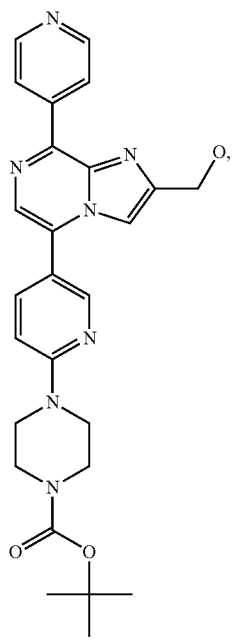

To a mixture of compound 87c (95.0 mg, 0.214 mmol), 4-(4,4,5,5-tetramethyl-1,3,2-dioxaborolan-2-yl)pyridine (48.2 mg, 0.235 mmol), Cs$_2$CO$_3$ (174 mg, 0.534 mmol), and Pd(dppf)$_2$.CH$_2$Cl$_2$ (17.5 mg, 0.0214 mmol) in 1,4-dioxane (3 mL) was added 1.5 mL of water. The resulting mixture was stirred at 90° C. for 4 h. After cooling to rt, the mixture was treated with EtOAc (30 mL) and washed with H$_2$O (2×10 mL) and brine (10 mL). Removal of the solvent gave a residue, which was purified by flash column chromatography on silica gel (0-6% MeOH/DCM) to give compound 87d as a bright yellow-green solid. $^1$H-NMR (CDCl$_3$; 400 MHz) δ 8.84 (br. s., 2H), 8.65 (d, J=4.9 Hz, 2H), 8.51 (s, 1H), 7.97 (s, 1H), 7.87 (s, 1H), 7.82 (d, J=8.8 Hz, 1H), 6.82 (d, J=8.8 Hz, 1H), 4.96 (s, 2H), 3.66-3.75 (m, 4H), 3.55-3.66 (m, 4H), 3.00 (br. s., 1H), 1.51 (s, 9H). Mass spectrum (LCMS, ESI pos.): Calcd. for C$_{26}$H$_{29}$N$_2$O$_3$, 488.2 (M+H). found 488.2.

E. tert-Butyl 4-(5-(8-(pyridin-4-yl)-2-((quinolin-2-yloxy)methyl)imidazo[1,2-a]pyrazin-5-yl)pyridin-2-yl)piperazine-1-carboxylate, 87e

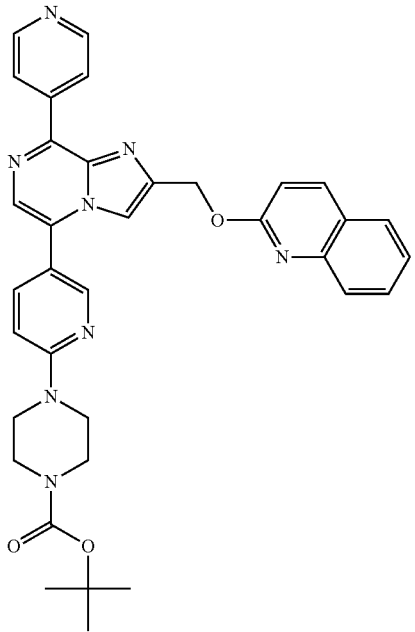

To a mixture of compound 87d (80.0 mg, 0.164 mmol), 2-chloroquinoline (40.3 mg, 0.246 mmol) and 18-crown-6 (43.8 mg, 0.164 mmol) in 5 mL of THF at rt was added potassium tert-butoxide (0.328 mL, 0.328 mmol, 1.0M in t-BuOH). The resulting mixture was heated to 60° C. and continued to stir for 0.5 h. After cooling to rt, the mixture was treated with 30 mL of EtOAc and washed with water (2×10 mL) and brine (10 mL). Removal of the solvent under reduced pressure followed by purification of the resultant residue by flash column chromatography on silica gel (0-4% MeOH/DCM) gave compound 87e as a yellow solid. $^1$H-NMR (CDCl$_3$; 400 MHz) δ 8.82 (br. s., 2H), 8.70 (br. s., 2H), 8.51 (br. s., 1H), 7.91-8.09 (m, 3H), 7.70-7.91 (m, 3H), 7.64 (t, J=7.2 Hz, 1H), 7.41 (t, J=6.8 Hz, 1H), 6.99 (d, J=8.6 Hz, 1H), 6.79 (d, J=8.6 Hz, 1H), 5.84 (s, 2H), 3.70 (br. s., 4H), 3.60 (br. s., 4H), 1.51 (s, 9H). Mass spectrum (LCMS, ESI pos.): Calcd. for C$_{35}$H$_{34}$N$_8$O$_3$, 615.3 (M+H). found 615.2.

F. 2-((5-(6-(piperazin-1-yl)pyridin-3-yl)-8-(pyridin-4-yl)imidazo[1,2-a]pyrazin-2-yl)methoxy)quinoline trifluoroacetic acid salt, Cpd 120

To a mixture of compound 87e (60.0 mg, 0.0976 mmol) in 3 mL of DCM at rt was added TFA (0.50 mL). The resulting mixture was stirred at rt for 1 h. The solvent was removed under reduced pressure and the residue was triturated with Et$_2$O. The solid was collected by filtration and washed with Et$_2$O. After drying under reduced pressure, the title compound 120 was obtained as an orange solid. $^1$H-NMR (CD$_3$OD; 400 MHz) 9.36 (d, J=6.1 Hz, 2H), 8.92 (d, J=6.1 Hz, 2H), 8.62 (s, 1H), 8.30 (s, 1H), 8.05-8.20 (m, 3H), 7.82 (t, J=7.3 Hz, 2H), 7.66 (t, J=7.8 Hz, 1H), 7.43 (t, J=7.3 Hz, 1H), 7.14 (d, J=8.8 Hz, 1H), 7.01 (d, J=8.8 Hz, 1H), 5.82 (s, 2H), 3.96-4.04 (m, 4H), 3.34-3.41 (m, 4H). Mass spectrum (LCMS, ESI pos.): Calcd. for C$_{30}$H$_{26}$N$_8$O, 515.2 (M+H). found 515.2.

Following the procedures described in Example 87 above, and substituting suitably selected and substituted reagents, starting materials and conditions as would be readily apparent to those skilled in the art, the following representative compounds of the present invention were prepared.

| Cpd | Characterization |
|---|---|
| 119 | 2-((8-(1H-Benzo[d]imidazol-6-yl)-5-(6-(piperazin-1-yl)pyridin-3-yl)imidazo[1,2-a]pyrazin-2-yl)methoxy)quinoline trifluoroacetic acid salt<br>$^1$H-NMR (400 MHz, CD$_3$OD) δ (ppm): 9.40 (d, J = 16.9 Hz, 2H), 8.90 (dd, J = 8.8, 1.2 Hz, 1H), 8.58 (d, J = 2.2 Hz, 1H), 8.21 (s, 1H), 8.16 (d, J = 9.0 Hz, 1H), 7.96-8.08 (m, 3H), 7.82 (t, J = 7.9 Hz, 2H), 7.63-7.69 (m, 1H), 7.40-7.46 (m, 1H), 7.14 (d, J = 9.0 Hz, 1H), 7.01 (d, J = 8.8 Hz, 1H), 5.79 (s, 2H), 3.95-4.02 (m, 4H), 3.35-3.41 (m, 4H).<br>Mass Spectrum (LCMS, ESI pos.) Calcd. For C$_{32}$H$_{27}$N$_9$O 554.2 (M + H), Found 554.2. |

Example 88

4-(5-(6-(piperazin-1-yl)pyridin-3-yl)-2-((quinolin-2-yloxy)methyl)imidazo[1,2-a]pyrazin-8-yl)piperazin-2-one trifluoroacetic acid salt (Cpd 115)

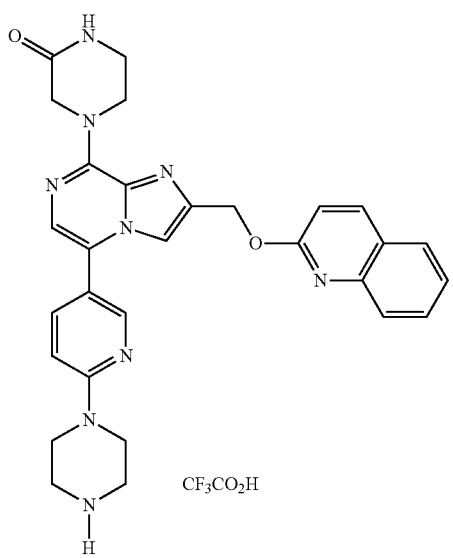 [SMILES: O=C1CN(c2ncc(-c3ccc(N4CCNCC4)nc3)n3cc(COc4ccc5ccccc5n4)nc23)CCN1 ; "CF3CO2H"]

A. tert-Butyl 4-(5-(2-(hydroxymethyl)-8-(3-oxopiperazin-1-yl)imidazo[1,2-a]pyrazin-5-yl)pyridin-2-yl)piperazine-1-carboxylate, 88a

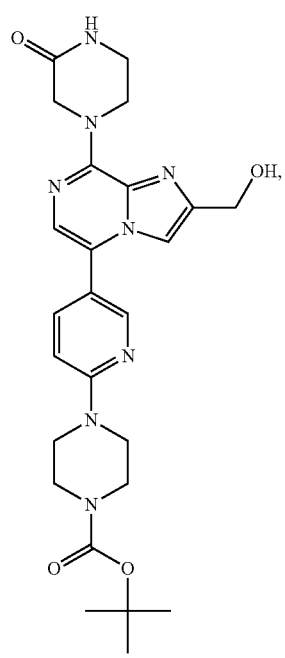

A mixture of compound 87c (90.0 mg, 0.202 mmol), piperazin-2-one (40.5 mg, 0.405 mmol) and K$_2$CO$_3$ (55.9 mg, 0.405 mmol) in 2.5 mL of DMF was stirred at 130° C. for 6 h under an Argon atmosphere. After cooling to rt, the mixture was treated with 30 mL of EtOAc and washed with saturated NH$_4$Cl (20 mL), water (20 mL), brine (10 mL) and then dried over Na$_2$SO$_4$. The solvent was removed under reduced pressure and the residue was purified by flash column chromatography on silica gel (0-7 MeOH/DCM) to give compound 88a as an off white solid. $^1$H-NMR (CDCl$_3$, 400 MHz): δ 8.34 (d, J=2.4 Hz, 1H), 7.67 (dd, J=8.8, 2.4 Hz, 1H), 7.54 (s, 1H), 7.30 (s, 1H), 6.76 (d, J=8.8 Hz, 1H), 6.23 (br. s., 1H), 4.89 (s, 2H), 4.80 (d, J=5.4 Hz, 2H), 4.55 (t, J=5.3 Hz, 2H), 3.55-3.69 (m, 10H), 1.50 (s, 9H). Mass spectrum (LCMS, ESI pos.): Calcd. for C$_{25}$H$_{32}$N$_8$O$_4$, 509.2 (M+H). found 509.2.

B. 4-(5-(6-(piperazin-1-yl)pyridin-3-yl)-2-((quinolin-2-yloxy)methyl)imidazo[1,2-a]pyrazin-8-yl)piperazin-2-one trifluoroacetic acid salt, Cpd 115

The title compound 115 is prepared from compound 88a using the methods described in Example 87, Steps E and F. $^1$H-NMR (CD$_3$OD, 400 MHz): δ 8.38 (d, J=2.2 Hz, 1H), 8.14 (d, J=9.0 Hz, 1H), 7.90 (s, 1H), 7.86 (dd, J=8.9, 2.3 Hz, 1H), 7.81 (s, 1H), 7.79 (s, 1H), 7.65 (td, J=7.6, 1.3 Hz, 1H), 7.42 (t, J=7.9 Hz, 1H), 7.30 (s, 1H), 7.06 (d, J=8.8 Hz, 1H), 6.97 (d, J=8.8 Hz, 1H), 5.65 (s, 2H), 4.75 (s, 2H), 4.60 (t, J=5.3 Hz, 2H), 3.89-3.98 (m, 4H), 3.54 (t, J=5.3 Hz, 2H), 3.33-3.39 (m, 4H). Mass spectrum (LCMS, ESI pos.): Calcd. for C$_{28}$H$_{23}$N$_5$O$_4$, 536.2 (M+H). found 536.3.

Following the procedures described in Example 88 above, and substituting suitably selected and substituted reagents, starting materials and conditions as would be readily apparent to those skilled in the art, the following representative compounds of the present invention were prepared.

| Cpd | Characterization |
|---|---|
| 37 | 1-(4-(5-(6-(Piperazin-1-yl)pyridin-3-yl)-2-((quinolin-2-yloxy)methyl)imidazo[1,2-a]pyrazin-8-yl)piperazin-1-yl)ethanone trifluoroacetic acid salt<br>$^1$H-NMR (400 MHz, CD$_3$OD) δ (ppm): 8.38 (d, J = 2.2 Hz, 1H), 8.13 (d, J = 8.8 Hz, 1H), 7.77-7.93 (m, 4H), 7.65 (td, J = 7.7, 1.2 Hz, 1H), 7.39-7.47 (m, 1H), 7.30 (s, 1H), 7.06 (d, J = 8.8 Hz, 1H), 6.96 (d, J = 8.8 Hz, 1H), 5.64 (s, 2H), 4.30 (m, 2H), 4.16-4.25 (m, 2H), 3.88-3.99 (m, 4H), 3.68-3.83 (m, 4H), 3.33-3.41 (m, 4H), 2.17 (s, 3H).<br>Mass Spectrum (LCMS, ESI pos.) Calcd. For C$_{31}$H$_{33}$N$_9$O$_2$: 564.3 (M + H), Found 564.3. |
| 112 | 2-((8-(4-Methoxypiperidin-1-yl)-5-(6-(piperazin-1-yl)pyridin-3-yl)imidazo[1,2-a]pyrazin-2-yl)methoxy)quinoline trifluoroacetic acid salt<br>$^1$H-NMR (400 MHz, CD$_3$OD) δ (ppm): 8.38 (d, J = 2.2 Hz, 1H), 8.14 (d, J = 8.8 Hz, 1H), 7.94 (s, 1H), 7.76-7.91 (m, 3H), 7.61-7.70 (m, 1H), 7.39-7.48 (m, 1H), 7.18 (s, 1H), 7.07 (d, J = 8.8 Hz, 1H), 6.94-7.01 (m, 1H), 5.66 (s, 2H), 4.53-4.68 (m, 2H), 4.11-4.26 (m, 2H), 3.90-4.01 (m, 4H), 3.61-3.70 (m, 1H), 3.40-3.46 (m, 3H), 3.34-3.40 (m, 4H), 2.05-2.17 (m, 2H), 1.76-1.90 (m, 2H).<br>Mass Spectrum (LCMS, ESI pos.) Calcd. For C$_{31}$H$_{34}$N$_8$O$_2$: 551.3 (M + H), Found 551.3. |

Example 89

4-(5-(6-(Piperazin-1-yl)pyridin-3-yl)-2-((quinolin-2-yloxy)methyl)imidazo[1,2-a]pyrazin-8-yl)thiomorpholine 1,1-dioxide trifluoroacetic acid salt (Cpd 117)

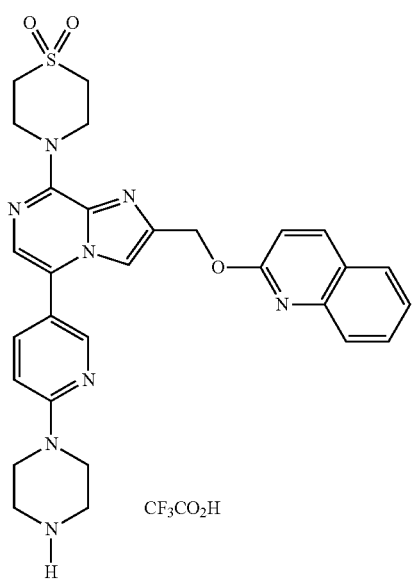 [SMILES: O=S1(=O)CCN(c2ncc(-c3ccc(N4CCNCC4)nc3)n3cc(COc4ccc5ccccc5n4)nc23)CC1 ; "CF3CO2H"]

A. Ethyl 5-(6-(4-(tert-butoxycarbonyl)piperazin-1-yl)pyridin-3-yl)-8-(1,1-dioxidothiomorpholino)imidazo[1,2-a]pyrazine-2-carboxylate, 89a

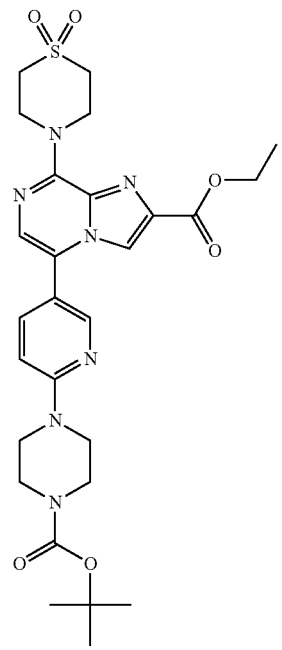

A mixture of compound 1b (100 mg, 0.205 mmol), thiomorpholine 1,1-dioxide (55.5 mg, 0.411 mmol) and DIEA (70.8 μL, 0.411 mmol) in 3 mL of ACN was stirred at 80° C. for 2 d under an Argon atmosphere. After cooling to rt, the mixture was concentrated under reduced pressure and the residue was purified by flash column chromatography on silica gel (0-40 EtOAc/DCM) to give compound 89a as a yellow solid. $^1$H-NMR (CDCl$_3$; 400 MHz) δ 8.36 (s, 1H), 8.14 (s, 1H), 7.67 (d, J=8.8 Hz, 1H), 7.37 (s, 1H), 6.80 (d, J=8.8 Hz, 1H), 4.86 (br. s., 4H), 4.42 (q, J=7.1 Hz, 2H), 3.67 (br. s., 4H), 3.60 (br. s., 4H), 3.19 (br. s., 4H), 1.51 (s, 9H), 1.40 (t, J=7.1 Hz, 3H). Mass spectrum (LCMS, ESI pos.): Calcd. for $C_{27}H_{35}N_7O_6S$, 586.2 (M+H). found 586.3.

B. tert-Butyl 4-(5-(8-(1,1-dioxidothiomorpholino)-2-(hydroxymethyl)imidazo[1,2-a]pyrazin-5-yl)pyridin-2-yl)piperazine-1-carboxylate, 89b

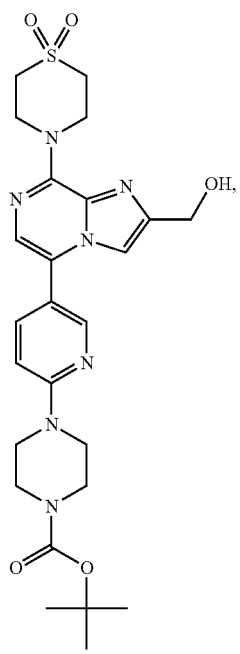

89b

To a solution of compound 89a (107 mg, 0.183 mmol) in 18 mL of THF at 0° C. was added LiAlH$_4$ (0.183 mL, 0.183 mmol, 1.0M in THF). The reaction was stirred at 0° C. for 3 h. The mixture was treated with 20 mL of saturated NH$_4$Cl solution and then extracted with EtOAc (3×20 mL). The combined organic layers were washed with brine (10 mL), dried over Na$_2$SO$_4$, and filtered. The solvent was evaporated under reduced pressure and the residue was purified by flash column chromatography on silica gel (0-100% EtOAc/heptane) to give compound 89b as an off white solid. $^1$H-NMR (2:1 CDCl$_3$/CD$_3$OD; 400 MHz) δ: 8.34 (s, 1H), 7.76 (d, J=8.8 Hz, 1H), 7.65 (s, 1H), 7.34 (s, 1H), 6.88 (d, J=8.8 Hz, 1H), 4.78 (br. s., 6H), 3.68 (d, J=3.2 Hz, 4H), 3.60 (br. s., 4H), 3.23 (br. s., 4H), 1.51 (s, 9H). Mass spectrum (LCMS, ESI pos.): Calcd. for $C_{25}H_{33}N_7O_5S$, 544.2 (M+H). found 544.3.

C. 4-(5-(6-(piperazin-1-yl)pyridin-3-yl)-2-((quinolin-2-yloxy)methyl)imidazo[1,2-a]pyrazin-8-yl)thiomorpholine 1,1-dioxide trifluoroacetic acid salt, Cpd 117

The title compound was prepared from compound 89b using the methods described in Example 87, Steps E and F. $^1$H-NMR (CD$_3$OD, 400 MHz): δ 8.38 (d, J=2.2 Hz, 1H), 8.13 (d, J=8.8 Hz, 1H), 7.83-7.89 (m, 2H), 7.77-7.82 (m, 2H), 7.64 (td, J=7.7, 1.5 Hz, 1H), 7.39-7.44 (m, 1H), 7.36 (s, 1H), 7.06 (d, J=8.8 Hz, 1H), 6.96 (d, J=8.8 Hz, 1H), 5.64 (s, 2H), 4.76 (br. s., 4H), 3.87-3.96 (m, 4H), 3.33-3.37 (m, 4H), 3.18-3.26 (m, 4H). Mass spectrum (LCMS, ESI pos.): Calcd. for $C_{29}H_{30}N_8O_3S$, 571.2 (M+H). found 571.3.

Following the procedures described in Example 89 above, and substituting suitably selected and substituted reagents, starting materials and conditions as would be readily apparent to those skilled in the art, the following representative compound of the present invention was prepared.

| Cpd | Characterization |
|---|---|
| 118 | 1-(5-(6-(Piperazin-1-yl)pyridin-3-yl)-2-((quinolin-2-yloxy)methyl)imidazo[1,2-a]pyrazin-8-yl)piperidin-4-ol trifluoroacetic acid salt<br>$^1$H-NMR (400 MHz, CD$_3$OD) δ (ppm): 8.38 (d, J = 2.4 Hz, 1H), 8.16 (d, J = 8.8 Hz, 1H), 8.00 (s, 1H), 7.86 (dd, J = 8.8, 2.4 Hz, 1H), 7.76-7.84 (m, 2H), 7.62-7.70 (m, 1H), 7.40-7.47 (m, 1H), 7.13 (s, 1H), 7.09 (d, J = 9.0 Hz, 1H), 6.99 (d, J = 8.8 Hz, 1H), 5.69 (s, 2H), 4.67-4.80 (m, 2H), 4.19-4.30 (m, 2H), 4.09 (dt, J = 7.2, 3.6 Hz, 1H), 3.93-4.00 (m, 4H), 3.34-3.40 (m, 4H), 2.08-2.18 (m, 2H), 1.75-1.86 (m, 2H).<br>Mass Spectrum (LCMS, ESI pos.) Calcd. For $C_{30}H_{32}N_8O_2$: 537.3 (M + H), Found 537.1. |

Example 90

(E)-2-(2-(5-(6-(piperazin-1-yl)pyridin-3-yl)-8-(tetrahydro-2H-pyran-4-yl)imidazo[1,2-a]pyrazin-2-yl)vinyl)quinoline trifluoroacetic acid salt (Cpd 80)

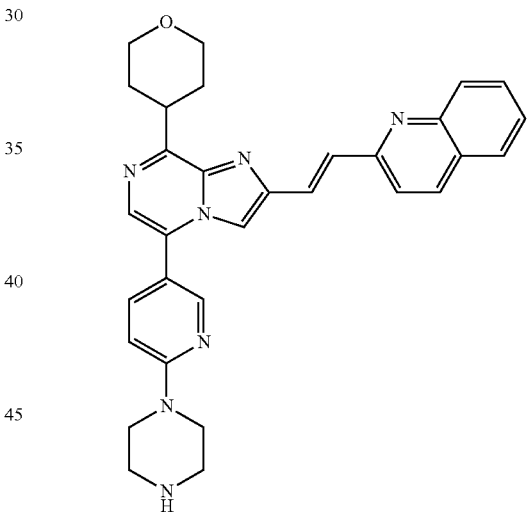

A. 1-(5-Bromopyridin-2-yl)piperazine, 90a

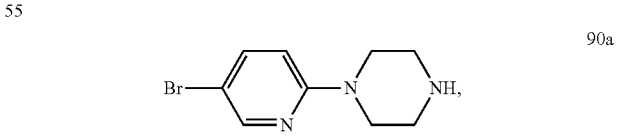

90a

A mixture of 5-bromo-2-chloropyridine (110 g, 573 mmol) and piperazine (99.1 g, 1.15 mol) was stirred overnight at 130° C. The reaction mixture was concentrated under reduced pressure. The residue was dissolved in water (200 mL) and then extracted with DCM (3×200 mL). The combined organic layers were concentrated under reduced pressure to obtain compound 90a as a white solid (105 g, 76% yield). Mass Spectrum (LCMS, ESI pos.): Calcd. for $C_9H_{12}BrN_3$: 242.0 (M+H). found 242.0.

B. tert-Butyl 4-(5-bromopyridin-2-yl)piperazine-1-carboxylate, 90b

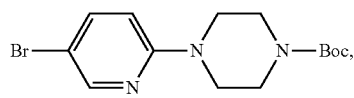

90b

To a solution of compound 90a (125 g, 516 mmol) in DCM (300 mL), TEA (104 g, 1.03 mol) was added, followed by $(BOC)_2O$ (135 g, 619 mmol) in portions with stirring at 0° C. The resulting mixture was stirred overnight at room temperature. The reaction was then quenched with water (100 mL), and the product was extracted with DCM (3×150 mL). The combined organic layers were concentrated under reduced pressure to obtain compound 90b as a white solid (125 g, 71% yield). Mass Spectrum (LCMS, ESI pos.): Calcd. for $C_{14}H_{20}BrN_3O_2$: 342.1 (M+H). found 342.1.

C. tert-Butyl 4-(5-(4,4,5,5-tetramethyl-1,3,2-dioxaborolan-2-yl)pyridin-2-yl), 90c piperazine-1-carboxylate

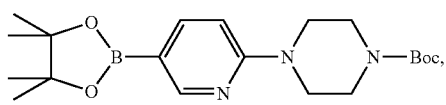

90c

A solution of compound 90b (125 g, 366 mmol) in DMF (1.30 L) was treated with, 4,4,4',4',5,5,5',5'-octamethyl-2,2'-bi(1,3,2-dioxaborolane) (186 g, 732 mmol), $Pd(OAc)_2$ (4.09 g, 18.3 mmol), $PPh_3$ (19.2 g, 73.2 mmol) and KOAc (108 g, 1.10 mol) under a nitrogen atmosphere. The resulting mixture was stirred overnight at 80° C. Upon cooling to room temperature, the solids were collected by filtration. The filtrate was concentrated under reduced pressure, and the resultant residue was purified by flash column chromatography on silica gel (EtOAc/petroleum ether (1:50 v/v)) to obtain compound 90c as a white solid (80.0 g, 56% yield). Mass Spectrum (LCMS, ESI pos.): Calcd. for $C_{20}H_{32}BN_3O_4$: 390.2 (M+H). found 390.2.

D. 3,5-Dibromo-2-chloropyrazine, 90d

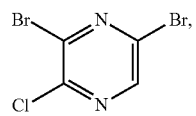

90d

To a solution of 3,5-dibromopyrazin-2-amine (234 g, 932 mmol) in DCM (700 mL) and titanium (IV) chloride (174 g, 926 mmol), tert-butyl nitrite (572 g, 5.55 mol) was slowly added. The resulting mixture was stirred for 2 h at room temperature and treated with water (500 mL). The resulting mixture was extracted with DCM (3×500 mL). The combined organic layers were concentrated under reduced pressure. The resultant residue was purified by flash column chromatography on silica gel (EtOAc/petroleum ether (1:50 v/v)) to obtain compound 90d as colorless oil (210 g, 83% yield). Mass Spectrum (LCMS, ESI pos.): Calcd. for $C_4HBr_2ClN_2$: 272.8 (M+H). found 272.6.

E. 6-Bromo-3-chloropyrazin-2-amine, 90e

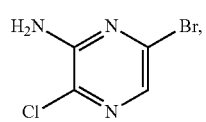

90e

Into a 250 mL sealed tube was placed compound 90d (50.0 g, 184 mmol) and $NH_4OH$ (150 mL). The resulting mixture was stirred overnight at 100° C. Upon cooling, a solid was collected by filtration and dried in an oven under reduced pressure to obtain the compound 90e as a grey solid (28.0 g, 66% yield), which was used in next step without further purification.

F. tert-Butyl 4-(5-(6-amino-5-chloropyrazin-2-yl)pyridin-2-yl)piperazine-1-carboxylate, 90f

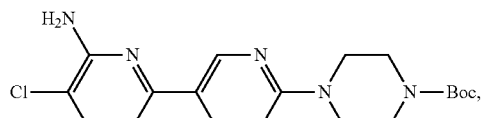

90f

Into a 2 L 4-necked round-bottom flask, purged and maintained with an inert atmosphere of nitrogen, was placed a solution of compound 90e (42.8 g, 206 mmol) in 1,4-dioxane (1 L), compound 90b (80.0 g, 206 mmol), $Pd(dppf)Cl_2$ (7.53 g, 10.3 mmol) and $Cs_2CO_3$ (167 g, 514 mmol). The reaction mixture was stirred overnight at 90° C. Upon cooling, the reaction was quenched with water (100 mL). The resulting mixture was extracted with DCM. The combined organic layers were dried over $Na_2SO_4$, filtered and concentrated under reduced pressure. The resultant residue was purified by flash column chromatography on silica gel (DCM/MeOH (100:3 v/v)) to obtain compound 90f as a yellow solid (23.0 g, 29% yield). Mass Spectrum (LCMS, ESI pos.): Calcd. for $C_{18}H_{23}ClN_6O_2$: 391.2 (M+H). found 391.1.

G. Ethyl 5-(6-(4-(tert-butoxycarbonyl)piperazin-1-yl)pyridin-3-yl)-8-chloroimidazo[1,2-a]pyrazine-2-carboxylate, 90g

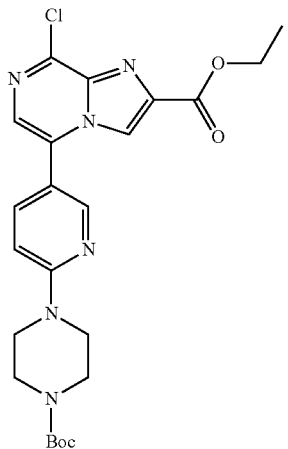 [SMILES: CCOC(=O)c1cn2c(-c3ccc(N4CCN(C(=O)OC(C)(C)C)CC4)nc3)cnc(Cl)c2n1]

Into a 50 mL sealed tube, was placed a solution of compound 90f (3.50 g, 8.53 mmol) in ethylene glycol dimethyl ether (35 mL). To the stirring mixture, ethyl 3-bromo-2-oxopropanoate (5.25 g, 26.9 mmol) was added drop-wise at 0° C. The reaction mixture was stirred overnight at 65° C. and concentrated under reduced pressure. The residue was purified by flash column chromatography on silica gel (EtOAc/petroleum ether (3:1 v/v)) to obtain compound 90g as a yellow solid (560 mg, 13% yield). Mass Spectrum (LCMS, ESI pos.): Calcd. for $C_{23}H_{29}ClN_6O_4$: 487.0 (M+H). found 487.1.

H. Ethyl 5-(6-(4-(tert-butoxycarbonyl)piperazin-1-yl)pyridin-3-yl)-8-(3,6-dihydro-2H-pyran-4-yl)imidazo[1,2-a]pyrazine-2-carboxylate, 90h

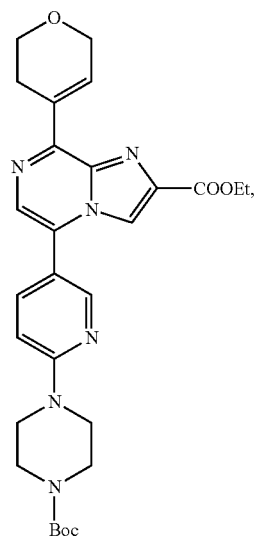

Compound 90g (1.08 g, 2.10 mmol) was subjected to Suzuki coupling with 2-(3,6-dihydro-2H-pyran-4-yl)-4,4,5,5-tetramethyl-1,3,2-dioxaborolane using the method described in Example 87, Step D to obtain compound 90h as a yellow solid (520 mg, 44% yield). Mass Spectrum (LCMS, ESI pos.): Calcd. for $C_{28}H_{34}N_6O_5$: 535.3 (M+H). found: 535.6.

I. Ethyl 5-(6-(4-(tert-butoxycarbonyl)piperazin-1-yl)pyridin-3-yl)-8-(tetrahydro-2H-pyran-4-yl)imidazo[1,2-a]pyrazine-2-carboxylate, 90i

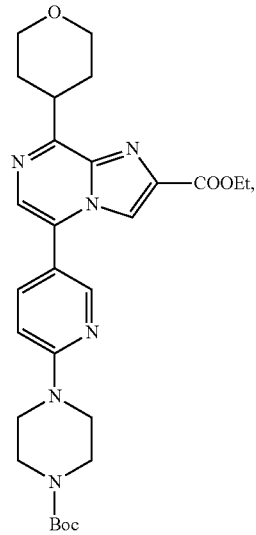

A solution of compound 90h (470 mg, 0.830 mmol) in MeOH (2 mL) and 10% palladium on carbon (300 mg) was placed under a $H_2$ atmosphere using a $H_2$ balloon. The reaction mixture was stirred overnight at 35° C. A solid was removed by filtration. The filtrate was concentrated under reduced pressure to obtain compound 90i as a gray solid (465 mg, 99% yield). Mass Spectrum (LCMS, ESI pos.): Calcd. for $C_{28}H_{36}N_6O_5$: 537.3 (M+H). found: 537.6.

J. tert-Butyl 4-(5-(2-(hydroxymethyl)-8-(tetrahydro-2H-pyran-4-yl)imidazo[1,2-a]pyrazin-5-yl)pyridin-2-yl)piperazine-1-carboxylate, 90j

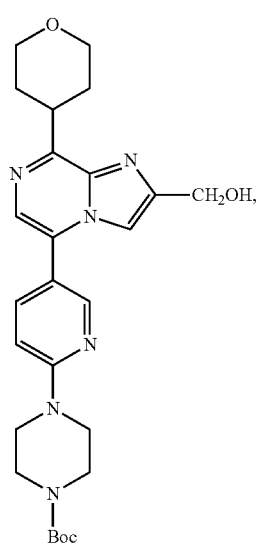

Compound 90j (510 mg, 0.950 mmol) was reacted with LiAlH$_4$ as described in Example 87, Step C to obtain compound 90j as a yellow solid (370 mg, 79% yield). Mass Spectrum (LCMS, ESI pos.): Calcd. for C$_{26}$H$_{34}$N$_6$O$_4$: 495.3 (M+H). found: 495.6.

K. tert-Butyl 4-(5-(2-formyl-8-(tetrahydro-2H-pyran-4-yl)imidazo[1,2-a]pyrazin-5-yl)pyridin-2-yl)piperazine-1-carboxylate, 90k

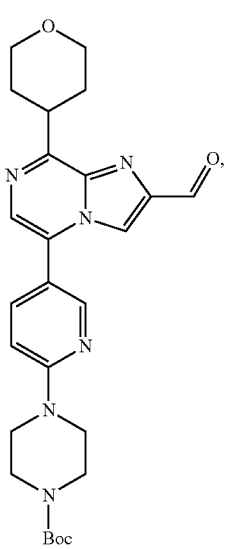

90k

Compound 90j (100 mg, 0.200 mmol) was reacted with IBX as described in Example 2, Step A to obtain compound 90k as a yellow solid (80.0 mg, 80% yield). Mass Spectrum (LCMS, ESI pos.): Calcd. for C$_{26}$H$_{32}$N$_6$O$_4$: 493.2 (M+H). found: 493.6.

L. (E)-2-(2-(5-(6-(piperazin-1-yl)pyridin-3-yl)-8-(tetrahydro-2H-pyran-4-yl)imidazo[1,2-a]pyrazin-2-yl)vinyl)quinoline trifluoroacetic acid salt, Cpd 80

Into an 8 mL sealed tube was placed a solution of compound 90k (160 mg, 0.330 mmol) in DMF (1 mL), 2-methylquinoline (55.8 mg, 0.390 mmol) and chlorotrimethylsilane (106 mg, 0.980 mmol). The reaction mixture was stirred overnight at 80° C. and then concentrated under reduced pressure to give approximately 150 mg of crude product, which was then purified by Prep-HPLC with the following conditions: (1#-PreP-HPLC-005(Waters)): Column, SunFire Prep C18, 19*150 mm, 5 µm; mobile phase, water with 0.05% TFA and CH$_3$CN (10% CH$_3$CN up to 25% in 10 min, up to 100% in 2 min, down to 10% in 2 min); Detector, UV 254 nm. The purification resulted in the title compound 80 as a yellow solid (63.2 mg, 36% yield). $^1$H-NMR (400 MHz, DMSO-d$_6$) δ (ppm): 8.94 (s, 1H), 8.57-8.52 (m, 2H), 8.40 (s, 1H), 8.11-8.03 (m, 5H), 7.87-7.81 (m, 3H), 7.65 (t, J=6.8 Hz, 1H), 7.17 (d, J=8.4 Hz, 1H), 4.58-4.57 (m, 4H), 3.65-3.59 (m, 4H), 3.35-3.18 (m, 5H), 2.10-1.91 (m, 4H). Mass Spectrum (LCMS, ESI pos.): Calcd. for C$_{31}$H$_{31}$N$_7$O: 518.3 (M+H). Found 518.3.

Example 91

2-((5-(6-(piperazin-1-yl)pyridin-3-yl)-8-(tetrahydro-2H-pyran-4-yl)imidazo[1,2-a]pyrazin-2-yl)methoxy) quinoline trifluoroacetic acid salt (Cpd 83)

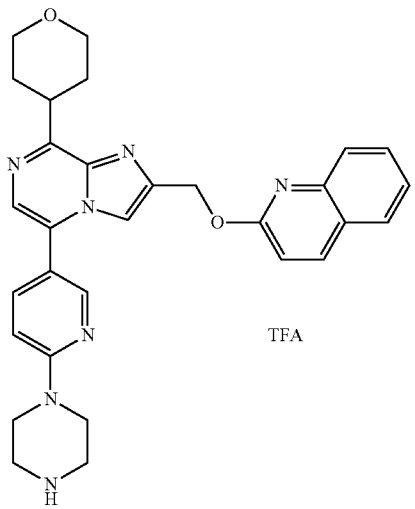 [SMILES: c1ccc2nc(OCc3cn4c(-c5ccc(N6CCNCC6)nc5)cnc(C5CCOCC5)c4n3)ccc2c1]

A. tert-Butyl 4-(5-(2-((quinolin-2-yloxy)methyl)-8-(tetrahydro-2H-pyran-4-yl)imidazo[1,2-a]pyrazin-5-yl)pyridin-2-yl)piperazine-1-carboxylate, 91a

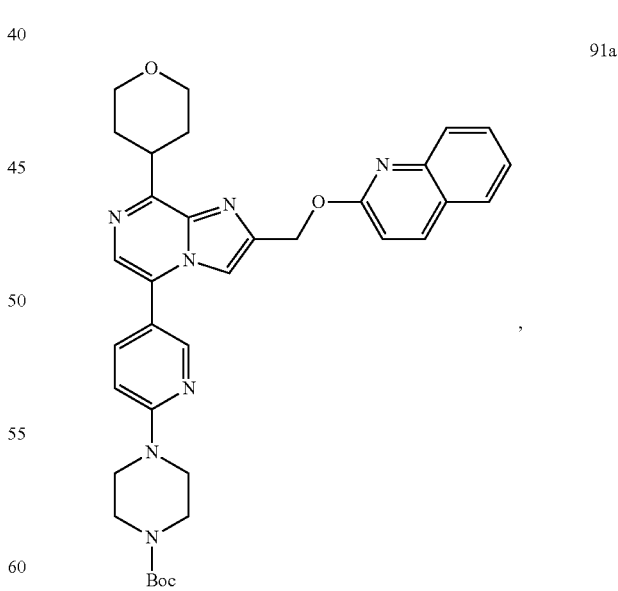

91a

Into a 10 mL round-bottom flask was placed a solution of compound 90j (150 mg, 0.300 mmol) in DMF (2 mL), followed by the addition of sodium hydride (30.0 mg, 1.25 mmol) at 0° C. The mixture was stirred for 15 min at 0° C., and 2-chloroquinoline (74.2 mg, 0.460 mmol) was added.

The reaction mixture was stirred overnight at 70° C. Upon cooling, the reaction was quenched with water. The resulting mixture was extracted with DCM (3×10 mL). The combined organic layers were concentrated under reduced pressure. The resultant residue was purified by flash column chromatography on silica gel (EtOAc/petroleum ether (1:3 v/v)) to obtain compound 91a as a light yellow solid (130 mg, 69% yield). Mass Spectrum (LCMS, ESI pos.): Calcd. for $C_{35}H_{39}N_7O_4$: 622.3 (M+H). found: 622.2.

B. 2-((5-(6-(piperazin-1-yl)pyridin-3-yl)-8-(tetrahydro-2H-pyran-4-yl)imidazo[1,2-a]pyrazin-2-yl)methoxy)quinoline trifluoroacetic acid salt, Cpd 83

Compound 91a (130 mg, 0.210 mmol) was treated with TFA as described in Example 87, Step F to obtain the title compound 83 as a light yellow solid (61.7 mg, 55% yield). $^1$H-NMR (300 MHz, DMSO-$d_6$) δ (ppm): 8.84 (s, 1H), 8.51 (s, 1H), 8.27 (d, J=9.0 Hz, 1H), 8.13 (s, 1H), 8.03 (dd, J=2.4 Hz, 8.7 Hz, 1H), 7.90 (d, J=8.1 Hz, 1H), 7.86 (s, 1H), 7.81 (d, J=8.7 Hz, 1H), 7.72-7.67 (m, 1H), 7.49-7.44 (m, 1H), 7.12 (d, J=9.0 Hz, 1H), 7.07 (d, J=9.0 Hz, 1H), 5.65 (s, 2H), 4.03-4.00 (m, 2H), 3.87-3.78 (m, 5H), 3.61-3.54 (m, 2H), 3.28-3.20 (m, 4H), 2.01-1.87 (m, 4H). Mass Spectrum (LCMS, ESI pos.) Calcd. for $C_{30}H_{31}N_7O_2$: 522.3 (M+H). Found 522.3.

Biological Examples

In Vitro Assays

Example 1

In Vitro Assay PDE10a

Rat recombinant PDE10a (rPDE10a) was expressed in Sf9 cells using a recombinant rPDE10a baculovirus construct. Cells were harvested after 48 h of infection and the rPDE10a protein was purified by metal chelate chromatography on Ni-sepharose 6FF. Tested compounds were dissolved and diluted in 100% DMSO to a concentration 100 fold of the final concentration in the assay. Compound dilutions (0.4 μL) were added in 384 well plates to 20 μL of incubation buffer (50 mM Tris pH 7.8, 8.3 mM $MgCl_2$, 1.7 mM EGTA). 10 μL of rPDE10a enzyme in incubation buffer was added and the reaction was started by addition of 10 μL substrate to a final concentration of 60 nM cAMP and 0.008 μCi $^3$H-cAMP. The reaction was incubated for 60 min at rt. After incubation, the reaction was stopped with 20 μL of 17.8 mg/mL PDE SPA beads. After sedimentation of the beads during 30 min the radioactivity was measured in a Perkin Elmer Topcount scintillation counter and results were expressed as cpm. For blank values the enzyme was omitted from the reaction and replaced by incubation buffer. Control values were obtained by addition of a final concentration of 1% DMSO instead of compound. A best fit curve was fitted by a minimum sum of squares method to the plot of % of control value subtracted with blank value versus compound concentration and the half maximal inhibitory concentration ($IC_{50}$) value was derived from this curve. Resultant data is shown in Table 3.

Example 2

In Vitro hPDE10a

Human recombinant PDE10A2 was expressed in Sf9 cells, using a recombinant baculovirus construct containing the full length sequence containing a 6×His sequence following the start Met to allow metal affinity purification of the recombinant protein. Cells were harvested and the phosphodiesterase protein was purified by metal chelate chromatography on Ni-sepharose 6FF.

The affinity of the compounds of Formula (I) for phophodiesterases (PDE) was measured by a scintillation proximity assay (SPA). PDE Yttrium Silicate SPA beads allow PDE activity to be measured by direct binding of the primary phosphate groups of non-cyclic AMP or GMP to the beads via a complex iron chelation mechanism. The amount of bound tritiated product ([$^3$H]-AMP) is measured by liquid scintillation counting.

The compounds were dissolved and diluted in 100% DMSO in polystyrene plates to a concentration of 100-fold the final concentration in the assay. Human PDE10A enzyme solution (10 μL) was added to 20 μL, of incubation buffer (50 mM Tris pH 7.8, 8.3 mM $MgCl_2$, 1.7 mM EGTA), 10 μL, substrate solution consisting of a mixture of non-tritiated and tritiated substrate (60 nM cAMP, 0.008 μCi $^3$H-cAMP), and 0.4 μL, compound in 100% DMSO in a 384-well plate, and incubated for 60 min at room temperature. After incubation, the reaction was stopped with 20 μL, of stop solution, consisting of PDE SPA beads (17.8 mg beads/mL in 18 mM zinc sulphate). After sedimentation of the beads for 30 min, the radioactivity was measured in a Perkin Elmer Topcount scintillation counter and results were expressed as cpm. To measure the low control, no enzyme was added to the reaction mixture.

Data were calculated as the percentage of inhibition of total activity measured in the absence of test compound (% control). A best-fit curve was fitted by a minimum sum of squares method to the plot of % Control vs compound concentration, from which an $IC_{50}$ value (inhibitory concentration causing 50% inhibition of hydrolysis) was obtained. Resultant data is shown in Table 2.

TABLE 2

| Cpd No. | rPDE10a2 IC50 (nM) | hPDE10a2 IC50 (nM) |
| --- | --- | --- |
| 1 | 95 | 85 |
| 2 | 20 | 30 |
| 3 | 9 | 5 |
| 5 | 6 | 7 |
| 6 | 14 | 12 |
| 7 | 16 | 6 |
| 8 | 9 | 2 |
| 9 | 2 | 1 |
| 10 | 16 | 12 |
| 11 | 9 | 7 |
| 12 | 4 | 2 |
| 14 | 11 | 6 |
| 15 | 51 | 30 |
| 17 | 3 | 3 |
| 18 | 102 | 83 |
| 19 | 15 | 18 |
| 20 | 26 | 8 |
| 21 | 31 | 25 |
| 22 | 9 | 9 |
| 23 | 6 | 8 |
| 24 | 5 | 3 |
| 25 | 3 | 2 |
| 26 | 8 | 6 |
| 27 | 2 | 2 |
| 29 | 15 | 24 |
| 30 | 10 | 17 |
| 31 | 115 | 1 |
| 32 | 6 | 12 |
| 33 | 23 | 21 |
| 34 | 13 | 5 |
| 35 | 12 | 7 |
| 36 | 23 | 17 |

TABLE 2-continued

| Cpd No. | rPDE10a2 IC50 (nM) | hPDE10a2 IC50 (nM) |
|---|---|---|
| 37 | 11 | 4 |
| 38 | 7 | 2 |
| 39 | 8 | 5 |
| 40 | 20 | 10 |
| 41 | 21 | 19 |
| 42 | 2 | 1 |
| 43 | 7 | 3 |
| 44 | 9 | 14 |
| 45 | 23 | 20 |
| 46 | 4 | 7 |
| 47 | 15 | 34 |
| 48 | 37 | 11 |
| 49 | 98 | 155 |
| 50 | 17 | 18 |
| 51 | 5 | 4 |
| 54 | 1 | 1 |
| 56 | 15 | 14 |
| 57 | 48 | 46 |
| 58 | 132 | 91 |
| 59 | 19 | 14 |
| 61 | 6 | |
| 62 | 16 | |
| 63 | <1.0 | |
| 64 | 22 | 13 |
| 65 | 60 | 38 |
| 66 | 3 | 2 |
| 67 | 4 | 5 |
| 69 | 4 | 4 |
| 70 | 1 | 2 |
| 71 | 63 | 44 |
| 72 | 46 | 31 |
| 73 | 40 | 26 |
| 74 | <1.0 | 1 |
| 75 | <1.0 | <1.0 |
| 76 | 3 | 2 |
| 77 | <30 | 1 |
| 78 | <1.0 | 1 |
| 79 | 33 | 7 |
| 80 | 562 | 617 |
| 81 | 91 | 245 |
| 82 | 245 | 282 |
| 83 | 269 | 316 |
| 84 | 8 | 16 |
| 85 | 2 | 1 |
| 86 | 16 | 14 |
| 87 | 2 | 1 |
| 88 | 12 | 9 |
| 90 | 1 | 2 |
| 91 | 3 | 12 |
| 92 | 3 | 6 |
| 93 | 10 | 13 |
| 94 | 3 | 8 |
| 95 | <1.0 | 5 |
| 96 | <1.0 | 3 |
| 97 | 1 | 1 |
| 98 | 52 | 58 |
| 99 | 204 | 224 |
| 100 | 38 | 29 |
| 101 | 20 | 15 |
| 102 | 17 | 35 |
| 103 | 617 | 676 |
| 104 | 68 | 129 |
| 105 | 22 | 50 |
| 106 | 15 | 89 |
| 107 | 2 | 2 |
| 108 | 23 | 35 |
| 109 | 87 | 110 |
| 110 | 288 | 407 |
| 111 | 562 | 955 |
| 112 | 95 | 89 |
| 113 | 151 | 224 |
| 114 | 1995 | 1349 |
| 115 | 40 | 85 |
| 116 | 3631 | 2630 |
| 117 | 32 | 56 |
| 118 | 30 | 78 |
| 119 | 26 | 54 |
| 120 | 15 | 20 |
| 121 | 83 | 59 |
| 122 | 8 | 9 |
| 123 | 8 | 19 |
| 124 | 123 | 115 |
| 125 | 339 | 309 |
| 126 | 13 | 34 |
| 127 | 30 | 62 |
| 128 | 31 | 30 |
| 129 | 27 | 31 |
| 130 | 16 | 42 |
| 131 | 11 | 51 |
| 132 | 871 | 1622 |

Example 3

PDE10a-Brain Permeability Assay

A. PDE10a-Perfused Brain Permeability Study Protocol

The purpose of the perfused blood brain barrier acute PK studies was to determine whether a compound post-administration was able to cross the blood brain barrier, and to then quantitate the drug levels in plasma relative to brain. Whole body perfusion of saline after plasma blood collection improved estimate errors due to drug remaining in the capillaries of the brain. It has been suggested in the scientific literature that compounds that do not accumulate in the brain tissue may possess fewer potential CNS side effects. Therefore, it is an objective of the present invention to identify compounds of Formula (I) that do not accumulate in the brain tissue where they may exert CNS effects.

Drug administration by oral gavage, subcutaneous injection or intravenous was carried out using male Sprague Dawley rats under IACUC protocol (SH-MET3010). Male Sprague Dawley rats (Charles River) ~300-350 g were maintained on a 4% standard rodent diet (Test Diet 5001). They are allowed ad libitum access to water and food. Room temperature was maintained at 64° F. and humidity at 30-70%.

Three animals per compound were provided a dose of 2 mg/mL in 20% HpbCD/Tris pH 8 by tail i.v. or 30 mpk p.o. or s.c. in 20% HpbCD/Tris pH 8, with PDE10a antagonists. A first blood sample was collected at 30 min via retro-orbital sinus (anesthetic by 70% $CO_2$/30% $O_2$) into heparinzed plasma separator tubes. The blood was centrifuged and 100 uL plasma was placed into a 96 well plate and saved on dry ice.

After the 120 min, the final blood sample was collected via retro-orbital sinus under anesthesia by IP 0.5 cc injection of a 4/1 mixture of Ketaset: AnaSed [(prepared 10 mL Ketaset (100 mg/mL Ketamine)+2.5 mL AnaSed (20 mg/mL Xylazine)]. The rats were then perfused with 400 mL heparinized saline (10,000 units/L) through the left ventricle of the heart; the brains were then removed (not including the medulla), weighed and homogenized in PBS (4 mL/g tissue). The samples were stored at −80° C. and submitted for chemical analysis of blood and brain concentrations. Endpoints of sample analysis consists of the plasma concentrations at 30 and 120 min, plus brain concentrations at 120 min. Resultant data is shown in Table 3.

B. PDE10a-Non-Perfused Brain Permeability Study Protocol

The purpose of the acute PK/Brain Permeability Studies was to determine whether a compound post-administration was able to cross the blood brain barrier, and then to quantitate the drug levels in plasma relative to brain. It has been suggested in the scientific literature that compounds that do not accumulate in the brain tissue may possess fewer potential CNS side effects. Single dose 2 mg/kg (i.v.) PK/brain permeability studies using male Sprague Dawley rats were carried out under IACUC protocol (SH-MET3010). Male Sprague Dawley rats (Charles River) weighing ~300-350 g were maintained on a 4% standard rodent diet (Test Diet 5001). They were allowed ad libitum access to water and food. The room temperature was maintained at 64° F. and humidity at 30-70%. Compounds were prepared 2 mg/mL in 20% HpbCD/Tris pH 8 for tail intravenous dosing at a dose volume for each rat at 1 mL/kg.

Three animals per compound were injected at a dose of 2 mg/kg tail i.v. with a PDE10a antagonist compound of the instant invention. Blood samples were collected at 30 and 120 min via retro-orbital sinus (anesthetic by 70% $CO_2$/30% $O_2$) into heparinzed plasma separator tubes. The blood was centrifuged and 100 mL plasma was placed into a 96 well plate and saved on dry ice. After the 120 min blood samples were collected, each rat was euthanized in a 100% $CO_2$ chamber, the brain (not including the medulla) and pancreas were removed, rinsed with PBS, weighed, and homogenized in PBS (4 mL/g tissue). 100 uL samples of tissue homogenates and 100 uL of compounds formulation were also placed in polyethylene tubes. The samples were stored at –80° C. and submitted for chemical analysis of blood and brain concentrations.

Endpoints of sample analysis consist of the plasma concentrations at 30 and 120 min, plus brain and pancreas concentrations at 120 min. Resultant data is shown in Table 3.

TABLE 3

Brain/Plasma ratios* of PDE10a compounds

| Cpd No. | Ratio Br/Pl Mean 2 h | Plasma conc 2 h (ng/mL) | Brain conc 2 h (ng/g) |
|---|---|---|---|
| 5 | 0.02 | 1117 | 18.4 |
| 14 | 0.07 | 503 | 35.5 |
| 16 | 0 | 141.8 | 0 |
| 55 | 0 | 118 | 0 |
| 63 | 0 | 2 | 0 |
| 69 | 1 | 73.6 | 36.1 |
| 74 | 0 | 58 | 0 |
| 76 | 0 | 115 | 0 |
| 91 | 0.55 | 209 | 112 |
| 92 | 0.77 | 135 | 78.3 |
| 93 | 0 | 98 | 0 |
| 95 | 0 | 113 | 0 |
| 97 | 0 | 84 | 0 |
| 107 | 0 | 22.5 | 0 |
| 109 | 0.03 | 225.5 | 8.15 |
| 110 | 0 | 4.63 | 0 |
| 119 | 2.99 | 53.77 | 108.33 |
| 121 | 1.55 | 55.1 | 81.5 |
| 122 | 3.18 | 35.6 | 98.17 |
| 125 | 1.2 | 45.87 | 54.88 |
| 126 | 2.26 | 22.37 | 49.28 |
| 128 | 0.58 | 16.44 | 1.85 |
| 129 | 2.07 | 10.99 | 21.92 |
| 131 | 2.04 | 28.07 | 57.33 |

*Perfused or non-perfused brain

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:

1. A compound of Formula (I)

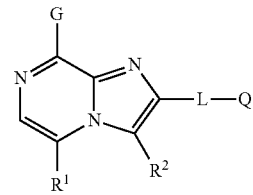

Formula (I)

wherein

G is a substituent selected from the group consisting of

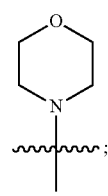

g-1

$R^1$ is (i) hydrogen;

(ii) a substituent selected from the group consisting of pyridinyl, 1H-pyrazol-4-yl, 5-pyrimidinyl, 5-hydroxy-1,2,4-oxadiazol-3-yl, 1H-imidazo[4,5-b]pyridin-6-yl, 2-hydroxy-1H-imidazo[4,5-b]pyridin-6-yl, and a ring 1-a to 1-h

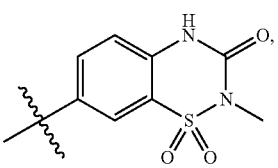

1-a

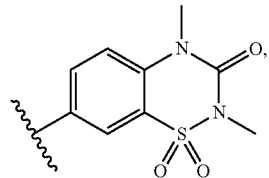

1-b

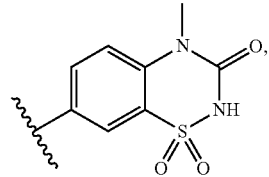

1-c

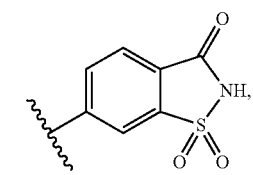

1-d

-continued

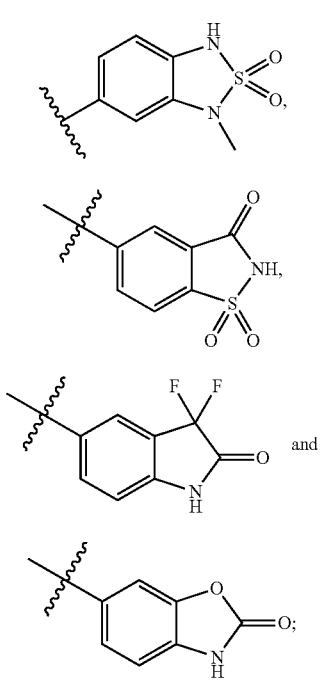

1-e 1-f 1-g 1-h and wherein the pyridinyl and 5-pyrimidinyl rings of group (iii) are optionally substituted with one substituent selected from the group consisting of $C_{1-4}$alkyl, carboxy($C_{1-4}$)alkyl, aminocarbonyl, aminosulfonyl, 1,2,3,6-tetrahydropyridin-4-yl, carboxy, amino, dimethylamino, carboxymethylamino, piperidin-4-yl, piperazin-1-yl, 4-methylpiperazin-1-yl, morpholin-4-yl, $C_{1-4}$alkylsulfonylamino, $C_{1-4}$alkylsulfonylaminocarbonyl, 5-hydroxy-1,2,4-oxadiazol-3-yl, 1,2,4-oxadiazol-5(4H)-one-3-yl, tetrazolyl, triazolyl, or triazolylthio; wherein said tetrazolyl, and triazolyl are optionally substituted with one hydroxy or $C_{1-4}$alkoxy substituent;

and wherein said pyridinyl of group (iii) is optionally further substituted with one or two substituents selected from the group consisting of fluoro, chloro, and hydroxy;

wherein said 1H-pyrazol-4-yl of group (iii) is optionally substituted at the 1-position with methoxy-ethyl or carboxy($C_{1-4}$)alkyl;

(iii) phenyl optionally substituted at the 4-position with one substituent that is $C_{1-4}$alkoxycarbonyl, $C_{1-4}$alkylcarbonylaminosulfonyl, $C_{1-4}$alkylaminosulfonyl, (2-hydroxyethyl)aminosulfonyl, aminosulfonyl, $C_{1-4}$alkylsulfonylaminocarbonyl, carboxy, —O(CH$_2$CH$_2$O)$_{2-5}$CH$_3$, —OCH$_2$OCH$_3$, carboxy($C_{1-4}$)alkylaminocarbonyl, 2-carboxypyrrolidin-1-ylcarbonyl, carboxy($C_{1-4}$)alkylcarbonylamino, $C_{1-4}$alkylsulfonylaminocarbonylamino, carboxy($C_{1-4}$)alkylamino, bis(2-hydroxyethyl)aminocarbonylamino, (2-hydroxyethyl)aminocarbonylamino, 1,1,1,3,3,3-hexafluoro-2-hydroxypropan-2-yl, 4-carboxypiperidin-1-yl, piperazin-1-yl, triazolylthio, tetrazolyl, triazolyl, imidazolyl, or oxazolyl; wherein said tetrazolyl, triazolyl, imidazolyl, or oxazolyl substituents are optionally independently substituted with one or two substituents selected from the group consisting of $C_{1-4}$alkyl and hydroxy;

and wherein said phenyl ring of group (iii) is optionally independently further substituted with one or two substituents selected from the group consisting of $C_{1-4}$alkyl, $C_{1-4}$alkoxy, and fluoro;

(iv) phenyl substituted at the 4-position with one substituent that is r-1, r-2, or r-3;

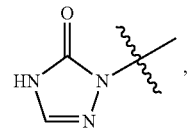

r-1

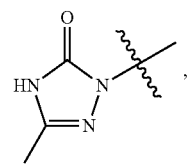

r-2

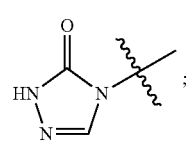

r-3 wherein said phenyl ring of group (iv) is optionally further substituted with one additional fluoro substituent;

(v) phenyl substituted at the 4-position with p-1 or p-2;

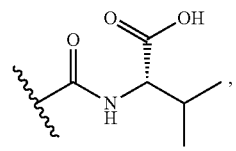

p-1

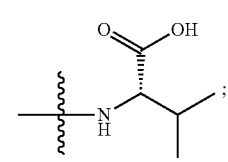

p-2 or (vi) piperidin-4-yl optionally substituted at the 1-position with aminosulfonyl or carboxy($C_{1-4}$)alkyl;

$R^2$ is hydrogen; or $R^2$ is chloro when L is azetidin-1-yl;

L is a bivalent linker that is ethyl, E-ethenyl, ethynyl, trans-1,3-cyclobutyl, cis-1,3-cyclobutyl, azetidinyl, —CH$_2$X—, or —NHC(O)—; wherein X is O or S;

Q is quinolin-2-yl, pyridinyl, pyrimidinyl, quinazolin-2-yl, benzimidazol-2-yl, or benzothiazol-2-yl;

wherein said Q is optionally independently substituted with one or two substituents selected from the group consisting of $C_{1-4}$alkyl, carboxy-methoxy, $C_{1-4}$alkoxy, and carboxy;

or an enantiomer, diastereomer, or pharmaceutically acceptable salt form thereof.

2. The compound of claim 1 wherein $R^1$ is (i) hydrogen;

(ii) a substituent selected from the group consisting of pyridinyl, 1H-pyrazol-4-yl, 5-pyrimidinyl, 5-hydroxy-1,2,4-oxadiazol-3-yl, 1H-imidazo[4,5-b]pyridin-6-yl, 2-hydroxy-1H-imidazo[4,5-b]pyridin-6-yl, and a ring 1-a to 1-h

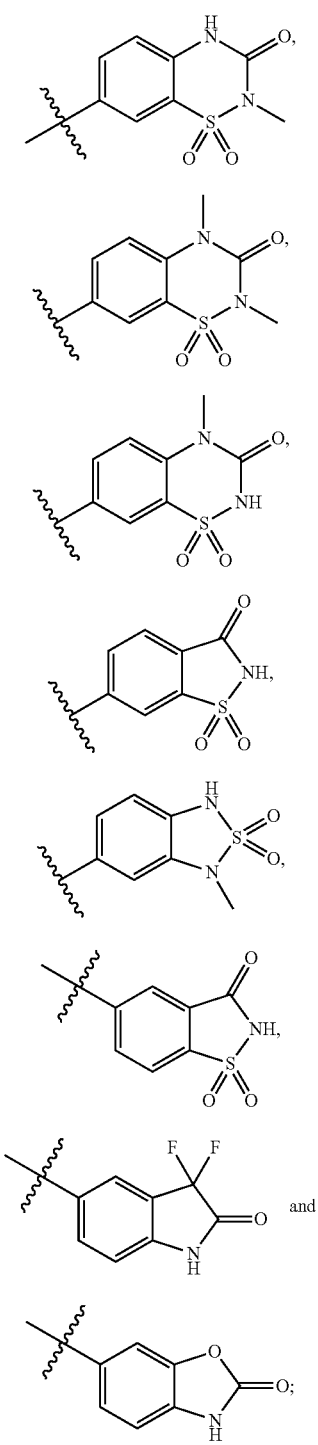

1-a 1-b 1-c 1-d 1-e 1-f 1-g 1-h wherein the pyridinyl and 5-pyrimidinyl rings of group (iii) are optionally substituted with one substituent selected from the group consisting of $C_{1-4}$alkyl, carboxy($C_{1-4}$) alkyl, aminocarbonyl, aminosulfonyl, 1,2,3,6-tetrahydropyridin-4-yl, carboxy, amino, dimethylamino, carboxymethylamino, 4-methylpiperazin-1-yl, morpholin-4-yl, $C_{1-4}$alkylsulfonylamino, $C_{1-4}$alkylsulfonylaminocarbonyl, 1,2,4-oxadiazol-5 (4H)-one-3-yl, tetrazolyl, triazolyl, or triazolylthio;

wherein said tetrazolyl and triazolyl are optionally substituted with one hydroxy substituent;

and wherein said pyridinyl of group (iii) is optionally further substituted with one or two substituents selected from the group consisting of fluoro, chloro, and hydroxy;

wherein said 1H-pyrazol-4-yl of group (iii) is optionally substituted at the 1-position with methoxy-ethyl or carboxy($C_{1-4}$)alkyl;

(iii) phenyl optionally substituted at the 4-position with one substituent that is $C_{1-4}$alkoxycarbonyl, $C_{1-4}$alkylcarbonylaminosulfonyl, (2-hydroxyethyl)aminosulfonyl, aminosulfonyl, $C_{1-4}$alkylsulfonylaminocarbonyl, carboxy, —O(CH$_2$CH$_2$O)$_{2-5}$CH$_3$, —OCH$_2$OCH$_3$, carboxy($C_{1-4}$)alkylaminocarbonyl, 2-carboxypyrrolidin-1-ylcarbonyl, carboxy ($C_{1-4}$)alkylcarbonylamino, $C_{1-4}$alkylsulfonylaminocarbonylamino, carboxy($C_{1-4}$)alkylamino, bis(2-hydroxyethyl) aminocarbonylamino, (2-hydroxyethyl) aminocarbonylamino, 1,1,1,3,3,3-hexafluoro-2-hydroxypropan-2-yl, 4-carboxypiperidin-1-yl, piperazin-1-yl, triazolylthio, tetrazolyl, triazolyl, imidazolyl, or oxazolyl;

wherein said tetrazolyl, triazolyl, imidazolyl, or oxazolyl substituents are optionally independently substituted with one or two substituents selected from the group consisting of $C_{1-4}$alkyl and hydroxy;

and wherein said phenyl ring of group (iii) is optionally independently further substituted with one or two substituents selected from the group consisting of $C_{1-4}$alkyl, $C_{1-4}$alkoxy, and fluoro;

(iv) phenyl substituted at the 4-position with one substituent that is r-1 or r-3;

r-1

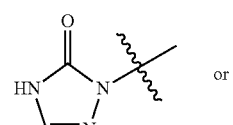

or r-3

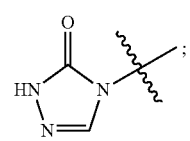

wherein said phenyl ring of group (iv) is optionally further substituted with one additional fluoro substituent;

(v) phenyl substituted at the 4-position with p-1 or p-2;

p-1

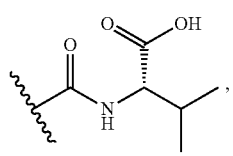

-continued

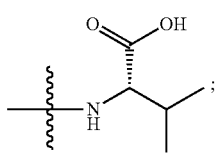
p-2 or (vi) piperidin-4-yl optionally substituted at the 1-position with aminosulfonyl.

3. The compound of claim 2 wherein $R^1$ is (i) hydrogen;

(ii) a substituent selected from the group consisting of pyridinyl, 1H-pyrazol-4-yl, 5-pyrimidinyl, 5-hydroxy-1,2,4-oxadiazol-3-yl, 1H-imidazo[4,5-b]pyridin-6-yl, 2-hydroxy-1H-imidazo[4,5-b]pyridin-6-yl, and a ring 1-a to 1-h

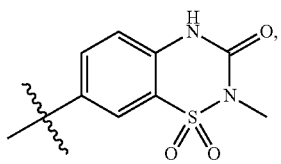
1-a

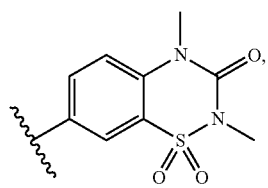
1-b

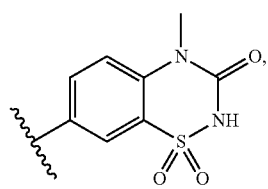
1-c

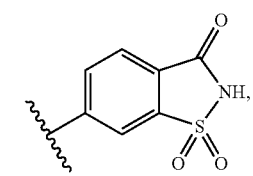
1-d

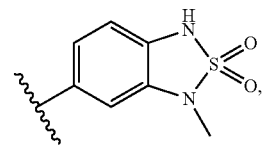
1-e

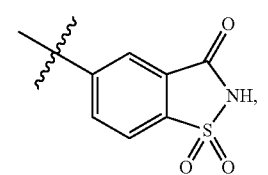
1-f

-continued

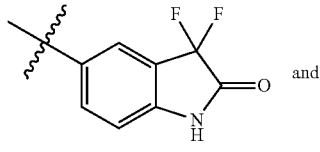
1-g and

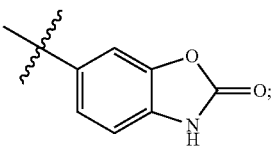
1-h wherein the pyridinyl and 5-pyrimidinyl rings of group (iii) are optionally substituted with one substituent selected from the group consisting of $C_{1-4}$alkyl, carboxy($C_{1-4}$) alkyl, aminocarbonyl, aminosulfonyl, 1,2,3,6-tetrahydropyridin-4-yl, carboxy, amino, dimethylamino, carboxymethylamino, 4-methylpiperazin-1-yl, morpholin-4-yl, $C_{1-4}$alkylsulfonylamino, $C_{1-4}$alkylsulfonylaminocarbonyl, 1,2,4-oxadiazol-5 (4H)-one-3-yl, tetrazolyl, triazolyl, or triazolylthio; wherein said tetrazolyl and triazolyl are optionally substituted with one hydroxy substituent;

and wherein said pyridinyl of group (iii) is optionally further substituted with one or two substituents selected from the group consisting of fluoro, chloro, and hydroxy;

wherein said 1H-pyrazol-4-yl of group (iii) is optionally substituted at the 1-position with methoxy-ethyl or carboxy($C_{1-4}$)alkyl;

(iii) phenyl optionally substituted at the 4-position with one substituent that is $C_{1-4}$alkoxycarbonyl, $C_{1-4}$alkylcarbonylaminosulfonyl, (2-hydroxyethyl)aminosulfonyl, aminosulfonyl, $C_{1-4}$alkylsulfonylaminocarbonyl, carboxy, —O(CH$_2$CH$_2$O)$_{2-5}$CH$_3$, —OCH$_2$OCH$_3$, carboxy($C_{1-4}$)alkylaminocarbonyl, 2-carboxypyrrolidin-1-ylcarbonyl, carboxy ($C_{1-4}$)alkylcarbonylamino, $C_{1-4}$alkylsulfonylaminocarbonylamino, carboxy($C_{1-4}$)alkylamino, bis(2-hydroxyethyl) aminocarbonylamino, (2-hydroxyethyl) aminocarbonylamino, 1,1,1,3,3,3-hexafluoro-2-hydroxypropan-2-yl, 4-carboxypiperidin-1-yl, piperazin-1-yl, triazolylthio, tetrazolyl, triazolyl, imidazolyl, or oxazolyl;

wherein said tetrazolyl, triazolyl, imidazolyl, or oxazolyl substituents are optionally independently substituted with one or two substituents selected from the group consisting of $C_{1-4}$alkyl and hydroxy;

and wherein said phenyl ring of group (iii) is optionally independently further substituted with one or two substituents selected from the group consisting of $C_{1-4}$alkyl, $C_{1-4}$alkoxy, and fluoro;

(iv) phenyl substituted at the 4-position with one substituent that is r-1 or r-3;

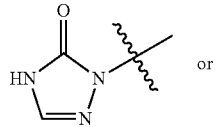
r-1 or

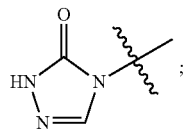 r-3 wherein said phenyl ring of group (iv) is optionally further substituted with one additional fluoro substituent; or (v) phenyl substituted at the 4-position with p-1 or p-2;

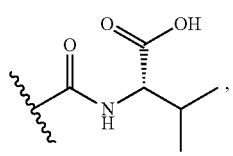 p-1

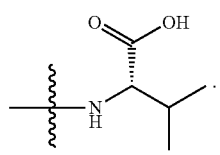 p-2

4. The compound of claim 1 wherein $R^2$ is hydrogen.

5. The compound of claim 1 wherein L is a bivalent linker that is ethyl, E-ethenyl, ethynyl, trans-1,3-cyclobutyl, cis-1,3-cyclobutyl, azetidinyl, —CH$_2$X—, or —NHC(O)—; wherein X is O or S.

6. The compound of claim 5 wherein L is a bivalent linker that is ethyl, E-ethenyl, ethynyl, trans-1,3-cyclobutyl, azetidinyl, or —CH$_2$X—; wherein X is O or S.

7. The compound of claim 1 wherein Q is quinolin-2-yl, pyridinyl, pyrimidinyl, benzimidazol-2-yl, or benzothiazol-2-yl; wherein said Q is optionally independently substituted with one or two substituents selected from the group consisting of $C_{1-4}$alkyl, carboxy-methoxy, $C_{1-4}$alkoxy, and carboxy.

8. The compound of claim 7 wherein Q is quinolin-2-yl, pyridinyl, benzimidazol-2-yl, or benzothiazol-2-yl; wherein said Q is optionally independently substituted with one substituent selected from the group consisting of $C_{1-4}$alkyl, carboxy-methoxy, $C_{1-4}$alkoxy, and carboxy.

9. A compound of Formula (I)

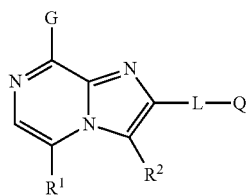

Formula (I)

wherein

G is

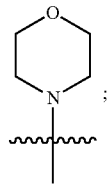 g-1

$R^1$ is (i) hydrogen;

(ii) a substituent selected from the group consisting of pyridinyl, 1H-pyrazol-4-yl, 5-pyrimidinyl, 5-hydroxy-1,2,4-oxadiazol-3-yl, 1H-imidazo[4,5-b]pyridin-6-yl, 2-hydroxy-1H-imidazo[4,5-b]pyridin-6-yl, and a ring 1-a to 1-h

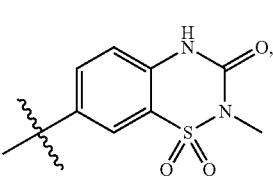 1-a

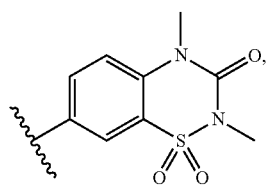 1-b

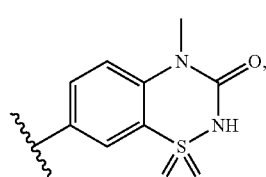 1-c

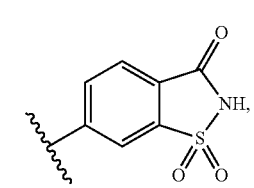 1-d

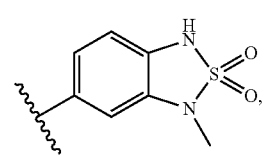 1-e

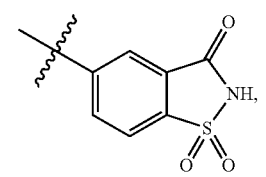 1-f

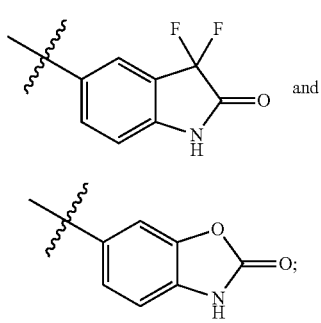

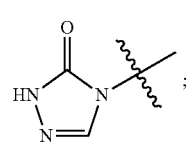

wherein the pyridinyl and 5-pyrimidinyl rings of group (iii) are optionally substituted with one substituent selected from the group consisting of $C_{1-4}$alkyl, carboxy($C_{1-4}$)alkyl, aminocarbonyl, aminosulfonyl, 1,2,3,6-tetrahydropyridin-4-yl, carboxy, amino, dimethylamino, carboxymethylamino, 4-methylpiperazin-1-yl, morpholin-4-yl, $C_{1-4}$alkylsulfonylamino, $C_{1-4}$alkylsulfonylaminocarbonyl, 1,2,4-oxadiazol-5(4H)-one-3-yl, tetrazolyl, triazolyl, or triazolylthio; wherein said tetrazolyl and triazolyl are optionally substituted with one hydroxy substituent;

and wherein said pyridinyl of group (iii) is optionally further substituted with one or two substituents selected from the group consisting of fluoro, chloro, and hydroxy;

wherein said 1H-pyrazol-4-yl of group (iii) is optionally substituted at the 1-position with methoxy-ethyl or carboxy($C_{1-4}$)alkyl;

(iii) phenyl optionally substituted at the 4-position with one substituent that is $C_{1-4}$alkoxycarbonyl, $C_{1-4}$alkylcarbonylaminosulfonyl, (2-hydroxyethyl)aminosulfonyl, aminosulfonyl, $C_{1-4}$alkylsulfonylaminocarbonyl, carboxy, —O(CH$_2$CH$_2$O)$_{2-5}$CH$_3$, —OCH$_2$OCH$_3$, carboxy($C_{1-4}$)alkylaminocarbonyl, 2-carboxypyrrolidin-1-ylcarbonyl, carboxy($C_{1-4}$)alkylcarbonylamino, $C_{1-4}$alkylsulfonylaminocarbonylamino, carboxy($C_{1-4}$)alkylamino, bis(2-hydroxyethyl)aminocarbonylamino, (2-hydroxyethyl)aminocarbonylamino, 1,1,1,3,3,3-hexafluoro-2-hydroxypropan-2-yl, 4-carboxypiperidin-1-yl, piperazin-1-yl, triazolylthio, tetrazolyl, triazolyl, imidazolyl, or oxazolyl;

wherein said tetrazolyl, triazolyl, imidazolyl, or oxazolyl substituents are optionally independently substituted with one or two substituents selected from the group consisting of $C_{1-4}$alkyl and hydroxy;

and wherein said phenyl ring of group (iii) is optionally independently further substituted with one or two substituents selected from the group consisting of $C_{1-4}$alkyl, $C_{1-4}$alkoxy, and fluoro;

(iv) phenyl substituted at the 4-position with one substituent that is r-1 or r-3;

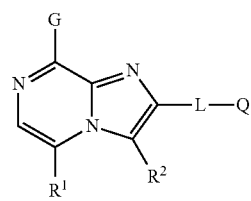

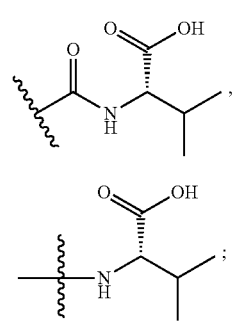

wherein said phenyl ring of group (iv) is optionally further substituted with one additional fluoro substituent;

(v) phenyl substituted at the 4-position with p-1 or p-2;

or (vi) piperidin-4-yl optionally substituted at the 1-position with aminosulfonyl;

$R^2$ is hydrogen;

L is a bivalent linker that is ethyl, E-ethenyl, ethynyl, trans-1,3-cyclobutyl, cis-1,3-cyclobutyl, azetidinyl, —CH$_2$X—, or —NHC(O)—; wherein X is O or S;

Q is quinolin-2-yl, pyridinyl, pyrimidinyl, benzimidazol-2-yl, or benzothiazol-2-yl; wherein said Q is optionally independently substituted with one or two substituents selected from the group consisting of $C_{1-4}$alkyl, carboxy-methoxy, $C_{1-4}$alkoxy, and carboxy;

or an enantiomer, diastereomer, or pharmaceutically acceptable salt form thereof.

10. A compound of Formula (I)

Formula (I)

wherein
G is

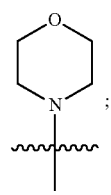

R[1] is
(i) hydrogen;
(ii) a substituent selected from the group consisting of pyridinyl, 1H-pyrazol-4-yl, 5-pyrimidinyl, 5-hydroxy-1,2,4-oxadiazol-3-yl, 1H-imidazo[4,5-b]pyridin-6-yl, 2-hydroxy-1H-imidazo[4,5-b]pyridin-6-yl, and a ring 1-a to 1-h

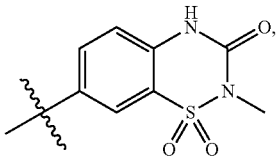
1-a

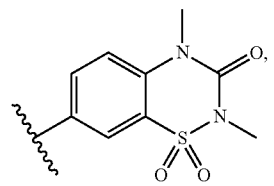
1-b

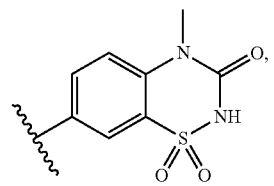
1-c

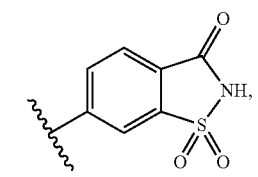
1-d

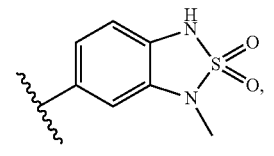
1-e

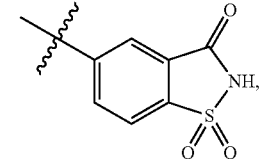
1-f

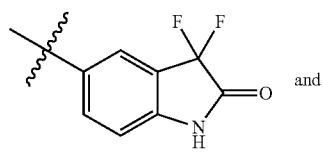
1-g

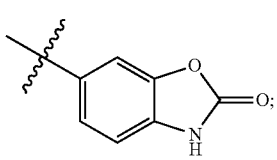
1-h wherein the pyridinyl and 5-pyrimidinyl rings of group (iii) are optionally substituted with one substituent selected from the group consisting of $C_{1-4}$alkyl, carboxy($C_{1-4}$)alkyl, aminocarbonyl, aminosulfonyl, 1,2,3,6-tetrahydropyridin-4-yl, carboxy, amino, dimethylamino, carboxymethylamino, 4-methylpiperazin-1-yl, morpholin-4-yl, $C_{1-4}$alkylsulfonylamino, $C_{1-4}$alkylsulfonylaminocarbonyl, 1,2,4-oxadiazol-5(4H)-one-3-yl, tetrazolyl, triazolyl, or triazolylthio; wherein said tetrazolyl and triazolyl are optionally substituted with one hydroxy substituent;

and wherein said pyridinyl of group (iii) is optionally further substituted with one or two substituents selected from the group consisting of fluoro, chloro, and hydroxy;

wherein said 1H-pyrazol-4-yl of group (iii) is optionally substituted at the 1-position with methoxy-ethyl or carboxy($C_{1-4}$)alkyl;

(iii) phenyl optionally substituted at the 4-position with one substituent that is $C_{1-4}$alkoxycarbonyl, $C_{1-4}$alkylcarbonylaminosulfonyl, (2-hydroxyethyl)aminosulfonyl, aminosulfonyl, $C_{1-4}$alkylsulfonylaminocarbonyl, carboxy, —O(CH$_2$CH$_2$O)$_{2-5}$CH$_3$, —OCH$_2$OCH$_3$, carboxy($C_{1-4}$)alkylaminocarbonyl, 2-carboxypyrrolidin-1-ylcarbonyl, carboxy($C_{1-4}$)alkylcarbonylamino, $C_{1-4}$alkylsulfonylaminocarbonylamino, carboxy($C_{1-4}$)alkylamino, bis(2-hydroxyethyl)aminocarbonylamino, (2-hydroxyethyl)aminocarbonylamino, 1,1,1,3,3,3-hexafluoro-2-hydroxypropan-2-yl, 4-carboxypiperidin-1-yl, piperazin-1-yl, triazolylthio, tetrazolyl, triazolyl, imidazolyl, or oxazolyl;

wherein said tetrazolyl, triazolyl, imidazolyl, or oxazolyl substituents are optionally independently substituted with one or two substituents selected from the group consisting of $C_{1-4}$alkyl and hydroxy;

and wherein said phenyl ring of group (iii) is optionally independently further substituted with one or two substituents selected from the group consisting of $C_{1-4}$alkyl, $C_{1-4}$alkoxy, and fluoro;

(iv) phenyl substituted at the 4-position with one substituent that is r-1 or r-3;

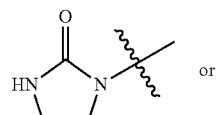 or
r-1

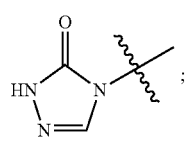 ;
r-3 wherein said phenyl ring of group (iv) is optionally further substituted with one additional fluoro substituent; or (v) phenyl substituted at the 4-position with p-1 or p-2;

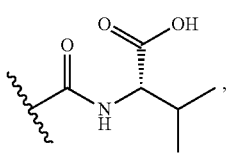
p-1

-continued

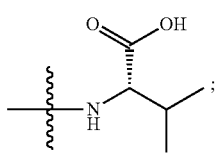
p-2

R² is hydrogen;

L is a bivalent linker that is ethyl, E-ethenyl, ethynyl, trans-1,3-cyclobutyl, cis-1,3-cyclobutyl, azetidinyl, —CH₂X—, or —NHC(O)—; wherein X is O or S;

Q is quinolin-2-yl, pyridinyl, pyrimidinyl, benzimidazol-2-yl, or benzothiazol-2-yl; wherein said Q is optionally independently substituted with one or two substituents selected from the group consisting of $C_{1-4}$alkyl, carboxy-methoxy, $C_{1-4}$alkoxy, and carboxy;

or an enantiomer, diastereomer, or pharmaceutically acceptable salt form thereof.

11. A compound of Formula (I)

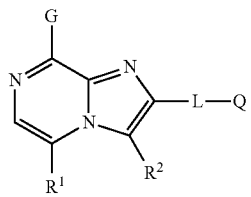
Formula (I)

wherein

G is

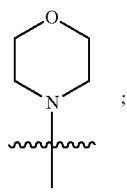
g-1

R¹ is (i) hydrogen;

(ii) a substituent selected from the group consisting of pyridinyl, 1H-pyrazol-4-yl, 5-pyrimidinyl, 5-hydroxy-1,2,4-oxadiazol-3-yl, 1H-imidazo[4,5-b]pyridin-6-yl, 2-hydroxy-1H-imidazo[4,5-b]pyridin-6-yl, and a ring 1-a to 1-h

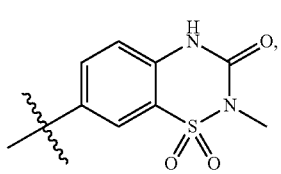
1-a

-continued

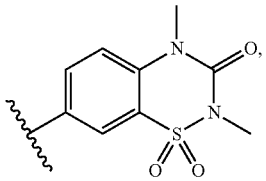
1-b

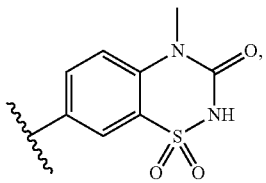
1-c

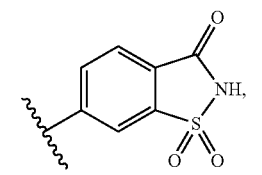
1-d

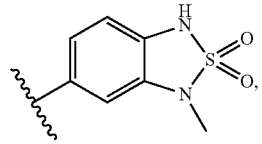
1-e

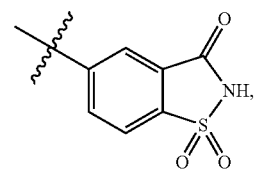
1-f

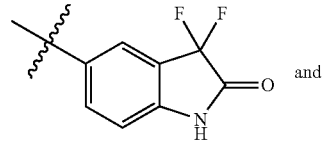
1-g
and

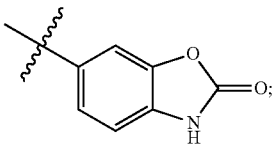
1-h wherein the pyridinyl and 5-pyrimidinyl rings of group (iii) are optionally substituted with one substituent selected from the group consisting of $C_{1-4}$alkyl, carboxy($C_{1-4}$)alkyl, aminocarbonyl, aminosulfonyl, 1,2,3,6-tetrahydropyridin-4-yl, carboxy, amino, dimethylamino, carboxymethylamino, 4-methylpiperazin-1-yl, morpholin-4-yl, $C_{1-4}$alkylsulfonylamino, $C_{1-4}$alkylsulfonylaminocarbonyl, 1,2,4-oxadiazol-5(4H)-one-3-yl, tetrazolyl, triazolyl, or triazolylthio; wherein said tetrazolyl and triazolyl are optionally substituted with one hydroxy substituent;

and wherein said pyridinyl of group (iii) is optionally further substituted with one or two substituents selected from the group consisting of fluoro, chloro, and hydroxy;

wherein said 1H-pyrazol-4-yl of group (iii) is optionally substituted at the 1-position with methoxy-ethyl or carboxy($C_{1-4}$)alkyl;

(iii) phenyl optionally substituted at the 4-position with one substituent that is $C_{1-4}$alkoxycarbonyl, $C_{1-4}$alkylcarbonylaminosulfonyl, (2-hydroxyethyl)aminosulfonyl, aminosulfonyl, $C_{1-4}$alkylsulfonylaminocarbonyl, carboxy, —O($CH_2CH_2O)_{2-5}CH_3$, —$OCH_2OCH_3$, carboxy($C_{1-4}$)alkylaminocarbonyl, 2-carboxypyrrolidin-1-ylcarbonyl, carboxy($C_{1-4}$)alkylcarbonylamino, $C_{1-4}$alkylsulfonylaminocarbonylamino, carboxy($C_{1-4}$)alkylamino, bis(2-hydroxyethyl)aminocarbonylamino, (2-hydroxyethyl)aminocarbonylamino, 1,1,1,3,3,3-hexafluoro-2-hydroxypropan-2-yl, 4-carboxypiperidin-1-yl, piperazin-1-yl, triazolylthio, tetrazolyl, triazolyl, imidazolyl, or oxazolyl;

wherein said tetrazolyl, triazolyl, imidazolyl, or oxazolyl substituents are optionally independently substituted with one or two substituents selected from the group consisting of $C_{1-4}$alkyl and hydroxy;

and wherein said phenyl ring of group (iii) is optionally independently further substituted with one or two substituents selected from the group consisting of $C_{1-4}$alkyl, $C_{1-4}$alkoxy, and fluoro;

(iv) phenyl substituted at the 4-position with one substituent that is r-1 or r-3;

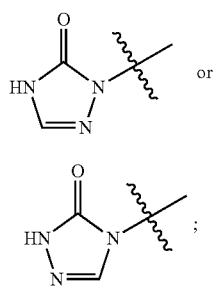

r-1

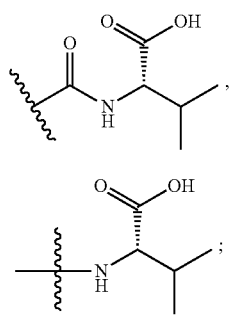

r-3 wherein said phenyl ring of group (iv) is optionally further substituted with one additional fluoro substituent; or (v) phenyl substituted at the 4-position with p-1 or p-2;

p-1

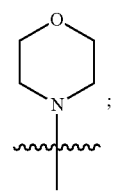

p-2

L is a bivalent linker that is -ethyl, E-ethenyl, ethynyl, trans-1,3-cyclobutyl, azetidinyl, or —$CH_2X$; wherein X is O or S;

Q is quinolin-2-yl, pyridinyl, benzimidazol-2-yl, or benzothiazol-2-yl;

wherein said Q is optionally independently substituted with one substituent selected from the group consisting of $C_{1-4}$alkyl, carboxy-methoxy, $C_{1-4}$alkoxy, and carboxy;

or an enantiomer, diastereomer, or pharmaceutically acceptable salt form thereof.

12. A compound of Formula (I)

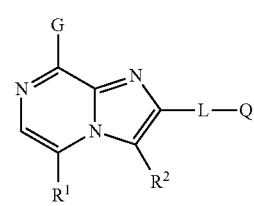

Formula (I)

wherein

G is

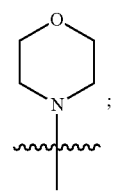

g-1

$R^1$ is (i) hydrogen;

(ii) a substituent selected from the group consisting of pyridinyl, 1H-pyrazol-4-yl, 5-pyrimidinyl, 5-hydroxy-1,2,4-oxadiazol-3-yl, 1H-imidazo[4,5-b]pyridin-6-yl, 2-hydroxy-1H-imidazo[4,5-b]pyridin-6-yl, and a ring 1-a to 1-h

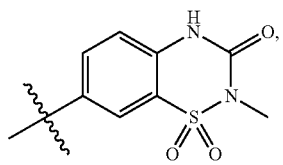

1-a

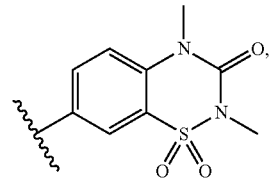

1-b

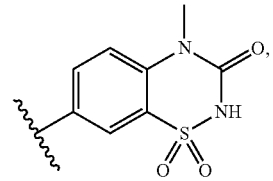

1-c

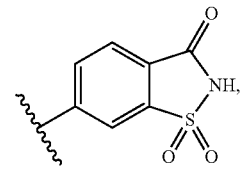

1-d

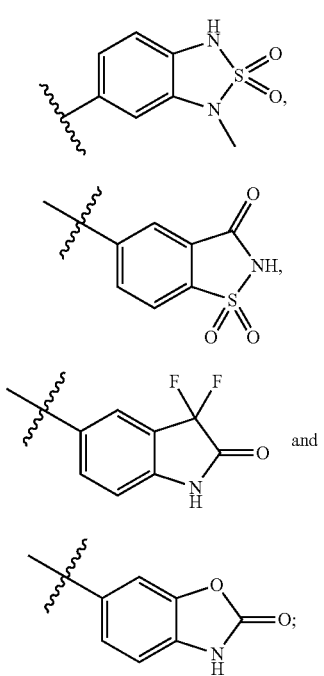

1-e 1-f 1-g 1-h wherein the pyridinyl and 5-pyrimidinyl rings of group (iii) are optionally substituted with one substituent selected from the group consisting of $C_{1-4}$alkyl, carboxy($C_{1-4}$)alkyl, aminocarbonyl, aminosulfonyl, 1,2,3,6-tetrahydropyridin-4-yl, carboxy, amino, dimethylamino, carboxymethylamino, 4-methylpiperazin-1-yl, morpholin-4-yl, $C_{1-4}$alkylsulfonylamino, $C_{1-4}$alkylsulfonylaminocarbonyl, 1,2,4-oxadiazol-5(4H)-one-3-yl, tetrazolyl, triazolyl, or triazolylthio; wherein said tetrazolyl and triazolyl are optionally substituted with one hydroxy substituent;

and wherein said pyridinyl of group (iii) is optionally further substituted with one or two substituents selected from the group consisting of fluoro, chloro, and hydroxy;

wherein said 1H-pyrazol-4-yl of group (iii) is optionally substituted at the 1-position with methoxy-ethyl or carboxy($C_{1-4}$)alkyl;

(iii) phenyl optionally substituted at the 4-position with one substituent that is $C_{1-4}$alkoxycarbonyl, $C_{1-4}$alkylcarbonylaminosulfonyl, (2-hydroxyethyl)aminosulfonyl, aminosulfonyl, $C_{1-4}$alkylsulfonylaminocarbonyl, carboxy, —O(CH$_2$CH$_2$O)$_{2-5}$CH$_3$, —OCH$_2$OCH$_3$, carboxy($C_{1-4}$)alkylaminocarbonyl, 2-carboxypyrrolidin-1-ylcarbonyl, carboxy($C_{1-4}$)alkylcarbonylamino, $C_{1-4}$alkylsulfonylaminocarbonylamino, carboxy($C_{1-4}$)alkylamino, bis(2-hydroxyethyl)aminocarbonylamino, (2-hydroxyethyl)aminocarbonylamino, 1,1,1,3,3,3-hexafluoro-2-hydroxypropan-2-yl, 4-carboxypiperidin-1-yl, piperazin-1-yl, triazolylthio, tetrazolyl, triazolyl, imidazolyl, or oxazolyl;

wherein said tetrazolyl, triazolyl, imidazolyl, or oxazolyl substituents are optionally independently substituted with one or two substituents selected from the group consisting of $C_{1-4}$alkyl and hydroxy;

and wherein said phenyl ring of group (iii) is optionally independently further substituted with one or two substituents selected from the group consisting of $C_{1-4}$alkyl, $C_{1-4}$alkoxy, and fluoro;

(iv) phenyl substituted at the 4-position with one substituent that is r-1 or r-3;

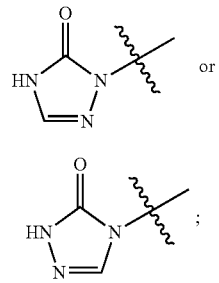

r-1 r-3 wherein said phenyl ring of group (iv) is optionally further substituted with one additional fluoro substituent; or (v) phenyl substituted at the 4-position with p-1 or p-2;

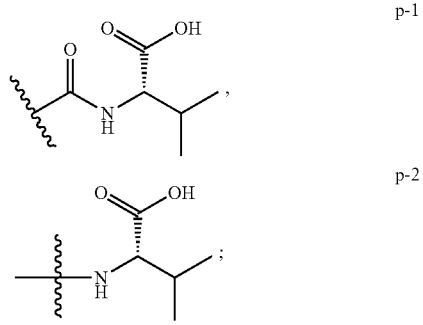

p-1 p-2

$R^2$ is hydrogen;

L is a bivalent linker that is ethyl, E-ethenyl, ethynyl, trans-1,3-cyclobutyl, azetidinyl, or —CH$_2$X—; wherein X is O or S;

Q is quinolin-2-yl, pyridinyl, benzimidazol-2-yl, or benzothiazol-2-yl;

wherein said Q is optionally independently substituted with one substituent selected from the group consisting of $C_{1-4}$alkyl, carboxy-methoxy, $C_{1-4}$alkoxy, and carboxy;

or an enantiomer, diastereomer, or pharmaceutically acceptable salt form thereof.

13. A compound of Formula (I)

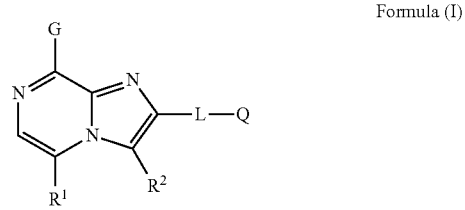

Formula (I)

selected from the group consisting of

Cpd 1, the compound of Formula (I) wherein G is g-1, $R^1$ is 4-carboxyphenyl, $R^2$ is hydrogen, L is cis-cyclobutyl, and Q is quinolin-2-yl;

Cpd 2, the compound of Formula (I) wherein G is g-1, $R^1$ is 4-(1,1,1,3,3,3-hexafluoro-2-hydroxy-propan-2-yl)phenyl, $R^2$ is hydrogen, L is E-ethenyl, and Q is quinolin-2-yl;

Cpd 3, the compound of Formula (I) wherein G is g-1, $R^1$ is 4-carboxy-3-fluorophenyl, $R^2$ is hydrogen, L is E-ethenyl, and Q is quinolin-2-yl;

Cpd 4, the compound of Formula (I) wherein G is g-1, $R^1$ is 4-carboxy-3-methoxyphenyl, $R^2$ is hydrogen, L is E-ethenyl, and Q is quinolin-2-yl;

Cpd 5, the compound of Formula (I) wherein G is g-1, $R^1$ is 4-carboxyphenyl, $R^2$ is hydrogen, L is trans-cyclobutyl, and Q is quinolin-2-yl;

Cpd 6, the compound of Formula (I) wherein G is g-1, $R^1$ is 5-carboxypyridin-2-yl, $R^2$ is hydrogen, L is E-ethenyl, and Q is quinolin-2-yl;

Cpd 7, the compound of Formula (I) wherein G is g-1, $R^1$ is 4-carboxyphenyl, $R^2$ is hydrogen, L is E-ethenyl, and Q is 6-methoxypyridin-2-yl;

Cpd 8, the compound of Formula (I) wherein G is g-1, $R^1$ is H, $R^2$ is hydrogen, L is E-ethenyl, and Q is 4-carboxyquinolin-2-yl;

Cpd 9, the compound of Formula (I) wherein G is g-1, $R^1$ is 1-carboxymethyl-pyrazol-4-yl, $R^2$ is hydrogen, L is ethynyl, and Q is quinolin-2-yl;

Cpd 10, the compound of Formula (I) wherein G is g-1, $R^1$ is 4-carboxyphenyl, $R^2$ is hydrogen, L is ethynyl, and Q is pyridin-2-yl;

Cpd 11, the compound of Formula (I) wherein G is g-1, $R^1$ is 4-carboxyphenyl, $R^2$ is hydrogen, L is ethynyl, and Q is benzothiazol-2-yl;

Cpd 12, the compound of Formula (I) wherein G is g-1, $R^1$ is 4-(methanesulfonylaminocarbonyl)phenyl, $R^2$ is hydrogen, L is —CH$_2$S-Q, and Q is quinolin-2-yl;

Cpd 13, the compound of Formula (I) wherein G is g-1, $R^1$ is 4-carboxyphenyl,
L is —CH$_2$S-Q, and Q is quinolin-2-yl;

Cpd 14, the compound of Formula (I) wherein G is g-1, $R^1$ is 4-(4-carboxypiperidin-1-yl)phenyl, $R^2$ is hydrogen, L is E-ethenyl, and Q is quinolin-2-yl;

Cpd 15, the compound of Formula (I) wherein G is g-1, $R^1$ is

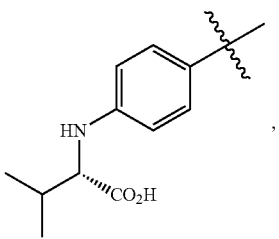 [SMILES: *c1ccc(N[C@H](C(=O)O)C(C)C)cc1]

$R^2$ is hydrogen, L is E-ethenyl, and Q is quinolin-2-yl;

Cpd 16, the compound of Formula (I) wherein G is g-1, $R^1$ is 4-carboxyphenyl, $R^2$ is hydrogen, L is E-ethenyl, and Q is quinolin-2-yl;

Cpd 17, the compound of Formula (I) wherein G is g-1, $R^1$ is 4-carboxyphenyl, $R^2$ is hydrogen, L is ethyl, and Q is quinolin-2-yl;

Cpd 18, the compound of Formula (I) wherein G is g-1, $R^1$ is 4-(CH$_3$(OCH$_2$CH$_2$)$_2$O)phenyl, $R^2$ is hydrogen, L is E-ethenyl, and Q is quinolin-2-yl Cpd 19, the compound of Formula (I) wherein G is g-1, $R^1$ is

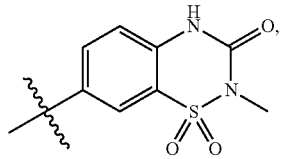

1-a $R^2$ is hydrogen, L is E-ethenyl, and Q is quinolin-2-yl;

Cpd 20, the compound of Formula (I) wherein G is g-1, $R^1$ is

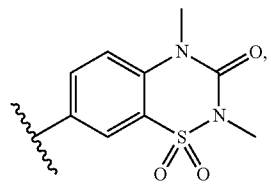

1-b $R^2$ is hydrogen, L is E-ethenyl, and Q is quinolin-2-yl;

Cpd 21, the compound of Formula (I) wherein G is g-1, $R^1$ is

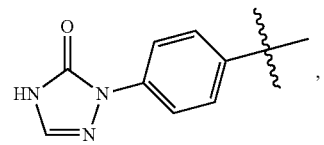 [SMILES: *c1ccc(-n2nc[nH]c2=O)cc1]

$R^2$ is hydrogen, L is ethyl, and Q is quinolin-2-yl;

Cpd 22, the compound of Formula (I) wherein G is g-1, $R^1$ is 4-(2-carboxyethylamino)phenyl, $R^2$ is hydrogen, L is E-ethenyl, and Q is quinolin-2-yl;

Cpd 23, the compound of Formula (I) wherein G is g-1, $R^1$ is 4-(2-carboxyethylamino)phenyl, $R^2$ is hydrogen, L is ethyl, and Q is quinolin-2-yl;

Cpd 24, the compound of Formula (I) wherein G is g-1, $R^1$ is

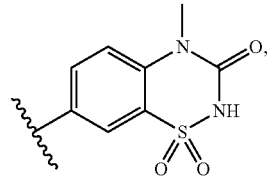

1-c $R^2$ is hydrogen, L is E-ethenyl, and Q is quinolin-2-yl;

Cpd 25, the compound of Formula (I) wherein G is g-1, $R^1$ is 5-(methanesulfonylaminocarbonyl)pyridin-3-yl, $R^2$ is hydrogen, L is E-ethenyl, and Q is quinolin-2-yl;

Cpd 26, the compound of Formula (I) wherein G is g-1, $R^1$ is 2,4-dihydroxy-oxazol-5-yl, $R^2$ is hydrogen, L is ethyl, and Q is quinolin-2-yl;

Cpd 27, the compound of Formula (I) wherein G is g-1, $R^1$ is 5-carboxypyridin-3-yl, $R^2$ is hydrogen, L is E-ethenyl, and Q is quinolin-2-yl;

Cpd 28, the compound of Formula (I) wherein G is g-1, $R^1$ is 5-(5-hydroxy-1,2,4-oxadiazol-3-yl)pyridin-3-yl, $R^2$ is hydrogen, L is E-ethenyl, and Q is quinolin-2-yl;

Cpd 29, the compound of Formula (I) wherein G is g-1, R$^1$ is 4-(carboxymethylamino)phenyl, R$^2$ is hydrogen, L is E-ethenyl, and Q is quinolin-2-yl;

Cpd 30, the compound of Formula (I) wherein G is g-1, R$^1$ is 4-(carboxymethylamino)phenyl, R$^2$ is hydrogen, L is ethyl, and Q is quinolin-2-yl;

Cpd 31, the compound of Formula (I) wherein G is g-1, R$^1$ is 4-(CH$_3$(OCH$_2$CH$_2$)$_2$O)phenyl, R$^2$ is hydrogen, L is ethyl, and Q is quinolin-2-yl;

Cpd 32, the compound of Formula (I) wherein G is g-1, R$^1$ is 4-(carboxyethylcarbonylamino)phenyl, R$^2$ is hydrogen, L is E-ethenyl, and Q is quinolin-2-yl;

Cpd 33, the compound of Formula (I) wherein G is g-1, R$^1$ is 4-(1-methyl-5-hydroxy-1,2,4-triazol-3-yl)phenyl, R$^2$ is hydrogen, L is ethyl, and Q is quinolin-2-yl;

Cpd 34, the compound of Formula (I) wherein G is G is g-1, R$^1$ is

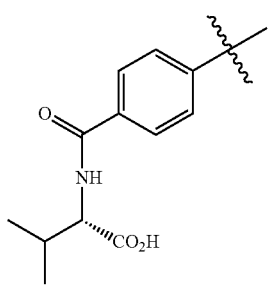 [SMILES: *c1ccc(C(=O)N[C@H](C(=O)O)C(C)C)cc1]

R$^2$ is hydrogen, L is ethyl, and Q is quinolin-2-yl;

Cpd 35, the compound of Formula (I) wherein G is g-1, R$^1$ is 4-(2(S)-carboxypyrrolidin-1-ylcarbonyl)phenyl, R$^2$ is hydrogen, L is ethyl, and Q is quinolin-2-yl;

Cpd 36, the compound of Formula (I) wherein G is g-1, R$^1$ is 4-(1H-1,2,3-triazol-4-ylthio)phenyl, R$^2$ is hydrogen, L is ethyl, and Q is quinolin-2-yl Cpd 37, the compound of Formula (I) wherein G is g-1, R$^1$ is 4-(carboxyethylcarbonylamino)phenyl, R$^2$ is hydrogen, L is ethyl, and Q is quinolin-2-yl;

Cpd 38, the compound of Formula (I) wherein G is g-1, R$^1$ is 4-(carboxyethylaminocarbonyl)phenyl, R$^2$ is hydrogen, L is ethyl, and Q is quinolin-2-yl;

Cpd 39, the compound of Formula (I) wherein G is g-1, R$^1$ is 4-(carboxyethylaminocarbonyl)phenyl, R$^2$ is hydrogen, L is E-ethenyl, and Q is quinolin-2-yl;

Cpd 40, the compound of Formula (I) wherein G is g-1, R$^1$ is 4-(methanesulfonylaminocarbonylamino)phenyl, R$^2$ is hydrogen, L is ethyl, and Q is quinolin-2-yl;

Cpd 41, the compound of Formula (I) wherein G is g-1, R$^1$ is 3,5-dimethyl-4-methoxymethoxy-phenyl, R$^2$ is hydrogen, L is E-ethenyl, and Q is quinolin-2-yl;

Cpd 42, the compound of Formula (I) wherein G is g-1, R$^1$ is

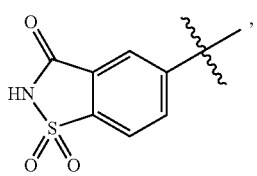 [SMILES: *c1ccc2c(c1)C(=O)NS2(=O)=O]

R$^2$ is hydrogen, L is E-ethenyl, and Q is quinolin-2-yl;

Cpd 43, the compound of Formula (I) wherein G is g-1, R$^1$ is

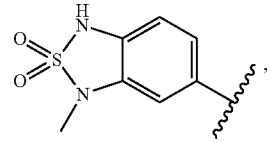 [SMILES: *c1ccc2c(c1)N(C)S(=O)(=O)N2]

R$^2$ is hydrogen, L is E-ethenyl, and Q is quinolin-2-yl;

Cpd 44, the compound of Formula (I) wherein G is g-1, R$^1$ is

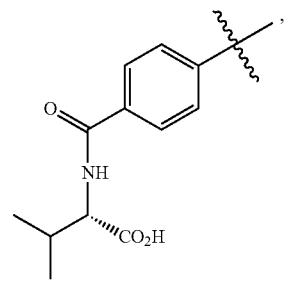 [SMILES: *c1ccc(C(=O)N[C@H](C(=O)O)C(C)C)cc1]

R$^2$ is hydrogen, L is E-ethenyl, and Q is quinolin-2-yl;

Cpd 45, the compound of Formula (I) wherein G is g-1, R$^1$ is 4-(2(S)-carboxypyrrolidin-1-ylcarbonyl)phenyl, R$^2$ is hydrogen, L is E-ethenyl, and Q is quinolin-2-yl;

Cpd 46, the compound of Formula (I) wherein G is g-1, R$^1$ is 4-(carboxymethylaminocarbonyl)phenyl, R$^2$ is hydrogen, L is ethyl, and Q is quinolin-2-yl;

Cpd 47, the compound of Formula (I) wherein G is g-1, R$^1$ is 4-(1-methyl-5-hydroxy-1,2,4-triazol-3-yl)phenyl, R$^2$ is hydrogen, L is E-ethenyl, and Q is quinolin-2-yl;

Cpd 48, the compound of Formula (I) wherein G is g-1, R$^1$ is 2,4-dihydroxy-oxazol-5-yl, R$^2$ is hydrogen, L is E-ethenyl, and Q is quinolin-2-yl;

Cpd 49, the compound of Formula (I) wherein G is g-1, R$^1$ is 2-methyl-4-isopropylaminosulfonyl-phenyl, R$^2$ is hydrogen, L is E-ethenyl, and Q is quinolin-2-yl;

Cpd 50, the compound of Formula (I) wherein G is g-1, R$^1$ is 4-(carboxymethylaminocarbonyl)phenyl, L is E-ethenyl, and Q is quinolin-2-yl;

Cpd 51, the compound of Formula (I) wherein G is g-1, R$^1$ is 4-(3-hydroxy-1H-1,2,4-triazol-1-yl)phenyl, R$^2$ is hydrogen, L is ethyl, and Q is quinolin-2-yl, Cpd 52, the compound of Formula (I) wherein G is g-1, R$^1$ is 6-(3-hydroxy-1H-1,2,4-triazol-1-yl)pyridin-3-yl, R$^2$ is hydrogen, L is E-ethenyl, and Q is quinolin-2-yl;

Cpd 53, the compound of Formula (I) wherein G is g-1, R$^1$ is 4-(5-hydroxy-1H-1,2,3,4-tetrazol-1-yl)phenyl, R$^2$ is hydrogen, L is ethyl, and Q is quinolin-2-yl;

Cpd 54, the compound of Formula (I) wherein G is g-1, R$^1$ is

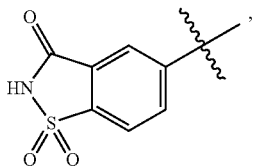 [SMILES: *c1ccc2c(c1)C(=O)NS2(=O)=O]

R² is hydrogen, L is ethyl, and Q is quinolin-2-yl;

Cpd 55, the compound of Formula (I) wherein G is g-1, R¹ is 4-(5-hydroxy-1H-tetrazol-1-yl)phenyl, R² is hydrogen, L is E-ethenyl, and Q is quinolin-2-yl;

Cpd 56, the compound of Formula (I) wherein G is g-1, R¹ is 4-(3-hydroxy-1H-1,2,4-triazol-1-yl)phenyl, R² is hydrogen, L is E-ethenyl, and Q is quinolin-2-yl;

Cpd 57, the compound of Formula (I) wherein G is g-1, R¹ is 4-(2,5-dihydroxy-imidazol-4-yl)phenyl, R² is hydrogen, L is E-ethenyl, and Q is quinolin-2-yl;

Cpd 58, the compound of Formula (I) wherein G is g-1, R¹ is

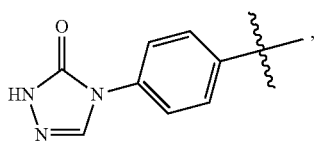 [SMILES: *c1ccc(-n2cn[nH]c2=O)cc1]

R² is hydrogen, L is E-ethenyl, and Q is quinolin-2-yl;

Cpd 59, the compound of Formula (I) wherein G is g-1, R¹ is

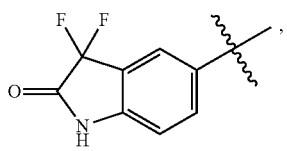 [SMILES: *c1ccc2c(c1)C(F)(F)C(=O)N2]

R² is hydrogen, L is ethyl, and Q is quinolin-2-yl;

Cpd 60, the compound of Formula (I) wherein G is g-1, R¹ is 5-(1H-tetrazol-5-yl)pyridin-3-yl, R² is hydrogen, L is E-ethenyl, and Q is quinolin-2-yl;

Cpd 61, the compound of Formula (I) wherein G is g-1, R¹ is 4-(methanesulfonylaminocarbonyl)phenyl, R² is hydrogen, L is ethyl, and Q is quinolin-2-yl;

Cpd 62, the compound of Formula (I) wherein G is g-1, R¹ is 4-(methanesulfonylaminocarbonyl)phenyl, R² is hydrogen, L is E-ethenyl, and Q is quinolin-2-yl;

Cpd 63, the compound of Formula (I) wherein G is g-1, R¹ is 4-(methylcarbonylaminosulfonyl)phenyl, R² is hydrogen, L is ethyl, and Q is quinolin-2-yl;

Cpd 64, the compound of Formula (I) wherein G is g-1, R¹ is

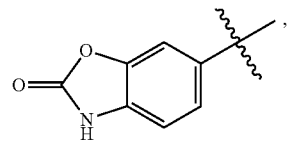 [SMILES: *c1ccc2[nH]c(=O)oc2c1]

R² is hydrogen, L is ethyl, and Q is quinolin-2-yl;

Cpd 65, the compound of Formula (I) wherein G is g-1, R¹ is

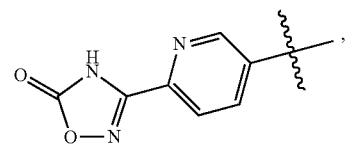 [SMILES: *c1ccc(-c2noc(=O)[nH]2)nc1]

R² is hydrogen, L is ethyl, and Q is quinolin-2-yl;

Cpd 66, the compound of Formula (I) wherein G is g-1, R¹ is 6-(carboxymethylamino)pyridin-3-yl, R² is hydrogen, L is E-ethenyl, and Q is quinolin-2-yl;

Cpd 67, the compound of Formula (I) wherein G is g-1, R¹ is 6-(4H-1,2,4-triazol-3-yl)pyridin-3-yl, R² is hydrogen, L is ethyl, and Q is quinolin-2-yl;

Cpd 68, the compound of Formula (I) wherein G is g-1, R¹ is

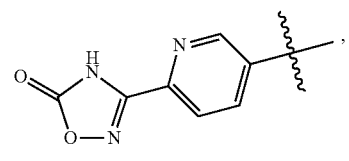 [SMILES: *c1ccc(-c2noc(=O)[nH]2)nc1]

R² is hydrogen, L is —CH₂O-Q, and Q is quinolin-2-yl;

Cpd 69, the compound of Formula (I) wherein G is g-1, R¹ is 4-(methylcarbonylaminosulfonyl)phenyl, R² is hydrogen, L is E-ethenyl, and Q is quinolin-2-yl;

Cpd 70, the compound of Formula (I) wherein G is g-1, R¹ is 6-(1H-tetrazol-5-yl)pyridin-3-yl, R² is hydrogen, L is —CH₂S-Q, and Q is quinolin-2-yl;

Cpd 71, the compound of Formula (I) wherein G is g-1, R¹ is 4-(bis-(2-hydroxyethyl)aminocarbonylamino)phenyl, R² is hydrogen, L is E-ethenyl, and Q is quinolin-2-yl;

Cpd 72, the compound of Formula (I) wherein G is g-1, R¹ is 4-((2-hydroxyethyl)aminocarbonylamino)phenyl, R² is hydrogen, L is E-ethenyl, and Q is quinolin-2-yl;

Cpd 73, the compound of Formula (I) wherein G is g-1, R¹ is 4-(2-hydroxyethylaminosulfonyl)phenyl, R² is hydrogen, L is E-ethenyl, and Q is quinolin-2-yl;

Cpd 74, the compound of Formula (I) wherein G is g-1, R¹ is $R^2$ is hydrogen, L is ethyl, and Q is quinolin-2-yl;

Cpd 75, the compound of Formula (I) wherein G is g-1, $R^1$ is 5-hydroxy-1,2,4-oxadiazol-3-yl, $R^2$ is hydrogen, L is —CH$_2$O-Q, and Q is quinolin-2-yl;

Cpd 76, the compound of Formula (I) wherein G is g-1, $R^1$ is 6-(methanesulfonylaminocarbonyl)pyridin-3-yl, $R^2$ is hydrogen, L is —CH$_2$O-Q, and Q is quinolin-2-yl;

Cpd 77, the compound of Formula (I) wherein G is g-1, $R^1$ is 6-(1H-tetrazol-5-yl)pyridin-3-yl, L is ethyl, and Q is quinolin-2-yl;

Cpd 78, the compound of Formula (I) wherein G is g-1, $R^1$ is 6-(methanesulfonylamino)pyridin-3-yl, $R^2$ is hydrogen, L is ethyl, and Q is quinolin-2-yl;

Cpd 79, the compound of Formula (I) wherein G is g-1, $R^1$ is 2-hydroxy-1H-imidazo[4,5-b]pyridin-6-yl, $R^2$ is hydrogen, L is ethyl, and Q is quinolin-2-yl;

Cpd 84, the compound of Formula (I) wherein G is g-1, $R^1$ is 6-aminocarbonyl-pyridin-3-yl, $R^2$ is hydrogen, L is —CH$_2$O-Q, and Q is quinolin-2-yl;

Cpd 85, the compound of Formula (I) wherein G is g-1, $R^1$ is 6-(methanesulfonylamino)pyridin-3-yl, $R^2$ is hydrogen, L is —CH$_2$O-Q, and Q is quinolin-2-yl;

Cpd 86, the compound of Formula (I) wherein G is g-1, $R^1$ is 6-aminosulfonyl-pyridin-3-yl, $R^2$ is hydrogen, L is —CH$_2$O-Q, and Q is quinolin-2-yl;

Cpd 87, the compound of Formula (I) wherein G is g-1, $R^1$ is 4-aminosulfonyl-phenyl, $R^2$ is hydrogen, L is —CH$_2$O-Q, and Q is quinolin-2-yl;

Cpd 88, the compound of Formula (I) wherein G is g-1, $R^1$ is 4-(methylcarbonylaminosulfonyl)phenyl, $R^2$ is hydrogen, L is —CH$_2$O-Q, and Q is quinolin-2-yl;

Cpd 89, the compound of Formula (I) wherein G is g-1, $R^1$ is 6-(methanesulfonylamino)pyridin-3-yl, $R^2$ is hydrogen, L is E-ethenyl, and Q is quinolin-2-yl;

Cpd 90, the compound of Formula (I) wherein G is g-1, $R^1$ is 4-(1H-tetrazol-5-yl)phenyl, $R^2$ is hydrogen, L is —CH$_2$O-Q, and Q is quinolin-2-yl;

Cpd 91, the compound of Formula (I) wherein G is g-1, $R^1$ is 6-(4H-1,2,4-triazol-3-yl)pyridin-3-yl, $R^2$ is hydrogen, L is E-ethenyl, and Q is quinolin-2-yl;

Cpd 92, the compound of Formula (I) wherein G is g-1, $R^1$ is 6-(3H-1,2,3-triazol-4-ylthio)pyridin-3-yl, $R^2$ is hydrogen, L is —CH$_2$O-Q, and Q is quinolin-2-yl;

Cpd 93, the compound of Formula (I) wherein G is g-1, $R^1$ is 1H-imidazo[4,5-b]pyridin-6-yl, $R^2$ is hydrogen, L is E-ethenyl, and Q is quinolin-2-yl;

Cpd 94, the compound of Formula (I) wherein G is g-1, $R^1$ is 2-hydroxy-1H-imidazo[4,5-b]pyridin-6-yl, $R^2$ is hydrogen, L is E-ethenyl, and Q is quinolin-2-yl;

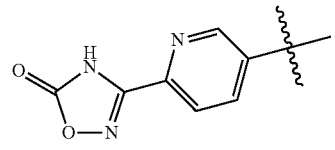 [SMILES: *c1ccc(-c2noc(=O)[nH]2)nc1]

Cpd 95, the compound of Formula (I) wherein G is g-1, $R^1$ is

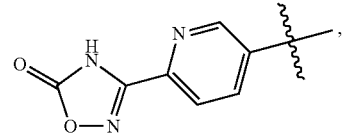 [SMILES: *c1ccc(-c2noc(=O)[nH]2)nc1]

$R^2$ is hydrogen, L is E-ethenyl, and Q is quinolin-2-yl;

Cpd 96, the compound of Formula (I) wherein G is g-1, $R^1$ is 6-(1H-tetrazol-5-yl)pyridin-3-yl, $R^2$ is hydrogen, L is E-ethenyl, and Q is quinolin-2-yl;

Cpd 97, the compound of Formula (I) wherein G is g-1, $R^1$ is 6-(1H-tetrazol-5-yl)pyridin-3-yl, $R^2$ is hydrogen, L is —CH$_2$O-Q, and Q is quinolin-2-yl;

Cpd 98, the compound of Formula (I) wherein G is g-1, $R^1$ is 6-(piperazin-1-yl)pyridin-3-yl, $R^2$ is hydrogen, L is —CH$_2$O-Q, and Q is quinolin-2-yl;

Cpd 99, the compound of Formula (I) wherein G is g-1, $R^1$ is 6-(piperazin-1-yl)pyridin-3-yl, $R^2$ is hydrogen, L is

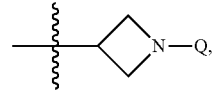

and Q is quinolin-2-yl;

Cpd 100, the compound of Formula (I) wherein G is g-1, $R^1$ is 6-(4H-1,2,4-triazol-3-ylthio)pyridin-3-yl, $R^2$ is hydrogen, L is —CH$_2$O-Q, and Q is quinolin-2-yl;

Cpd 101, the compound of Formula (I) wherein G is g-1, $R^1$ is 6-(carboxymethyl)pyridin-3-yl, $R^2$ is hydrogen, L is —CH$_2$O-Q, and Q is quinolin-2-yl;

Cpd 102, the compound of Formula (I) wherein G is g-1, $R^1$ is 6-(piperazin-1-yl)pyridin-3-yl, $R^2$ is hydrogen, L is ethyl, and Q is quinolin-2-yl;

Cpd 103, the compound of Formula (I) wherein G is g-1, $R^1$ is 6-(piperazin-1-yl)pyridin-3-yl, $R^2$ is hydrogen, L is E-ethenyl, and Q is pyrimidin-2-yl;

Cpd 104, the compound of Formula (I) wherein G is g-1, $R^1$ is 6-(piperazin-1-yl)pyridin-3-yl, $R^2$ is hydrogen, L is E-ethenyl, and Q is quinazolin-2-yl;

Cpd 105, the compound of Formula (I) wherein G is g-1, $R^1$ is 6-(piperazin-1-yl)pyridin-3-yl, $R^2$ is hydrogen, L is E-ethenyl, and Q is quinolin-2-yl;

Cpd 106, the compound of Formula (I) wherein G is g-1, $R^1$ is 6-(piperidin-4-yl)pyridin-3-yl, $R^2$ is hydrogen, L is —CH$_2$O-Q, and Q is quinolin-2-yl;

Cpd 107, the compound of Formula (I) wherein G is g-1, $R^1$ is 6-(carboxymethylamino)pyridin-3-yl, $R^2$ is hydrogen, L is —CH$_2$O-Q, and Q is quinolin-2-yl;

Cpd 108, the compound of Formula (I) wherein G is g-1, $R^1$ is 6-(1,2,3,6-tetrahydropyridin-4-yl)pyridin-3-yl, $R^2$ is hydrogen, L is —CH$_2$O-Q, and Q is quinolin-2-yl;

Cpd 109, the compound of Formula (I) wherein G is g-1, $R^1$ is 1-(aminosulfonyl)piperidin-4-yl, $R^2$ is hydrogen, L is —CH$_2$O-Q, and Q is quinolin-2-yl;

Cpd 110, the compound of Formula (I) wherein G is g-1, $R^1$ is 1-(carboxymethyl)piperidin-4-yl, $R^2$ is hydrogen, L is —CH$_2$O-Q, and Q is quinolin-2-yl;

Cpd 111, the compound of Formula (I) wherein G is g-1, $R^1$ is piperidin-4-yl, $R^2$ is hydrogen, L is —CH$_2$O-Q, and Q is quinolin-2-yl;

Cpd 114, the compound of Formula (I) wherein G is g-1, $R^1$ is 6-(piperazin-1-yl)pyridin-3-yl, $R^2$ is hydrogen, L is

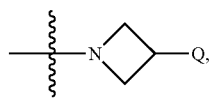

and Q is quinolin-2-yl;

Cpd 116, the compound of Formula (I) wherein G is g-1, $R^1$ is 6-(piperazin-1-yl)pyridin-3-yl, $R^2$ is hydrogen, L is —$CH_2$O-Q, and Q is pyrimidin-2-yl;

Cpd 121, the compound of Formula (I) wherein G is g-1, $R^1$ is 2-(piperazin-1-yl)pyrimidin-5-yl, $R^2$ is hydrogen, L is —$CH_2$O-Q, and Q is quinolin-2-yl;

Cpd 122, the compound of Formula (I) wherein G is g-1, $R^1$ is 6-aminopyridin-3-yl, $R^2$ is hydrogen, L is —$CH_2$O-Q, and Q is quinolin-2-yl;

Cpd 123, the compound of Formula (I) wherein G is g-1, $R^1$ is 2-(4-methylpiperazin-1-yl)pyrimidin-5-yl, $R^2$ is hydrogen, L is —$CH_2$O-Q, and Q is quinolin-2-yl;

Cpd 124, the compound of Formula (I) wherein G is g-1, $R^1$ is 6-(piperazin-1-yl)pyridin-3-yl, $R^2$ is hydrogen, L is —$CH_2$O-Q, and Q is quinazolin-2-yl;

Cpd 125, the compound of Formula (I) wherein G is g-1, $R^1$ is 6-(piperazin-1-yl)pyridin-3-yl, $R^2$ is hydrogen, L is —NHC(O)-Q, and Q is quinolin-2-yl;

Cpd 126, the compound of Formula (I) wherein G is g-1, $R^1$ is 6-(piperazin-1-yl)pyridin-3-yl, $R^2$ is hydrogen, L is —$CH_2$O-Q, and Q is quinolin-2-yl;

Cpd 127, the compound of Formula (I) wherein G is g-1, $R^1$ is 6-dimethylamino-pyridin-3-yl, $R^2$ is hydrogen, L is —$CH_2$O-Q, and Q is quinolin-2-yl;

Cpd 128, the compound of Formula (I) wherein G is g-1, $R^1$ is 6-methylpyridin-3-yl, $R^2$ is hydrogen, L is —$CH_2$O-Q, and Q is quinolin-2-yl;

Cpd 129, the compound of Formula (I) wherein G is g-1, $R^1$ is pyridin-3-yl, $R^2$ is hydrogen, L is —$CH_2$O-Q, and Q is quinolin-2-yl;

Cpd 130, the compound of Formula (I) wherein G is g-1, $R^1$ is 6-(4-methylpiperazin-1-yl)pyridin-3-yl, $R^2$ is hydrogen, L is —$CH_2$O-Q, and Q is quinolin-2-yl;

Cpd 131, the compound of Formula (I) wherein G is g-1, $R^1$ is 6-(morpholin-4-yl)pyridin-3-yl, $R^2$ is hydrogen, L is —$CH_2$O-Q, and Q is quinolin-2-yl;

Cpd 132, the compound of Formula (I) wherein G is g-1, $R^1$ is 6-(piperazin-1-yl)pyridin-3-yl, $R^2$ is chloro, L is

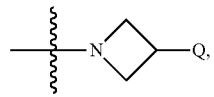

and Q is quinolin-2-yl;

Cpd 133, the compound of Formula (I) wherein G is g-1, $R^1$ is 6-carboxypyridin-3-yl, $R^2$ is hydrogen, L is E-ethenyl, and Q is quinolin-2-yl; g-1 is

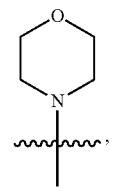

and pharmaceutically acceptable salt forms thereof.

14. A pharmaceutical composition comprising a compound of claim 1 or 13 and at least one of a pharmaceutically acceptable carrier, a pharmaceutically acceptable excipient, and a pharmaceutically acceptable diluent.

15. The pharmaceutical composition of claim 14, wherein the composition is a solid oral dosage form.

16. The pharmaceutical composition of claim 14, wherein the composition is a syrup, an elixir or a suspension.

17. A method of treating a psychosis, a cognitive disorder, a disorder of lipid metabolism, obesity or Type II diabetes, comprising administering to a subject in need thereof a therapeutically effective amount of the compound of claim 1 or 13.

18. The method of claim 17, wherein the disorder affected by the PDE10a enzyme is Type II diabetes.

19. A method of treating Type II diabetes comprising administering to a subject in need thereof a therapeutically effective amount of the composition of claim 14.

* * * * *